(12) United States Patent
O'Brien et al.

(10) Patent No.: US 6,865,926 B2
(45) Date of Patent: Mar. 15, 2005

(54) METHOD AND APPARATUS FOR SAMPLE ANALYSIS

(75) Inventors: Robert J. O'Brien, Clackamas, OR (US); Thomas R. Smith, Portland, OR (US)

(73) Assignee: State of Oregon Acting by and through the State Board of Higher Education on behalf of Portland State University, Portland, OR (US)

( * ) Notice: Subject to any disclaimer, the term of this patent is extended or adjusted under 35 U.S.C. 154(b) by 0 days.

(21) Appl. No.: 10/438,517

(22) Filed: May 14, 2003

(65) Prior Publication Data

US 2004/0035183 A1 Feb. 26, 2004

Related U.S. Application Data

(63) Continuation-in-part of application No. 09/770,942, filed on Jan. 25, 2001.
(60) Provisional application No. 60/448,411, filed on Feb. 18, 2003, and provisional application No. 60/177,923, filed on Jan. 25, 2000.

(51) Int. Cl.[7] .............................................. G01N 30/04
(52) U.S. Cl. ................................. 73/23.27; 73/23.42
(58) Field of Search ............................. 73/23.42, 23.27

(56) References Cited

U.S. PATENT DOCUMENTS

| | | | | |
|---|---|---|---|---|
| 2,839,152 A | * | 6/1958 | Tracht ...................... 73/864.86 |
| 3,240,052 A | * | 3/1966 | Reinecke et al. ........... 73/23.27 |
| 3,291,980 A | * | 12/1966 | Coates et al. ............... 73/23.37 |
| 3,712,111 A | * | 1/1973 | Llewellyn ................... 73/23.37 |
| 3,991,626 A | * | 11/1976 | Shair .......................... 73/23.4 |
| 4,033,171 A | * | 7/1977 | Karas et al. ................ 73/23.24 |
| 4,059,994 A | | 11/1977 | Annino et al. |
| 4,076,420 A | | 2/1978 | De Maeyer et al. |
| 4,095,455 A | * | 6/1978 | Karas et al. ................ 73/23.24 |
| 4,123,236 A | | 10/1978 | Hirschfeld et al. |
| 4,151,741 A | | 5/1979 | Schirrmeister |
| 4,165,644 A | | 8/1979 | Brandt et al. |
| 4,346,584 A | | 8/1982 | Boehringer |
| 4,517,824 A | * | 5/1985 | Quimby ..................... 73/23.42 |
| 4,658,637 A | | 4/1987 | Ollivaud et al. |
| 4,872,334 A | | 10/1989 | Watanabe |
| 4,962,662 A | * | 10/1990 | Berger ....................... 73/23.42 |
| 5,034,193 A | * | 7/1991 | Maroulis et al. ............. 422/89 |
| 5,099,743 A | | 3/1992 | Rounbehler et al. |
| 5,240,603 A | * | 8/1993 | Frank et al. ............... 210/198.2 |
| 5,305,232 A | * | 4/1994 | Chimowitz et al. .......... 702/32 |
| 5,340,476 A | * | 8/1994 | Berger et al. ............. 210/198.2 |
| 5,476,000 A | * | 12/1995 | Henderson et al. ........ 73/23.27 |
| 5,504,486 A | | 4/1996 | Bushman |
| 5,526,675 A | | 6/1996 | Ratton |
| 5,605,839 A | | 2/1997 | Simpson et al. |
| 5,624,846 A | * | 4/1997 | Hayashibe et al. ........... 436/50 |
| 5,668,735 A | | 9/1997 | Dominguez et al. |

(List continued on next page.)

FOREIGN PATENT DOCUMENTS

| | | |
|---|---|---|
| WO | WO 99/22868 | 1/1999 |
| WO | WO 01/55714 | 2/2001 |

OTHER PUBLICATIONS

Ocean Optics, Inc. 2003 Product Catalog, pp. 1–39 (2003).

*Primary Examiner*—Michael Cygan
(74) *Attorney, Agent, or Firm*—Klarquist Sparkman, LLP

(57) ABSTRACT

Methods and systems for analyzing samples, such as gas samples, are described. One method comprises providing a gas sample, increasing pressure applied to the gas sample to compress the sample to a smaller volume and provide a pneumatically focused gas sample, and analyzing the pneumatically focused gas sample using any of a variety of analytical techniques. Also disclosed are systems for gas analysis, including systems for analysis of pneumatically focused, and thereby concentrated, gas samples and for analysis of particulate matter in gas samples. Analytical systems constructed within personal computer cases also are disclosed.

26 Claims, 65 Drawing Sheets

U.S. PATENT DOCUMENTS

| | | | |
|---|---|---|---|
| 5,811,059 A | * | 9/1998 | Genovese et al. ............. 422/89 |
| 5,846,293 A | | 12/1998 | Rubey et al. |
| 5,859,360 A | | 1/1999 | Magni et al. |
| 5,918,257 A | * | 6/1999 | Mifsud et al. ............. 73/23.34 |
| 5,932,101 A | | 8/1999 | Kanel et al. |
| 6,027,758 A | * | 2/2000 | McHugh et al. ............ 426/615 |
| 6,062,065 A | | 5/2000 | Sugimoto et al. |
| 6,120,985 A | | 9/2000 | Laugharn et al. |
| 6,155,097 A | | 12/2000 | Arnold |
| 6,301,952 B1 | * | 10/2001 | De Zeeuw et al. ........ 73/23.35 |
| 6,456,095 B1 | * | 9/2002 | Sorita et al. ................ 324/703 |
| 6,494,078 B1 | * | 12/2002 | Klee ......................... 73/23.35 |

* cited by examiner

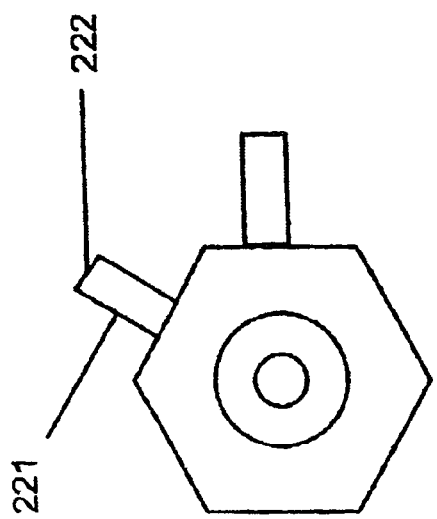
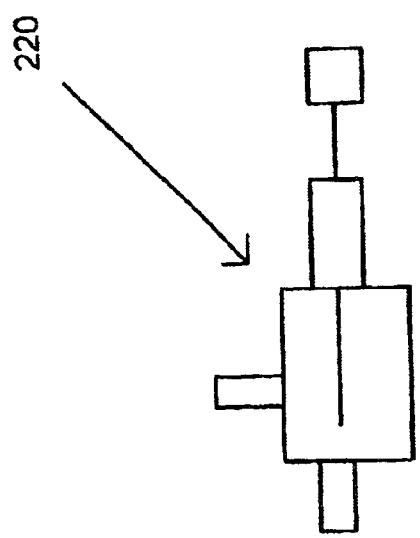
FIG. 11

METHOD AND APPARATUS FOR SAMPLE ANALYSIS

CROSS REFERENCE TO RELATED APPLICATIONS

This is a continuation-in-part of U.S. patent application Ser. No. 09/770,942, filed Jan. 25, 2001, and claims the benefit of U.S. Provisional Patent Application No. 60/177,923, filed Jan. 25, 2000 and U.S. Provisional Patent Application No. 60/448,411, filed Feb. 18, 2003, all of which applications are incorporated herein by reference.

FIELD

The present invention concerns analytical instruments and methods. More particularly, the invention concerns an apparatus for concentration and analysis of samples, particularly gas samples, and methods for monitoring/analyzing samples using the apparatus.

BACKGROUND

Volatile organic compounds (VOCs) as described by the United States Environmental Protection Agency (EPA) include components of fuels, solvents, and chemical feedstocks commonly used for internal combustion engine fuel, power and heat generation, cleaning, chemical, pharmaceutical, agricultural, semiconductor and other industries. VOCs are highly regulated in the U.S. and elsewhere in the world because they contribute to photochemical smog formation. A subset of VOC compounds includes those compounds designated by the EPA as toxic chemicals, including those compounds designated as Air Toxics. "Air Toxics" are harmful to breathe. As such they are regulated by the EPA in ambient and indoor air, and by OSHA in the workplace.

Atmospheric VOCs and/or Air Toxics are currently measured under USEPA guidance at regular times and places as part of the Photochemical Assessment Monitoring Stations (PAMS). These VOCs may be measured according to EPA Method TO-14A using samples collected in special canisters. Another method for measuring Air Toxics or VOCs uses active sampling into sorbent tubes using EPA Method TO-17. In either case the canisters or sorbent tubes are then transported to a gas chromatography laboratory for analysis using (for instance) thermal desorption of the adsorbent cartridges, or flushing or pumping from the canisters. This is followed by cryogenic or some other type of cooling. Detailed instructions on these procedures are freely available from the USEPA, which publishes the TO-xx methods. Gas chromatography methods for air analysis are recently summarized in an extensive review article written by Detlev Helmig, entitled "Air Analysis by Gas Chromatography," Journal of Chromatography A, 843:129–146 (1999).

Harmful or toxic chemicals based upon organic chemicals typically have a carbon skeleton and usually are derived from petroleum. The simplest members of this wide range of compounds are hydrocarbons (HC's), compounds containing only the elements carbon and hydrogen. Hydrocarbons consist of alkanes (all single bonds), alkenes (at least one carbon/carbon double bond), alkynes (at least one carbon/carbon triple bond), and aromatics, which contain conjugated carbon/carbon double bonds, and are derivatives of benzene, $C_6H_6$. These bonding functionalities may exist in combination with one another, making an individual hydrocarbon belong to more than one class. There is no strict upper limit to the molecular weight, molecular size, or carbon number of such compounds. As the carbon number increases, the compounds have decreasing vapor pressure and, if present in the atmosphere at all, are increasingly present in suspended particulate matter rather than as gases. Table I provides exemplary members of each HC family.

TABLE I

Examples of Hydrocarbons Classified as VOCs

| Alkanes | Alkenes | Alkynes | Aromatics |
|---|---|---|---|
| 1. Methane ($CH_4$) | 1. Ethene ($C_2H_4$) | 1. Ethyne ($C_2H_2$) | 1. Benzene ($C_6H_6$) |
| 2. Ethane ($C_2H_6$) | 2. Propene ($C_3H_6$) | 2. Propyne ($C_3H_4$) | 2. Methylbenzene ($C_7H_8$), i.e., toluene |
| 3. Propane ($C_3H_8$) | 3. Butene ($C_4H_8$), which exists in isometric forms | 3. Butyne ($C_4H_6$), which exists in isometric forms | 3. Ethylbenzene ($C_8H_{10}$) |
| 4. Butane ($C_4H_{10}$), which exists in isometric forms | 4. Butadiene ($C_4H_6$) | | 4. Dimethylbenzene ($C_8H_{10}$), i.e., xylene, which exists in isomeric forms |
| | | | 5. Naphthalene ($C_{10}H_8$) |

Other VOC compounds include carbon, hydrogen, and at least one other element, especially including (but not limited to) the elements oxygen, sulfur, nitrogen, phosphorus, and the halogens, such as fluorine, chlorine, bromine and iodine. Such compounds are used in the chemical, electronics, agricultural, and many other industries as solvents, pesticides, drugs, and so forth. Compounds containing the elements C, H, and O are sometimes called oxygenated volatile organic compounds, OVOCs. Table II provides a few exemplary members of this extended VOC family.

TABLE II

Examples of VOCs other than Pure Hydrocarbons

| Oxygen-containing OVOCs | Sulfur-Containing | Halogen-Containing |
|---|---|---|
| 1. Aldehydes | 1. Sulfides | 1. Chlorocarbons (e.g., $CHCL_3$, $CH_2Cl_2$, $CH_3Cl$, $CH_3CCl_3$, $C_2Cl_4$) |
| 2. Ketones | 2. Sulfates | 2. Halons (e.g., $CH_3Br$, $CH_3I$) |
| 3. Acids | 3. Mercaptans | 3. Chlorofluorocarbons (e.g., $CCl_2F_2$, $CClF_3$, $CCl_4$, $CF_4$) |
| 4. Ethers | 4. Thiols | |
| 5. Alcohols | | |

A partial listing of chemical compounds found in the atmosphere is Chemical Compounds in the Atmosphere, (1978) Academic Press, T. E. Graedel. This book lists many hundreds of such compounds known when it was published more than 20 years ago.

A major source of atmospheric hydrocarbons is automobile gasoline, which typically contains hydrocarbons having carbon numbers greater than 3. Methane, natural gas, is widespread and relatively constant in the atmosphere at concentrations of about 1.8 ppm by volume. Natural gas is about 95% methane and 5% ethane. Propane makes up the bulk of liquefied petroleum gas (LPG). Gasoline and diesel fuel and their resulting combustion byproducts together contain more than 200 individual hydrocarbons. See Fraser et al., "Air Quality Model Data Evaluation for Organics. 4. C2–C36 Non-aromatic Hydrocarbons," Environ. Sci. Technol., 31:2356–2367 (1997). Since these compounds, along with oxides of nitrogen also produced in combustion, react chemically in the atmosphere to produce smog, there is worldwide interest in controlling their atmospheric emission, and in measuring their individual (speciated) concentrations.

Air Toxics are compounds directly harmful to human health, and the EPA has many regulations dealing with their emission and atmospheric concentration. Efficient measuring of ambient concentrations is highly important. All ambient gaseous compounds also appear in human breath since they are inhaled. In addition, metabolic processes add additional volatile compounds to exhaled breath, such as ethanol, acetone, isoprene, pentane and others. Study of metabolic processes of respiratory organisms and diagnosis of disease would benefit greatly from automated VOC analysis in exhaled air. Chromatographic analysis of anesthesia environments such as hospitals has been reviewed by A Uyanik in Journal of Chromatography B 693 (1997) 1–9. From this review it is clear that a sensitive, inexpensive, compact gas chromatograph would be a useful tool for operating rooms and associated environments.

Sick Building Syndrome involves poorly characterized human diseases and ailments associated with outgassing of toxic materials in the indoor environment. Sources of such toxic materials can include carpets, drapes, particle board, etc. Harmful fungi and bacteria which can thrive in moist or poorly ventilated environments often emit characteristic VOC or OVOC compounds (e.g. heptanol) which, although they may not be toxic themselves, can serve as indicators of the presence and abundance of such harmful organisms.

Chemical synthesis or process streams, clean rooms and other industrial areas require automated, sensitive gas analysis procedures which may be routinely implemented for reasonable costs. Other areas which would benefit from highly sensitive analytical air analysis methods would be those areas dealing with naturally occurring and artificially applied pheromones for insect attraction and/or control.

In sampling trace level VOCs, air toxics, metabolites or other analytes such as particulates in the atmosphere, in breath, or other gaseous environments, the concentration of target analytes often is below the detection limit of a particular analytical technique. Such analysis is often termed trace gas analysis. A wide range of concentrations may be present, for instance from 1 ppmV (1 part per million by volume) down to 1 pptV—a range of one million. For instance, in gas chromatography, a flame ionization detector cannot detect many VOCs of ambient atmospheres or in breath samples unless they are concentrated. Two concentration methods are commonly employed: (a) cryogenic focusing/concentration and (b) adsorbent focusing/concentration. In each method an air sample of the desired volume is passed through an accumulation chamber, which consists of:

(a) a 'U-tube' immersed in a cryogenic liquid, such as liquid oxygen or air, or which is otherwise cooled sufficiently that some or all of the target analytes condense to liquids or solids within the U-tube trap, also referred to herein as a cryotrap. Most of the air sample does not condense and therefore passes through the trap; or (b) a sorbent-filled trap, which absorbs or adsorbs some or all of the target analytes, allowing most of the sample to pass through. Such traps can operate at ambient temperature or below.

Either procedure concentrates the desired analytes to a concentration much higher than their original concentration in the air sample. After the desired air volume has passed through the trap, yielding sufficient analyte, the trap is heated to transfer the concentrated analytes into a chromatographic column or other analytical device.

Both of these procedures are commonly used in the field of atmospheric analysis, air pollution, etc. However, each has drawbacks, which makes them less amenable to automating an air-monitoring instrument, especially for field use. In the case of cryogenic focusing, the cryogenic liquid must be stored on site and pumped as needed for cryogenic focusing. Although electrically cooled devices are available, such devices typically cannot obtain sufficiently low temperatures to collect all of the VOCs that can be condensed by cryogenic focusing. Another problem with cryofocusing is the large amount of atmospheric materials, particularly water and carbon dioxide, which are trapped along with desired analytes, unless separately removed before the cryotrap. Yet another problem with cryofocusing is that such instruments typically reside in laboratories to which samples must be transported in special containers. Although such transport has been extensively studied, there remains the possibility of sample modification so that spurious compounds may either be added to or subtracted from transported and/or stored samples. For sorbent-filled traps, the sorbent material must adsorb and desorb a wide range of potential analytes because the target analyte volatilities vary greatly. A strongly absorbent material may collect all analytes, but temperatures high enough to cause desorption of the least volatile analytes may cause decomposition of analytes or the absorbent collecting material itself. A less absorbent material may sorb and desorb the heavier analytes, but not collect the more volatile analytes, which therefore are not completely collected. Another problem with sorption is the tendency for the material to desorb over a period of time when heated. This can require refocusing with cryogens or other methods during analysis. Sorbent and cryofocusing can be used in combination. A final problem with adsorbents is possible chemical reaction or decomposition of the target analytes during collection, transport or storage of the adsorbent cartridges, or the presence of artifacts acquired on the adsorbents before or after sampling. Such artifacts are not uncommon in atmospheric sampling and often lead to spurious conclusions about atmospheric trace-gas composition. Ambient air sampling and breath analysis would benefit greatly from in-situ, continuous, real time analytical instrumentation. Such instrumentation is not widely available nor currently practical.

Gas chromatography methods for air analysis are recently summarized in an extensive review article written by Detlev Helmig, entitled "Air Analysis by Gas Chromatography," Journal of Chromatography A, 843:129–146 (1999), which is incorporated herein by reference. Helmig's review substantiates the conclusion that only two primary methods are known for concentrating analytes in an ambient air sample, cryofocusing and absorbent traps. These methods are poorly amenable to developing remotely operated, continuous sampling methods for ambient air although such methods have been reported. For instance J P Greenberg, B Lee, D Helmig and P R Zimmerman have described a "Fully automated gas chromatograph-flame ionization detector system for the in situ determination of atmospheric non-methane hydrocarbons at low parts per trillion concentration" in Journal of Chromatography A 676 (1994) pp. 389–98. This system was designed to (1) rapidly trap air samples of up to 4 liters volume to allow for sub-parts per trillion detection limits, (2)

eliminate interferences from ambient ozone, water vapor and carbon dioxide, and (3) reduce to negligible levels any contamination in the analytical systems, and (4) allow for continuous unattended operation. This instrument used cryogenic sample freeze-out and was successfully employed for measurements in the state of Hawaii. However, it apparently has seen limited additional use since that time, probably because of its cost, complexity and use of cryogenic fluids.

Other pertinent areas include breath analysis. For instance, U.S. Pat. No. 5,293,875, "In-vivo Measurement of End-tidal Carbon Mono xide Concentration Apparatus and Methods" describes a noninvasive device and methods for measuring the end-tidal carbon monoxide concentration in a patient's breath, particularly newborn and premature infants. The patient's breath is monitored. An average carbon monoxide concentration is determined based on an average of discrete samples in a given time period. An easy to use microcontroller-based device containing a carbon dioxide detector, a carbon monoxide detector and a pump for use in a hospital, home, physician's office or clinic by persons not requiring high skill and training is described.

K D Oliver and 7 co-authors of Mantech Environmental, the USEPA, XonTech and Varian Chromatographic Systems have described a "Technique for Monitoring Toxic VOCs in Air: Sorbent Preconcentration, Closed-Cycle Cooler Cryofocusing and GC/MS analysis" in Environmental Science and Technology 30 (1996) 1939–1945. This powerful but very complex, automated system usually is attended by various operators and has seen only intermittent field use, perhaps due to operational expense and complexity.

Air pollution is increasingly regulated throughout the world. Knowing the source of pollution emissions is essential to this regulatory process so that regulation can be efficient and cost effective. One method for determining air pollution sources is source characterization. That is, individual sources are surveyed either by direct measurements of emissions or by apportionation by generic emission factors. Usually local, regional, or national pollution control agencies maintain emission inventories and issue emission permits. Such emission inventories are widely viewed as unreliable. Once emission factors for a variety of pollutant species, including VOCs, are available, individual measurements of atmospheric VOCs at any site can be assigned quantitatively to the major sources by mathematical processes referred as Source Apportionment or Chemical Element Balances. Efficient, cost-effective measurements of ambient VOCs, Air Toxics, and other pollutant concentrations will allow this source apportionment procedure to be carried out more efficiently. Beyond source apportionment, recently developed computer programs (program UNMIX developed by Dr. Ronald Henry of the University of Southern California) now allow sources to be determined from ambient VOC measurements without any direct source information. (See ScienceNewsOnline Jun. 28, 1997 and the USC Chronicle Sep. 1, 1997, included herein) As Dr. Henry describes it, these programs allow the ambient air data to analyze itself. This extremely powerful new mathematical technique would benefit greatly from lowcost, and therefore frequent measurements of VOCs and other such compounds in polluted air.

In addition to the organic compounds discussed above, there is a need for the determination of various inorganic atmospheric constituents. A few examples are NO, $NO_2$, $SO_2$, $H_2S$, $O_3$, CO, etc. Many of these have specific instrumental methods and measurement devices devoted specifically to their determination, for instance in automobile testing as well as in ambient air. A more general method involves measurement of one or more of such species (including VOC and OVOC compounds discussed above) by light absorption. This may occur typically in the ultraviolet, visible, or infrared. When species are present at very low concentrations, often long path lengths are used. This may involve meters or kilometers through the open atmosphere, or reflected paths in a localized instrument. Examples of such techniques are differential optical absorption spectroscopy (DOAS) and Fourier transform infrared spectroscopy (FTIR). Such instruments may determine one or many atmospheric components simultaneously using light at various suitable wavelengths.

Despite these previously developed techniques and inventions, there still is a need for an apparatus and method for continuous, and remote if desired, concentration and analysis of gaseous samples. Such a method and apparatus, if available, would allow automation of methods for analyzing analytes in a gaseous sample, such as air-pollution analysis, clinical breath analysis, metabolic studies, process streams, clean rooms, etc.

SUMMARY

The disclosed embodiments address the problems and shortcomings associated with the prior methods and apparatuses described in the Background section, and provide many advantages relative to prior methods and apparatuses directed to potentially continuous spectrometric or GC analysis of gaseous samples. For example, Pneumatic Focusing as described herein operates very rapidly as pressurization and transit of the sample through a chromatographic column are inherently very fast due to the high pressure driving the analysis. The speed of the analysis can be adjusted by adjusting a Pneumatic Focusing valve, which controls the column flow rate. All features can be controlled by a computer to optimize the most important parameters. Hence, the present technology allows for the development of portable, compact, fast, multi-detector, multi-column instruments that can be used, if desired, for continuously obtaining and analyzing a pneumatically focused gas sample.

The method does not require cryofocusing, or sorbent-trap focusing, as with prior methods, although it should be appreciated that the present method can be practiced in combination with cryofocusing and/or sorbent-trap focusing of analytes in laboratory or field use. For example, cryofocusing a sample after it has been pneumatically focused might provide better resolution than is achieved by practicing either method separately, particularly for the more volatile analytes being analyzed. In a chromatographic system, a sample is separated into components which then must be delivered to a suitable analytical device (such as a FID, an ECD, etc) for detection and quantification. Pneumatic Focusing is advantageous for concentrating such samples before injection into the chromatographic column. Pneumatic Focusing is equally applicable for direct introduction of a sample into an analytical device, such as a UV-VIS or IR absorption cell, in which case a chromatographic column need not be employed. One chief advantage and application of Pneumatic Focusing is it's applicability to trace gas measurements. Atmospheric trace gases range in concentration from methane (1.8 ppm in the global troposphere) down in concentration to a host of species at the ppt (0.000001 ppm) level in clean air. A similar concentration range is undoubtedly present in exhaled breath. Many such breath components are present in inhaled air, but a variety of exhaled metabolites are of real interest because of diagnostic information they could provide. Important metabolites and disease markers may be present at very low concentrations and may be difficult to distinguish from compounds already present in inhaled air.

Pneumatically focused chromatography represents a superior approach to prior measurements, such as those described above concerning EPA measurements. This is because Pneumatic Focusing is more easily automated for laboratory analysis of such VOCs or Air Toxics from canisters or sorbent tubes, or most especially, to real-time, continuous, in-the-field sampling of these gases wherein the problems and artifacts associated with sample collection, transport and storage are mitigated or eliminated altogether. The advantage of Pneumatic Focusing is that it is simpler, more easily automated, less prone to artifacts, more easily calibrated and can provide more extensive measurements of atmospheric VOCs, Air Toxics, breath components, etc. at less cost than with present methods.

A method for analyzing a gas sample comprises providing a gas sample, increasing pressure applied to the gas sample to compress the sample to a smaller volume and provide a pneumatically focused gas sample, and thereafter analyzing the pneumatically focused gas sample, such as by using a gas chromatograph or spectrometric cell. Typically, the gas sample is pneumatically focused prior to or concurrently with reaching a separatory column or spectrometric cell. The method is well suited for analyzing ambient air samples, both continuously, and can be, but does not necessarily have to be, run remotely using computer control and telemetric data transfer. Continuously sampling ambient air provides a method for real-time monitoring of indoor or outdoor air quality or for in-situ clinical analysis of breath samples from subjects or patients.

As used herein, Pneumatic Focusing generally means increasing the pressure of a gaseous sample from a starting pressure (e.g. atmospheric pressure) to a pressure of from about 100 psi to about 15,000 psi, more typically from about 200 psi to about 2,000 psi, with working embodiments having been practiced primarily at Pneumatic Focusing pressures of from about 250 psi to about 500 psi in the case of gas chromatography and from 150 psi to 2,000 psi in the case of absorption spectroscopy. Pneumatic Focusing can be carried out with a sample originating as a gas, in which case the sample may be focused (pressurized) in a sample cell or concurrently as it is introduced to a chromatographic column or spectrometric cell. Pneumatic Focusing may also be carried out with a liquid sample vaporized at an effective vaporization temperature upon introduction into a gas chromatograph or heated spectrometric cell. In either case high pressure in the sampling or analytical environment will serve to focus (concentrate) the sample for better detectability of the target analytes. One goal of Pneumatic Focusing is to allow introduction of large quantities of analytes into analytical devices. Another goal is the removal of undesired condensable vapors, such as water vapor. When used with gas chromatography we call this procedure Pneumatic Focusing Gas Chromatography (PFGC). The method also can comprise reducing the pressure of the carrier gas, such as to pressures below about 100 psi, simultaneously with or subsequent to the pneumatically focused sample being injected onto a separatory column so that the chromatography occurs at more normally employed pressures. In the case of spectroscopy, Pneumatic Focusing can mean continuously or discretely increasing the pressure of a gaseous sample either in, or before entrance into, a spectrometric cell so that absorbances are adjusted to an optimum level for enhanced signal-to-noise ratio and improved sensitivity. Pneumatic Focusing also can comprise suddenly increasing or decreasing the pressure between a higher and a lower pressure for observation of transient absorptions that are not observable at constant high or low pressure. In one working embodiment in a uv/visible light absorption cell, pressure was abruptly increased from ambient (~15 psi) to pressures ranging from 150 to 2000 psi. Pressure was also abruptly dropped within the same range of pressures. Transient absorbances occurring during these pressure transients can be useful in measuring concentrations of trace absorbers or in studying nucleation processes or in measuring concentrations of nucleating aerosols, such as biological aerosols, including spores. The apparatus where Pneumatic Focusing (or defocusing) is carried out can be either heated or cooled from ambient temperatures to prevent or enhance such aerosol nucleation, or to enhance or retard adsorption or absorption to the surfaces of the apparatus. The region of a device in which Pneumatic Focusing is carried out may include but is not limited to chromatographic columns, sample loops for chromatographic columns, spectrometric light absorption or scattering cells, electromagnetic waveguides, such as optical or infrared waveguides, etc.

Condensable vapors (such as water vapor which may interfere with an analysis) may be removed in a prefocusing prechamber if desired before the sample is introduced to the light absorption chamber or chromatographic column. Such vapors may be either discarded or analyzed separately by automated transfer to additional analytical devices.

Spectrometric measurements are normally interpreted in terms of the Beer-Lambert Law $I=I_o e^{-acl}$ or alternately $I=I_o 10^{-a'cl}$ where a is the absorption coefficient, c is the absorber's concentration and l is the path length. Using this law, previously measured and recorded absorption coefficients, a measured path length, and an experimentally measured absorbance Io/I, it is common practice to determine the concentration c of an analyte. Thus absorption responds to the product of concentration and path length.

In carrying out Spectrometric Pneumatic Focusing (SPF) it is possible to control with a combination of temperature and pressure the disposition of various condensable or adsorbable vapors in a confined sample or in a continuous sample stream. When pressure of a gaseous mixture is increased, as in Pneumatic Focusing, the absorptivity of target analytes may change in ways not obvious from a consideration of Beers Law. For instance, in preliminary investigations of Pneumatic Focusing Spectroscopy all of the following have been observed when pressure was gradually increased or decreased:

1. The absorbance increases linearly with pressure due to increasing concentration as expected from Beer's Law.
2. The absorbance increases proportional to the square root of the pressure ratio due to dimerization of the target analyte to produce a nonabsorbing dimer.
3. The absorbance increases proportional to the square of the pressure ratio due to absorption of dimers or collision complexes.
4. The absorbance increases and remains constant due to condensation of the target analyte to a liquid which is removed from the view of the absorbed light beam.
5. The absorbance may increase, decrease, or otherwise behave erratically due to phenomena not currently understood.
6. Continuous oscillations in cell transmission which were wavelength dependent.

When the Pneumatic Focusing pressure was increased or decreased suddenly additional phenomena have been observed, some of which may be due to nucleation and/or growth of light scattering aerosols.

Heating and/or cooling a separatory column subsequent to injecting the pneumatically focused sample also could be advantageous. For example, the method may involve cooling a head portion of the column prior to injecting the pneumatically focused sample onto the column and heating the column subsequent to injecting the pneumatically focused sample onto the column.

In chromatography plural eluting gasses can be used to elute the pneumatically focused sample. For example, the method may involve eluting a pneumatically focused sample with a first carrier gas, and then eluting the column with a second carrier gas. And, either the first or second gas (usually the second) may be a supercritical fluid. See S Pentoney et al., "Combined Gas and Supercritical Fluid Chromatography for the High Resolution Separation of Volatile and Nonvolatile Compounds," Journal of Chromatographic Science, 5:93–98 (1987). It could also be advantageous after Pneumatic Focusing to drop the column pressure to lower values and then gradually increase it again, gradually switching from a non-supercritical to a supercritical fluid for better elution of analytes through the column. Such approach could in some instances obviate the need for temperature programming of the column with resultant reduction in power requirements to facilitate portability and field operation.

The method can involve continuous sampling. This embodiment provides a considerable amount of data. This collection of data allows individual chromatograms, collected over time, to be averaged. This can, for example, provide a well-defined, stable baseline so that analyte peaks are easier to discern, identify and quantify, thereby increasing sensitivity. Once peak locations are established on a low-noise, averaged chromatogram, these peak locations may be used to unambiguously identify the position of individual low-intensity peaks on the individual chromatograms which formed the average. This can improve the sensitivity and lower the limit of detection.

The method can be practiced with various detectors. A working embodiment used a flame ionization detector. However, most commercially available detectors can be used in combination with a system for pneumatically focusing a gas sample as described herein. Additionally, the method can be practiced using plural separatory columns connected in series, or in parallel. The method can be used in combination with other techniques currently known or hereafter developed for focusing analytes in a gas sample. For example, Pneumatic Focusing can be done in combination with cryofocusing, absorbent focusing, or both. Pneumatic Focusing can also be carried out in a suitably designed spectrometric cell which also serves as the sample loop (injection volume) for a chromatographic or other system so that spectroscopic properties of the sample may be determined prior to separation and analysis chromatographically or by other means. Such approach would be beneficial, for instance, in determining the total hydrocarbon content of a VOC sample by application (without limitation) of nondispersive infrared analysis to the CH bond region of the spectrum. Gasses may be passed at high pressure through a spectrometric cell after separation and elution from a separatory column as well.

A gas chromatograph and gaseous sample analysis system also is disclosed. One embodiment of the system comprised: a sample loop for receiving a first volume of a gaseous sample; a separatory column fluidly connected to and downstream of the sample loop; an inline pressure-increasing valve downstream of the separatory column, which increases system pressure to pneumatically focus the gaseous sample and adjust flow rate through the system. Flow rate can be adjusted as desired to be substantially about the same linear flow rate through the system as prior to increasing the pressure with the inline valve, less than the linear flow rate through the system prior to increasing the pressure with the inline valve, or greater than the linear flow rate through the system prior to increasing the pressure with the inline valve; and a detector downstream of the pressure increasing valve for detecting analytes. The system can further comprise plural sample collection coils, and plural separatory columns, connected either in parallel or in series with appropriate switching, heart-cutting, 2-dimensional chromatographing or other manipulation of the analytes during separation and analysis. In one working embodiment, a single air sample distributed into two separate sample loops was simultaneously injected into two different separatory columns, one more suitable for VOC compounds and the other for OVOC compounds. In this way a broader range of compounds in polluted air or in human breath could be analyzed. For continuous monitoring of ambient air, the system typically includes a sample collection pump for continuously drawing the gaseous sample into the gas sample collection coil. The system has been automated by placing its operation under computer control. Moreover, the technique of pneumatically focusing can be used in combination with gas chromatographs located on microchips, which GCs should be modified to accept higher gas pressures.

For analysis of human breath, one working embodiment used a specially designed breath-sampling device. A 100 cc-glass syringe was fluidly connected to the previous dual column gas chromatograph. The last portion of a human breath was collected into the syringe by the subject breathing through a Teflon tube through a 4-way valve to inflate the syringe. This syringe exerts much less back pressure than the sample loop itself and is easier for a subject to breathe into. After the syringe was filled with breath, the 4-way valve was switched and the sample pump then drew the breath sample into the sample loops over a period of 20–40 seconds. Once the sample had passed from the sampling syringe into the sample loops it was pneumatically focused into the chromatograph for analysis of the VOCs and OVOCs and other compounds in the human breath. Such instrumentation will be useful in disease diagnosis or in analysis of metabolic processes in humans or other respiratory organisms. One advantage of this syringe sampler is minimal exposure of the syringe walls to the breath sample as the syringe remains 'closed' at all times except for the approximately 1 minute involved in sampling. Thus, current analytes or leftover analytes from previous samples have a minimum amount of time to exchange with the walls and be either removed from or added to a breath sample. An additional advantage is that the breath sample provider (such as a medical patient or subject) obtains visual feedback on the course of sample delivery and transfer to the chromatographic or other analysis device.

Also disclosed are Methods and systems for measuring the concentration of particulates, such as spores, in a gas sample are described. The disclosed methods constitute simple, inexpensive approaches that may be economically implemented on a widespread basis to provide early warning of the presence of potentially infectious spores. Such spores may be naturally present in some environments, such as mold-infected buildings or other environments, or could be deliberately introduced by terrorists or other criminals.

Also disclosed are methods of selectively condensing water vapor on biological aerosols present in indoor or outdoor air. In one embodiment, the condensation process is used to grow the size of such aerosols so that they can be individually visualized in a light beam and viewed with an inexpensive computer-based camera, commonly called a webcam.

In another aspect, instrumentation constructed within a personal computer case is provided. Such instrumentation includes pneumatic focusing systems (for chromatography and spectroscopy) and particle detection systems, as well as gas chromatography/mass spectrometry systems, and other spectrophotometers, such as infrared and fluorescence spectrophotometers. Examples of personal computer cases that may be used to construct the instrumentation include full towers, mid-towers, and desktop cases. Further examples of suitable personal computer cases include AT, BATX, ATX, MATX, LPX and microATX compatible cases. In a working embodiment, a pneumatic focusing gas chromatograph is constructed in an ATX compatible tower case.

BRIEF DESCRIPTION OF THE DRAWINGS

FIG. 1 is a schematic of a system for pneumatically focusing and analyzing a gaseous sample.

FIG. 2 is a schematic diagram of a one embodiment of a high pressure spectral analysis system.

FIG. 3 is a schematic diagram of a working embodiment of a device for continuously providing sample to a focusing system.

FIG. 4 is a cross sectional view of the system illustrated in FIG. 3.

FIG. 5 is a schematic diagram of a working embodiment of a check valve.

FIG. 6 is a schematic diagram of a continuous Pneumatic Focusing system.

FIG. 7 is a schematic of a chromatograph useful for making and using a disclosed embodiment of a chromatograph for pneumatically focusing samples.

FIG. 8 is a schematic drawing of an apparatus useful for injection of liquid samples for Pneumatic Focusing.

FIG. 9 is a schematic drawing of a pressure increasing/linear flow reducing valve.

FIG. 10 is a schematic drawing of a pressure increasing/linear flow reducing valve.

FIG. 11 is a schematic drawing of a needle valve for pressure/flow feedback.

FIG. 12 is a control circuit for an A/D board.

FIG. 13 is an amplifier circuit used to increase voltage of signals from an A/D board.

FIG. 14 is a schematic drawing of system for controlling valves.

FIG. 15 is a chromatogram illustrating a method for determining a true base line for chromatograms produced by a disclosed apparatus and method.

FIG. 16 is a graph of analog offset to an A/D board.

FIG. 17 is a graph of interpolation between digital readings on an A/D board.

FIG. 18 is an enlargement of the digital data from FIG. 17.

FIG. 19 is a block diagram of a program to integrate chromatographic peaks.

FIG. 20 shows output from the program integpro.bas.

FIG. 21 is a chromatogram illustrating using methane as an internal standard.

FIG. 22 is an apparatus to determine a true chromatographic baseline.

FIG. 23 is a schematic drawing of a pneumatic piston.

FIG. 24 is a graph illustrating the continuous, real-time collection of atmospheric data using a disclosed apparatus with the methane peak being attenuated by a factor of 100.

FIG. 25 is an averaged chromatogram as prepared for the 40 plural chromatograms of FIG. 24.

FIG. 26 is one chromatogram of the plural chromatograms provided by FIG. 24 with the methane peak being attenuated by a factor of 100.

FIG. 27 is a chromatogram produced using a dual column and an embodiment of a disclosed apparatus.

FIG. 28 is a chromatogram of a gasoline sample (0.000001 liters liquid gasoline in 847 liters of air with about 3 ppm methane) made at 200 psi using a disclosed apparatus and method.

FIG. 29 is a chromatogram of a gasoline sample (0.000001 liters liquid gasoline in 847 liters of air with about 3 ppm methane) made at 250 psi using a disclosed apparatus and method with the methane peak being attenuated by a factor of 10.

FIG. 30 is a chromatogram of a gasoline sample (0.000001 liters liquid gasoline in 847 liters of air with about 3 ppm methane) made at 350 psi using a disclosed apparatus and method with the methane peak being attenuated by a factor of 100.

FIG. 31 chromatogram of a gasoline sample (0.000001 liters liquid gasoline in 847 liters of air with about 3 ppm methane) made at 400 psi using a disclosed apparatus and method with the methane peak being attenuated by a factor of 100.

FIG. 32 chromatogram of a gasoline sample (0.000001 liters liquid gasoline in 847 liters of air with about 3 ppm methane) made at 500 psi using a disclosed apparatus and method.

FIG. 33 is a chromatogram of a gasoline sample (0.000001 liters liquid gasoline in 847 liters of air with about 3 ppm methane) made at 900 psi and 30 standard cubic centimeters/minute flow rate using a disclosed apparatus and method.

FIG. 34 is a chromatogram of a gasoline sample (0.000001 liters liquid gasoline in 847 liters of air with about 3 ppm methane) made at 900 psi and 40 standard cubic centimeters/minute flow rate using a disclosed apparatus and method.

FIG. 35 is a chromatogram of a gasoline sample (0.000001 liters liquid gasoline in 847 liters of air with about 3 ppm methane) made at 900 psi and 60 standard cubic centimeters/minute flow rate using a disclosed apparatus and method.

FIG. 36 is a chromatogram of ambient air in Portland, Oreg., during a period when wind speeds varied from about 30 miles per hour to about 80 miles per hour with the methane peak being attenuated by a factor of 100.

FIG. 37 is an average of 10 chromatograms taken during the wind storm before and after the chromatogram of FIG. 36 with the methane peak being attenuated by a factor of 100.

FIG. 38 is an average of 37 chromatograms of ambient air in Portland, Oreg., for polluted air as a reference to FIGS. 36 and 37 with the methane peak being attenuated by a factor of 100.

FIG. 39 is a circuit diagram for a disclosed system for sampling breath using a syringe.

FIG. 40 is a chromatogram of breath exhalations illustrating the reproducibility of the chromatograms.

FIG. 41 is a chromatogram of breath exhalations from another person.

FIG. 54 is a diagram showing a side view of another embodiment of a piston inlet.

I. Analytical Chemistry Terms Defined

Figure 1:
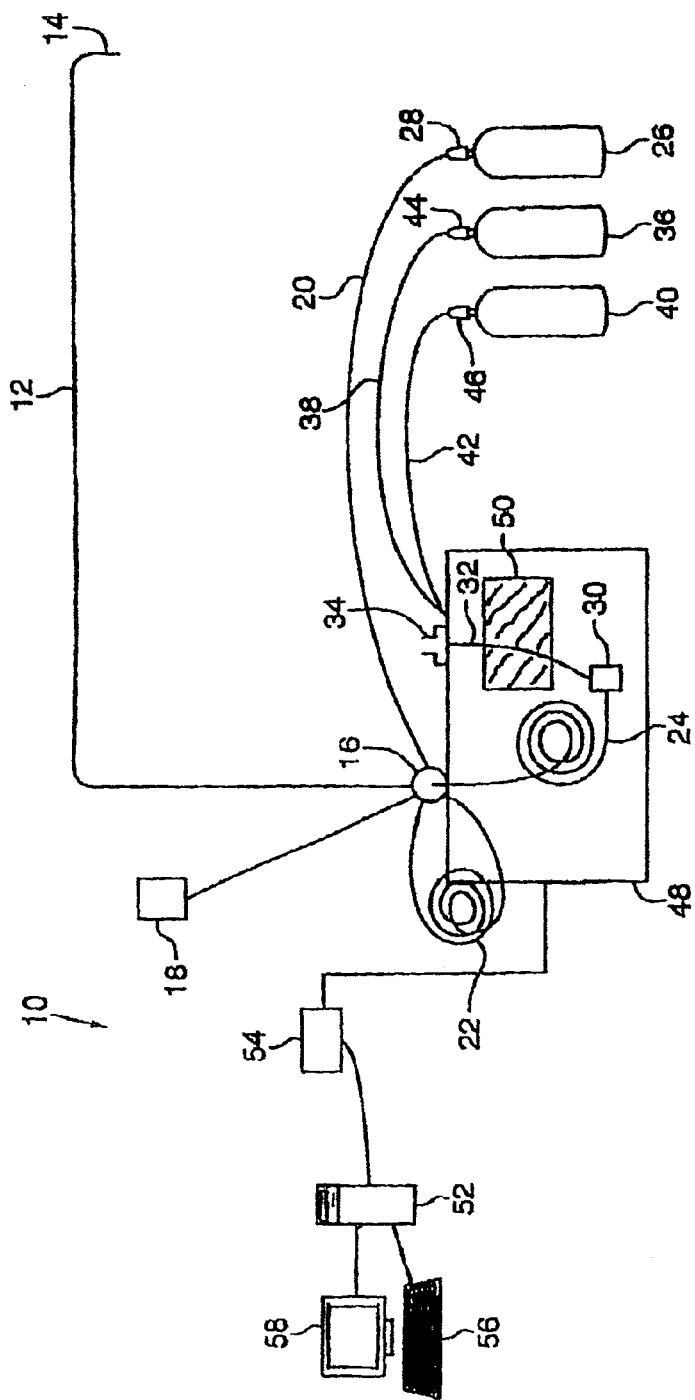

The field of analytical chemistry concerns itself with measurement of the concentrations of various substances. This can include either routine measurements using established techniques or the development of new or innovative techniques. In some cases these substances are present at very low concentrations. Such analysis then might be termed 'trace analysis'. Often times the substances whose concentration it is desired to measure are present in a matrix of other substances. Sometimes this matrix is quite large and complex. In this case it may be difficult to separate analytically the target substances from extraneous or perhaps even interfering substances. In all cases, those substances whose concentrations are desired of measurement are commonly called analytes. This definition is adopted for purposes of this patent application. Quite frequently the specific concentration of individual analytes needs to be measured. For instance, determining the concentration of ethane in the presence of ethane and ethyne.

Often individual analytes can be specifically identified by separating them from other analytes on a chromatographic column, or by causing them to absorb measurable quantities of light at a specific wavelength not absorbed by other analytes, etc. In other circumstances it is sufficient to measure the concentration of generic classes of analytes, such as methane (a specific chemical entity) and nonmethane (a potentially huge array of many 10's or 100's of individual) hydrocarbons often measured in the atmosphere or in auto exhaust. Analytical chemists often use the word determine to indicate the measurement of the specific concentration (such as in moles/liter, grams/liter, ug/m3, molecules/cc etc.) of an individual analyte. On the other hand, the word detect may mean to sense the presence but not the actual concentration of a specific analyte. Such common definitions are adopted for the purposes of this patent application. If an analyte cannot be sensed at all in a sample it is termed to be below the detection limit. This minimum is also referred to as the limit of detection LOD. In this case Pneumatic Focusing may be employed to make it detectable and to enable its determination. Often in analytical chemistry, theoretical equations are employed in such determinations, and often various types of standards are employed as well. These standards may be either internal (present naturally or by addition to the sample) or external (delivered to the analytical device separately from the sample).

II. Chromatography Types/Terms

1. Packed Column Gas chromatography refers to chromatography carried out with a packed metal, glass, or other column, typically ⅛" or ¼" in diameter. Head pressures are typically 30–60 psi and no flow restriction is used downstream from the column. A wide variety of commercial packing materials are used. Lengths are variable. Flow rates are typically 20–40 milliliters/minute. The use of such columns has declined with the advent of capillary column chromatography, but these are still commercially available, or can be packed in-house with commercially purchased packing materials.

2. Capillary Column Gas Chromatography uses longer, open tubular columns, the inside walls of which are coated with some type of adsorbent or absorbent material. Lengths are typically from 30–105 meters. Inside diameters typically range from 0.18 mm to 0.53 mm. Flow rates are typically 1–2 milliliters/minute, with head pressures of 30–60 psi. Makeup gas often is used with these columns to increase the flow rate into (for instance) a FID detector. These columns are available commercially.

3. Packed Capillary Column Gas Chromatography uses narrow-bore capillary columns, which are packed with very small beads of varying composition. A recent innovation, these are often packed in-house with commercially purchased materials. Since these columns are very narrow and packed tightly, high head pressures are necessary to achieve adequate flows. This is sometimes termed High Pressure Gas Chromatography (HPGC).

4. Supercritical Fluid Chromatography (SFC), is similar to packed column or capillary column gas chromatography, except that the eluent is often CO2 at high enough pressure that it is a supercritical fluid. As such it has higher solution powers than a gas, but retains some of the gas phase's high diffusivity, which aids separations. By definition, the carrier is at high pressure to achieve supercritical fluidity. This is accomplished by a flow restrictor at the column end, either before or after the detector depending upon the application. Because of the flow restrictor at the end, the gas expands to atmospheric pressure, yielding a large volume flow rate under standard conditions. When first developed SFC was termed dense gas chromatography (e.g. J C Giddings, M N Myers and J W King, "Dense gas chromatography at pressures to 2000 atmospheres," Journal of Chromatographic Science 7 (1969) pp. 276–283. In some respects this chromatography is similar to liquid chromatography. R M Smith has reviewed the current status of SFC in the paper "Supercritical fluids in separation science—the dreams, the reality and the future" Journal of Chromatography A 856 (1999) pp. 83–115.

5. Solvating Gas Chromatography (SGC), in which there is no flow restrictor at the column end but the upstream head pressure is high enough to generate a supercritical eluent for part of the length of the column. At some point the pressure drops enough that the eluent (often CO2) changes from a supercritical fluid to a gas. See for instance Y Shen and M L. Lee "High speed solvating gas chromatography using packed capillaries containing sub-5 um particles," Journal of Chromatography A, 778(1997) pp. 31–42, 6. Liquid Chromatography (LC), which uses narrow bore or packed columns and liquid eluent(s). High pressures are required to force the liquid eluent through the column because of the higher viscosity of the liquid phase. Hence this is sometimes called high-pressure liquid chromatography (HPLC). Often two different eluents are gradually interchanged during the chromatogram (for instance from a less polar to a more polar eluent) in what is termed gradient elution.

Summary of High Pressure in Chromatography

High pressure in chromatography today is typically employed for one of two reasons:

1. is required so that the carrier fluid will pass through a separatory column in an acceptable length of time. (HPLC, HPGC)
2. is employed because of the enhanced solution capabilities of fluids at high pressure and also because of their ability in some cases to displace analytes from the separatory column, thereby enhancing movement of analytes which strongly adsorb to the column material. (SFC, SGC)

It is current wisdom that the high pressure required to force the liquid carrier through tightly packed particles in chromatography is an unavoidable evil associated with the high resolution which tightly packed particles generates. To quote Yufeng Shen and Milton L. Lee in the paper "High speed solvating gas chromatography using packed capillaries containing sub-5 um particles," Journal of Chromatography A, 778(1997) pp. 31–42, the main practical problem resulting from the use of small particles in LC is the large pressure drop along the column, which imposes special requirements on the LC instrumentation to handle high pressures. In supercritical fluid chromatography (SFC), the effect of the pressure drop on chromatographic performance is relatively complex [15–18] and affects both column efficiency and retention of solutes. The use of microparticles and the resultant high pressures in packed column GC (i.e SGC) introduces a practical difficulty in sample introduction. However, the well developed sample injection valves with small sample loops used in LC and SFC can minimize this problem (citing D. Tong, A M Barnes, K D Bartle, A A Clifford, J Microcol. Sep. 8 (1996) pp353–359). These authors recommend injection of small sample volumes because of the high pressure associated with HPLC, SFC or SGC. Thus the current wisdom is to consider high column pressures an undesirable but unavoidable consequence of tightly packed column materials which are useful for the high resolution they enable. Likewise, V Jain and J B Phillips in the Journal of Chromatographic Science 33 (1995) pp. 601–605 state The use of low sample capacity narrow-bore capillary columns puts great demands on sample introduction and detection. As the internal diameter of the column decreases, the maximum sample volume also drops rapidly. This small volume is hard to manipulate and often causes problems in column performance with small diameter capillary columns. Thus common perception in the field is that large samples are to be avoided. Such wisdom is certainly not correct in trace analysis, especially automated trace analysis.

In contrast to this conventional wisdom, Pneumatic Focusing allows very large samples to be introduced to a capillary column, and in working embodiments narrower columns produced better peak resolution than wider columns coated with the same material (e.g. alumina) even when very large samples were introduced. It appears that current wisdom has misjudged the usefulness of high pressure (Pneumatic Focusing) both in chromatography and in spectrometry. This is due, at least in part, to much the work in the art NOT being applied to trace level determinations and especially not to automated trace analysis. If adequate analyte concentrations are present in the sample, then Pneumatic Focusing will be less useful. Even then, however, it may allow better separation of complex mixtures into individual compounds (analytes) for instance such as in chromatography by reducing injection volumes and limiting injection band broadening.

III. Spectroscopy Types/Terms

Spectrometric measurements are normally interpreted in terms of the Beer-Lambert Law I=Ioe-a c l or alternately I=Io10-a c l where a is the absorption coefficient, c is the absorber's concentration and l is the path length. Using this law, previously measured and recorded absorption coefficients, a measured path length, and an experimentally measured absorbance Io/I, the concentration c of an analyte can be determined. Thus absorption responds to the product of concentration and path length. If an analyte is present at low concentration, especially in the atmosphere, sensitivity can be increased by using a long path length. This is especially important in gas phase measurements, especially in the atmosphere where it is important to determine the concentrations of very trace components. These concepts apply to measurements made at any wavelength, for instance microwave, IR, VIS, UV, etc. These considerations apply to many types of spectroscopy, including Differential Optical Absorbency Spectroscopy (DOAS), Fourier Transform Infrared Spectroscopy (FTIR) NOIR and other derivative and non-derivative measurements. Long path lengths are used in several ways:

1. A long physical path length is used. For instance a light beam, including a laser beam, may be propagated to a detector meters or even kilometers distant.
2. Similar to 1, but a reflector is used at a distance to reflect the beam back to a detector co-located with the beam source.
3. A folded path is used. In this application, such as in a White Cell, two mirrors are used to reflect a beam over a base path a number of times, thereby increasing the total path length. The number of reflections and the base path length (distance between the mirrors) is variable.
4. A waveguide is used to confine the light beam. In situations where a sample is contained in a tubular material with refractive index lower than the sample itself, complete internal refraction occurs and the beam may be effectively propagated over long distances to a detector. Recently, new Teflon formulations have been developed with refractive indices less than that of water and thereby form effective waveguides for absorption in aqueous samples. Metals, with real refractive indices <1 are potentially useful waveguides.

An important property of gas phase spectroscopy or spectrometry is a phenomenon known as pressure broadening wherein the height to width ratio of an absorption feature decreases with increasing total gas pressure. This broadening is caused by interactions between the analyte molecules and any other gas phase molecules present. Further, although Beer's Law is know to hold over a wide range of conditions, it is by no means followed under all conditions of pressure, concentration or intensity of the probe light source.

Although the concentration dependence of Beer's Law is well known, the current spectrometric art does not teach or suggest high sample pressures i.e. it does not teach or suggest Pneumatic Focusing trace analysis.

Summary of Pressurization in Absorption Spectroscopy

It is not recognized in the current art that for trace gas analysis, Pneumatic Focusing trace analysis of a sample will result in greater detectability. U.S. Pat. No. 4,749,276 describes a long path absorption cell whose prime novelty involves heating to prevent condensation of condensable vapors. This patent does refer to the cell being sealed so it can operate above atmospheric pressure. This patent states that:

It is an object of applicants' invention to produce a White-type cell, which can function to measure condensable gases at elevated pressure.

Note the use of the qualifier "condensable gas". It appears that the authors didn't consider the very high pressures of Pneumatic Focusing trace analysis, or that this method would be useful in the measurement of gases which would never condense even when compressed. That is, gases at such low partial pressure/concentration that their vapor pressure would not be exceeded even with very high pressurization. It appears that these authors did not envision Pneumatic Focusing as they fail to discuss precautions that must be taken to ensure that the cell does not explode when subjected to high pressures. Rather, they simply discuss 'sealing' the cell, providing no information of how high a pressure this cell could take or of any of the benefits or disadvantages of going to very high pressure. Further, as shown above, in Pneumatic Focusing trace analysis it would be advantageous to first pressurize the sample gas before introducing it into the long path absorption cell so that much of the IR absorbing water would be removed outside of the cell. This is important because water is opaque in many regions of the IR. If a sample containing water vapor was introduced into the above cell and then greatly pressurized, water would condense on whatever components were heated the least. If the temperature was so high as to completely prevent condensation, then water absorption of the IR beam would occur. If the temperature were not high enough to prevent water condensation then the cell could be damaged or corroded by the liquid water.

Spectrometric Effects of Pneumatic Focusing

Pneumatic Focusing trace analysis may be used either to replace or complement such path length absorption processes. Whereas an increase in path length can produce increased absorption and increased sensitivity, an increase in concentration through pressurization or Pneumatic Focusing can do the same. Such pressurization may be carried using a high pressure driving gas, such as in the exemplary chromatographic technology described here, or by means of a piston, compressor or other such device. Long path lengths, especially reflected paths, may be used in combination with Pneumatic Focusing. Waveguides will be useful with Pneumatic Focusing as the sample can be compressed to high pressures, generating a higher refractive index for the sample so that its refractive index became higher than that of the containment vessel, enabling complete internal reflection of a probe light beam. Can cool to enhance compression i.e., liquefy the sample.

Spectroscopic Details of Pneumatic Focusing

When air or other sample gases are compressed to higher pressures potential analytes are increased in concentration and condensables are separated so that both (if desired) can be subjected to separate analysis. In addition, any reactions which may be occurring within the gas sample are accelerated, since reaction rates are proportional to the product of the reactants' concentrations.

As an example, ozone reacts with alkenes in ambient air. If such air is pressurized, for instance by a factor of 10, these reactions will occur faster, in this case by a factor of 100. However, the rate of fractional alkene removal by the reactive ozone will be increased only by a factor of 10. Thus is it already known within the field of atmospheric measurements to remove ozone from a gas sample before either storing it for later analysis, or passing in into any sort of collection of focusing device. This standard technology may be applied to Pneumatic Focusing as well. Standard methods of ozone removal include reaction with added nitric oxide NO, or removal on some surface, such as a copper surface, or a glass fiber surface which has been coated with reactive potassium iodide.

Other pitfalls to be recognized or avoided in Pneumatic Focusing spectrometry include:

1. Absorbance commonly increases linearly with pressure due to increasing concentration as expected from Beer's Law, but this is not always the case.
2. Absorbance can increase proportional to the square root of the pressure ratio due to dimerization of the target analyte to produce a nonabsorbing dimer.
3. Absorbance can increase proportional to the square of the pressure ratio, which without limiting any invention to a theory of operation, may be due to absorption of dimers or collision complexes.
4. Absorbance can increase and remain constant due to condensation of the target analyte to a liquid which is removed from the view of the absorbed light beam.
5. Absorbance may increase, decrease, or otherwise behave erratically.
6. Broadening of the absorption lines can occur.
7. Interference from unwanted spectral bands of the sample (e.g. O4 absorptions) not present at the original sample pressure and whose intensity is dependent upon the focusing pressure can occur.
8. Transmitted light intensities can oscillate, perhaps randomly, indefinitely in time, but time averaging can be used to determine absorbances and concentrations.

II. Apparatus

FIG. 1 is a schematic of a working embodiment of a system useful for pneumatically focusing, and analyzing a gaseous sample using a gas chromatograph. The components of the system, and their connections, will be discussed with reference to FIG. 1. A more detailed description of certain components of the system also is provided.

FIG. 1 illustrates a chromatographic system 10. A working embodiment of system 10 as illustrated in FIG. 1 has been used for continuous, real time monitoring of ambient air. This system 10 has operated almost continuously for more than one year sampling ambient air for a total of >10,000 samples on the same alumina column. A sample line 12 having an outdoor sample inlet 14 was used to collect ambient air outside of a building. For this illustrated embodiment, the sample line was made of TEFLON, and was approximately 30 meters in length. A person of ordinary skill in the art will recognize that the sample line can be made from other materials, such as other plastic materials or metals, such as copper tubing. The length of the sample line is determined by application, and is not critical to the operation of the present system.

In this application a virtually instantaneous sample was taken. Such sample is most suitable for determining emission source distributions (which information is degraded by averaging over large sample volumes which have been impacted by varying sources). It is more common in the field of air sampling to use integrated samples. For instance, a gas canister is slowly filled over a period of 1, 2, 24, etc. hours and then transported for laboratory analysis. Or, air is passed slowly through an adsorbent cartridge for 1, 2, 24, etc. hours. In some applications this type of sampling might be preferred with PFGC. Time averaged sampling may be accomplished several ways (without limitation) using PFGC. For purposes of these examples, assume the sample analysis time to be 40 minutes.

1. Sample on an instantaneous time basis and then average individual chromatograms together before analysis. This yields a better signal-to-noise ratio and hence sensitivity or detection limit as discussed elsewhere than analyzing a single accumulated sample a single time. For instance 40 samples taken on a 40 minute basis may be averaged to compare with a single 24-hour integrated sample.
2. Sample on an instantaneous time basis but draw the air sample continuously into a collection/averaging volume during the 40 minute analysis time. If the sample rate were 10 cc/min and the averaging volume were 400 cc then the averaging time would be 40 minutes. Thus each 40 minute sample would be an average over that time period rather than an instantaneous sample taken every 40 minutes.

3. As in 2 but choose an integration averaging time (=volume/flow rate) of any desired time.

Sample line 12 was fluidly connected via a multiport sampling valve 16 to a sampling pump 18. Sampling pump 18 is used to, if desired, continuously draw gaseous samples, such as ambient air samples, into the sampling line 12. Further fluidly connected to the sampling valve 16 is a carrier gas inlet line 20, a sample loop 22 and a separatory column 24. Carrier gas inlet line 20 is fluidly connected to a carrier gas source, such as the carrier gas cylinder 26. In a working embodiment, the carrier gas was helium. Typically, a high-pressure regulator 28 is coupled to the carrier gas source for regulating the pressure delivered to the system by the carrier gas. Additionally, a VOC adsorbing filter, not illustrated but described elsewhere, was fluidly coupled inline between the high-pressure regulator and the multiport valve. A working embodiment used an activated carbon filter to remove VOCs and other impurities from the carrier gas so that they do not appear as spurious peaks in the chromatograms. This allowed lower grade and cheaper carrier gases, for instance 'balloon grade' helium, to be used. Since these filters can themselves restrict flow and cause pressure drop to the pneumatic chamber, a pressure gauge may be placed between the filter and the multiport valve so that pressures may be adjusted correctly independent of the regulator gauge and so that gradual clogging of the filter may be monitored.

Sample loop 22 is fluidly connected to two ports of the multiport sampling valve 16. The carrier gas is connected to the sampling valve 16 by carrier gas inlet line 20, which is fluidly connected to a first port of the valve 16. Separatory column 24 is fluidly connected to a port of the valve 16. The illustrated embodiment of the valve 16 had only two primary positions, a sampling position and an injection position. In the sampling position, sampling pump 18 continuously draws air through the sample line 12 and through the sample coil, while carrier gas from gas source 26 is delivered to valve 16 by sample line 20. In the sampling mode, carrier gas passes through the valve 16 and through the separatory column 24. In an injection position, valve 16 allows carrier gas to pass through sample loop 22. The carrier gas pushes the gas sample collected in the sample loop ahead of it, thereby pneumatically focusing the gaseous sample, and into the separatory column 24. Valve 16 can be manually operated, but preferably is operated by a control computer so that the sampling and analysis conducted by the system can be automated.

Downstream of the column 24 is a pressure increasing/ flow reducing valve 30. Actuating valve 30 increases fluid pressure in the line and reduces fluid linear velocity through the line. Thus, once a gaseous sample is pushed towards the column 24 by a carrier gas, the gas sample is compressed to a second smaller volume, and therefore analytes in the gas are concentrated. The pressure of the line can be maintained as, and subsequent to, the gaseous sample being injected onto the GC column. Compressing the gas sample can be used to condense certain materials, such as water, in the gaseous sample before the sample is injected onto the column. One important benefit of this system is that water condensed by Pneumatic Focusing can be condensed prior to entering the column and hence mostly prevented from entering the column. For instance, isothermally compressing the sample gas initially at 100% RH from 15 psi (atmospheric) to 300 psi (pneumatically focused) would condense 1–15/300 or 95% of the water. By appropriate valve switching, the vast majority of the sample water vapor would not enter the column or other analytical fashion. This illustrates the nonobvious design of Pneumatic Focusing.

Alternately, if it is desired to inject the gaseous and condensed water with the sample this may be accomplished several ways, such as:

1. The sample compression section may be heated sufficiently that water will not condense even at high pressures. Thermodynamic calculations or empirical tests can determine the appropriate temperature.
2. The carrier gas may continue to pass through the sample compression section long enough to reevaporate condensed water and other condensables and sweep them onto the head of the column.
3. 1 and 2 may be used in combination.

Alternately, the condensed water and any dissolved components may be collected through a separate port and subjected to additional chemical analysis either by direct spectroscopy, pH determination, or other measurement such as by additional chromatographic separation and analysis.

Column 24 is fluidly connected by sample conduit 32 to a detector, such as a FID detector, 34. Thus, gaseous sample that has been pneumatically focused and injected on the column 24 is diverted through detector 34. Plural detectors (not illustrated), either connected in series or in parallel, also can be used. If connected in series, then detectors that destroy the sample, such as a flame ionization detector (FID), should be last in the series. If detectors 34 are connected in parallel, then portions of the gaseous sample from column 24 are diverted, as desired, into such detectors.

FIG. 1 illustrates a system that utilized an FID 34. FID 34 was used because one primary use for the illustrated system, without limitation, is continuous sampling of VOCs in ambient air and in human breath. FIDs are especially well suited for detecting the minute quantities of VOCs in pneumatically focused samples produced. FIDs require both a fuel source and an oxidizer source. FIG. 1 illustrates fluidly connecting FID 34 to both a hydrogen (fuel) cylinder 36, via supply line 38, and to an oxidizer (oxygen) cylinder 40, via an oxidizer supply line 42. Both fuel cylinder 36 and oxidizer cylinder 40 include conventional pressure regulators 44 and 46, respectively.

Gaseous samples pneumatically focused are analyzed by desired chemical analysis instruments, such as the gas chromatograph 48 (e.g., a Varian 3400 gas chromatograph) illustrated in FIG. 1. The Varian 3400 gas chromatograph used in one working embodiment of the present system also included a keypad 50. An operator using the keypad entered chromatographic processing parameters into the chromatograph.

The entire operation of the present system was automated, and the working embodiment of the present system as illustrated in FIG. 1 was computer controlled. Computer 52, such as a 486 personal computer, was electrically coupled to the detector 34. Signals generated by the detector 34 were routed to computer 52 through an amplifier A/D converter 54. Computer programs, discussed below (source codes for which are attached hereto as an appendix) controlled the operation of the computer to determine when samples were collected and analyzed. As with any computer, input to computer 52 can be accomplished as desired, such as through a keyboard 56. Data generated/analyzed by the computer can be displayed, if desired, on a computer monitor 58. These data could be subjected to real-time, digital signal processing to reduce noise and improve signal to noise ratio. Such data, as well, could be subjected to real-time peak integration for direct reporting of analyte concentrations. Also, the computer 52 can be linked via a modem to a remote operating station, or can download data to an internet connection, if desired.

Certain of the components described above with reference to a working system will now be described in more detail. The system was made by modifying commercially available chromatographs, such as Varian 3000 series chromatographs. Models No. 3400 and 3700 were used to construct 2 working embodiments. However, virtually all known chromatographs can be modified to be useful for Pneumatically Focusing gas samples.

A person of ordinary skill in the art will recognize that working instruments could include elements in addition to those described below. Moreover, a person of ordinary skill in the art will recognize that the elements listed below could be modified from that described to include, for example, future-developed features. Further it should be realized that a more suitable, more saleable, more compact, etc., instrument could be designed, constructed, and built from scratch.

1. Compressed Gases/Delivery Cylinders

Compressed gases are used for a number of purposes, such as (a) to provide a carrier gas that carries the sample through a separatory column and/or (b) to provide a gas that fuels the flame, the electrical conductivity of which forms the basis for detecting analytes using flame ionization detection of individual, separated VOCs.

The carrier gas can be any gas deemed suitable for carrying samples through a separatory column. Working embodiments of the present apparatus have used helium (He) as the carrier gas. A number of other suitable and useful carrier gases can be used, depending upon the details of the application, including hydrogen (H2), nitrogen (N2), argon (Ar), carbon dioxide (CO2), ambient air, or any of a multitude of other gases, including gases doped with suitable internal standards. In one application, the carrier gas (e.g. CO2) may be compressed sufficiently to generate a supercritical fluid.

Suitable carrier gases may be used singly or in combination. Moreover, plural gases can be used in various combinations during the course of Pneumatically Focusing or analyzing samples. For example, the chromatogram initially could be generated using Pneumatic Focusing and initial column separation using helium. At some point, the carrier could either continuously or discontinuously, be changed from helium to, for example, supercritical fluid carbon dioxide. By this method, a carrier gas of varying composition over time could be developed. Changing the carrier gas in PFGC gradually from helium to supercritical carbon dioxide would allow eluting from the column those analytes which helium is not capable of eluting. This gradient elution could thereby allow an automated chromatograph to operate using a constant oven temperature. This allows considerable savings in complexity and electrical power for a remotely operating instrument. In this case, analyte separation and elution would be accomplished by a combination of factors, such as carrier gas composition, pressure, and flow rate, including supercritical fluidity of the carrier for part or all of the chromatogram. Another such approach would be to employ a liquid chromatograph. Chromatographic carrier gases can be contained at elevated pressures (1000–10000 psi) in compressed gas cylinders. In Pneumatic Focusing these compressed gases can serve to compress the pneumatically focused sample in the sample loop and into the chromatographic column. This could also be accomplished with a minimum of diffusional mixing between sample and Pneumatic Focusing/carrier gas through the use of a pneumatic piston described herein separately. Following delivery to the chromatographic column, each VOC component separated by the separatory column is consecutively eluted into a FID.

Figure 2:
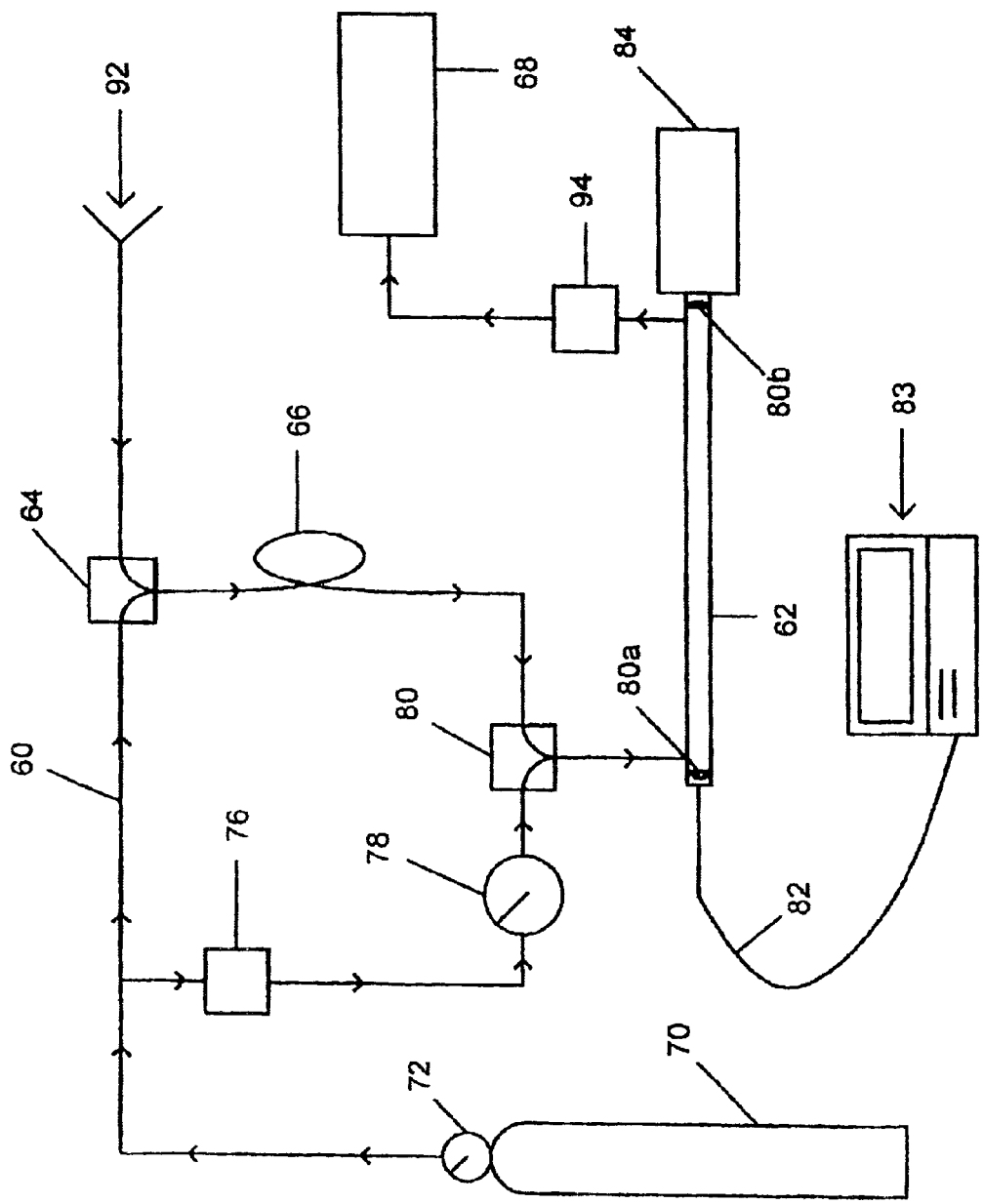

FIG. 2 illustrates a Pneumatic Focusing Spectrometric System 60 (PFSS). Components of this system were selected to withstand pressures of 15 to 2,500 psi as delivered by a compressed nitrogen cylinder. This system consists of a metal or glass light absorption cell 62 fluidly connected with Swagelok fittings and 3-way valves 64 and 80 to a sample containing loop (200' coil of ¼" od copper tubing) 66, a sample providing pump 68, a compressed nitrogen cylinder 70 and high pressure regulator 72 to deliver the Pneumatic Focusing pressure. Gas from cylinder 70 is delivered via a fluid conduit 74, through a 2-way valve 76 and pressure gauge 78. Gas from cylinder 70 is then routed via Whitey 3-way valve 80 to cell 62. Spectrometric measurements were provided by an Ocean Optics PC-2000 spectrometer (not illustrated) which consisted of a diode array card located inside a personal computer 83 running Windows98. Light to the cell 62 was provided by an Ocean Optics mini-FT2 combined UV-VIS light source 84 providing light from approximately 200 to 900 nm. Light was passed through the cell 62 using end windows consisting of UV-transparent fused silica lenses 80a, 80b from Edmund Optics #K45-693. Light was conveyed from the cell 62 to the diode array card within the computer 83 by an optical fiber 82 included with the PC-2000.

In a working embodiment, the valves, such as valves 64, 76 and 80, were operated manually. These valves could in continuous operation be operated by personal computer 82 containing the spectrometer.

One method (without limitation) for operating this Pneumatic Focusing spectrometric system PFSS is as follows:

1. The system 60 is assembled as illustrated in FIG. 2. All components described herein have withstood 2,000 psi focusing pressure, but appropriate precautions should always be taken in assembling such a system. This system was pressurized for the first week by an operator standing behind a ¼" section of safety glass. In FIG. 2 pressure gauge 78 allows the Pneumatic Focusing pressure to be determined. Typical operation (without limitation) is as follows.

2. A sample 13 drawn through ¼" Teflon tubing 90 leading from the sample inlet 92. In this set of tests various test gases contained in plastic bags were delivered to the PFSS at port 92.

3. Before initiation of spectrometric measurements, appropriate measurements of lamp and dark intensities are made. Such operations, familiar to practitioners of the spectrometric arts, are described in the Ocean Optics manual. Initially, the spectrometer is placed in 'Scope' mode and the lamp intensity (Io) is recorded and saved in computer memory. Since data at each wavelength are recorded with a 12-bit A/D board, the sampling time should be set such that approximately 3500 counts are displayed on the computer screen at the maximum point in the intensity curve. Any desired spectral averaging number may be selected as well. For many applications no averaging is required and the computer will update absorbance measurements every few seconds or so. Next, the optical fiber 82 is removed from the spectrometer cell 62 and light is blocked from entering it, such as by the operator's thumb. Under computer operation the operator's thumb would be replaced by a computer actuated shutter between the fiber 82 and the cell 62. This dark current is recorded and stored in computer memory. This forms Idark as is commonly employed in spectrometry, the concentration of an absorber is given by solving the equation:

$$A = \log((I_o - I_{dark})/(I - I_{dark})) = ac1$$

Thus absorber concentration is proportional to A which is computed automatically and displayed by the computer as a function of wavelength, in real time, on the computer screen. After these initial measurements the program is placed in absorbance mode.

1. With valves 64, 80 and 2-way valve 94 in the appropriate position, pump 68 draws air from a source through sample coil 66 and through spectrometric cell 62. Care should be taken that the entire sample coil 66 and cell 62 are filled by such sample. Since sample arrives at the spectrometer cell 62 last, this may be ascertained by observing the light absorption spectrum on the PC computer screen. In the case where no discernable absorption is present before Pneumatic Focusing a sufficient length of time should be allowed for sample to arrive.

1. When sample delivery is complete the initial absorbance may be recorded and saved to computer memory.

2. Valve 94 is thrown to the opposite closed position to isolate pump 68 from the system.

3. The sample is pneumatically focused to the desired pressure. This may be carried out without limitation as follows. The pressure regulator 72 is set for a pressure less than or equal to the starting, atmospheric pressure. Valve 64 is moved to the opposite position, fluidly connecting tank 70 through regulator 72 to sample coil 66, valve 80 and cell 62 (valve 76 remains closed). Then regulator 78 is slowly adjusted upward in pressure, allowing nitrogen pressure to build up in the sample loop and spectrometric cell 62, pneumatically focusing the sample contained therein. Absorption may be observed on the computer screen continuously during this process. When the system 60 has reached equilibrium (a few seconds, assuming pressure was increased gradually) the absorbance spectrum is recorded and saved to computer memory. In the process of sample focusing within the sample loop 66, condensed water will be formed, and if the process occurs slowly (as is advised for the purposes of these measurements), most will be removed on the walls of the sample loop 66 rather than enter the sample cell 62.

4. This process is repeated to produce a series of recorded spectra at various focusing pressures such as discussed in one of the examples below.

Figure 3:
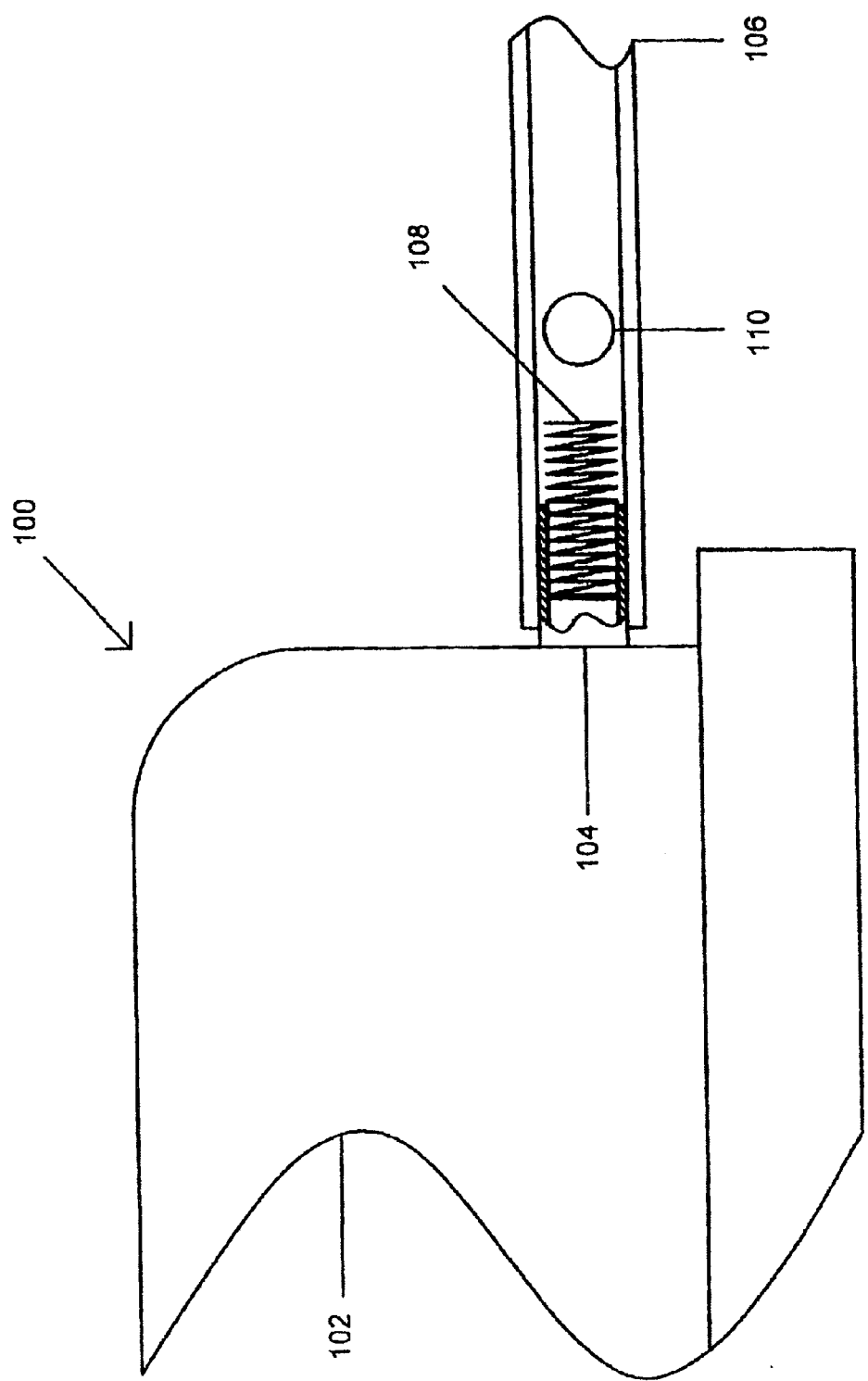
Figure 4:
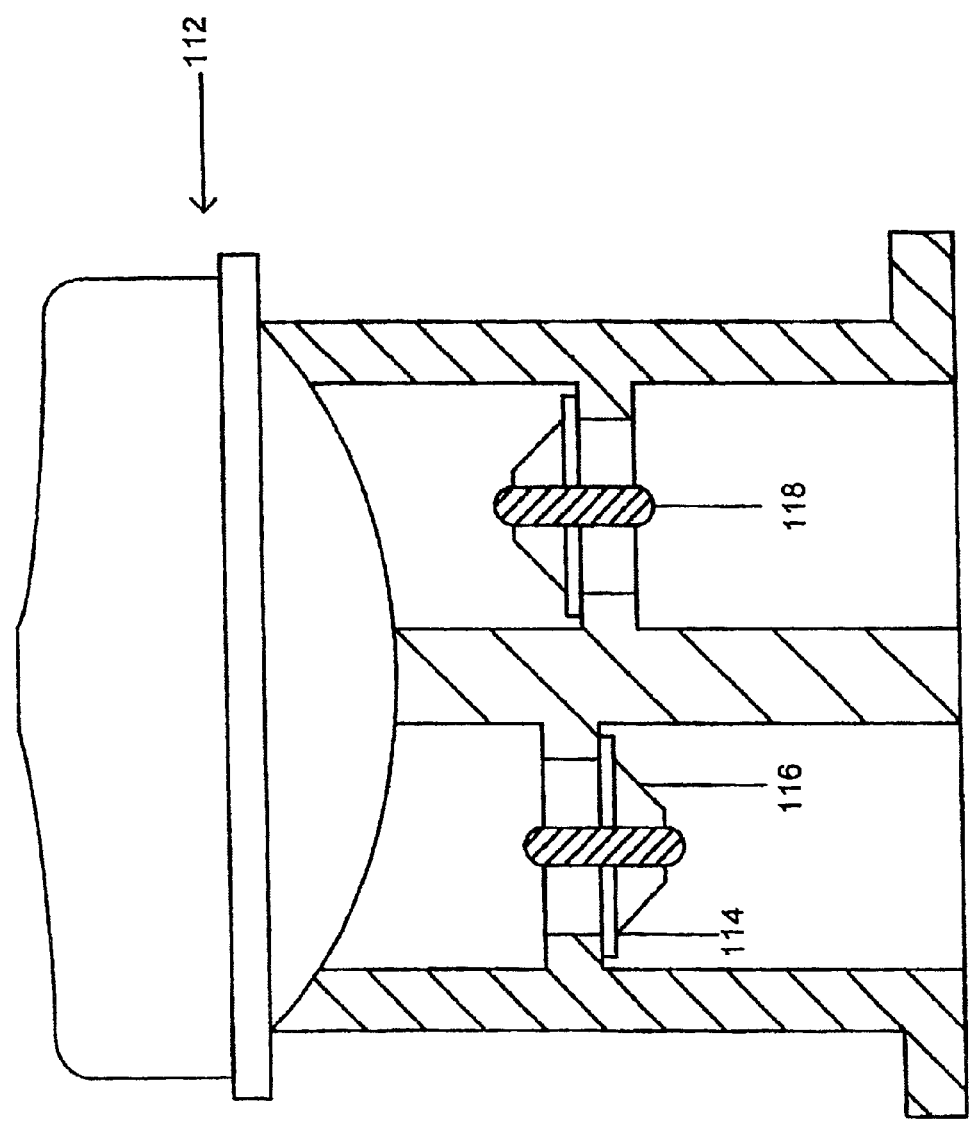

5. To terminate the process, regulator 72 is adjusted back to pressure less than 1 atmosphere, and pressure is bled from the system 60 by slowly opening either valve 64 or valve 94. In manual operation pump 68 may be removed before pressure is bled off to avoid displacing the rubber diaphragm inside the pump (this diaphragm is easily replaced). Alternately, check valves and bleed valves, such as illustrated in FIG. 3 and FIG. 4 may be bleed check valve employed.

6. If pressure is bled off slowly through valve 64 and no irreversible chemical reactions have occurred at focusing pressures, the spectra should retrace the results obtained during pressurization 7. If pressure is bled off through valve 94 the spectrometer should quickly return to a 'zero absorbance' reading as the non-absorbing, focusing nitrogen gas enters the spectrometric cell.

The PFSS illustrated in FIG. 2 can perform another function through the use of valve 76. In this operation compressed gas cylinder 70 is connected directly to cell 62 without passing through the sample loop 66. In this way the effect of pressure (pressure broadening) on any desired analyte may be determined with said analyte remaining at constant concentration. In this operation the analyte is first drawn through the sample chamber 62 as above. Once a stable absorption spectrum is obtained, valves 64, 94, 80 and 76 are reversed thereby connecting cylinder 70 through regulator 72 to sample chamber 62. Thus pressure administered from the compressed gas cylinder 70 serves to increase the pressure to which an analyte is exposed while maintaining constant analyte concentration. When carrying out these measurements sufficient time should be allowed for the analyte to diffuse into newly administered pressurization gas.

For samples containing water vapor, such as ambient air samples, focusing as described above will condense water vapor onto the walls of the sample coil 66. If removal in this manner is insufficient, a filter (not illustrated) may be included between the sample loop 66 and the cell 62. One caveat in water condensation is partitioning of water soluble analytes into the condensed water vapor. This process is described by Henry's Law.

An exemplary calculation of the nature of this affect is given here for acetone. The NIST web site (http://webbook.nist.gov/chemistry/) lists the Henry's Law coefficient for acetone solubility in water as kH=30 mole/(kg*bar) ~30 (mole/kg H$_2$O)/atm.

Consider 1 liter of ambient air that has 1% water vapor by volume. (Saturation at STP is about 3% so this is about 33% RH). Pressurization to 100 atmosphere would condense virtually all the water vapor. Using PV=nRT, this would produce:

$n$=0.01 atm*1 L/(0.082 L-atm/K-mole*298K)=4.1 e−4 mole H2O 4.1 e−4 mole*18 g/mole=7.4 e−3 g H2O=7.4 e−3 ml=7.4 uL H2O=7.4 e−6 kg H2O Assuming 1 ppb=1 e−9 atm of acetone compressed to 100 atm in the sample we have $n$=1 e−9 atm*1 L/(0.082 L-atm/K-mole*298K)=4.1 e−11 mole acetone KH=30(mole/kg H2O)/atm*7.4 e−6 kg H$_2$O*1 e−7 atm Acetone= 2.2 e−11 mole acetone.

Thus acetone would partition into the condensed phase about 1 liquid:2 gas at a Pneumatic Focusing pressure of 100 atm=1500 psi. The fraction partitioned would be negligible at 10 atm or 150 psi.

Benzene is much less soluble in water than acetone with KH=0.16. Thus benzene partitioning into water would be negligible even at 100 atm.

These calculations, based upon proportions, are independent of the volume of air pneumatically focused.

Pneumatic Focusing Spectrometry consumes significant quantities of the pressurization gas for a sample loop of 1 L volume. A more attractive approach (also applicable to PFGC) is to use without limitation any of a variety of piston-type devices. Four such embodiments have been developed or envisioned to date.

1. One such device was constructed using a piston/cylinder and a 12V electronic trailer jack (Atwood company) to provide the compression force. In a laboratory model, the jack was attached to a cast iron mount with stainless steel hose clamps. The cylinder, which contained an o-ring-sealed piston, was similarly attached. Application of 12V to the jack actuated piston, driving the contained air sample into either a spectrometric sample cell or onto the head of a GC column. In this fashion pressure was increased by the application of voltage to the pressure jack. Higher pressures could be generated using a longer piston.

2. A hydraulic cylinder of about 10 liters volume is compressed by a variable speed high torque motor. This large device would easily deliver sufficient sample for a spectrometric cell but would be larger than normally required for PFGC.

3. Another such device 100 (FIG. 6) employed a 12V (cigarette-lighter plug in type) compressor designed for inflating tires. This miniature compressor was equipped with coiled copper tubing 102 having inlet 104 through which cooling water flowed to prevent overheating. Tubing 102 also included an outlet 106. The compressor included a motor 108 and a gearing device 110. Motor 108 actuates piston 112 into reciprocating motion within cylinder 114. Cylinder 114 has a delivery conduit 116 having a gas flow outlet 118 and a liquid flow outlet 120. A flow regulating material, such as a glass wool plug 122, also can be used within conduit 116. Pressure is measured with gauge 124. The compressor was connected to a spectrometric cell through a section of Teflon tubing. A downstream valve below the spectrometric cell regulated flow rate through and pressure within the cell. With this device it was possible to feed a continuous air sample for spectrometric analysis to the cell at pressures ranging from 60 to 120 psi. Such tire pump, not being designed for continuous operation, could be replaced by a more suitable small compressor in actual practice and would deliver a higher Pneumatic Focusing pressure. Otherwise, such compressor could be used to deliver periodic samples by computer control to a chromatographic device. Since Pneumatic Focusing results in conversion of condensable gases (e.g. water) to liquids, it is possible to separate said condensed liquids from the non-condensed pneumatically focused air stream. Each of these two pneumatically focused samples could be directed to an appropriate detection device. For instance (without limitation) the liquid sample could sent to a liquid chromatograph and the gas sample to a gas chromatography alternately, both could be sent to different gas chromatographs, or to different columns in the same gas chromatograph. The aqueous fraction may be subjected to a variety of nondestructive micro determinations such as pH or specific ion electrode measurements. Persons familiar with the art will appreciate the extremely wide range of analytical possibilities for these two sample streams.

4. Another such prototype application would employ the small compressor as the continuous gas feed (carrier gas) to a chromatographic system. Since the compressor delivers ambient air, any compounds present in ambient air which collect on the head of the column would elute and form peaks during temperature programming of the column. Thus air could form both the analyte and the carrier gas.

2. Sample Collection Tubes

A gas sample is collected so that it can be pneumatically focused and injected onto a separatory column of a GC. This has been accomplished using coiled collection tubes typically made out of metal, such as copper. Copper has the advantage of catalytically destroying ozone which may be present in ambient air samples and which could remove alkene VOCs during Pneumatic Focusing (see above). Working embodiments have used one or more sample collection tubes connected in parallel for collecting samples. The collection tubes typically have been about ⅛ inch exterior diameter copper tubing approximately 50 feet in length. By increasing the length of the collection coil, or by coupling plural collection coils together in series or in parallel, a larger gas sample can be collected for injection onto a separatory column of the GC. In other working embodiments of Pneumatic Focusing a ¼ inch 50-foot length coil of copper tubing has been using with variable time delay injection under computer control. In this fashion the computer may inject from a single 0.5-liter sample loop actual volumes ranging from 0.05 liter to 0.5 liter. The larger the sample size introduced onto a separatory column, the potentially greater sensitivity that can be achieved. With larger samples higher pneumatically focusing pressures can be used if desired to maintain sample band width. Variable volume injection may be quantified by any of the internal standard methods described herein.

It will be recognized that injection of larger and larger samples may produce some loss in resolution and separation, especially for those compounds not collected at the column head.

A multiple injection technique also may be used. In this approach, rather than injecting a single large volume, say 500 cc of sample at once, the computer is programmed to inject a 50 cc sample 10 times. After each injection the sample pump pulls fresh sample into the sample loop. After injecting a computer controlled number of times the gas chromatograph is triggered to begin temperature programming. The result of this multiple injection approach is to generate 10 individually resolved methane peaks since methane is not held up by adsorption on the column. There then follows a range of compounds which are not resolved by the multiple injection technique. Finally individual peaks which were held up on the column head by the low initial temperature (in this case room temperature) emerge fully resolved and at an intensity 10 times that of an individual injection. Under computer control, such multiple injections could be carried out inversely proportional to the concentrations of target analytes. For instance, in air monitoring, if the air was highly polluted, a relatively small number of multiple injections could be made. If the air was slightly polluted, a relatively larger number of multiple injections could be made. The computer could determine pollution levels from each previous chromatogram and adjust the subsequent number of injections accordingly.

One method which is useful in improving resolution in capillary column chromatography has been described by Ziment Yan and J G Nikelly in Journal of High Resolution Chromatography 17 (1994) pp. 522–536: "The use of pre-columns for solvent focusing in capillary column gas chromatography." Such precolumns also will be useful in improving the manner in which pneumatically focused samples are introduced into a capillary column. This will be particularly but not solely useful in focusing samples which originated as liquid samples but which were vaporized upon introduction into a Pneumatic Focusing gas chromatograph.

Two factors typically are considered when determining the sample size and the degree to which the gas sample is pneumatically focused. These two factors are the sample volume and the compression ratio. For example, by both doubling the sample volume and doubling the pressure used to pneumatically focus the sample, to a first order approximation the result should be substantially the same peak resolution but twice the sensitivity, since the sample size has doubled, as achieved prior to doubling the sample volume and the focusing pressure. On the other hand if the sample volume is doubled, but the focusing pressure is maintained the same, then the integrated signal may be increased but the peak resolution and sensitivity may degrade, i.e., the peak width as displayed by the chromatogram would increase but not the peak height. Thus, Pneumatic Focusing results in narrower peaks that can be resolved from one another and provides a larger signal relative to instrument background noise. Pneumatic Focusing is enhanced by temperature programming. In previous examples those compounds retained on the column head would have enhanced sensitivity when two times the sample size was injected at a constant pressure. See example below. There is no clear upper limit to the degree of Pneumatic Focusing in terms of sample volume, pneumatically focused pressure and resultant sensitivity. Obvious limitations are the pressure limits of those system components exposed to the elevated pressures, separation efficiencies on the chromatographic column (if employed), and potential chemical reactions accelerated with pressure in the sample. These limits can be ascertained and perhaps improved by experimentation familiar to persons experienced in the chromatographic or spectrometric arts.

For air analysis, methane is one VOC that is both quite volatile and relatively constant in concentration. Other, less volatile VOCs, such as aromatics, tend to absorb, or stick, to the head of the column as the sample containing such materials is introduced onto the column. These less volatile VOCs are desorbed from the column by, for example, heating the column. Thus, the Pneumatic Focusing of less volatile VOCs may be less important than Pneumatic Focusing of more volatile VOCs. Methane is the first VOC to emerge from a separatory column due to its relatively high volatility, whereas aromatics such as toluene are, to some degree, additionally focused by their relatively lower volatility and relatively higher affinity for the separatory column. The Pneumatic Focusing effect can be enhanced by selectively cooling a section at the 'head' of the column to focus more volatile analytes, using a retention volume, a thickly coated precolumn, or any of several other approaches familiar to those experienced in the art.

In atmospheric analysis it is often desired to measure the methane concentration and the sum of all the nonmethane hydrocarbons. U.S. Pat. No. 4,102,648: "Measuring Non-Methane Hydrocarbon Contents in Gases" takes a sample gas which is divided into two portions, one being subjected to flame ionization detection to measure all hydrocarbons, the other one being passed through a tube having active carbon to remove all higher hydrocarbons by adsorption except methane. The resulting gas also is subjected to flame ionization detection and the difference in detection gives the non-methane impurities, either electrically as difference signal or graphically. The adsorber tube may be exchanged for another one while the former is cleaned and purged. A simple flame ionization detector is used alternatingly or two are operated in parallel to obtain the two readings. This now standard way to measure methane and the sum of non-methane HCs would benefit in higher sensitivity if adapted for Pneumatic Focusing since a higher signal would be achieved upon compression, allowing more accurate determination of the signal difference produced upon removing NMHCs.

Conventional wisdom in the field of air sampling, as discussed in the Background, is to cryofocus or absorbent focus samples (or both) from a fairly large volume to a significantly smaller volume. However, if a sufficiently large sample volume is first collected and thereafter injected onto a separatory column at conventional pressures, such as less than 100 psi, and more typically about 40 psi–60 psi, without pneumatically focusing the sample at pressures greater than pressures used for conventional GC analysis, then the first, most volatile materials in the sample are not focused, and hence are not resolved. However, VOCs that are less volatile may be resolved by adsorption and desorption from the separatory column, where desorption occurs as a result of heating the column. The significant advantage of Pneumatic Focusing for less volatile analytes is to pass a large volume of sample gas through the column in the most rapid fashion—which is at high pressure. Thus, even for materials that are primarily focused by absorption to the head of the column, increasing the pressure at which such samples are driven through the column significantly decreases processing times without sacrificing sensitivity or resolution for the column-focused analytes.

3. Columns

Virtually any known separating column can be used, along or in combination with other columns. Those familiar with the art will realize that some columns will be more appropriate for individual target analytes and that individual columns, coatings or packing materials, etc. may be more suitable than others for PFGC. One working embodiment of the present apparatus used an alumina VOC analysis column, distributed by J&W, (30 m×0.53 mm id) Model No. 115-3532 RT-alumina. This column has passed approximately 20,000 air samples without suffering unacceptable degradation in resolution. A similar Restek column, RT Alumina (60 m×0.32 mm id) Ser. No. 183,143 also was used and gave better resolution than the shorter, wider bore J&W alumina column. Another such working embodiment used a Supelcowax-10 fused silica capillary column serial #15702-10 (60 m×0.32 mm id×1.0 um film thickness) for OVOC analysis of ambient air and human breath. Without limitation, other columns that could be used for separating a pneumatically focused sample include packed columns, capillary columns, open tubular capillary tube having an interior wall coated with sorbent material, packed capillary column, alumina columns, and combinations thereof. In other applications, a liquid chromatography or SFC column could be used.

A portion of the separating column could be further cooled during separation of a pneumatically focused sample. The temperature at which the cooling would take place could be higher than for cyrofocusing, and instead such temperatures can be achieved by electrical means without using cryogenic materials, such as liquid oxygen, nitrogen or air. This "reduced temperature" focusing could be used to further focus a sample at a localized region of a separating column, usually at an upstream portion thereof, relative to flow of the carrier gas. Thus Pneumatic Focusing can obviate the need for cryogenic fluids in gas analysis. Two-dimensional and comprehensive GC, in which successive portions of the sample fluid passing through a first column are directed as refocused pulses into a second column gives significantly higher sample resolution and separation than a 1-dimensional GC. This technique is completely amenable to Pneumatic Focusing of the sample before introduction or during introduction into the first column.

4. Column Packing Materials

Virtually any known column packing material can be used in combination with the method of Pneumatic Focusing as described herein. Working embodiments typically used a column having an alumina absorbent coated on an inside wall thereof Other packing materials are described in Helmig's Air Analysis by Gas Chromatography, supra.

5. Detectors

A working system used a FID detector. However, persons of skill in the art will realize that Pneumatic Focusing as described herein can be used with other detectors. Standard types of chromatographic detectors other than FID detectors may be cheaper, more sensitive, or otherwise more appropriate for a particular application or instrument. Such detectors may either operate at the Pneumatic Focusing column pressure, or downstream of the flow regulating valve at pressures near atmospheric, as is the case for a FID. Descriptions of a selection of suitable detectors may be found in standard references, such as: "Detectors for Gas Chromatography," Hill and McMinn, John Wiley (1992), incorporated herein by reference; "Detectors in Gas Chromatography," Sevcik, Elsevier, (1976), incorporated herein by reference; and others. In particular, suitable detectors include, without limitation, photoionization (PID), infrared (IR or FTIR), electron capture (ECD), thermal conductivity (TCD), nitrogen phosphorous (NPD), flame photometric (FPD), UV/Visible or Raman scattering detectors. The thermal conductivity detector, TCD, is especially simple, inexpensive, and used widely. However, many TCDs have limited sensitivity relative to (e.g.) FIDs. Pneumatic Focusing of gaseous samples will greatly extend the range of uses of the TCD and other such detectors for gas analysis because of its ability to quickly and inexpensively increase target analyte concentrations. It also is possible to use more than one detector to analyze portions of a pneumatically focused and resolved sample.

Pneumatic Focusing is especially useful for sample introduction for so-called GC/MS analysis of analytes. In this case, as described elsewhere herein, column mass flow rate should be decreased after pneumatic injection by simultaneously dropping column head pressure and opening the downstream valve to allow an increased volumetric flow at the dropping column pressure.

Some compounds are more appropriately detected by chromatographic detectors other than the flame ionization detection (FID), or by using other analytical procedures, such as absorption or fluorescence spectroscopy. The present technology will apply equally as well to most such other gas analysis procedures, and can yield greater sensitivity for those analytical techniques which respond with greater sensitivity to a compressed sample.

Pneumatic Focusing can be applied to absorption spectroscopy. Spectrometric measurements are normally interpreted in terms of the Beer-Lambert Law $I=Io\ exp(-a\ c\ l)$ where a is the absorption coefficient, c is the absorber's concentration and 1 is the path length. Using this law, previously measured and recorded absorption coefficients, a measured path length, and an experimentally measured absorbance $\log(Io/I)$ the concentration c of an analyte can be determined. Thus absorption responds to the product of concentration and path length. If an analyte is present at low concentration, especially in the atmosphere, sensitivity can be increased by using a long path length. This is especially important in gas phase measurements, especially in the atmosphere where it is important to determine the concentrations of very trace components. These concepts apply to measurements:made-at any wavelength, for instance microwave, IR, VIS, UV, etc. These considerations apply to many types of spectroscopy, including Differential Optical Absorbance Spectroscopy (DOAS), Fourier Transform Infrared Spectroscopy (FTIR), other derivative and non-derivative measurements.

Pneumatic Focusing may be used either to replace or complement such path length absorption processes. Whereas an increase in path length can produce increased absorption and increased sensitivity, an increase in concentration through pressurization or Pneumatic Focusing can do the same. Such pressurization may be carried out using a high pressure driving gas, which pushes the sample air into an absorbance chamber, without entering the chamber itself, or by means of a piston, compressor or other such device. Long path lengths, especially reflected paths, may be used in combination with Pneumatic Focusing.

Waveguide absorption spectroscopy can also be effectively used with Pneumatic Focusing.

1. In one embodiment an optical waveguide may be used to measure the absorption of the water fraction of the sample produced by Pneumatic Focusing. Such absorptions would be most easily carried out in the uv or visible region where water is mostly transparent to the beam radiation so that trace dissolved analytes can be quantitatively determined.

2. In another embodiment the aqueous fraction may be exposed to nonpolar adsorbents coated on the interior surface of the waveguide. After analytes in the aqueous fraction of the Pneumatically Focused sample adsorb onto the coatings, the water may be removed from the tube by forced air drying and then the concentrations of the adsorbed species measured by waveguide IR or FTIR spectroscopy.

3. In another application the Pneumatically Focused gaseous fraction of the sample may be subjected to either uv, visible, IR or other wavelength absorption measurements in a waveguide, such as a metallic or metallic coated waveguide. In such applications the approximately linear increase in refractive index of the gaseous sample with pressurization could enable the total internal reflection of the propagated beam.

U.S. Pat. No. 5,892,861: "Coated optical waveguides as extremely long path sample cells" (April 1999) states that:

A very long sample cell for spectrophotometric measurements that can be used to extend sensitivity to very low levels of gaseous components, under about 50 parts per billion. The cell is an optical fiber positioned within the annular space of a housing, with a gas stream flowing along the annular space. The outer surface of the fiber is coated with a material, e.g., an adsorbent that concentrates at least one component of the gas stream at the interface of the fiber and annular space. An indispensable prerequisite is that the coating have a refractive index greater than that of the optical fiber core. Radiation is propagated along the core of the fiber, and the evanescent wave passes through the adsorbed component, ultimately changing the radiation detected at the output end of the fiber according to the nature and concentration of the component. What we have done is to construct an extremely long sample cell for spectrophotometric measurements using an optical waveguide, or optical fiber, as the underlying component.

This waveguide cell operates by adsorption or absorption of target analytes on the waveguide coating material. No provision is made for adjusting the flowing sample pressure in the waveguide absorption cell. In contrast, in the present disclosure the pressure could be adjusted to quite high levels by suitably strengthening the waveguide material or by providing a strong external cladding. The increased pressure may provide the following additional advantages over those claimed by U.S. Pat. No. 5,892,861.

1. Increased pressure may enhance adsorption of trace analytes in the sample stream.

2. Increasing pressure prior to entering the waveguide cell may remove condensable vapors within the sample (for instance, water) which could interfere with the absorption measurement.

3. Increasing and decreasing pressure within the cell may accelerate adsorption and desorption of the target analytes, resulting in faster time response.

4. In addition to 1–3 and in contrast to U.S. Pat. No. 5,892,861, the absorption may alternately be carried out homogeneously (without adsorption to a coating material) under the following conditions.

a. the gas to be analyzed is pressurized such that its refractive index reaches a much higher value. Such refractive index is generally proportional to pressure.

b. The waveguide itself, or any appropriate coating thereon has a refractive index greater than the compressed gas. Although such waveguide material may not now exist it should be developed.

Under these conditions the sample/waveguide will serve to transmit the analytical probe beam over long distances due to total internal reflection, resulting in high sensitivity. Furthermore, said waveguide can be coiled (with some loss in transmission), thereby producing an absorption cell which is more compact.

Thus Pneumatic Focusing technology will complement and extend the usefulness and sensitivity of waveguide absorption measurements such as disclosed by U.S. Pat. No. 5,892,861 and other such waveguide patents.

When air or other sample gases are compressed to higher pressures, any reactions which may be occurring within the gas sample likely are accelerated, since reaction rates are proportional to the product of the reactants' concentrations. As an example, ozone reacts with alkenes in ambient air. If such air is pressurized, for instance by a factor of 10, these reactions will occur faster, in this case by a factor of 100. However, the rate of fractional alkene removal per unit time by the reactive ozone will be increased only by a factor of 10. Thus is it known within the field of atmospheric measurements to remove ozone from a gas sample before either storing it for later analysis, or passing in into any sort of collection of focusing device. This standard technology may be applied to Pneumatic Focusing as well. Standard methods of ozone removal include reaction with added nitric oxide (NO) or removal on some surface, such as a copper surface, or a glass fiber surface which has been coated with reactive potassium iodide (KI). In a current disclosed embodiment a copper sample loop was employed.

Chemical reactions which remove analytes may present problems which must be addressed (for instance as described in the last paragraph). Such reactions may also be used to advantage in Pneumatic Focusing. One such example is the measurement of atmospheric nitric oxide (NO). A current popular method for measuring NO is $O_3$ to draw a air stream sample into an instrument while adding ozone $O_3$ from an ozone generator. This produces a chemiluminescent reaction $NO+O_3 \rightarrow NO_2^*$(in an excited electronic state)$\rightarrow NO_2$+light. The chemiluminescence emission, which may be detected by a phototube, is proportional in intensity to the product of the NO and $O_3$ concentrations. Since in many atmospheres both NO and $O_3$ are present together, Pneumatic Focusing (which accelerates the rate of this reaction proportional to the square of the pressurization ratio) will generate an emission whose time-varying intensity is proportional to the product $[O_3][NO]/[P]$. The term [P] in the denominator of this expression refers to quenching of the emitting state $NO_2^*$. Thus the fluorescence signal should increase proportional to pressure. Further, the integrated intensity is proportional to the concentration of whichever of these two molecular species is in lesser concentration (the limiting reagent). These two pieces of information will allow the individual concentrations of each to be inferred. This method is superior to existing chemiluminescence because it is simpler and provides information about both species' concentrations. Of course, its effectiveness depends upon both species being present. If only one is present (such as at night when the species present in excess may titrate away the other), then the absent species may be added. Unlike traditional chemiluminescence however, it need not be added in precisely regulated concentration.

For FID measurements, a fuel gas must be provided. Working systems used hydrogen ($H_2$) gas from compressed gas cylinders as fuel for the FID. There are other methods for providing the fuel gas for FIDs. For example, other embodiments could use any of several, commercially available electrolytic hydrogen generators. One example of such a commercially available generator is Restek Model No. 75-32, which is sold commercially by Restek, of Bellefonte, Pa. These electrolytic hydrogen generators are especially suitable for conditions where explosive hazard is a concern.

For FID detectors, air or oxygen may serve as a source of an oxidizer for the FID flame. Moreover, air or oxygen powers the pneumatically driven sampling valve 16 in FIG. 1. A working system used compressed cylinder air or oxygen. Other applications might use ambient air as a source of an oxidizer, which ambient air would be delivered to the FID by a compressor. Suitable compressors are commercially available, such as Model No. Jun-Air 200-1.5 BD2, from Restak, of Bellefonte, Pa. Such compressors also could produce compressed air as the carrier gas.

6. Pressure Regulators

Pressure regulators are used to deliver controlled flows of compressed gases, some of which are discussed above, at a substantially constant output pressure from the cylinders or compressors to the chromatographic instrument. Typically regulators are capable of delivering pressures above ambient from about 1 psi to about 4,000 psi above ambient pressure. Pressure regulators set to a predetermined, but substantially constant pressure, have been used in working embodiments. These pressure regulators also might be controlled by a computer. Computer-controlled pressure regulators would allow for pressure programming of either Pneumatic Focusing, chromatographic separation, or both. Special high pressure regulators can be used for the carrier gas or PF gas in Pneumatic Focusing.

7. Reagent Gas Clean-up Traps

Contaminant traps, particularly carrier gas traps, have been used in combination with working embodiments of the present apparatus. Such sample traps typically consisted of galvanized pipe and appropriate fittings for coupling to the carrier conduits used with the apparatus. The sample traps used with working embodiments typically are filled with materials, either alone or in combination, to remove impurities from the carrier gas (often helium), $O_2$ or $H_2$ for the FID. Examples of materials to be used include mixtures of molecular sieves, activated charcoal, and mixtures thereof. Other materials that remove impurities from the compressed gases sufficiently to allow the use of low-purity gases and thereby lower the operational costs of the instrument, also can be used.

Contaminant traps used with working embodiments were prepared by filling the trap with appropriate packing material, glass wool caps and frits, which prevent the packing material from being transported into the sample loop or chromatographic column. In one working embodiment cast iron pipe fittings were used to form a contaminant trap which was filled with activated charcoal for carrier gas cleanup. Working traps were baked in an oven with low helium, or other purge gas flow, at a temperature of, for example, about 100° C. Other temperatures can be used, if desired, to remove any adsorbed impurities before the first use, or after excessive amounts of impurities have built up by using the sample traps. Suitable traps can be made. Suitable sample traps also are commercially available, such as Restek Gas Management System or purifier tube, catalog No. 21660, available from Restek, of Bellefonte, Pa. Alternatively, high-purity compressed gas cylinders could be used.

8. Tubing for Transporting Compressed Gases

Tubing is needed to transport compressed gases from the compressed gas source to the chromatographic instrument.

Working embodiments of the present apparatus used ⅛ inch outer diameter metal tubing such as copper tubing, to transport compressed gases to the chromatographic instrument. Small diameter tubing is less expensive and is better able to withstand the high-pressure focusing gas associated with pneumatically focusing analytes in a sample. Tubing made from materials other than copper could be used as well. For example, tubing made from other metals, plastics, or combinations thereof, also can be used. The selection of an appropriate material for making such tubing will depend, in large part, on the particular application. Using high pressure in enclosed volumes carries a significant explosion safety issue. In any PFGC applications appropriate safety precautions must be employed.

9. Fittings for Connecting Components of the Apparatus

Standard taper pipe fittings and Swagelok brand fittings have been used with working embodiments of the present apparatus to connect various components of the regulators, traps, and tubing to the chromatographic apparatus. Persons of ordinary skill in the art will realize that other types or brands of fittings may work equally well and also may be cheaper or more suitable for a particular application.

10. Chromatograph

Figure 7:
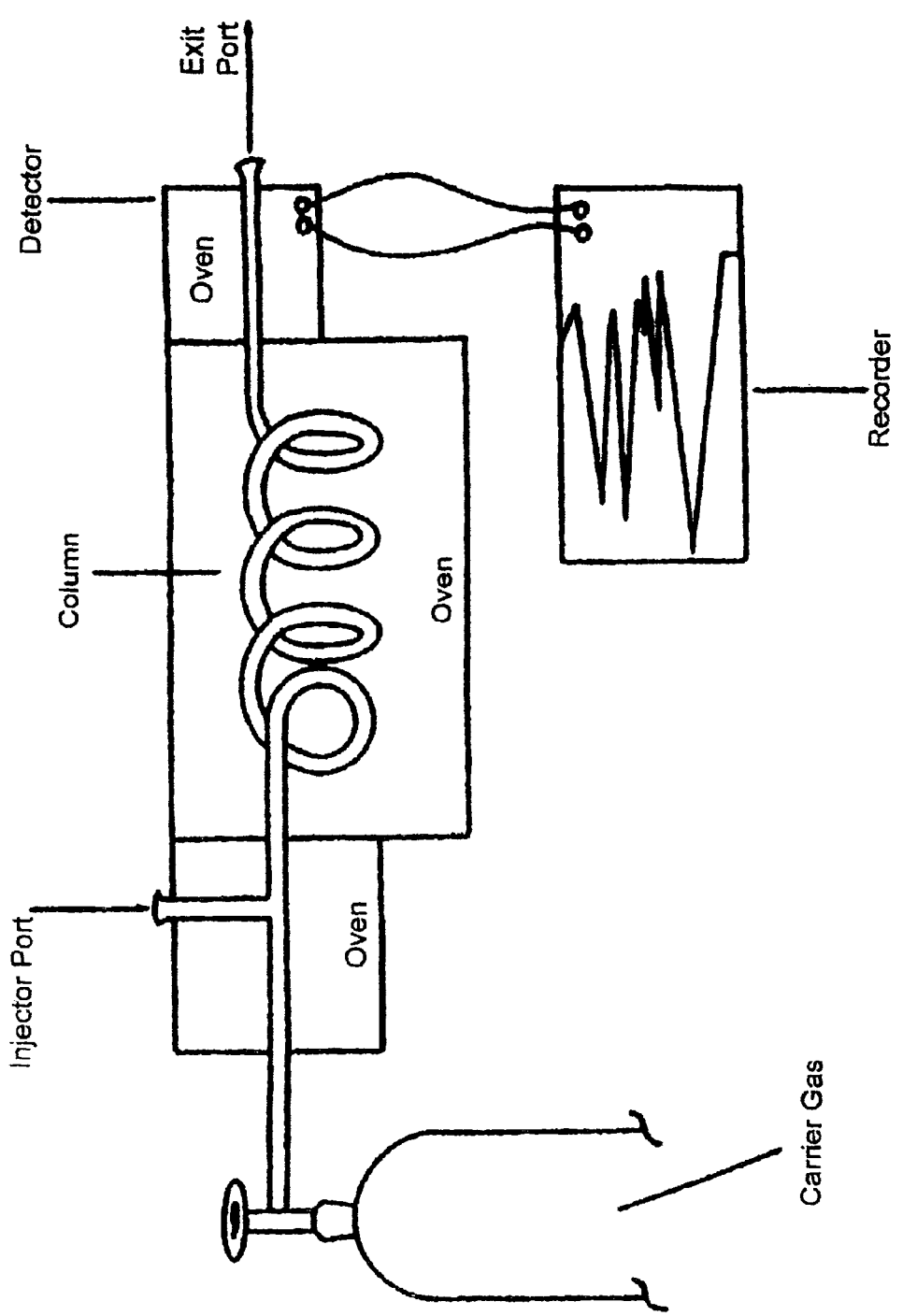

A schematic of a typical chromatograph is provided by FIG. 7, from Boyer's "Modern Experimental Biochemistry," Benjamin/Cummings Publishing Co. (1993). Two working embodiments of the present apparatus used in-house-modified Varian model 3400 and 3700 gas chromatographs with a factory-equipped flame ionization detectors. The Varian 3700 instrument was modified as follows for either gaseous or liquid samples.

Figure 8:
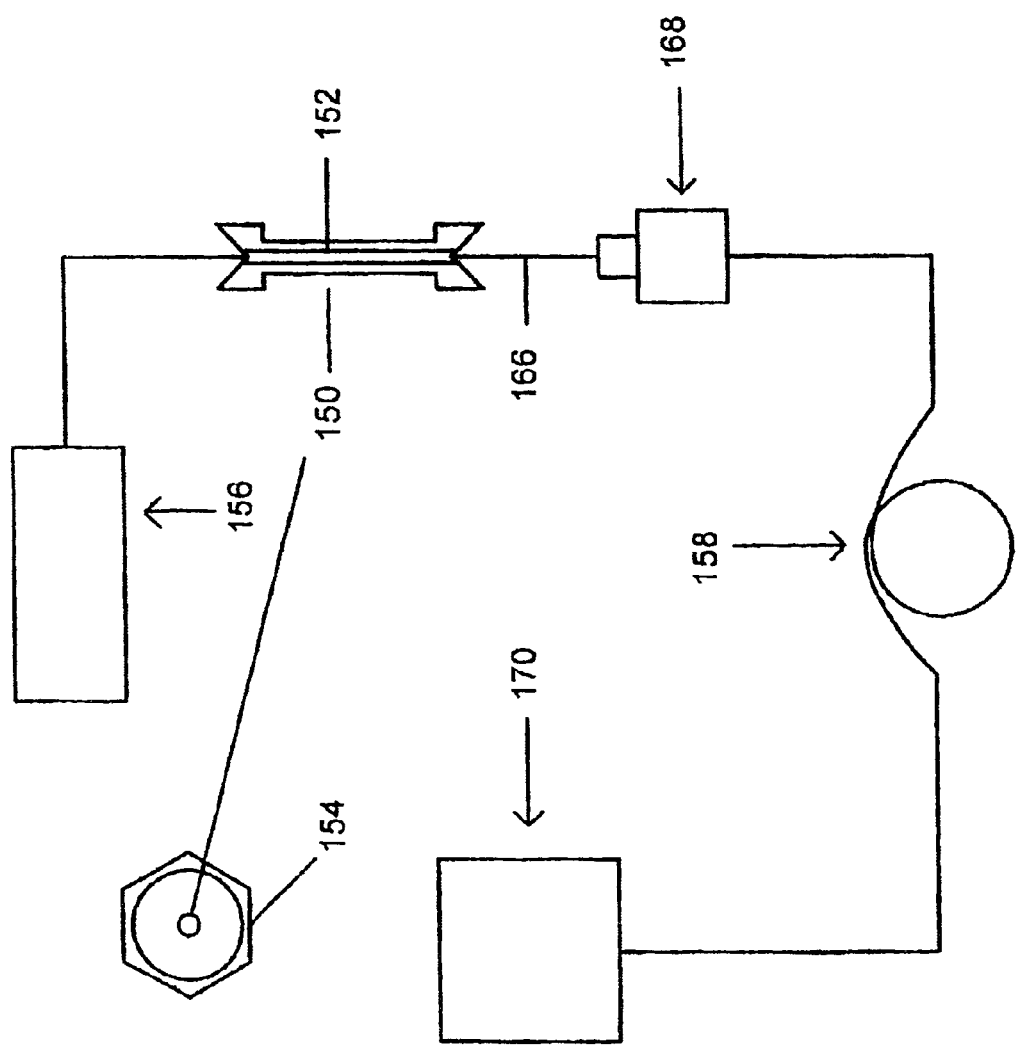

1. Liquid phase injection PFGC. Refer to FIG. 8. The standard syringe injection port 150 was modified for automated liquid injection as follows. The syringe injection/septum containing cap (not illustrated) was unscrewed and not used. The injection assembly was removed and the septum purge tubing was cut off. A brass tube 152 was machined to 0.259" od and ¹⁄₁₆" id and placed into this injector body 154, which transferred heat from the heated injection manifold to the ¹⁄₁₆" tubing leading from the sample injection valve 156 (Valco 8-port valve). Upon sample injection from the sample loop (not shown) to the chromatographic column 158 the liquid sample passed through the heated injection block and associated fittings and vaporized. A standard Swagelok ⅛" to ¹⁄₁₆" reducing union (#B-400-6-2) 160 was modified to additionally perform a check valve function by boring out the interior to accept a ⅛" stainless steel beebee 162. A plug was inserted from the large end to contain the beebee and the fitting was cross-drilled to accept an epoxied in pin 164 to contain the beebee. This check valve prevented backflow of column carrier gas into the downstream end of the sample loop upon sample injection. Sample from injection port 150 was coupled to column 158 by a Swagelok reducing union 168. FID 170 was operably coupled to the column 158. The vaporized liquid sample, i.e. a gas, was pneumatically focused by the high column pressure so that column flooding did not occur. Heat transfer/vaporization could be controlled by a combination of injection block 150 temperature, injector insert 152, tubing 166 id, and carrier flow rate. If desired, additional bypass plumbing could send only a portion of the carrier gas through injector 150.

2. Gas phase injection PFGC. The integral carrier gas flow control valves and syringe injection ports were disconnected from the carrier flow and need not be used to provide the gas-injection Pneumatic Focusing apparatus. These components would not be required if the gas sampling instrument were built initially, instead of being made by modifying existing chromatographs. Avoiding using carrier gas flow control valves and syringe injector ports would make the present instrument more compact and less expensive than currently available chromatographs that can be modified as described herein. Instead, the carrier gas is brought directly to one port of a multiple-port sampling valve. One working embodiment of the present apparatus used an 8-port sample valve, namely Valco Model A28UWP 8 port, ⅛", 2-position valve. Other commercially available multiport valves could be used, depending upon the application. For instance, in another working embodiment of this device, a similar 10 port valve was used, which allowed two samples in two sample loops to be simultaneously injected into two columns running into two separate detectors in a single gas chromatograph. This would allow compounds of varying chemical nature to be subjected to different levels of separation.

In some instances it would be more suitable, and perhaps less expensive, to use individual valves to perform these functions rather than a single multiport valve. For example, using plural individual valves instead of a single, multiport valve could allow greater and more precise control of the pneumatic sample focusing. An embodiment of this 3 three-way valve setup has been constructed using B41XS2 Swagelok valves capable of regulating pressure up to 2,500 psi. Electronic motor actuators constructed for that purpose controlled these valves. The carrier gas cylinder regulator controls carrier gas flow pressure. Working embodiments used a cylinder regulator. Cylinder regulators typically provided a gas pressure of from about 300 psi to about 500 psi. Although regulators that provide gas pressures of from about 300 psi to about 500 psi are described herein, other regulators that provide equal, and especially higher pressures, would be as desirable, or likely even more desirable. This would include pressures high enough to convert some carrier gases to supercritical fluids. Regulators providing gas pressures greater than about 400 psi would allow using either larger sample sizes, or greater Pneumatic Focusing (higher pressure) or both. This would provide better chromatographic resolution, higher sensitivity, or both. Of course, as pressure within the column is increased, a consequential decrease in resolution may occur due to slower diffusion rates, thereby producing an optimum pressure that may be found by a combination of theory and/or experiment.

At such head pressures, the carrier gas flows through the sampling valve directly to the column with the valve in the sample position. Flow rate through the column in a working embodiment of the apparatus was controlled by a PNEUMADYNE (nickel plated brass) valve CS70303. The PNEUMADYNE valve was placed on the downstream end of the chromatographic column but before the FID detector. The PNEUMADYNE valve includes silicone o-rings to withstand the high chromatographic oven temperatures (e.g. 200C). Another approach for regulation of high pressure flows would be as described by E J Guthrie and H E Schwartz in "Integral pressure restrictor for capillary SFC" Journal of Chromatographic Science 24 (1986) pp. 236–241.

In a working embodiment of the present apparatus the sample loop and column pressure were maintained substantially constant at about 300–500 psi through the chromatographic analysis. A more suitable and efficacious approach in some applications would be to drop the carrier gas pressure to a pressure more typical of conventional gas chromatography used for standard VOC analysis, such as to pressures of about 30 psi to about 60 psi, and open the flow-regulating valve to allow constant or reduced mass flow of eluting carrier gas and analytes into the detector, while maintaining the chromatographic column at lower pressure during the analysis. There are several reasons for this pressure reduction, including (1) to limit the carrier gas flow rate exiting the separatory column for subsequent analysis by, for example, a mass spectrometer, and (2) better resolution may be obtained at lower pressures, or (3) lower carrier flow rates would use less carrier gas and be more economical. Maintaining the chromatographic column at a lower pressure could provide greater separatory efficiency due to higher diffusion rates of the analyte/carrier gas mixture during elution. Also, with some types of detectors, especially mass spectrometers (MS), effluent should be limited to 1–2 standard cubic centimeters/minute. In the current technology, after expansion past the flow/pressure regulating valve at the end of the column, carrier flow increases to an adjusted value of 20–40 cubic centimeters/minute. In other practice different flow rates might be as suitable or more suitable. 40–60 cc/min was suitable for the FID employed in one working system, but likely would be unsuitable for an MS instrument. Splitting the flow out of the high-pressure capillary column might be disadvantageous for sensitivity, as less sample would enter the MS. Thus, dropping the carrier pressure and opening the valve under computer control after column injection is an important variation which would use the adsorptive property of the column to enhance sensitivity by increasing the relative partial pressure or mole fraction of the analytes in the carrier gas. Another application would allow pressure programming of the carrier gas, which would be especially suitable if the carrier were a supercritical fluid. Still another would be to carry out gradient elution with two or more carrier gases. Furthermore, after exiting the column, the flow could equally as well be split between a number of detectors arranged in a combination of parallel and series, depending upon their method of detection, thereby giving multiple responses for individual or varying analytes.

a. Pneumadyne Valve

Figure 9:
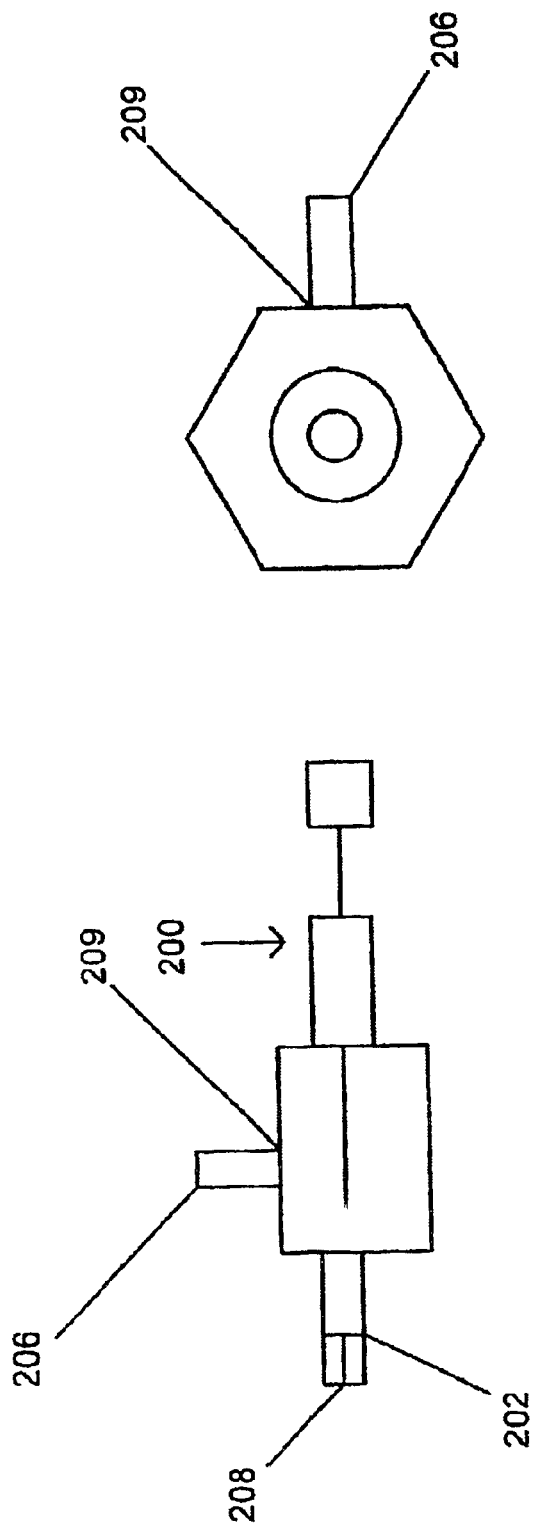
Figure 10:
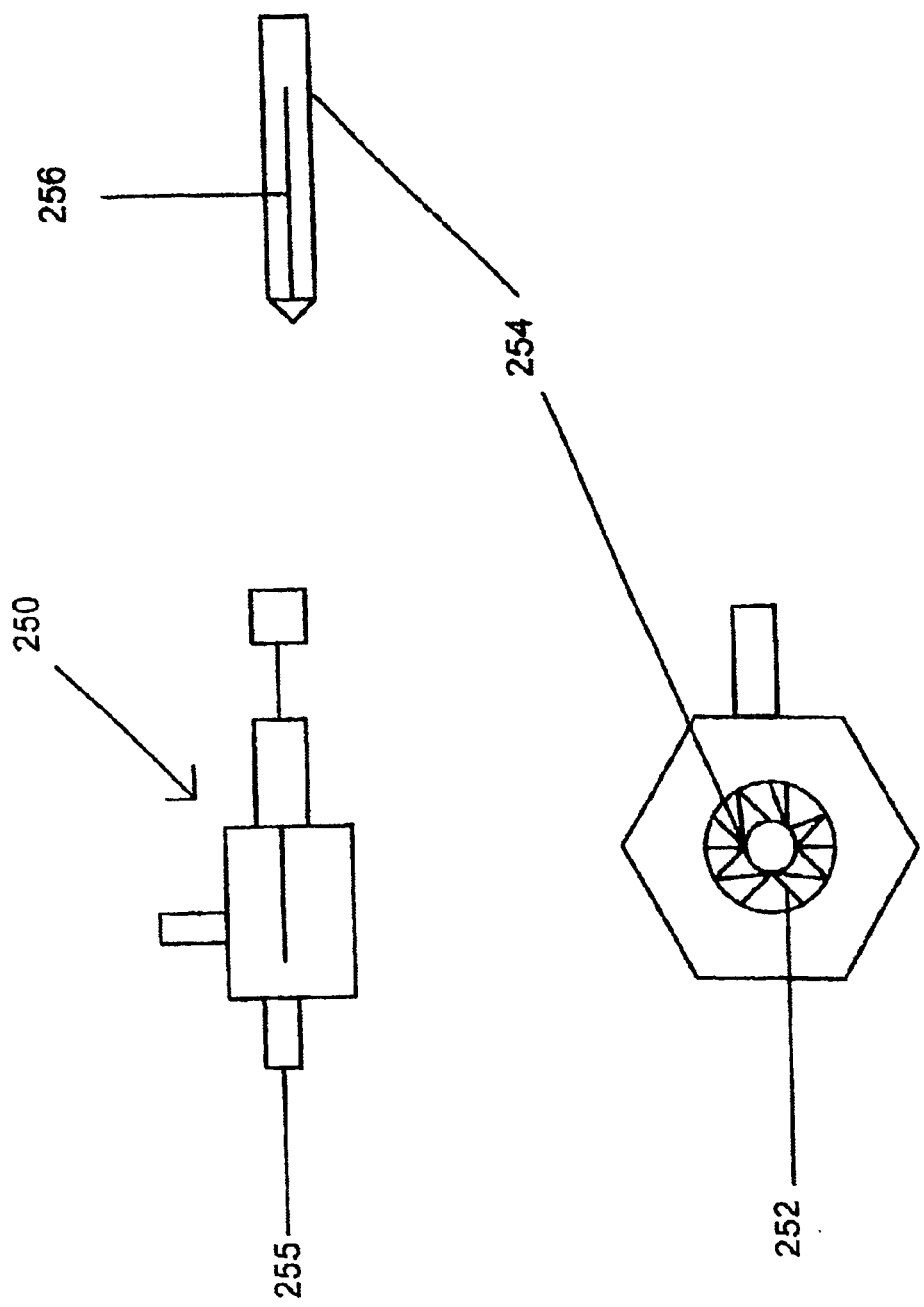

The PNEUMADYNE valve described above as received from the factory was modified (FIGS. 9 and 10) for use with the present system. More specifically, FIG. 9 shows a valve 200.

i. The inlet fitting 202, a $^{10}\!/_{32}$ tapered pipe fitting, was rethreaded with a $^{10}\!/_{32}$ dye for a straight $^{10}\!/_{32}$ thread, and machined to produce a tapered inlet. These modifications were made to allow its connection to the capillary column.

ii. The outlet fitting 206, a $^{10}\!/_{32}$ straight-threaded cavity was fitted with a hollow, $^{10}\!/_{32}$ stainless steel screw 208, permanently glued into the valve body. This modification was made to allow its connection to the short section of capillary column leading to the FID. High T glue withstood 280° C.

b. The PNEUMADYNE valve was connected to the outlet of the chromatographic column. This connection can be made in any suitable manner. In a working embodiment, the PNEUMADYNE valve 200 was connected to the outlet of the chromatographic column by inserting it through a SWAGELOK $^{1}\!/_{16}$" cap nut, then through a suitable graphite ferrule 208 and then inserting it into the rethreaded aperture to a point just above the tapered valve needle. The SWAGELOK nut was tightened onto the rethreaded valve inlet pipe, compressing the graphite ferrule into the tapered inlet prepared for that purpose and around the capillary column. This formed a hermetic seal, which was capable of withstanding the high pressures, i.e., in a working embodiment of from about 300 psi to about 1,500 psi, as required for Pneumatic Focusing and delivery of the sample, particularly air samples. In making this connection it is important not to project the capillary column so far into the valve that it will be contacted and crushed by the valve needle as the valve is sealed off. Commercially available PNEUMADYNE valves generally are not rated for the high pressures of the carrier gas system. But such pressures occur within the valve only upstream of the flow-controlling needle. The pressure of the carrier gas drops past the needle to much lower values as such gas, or gasses, pass through the valve body and enter the outlet capillary tube, which carries any gas or gasses to the FID with little back pressure.

c. This commercial Pneumadyne valve performed satisfactorily in the working embodiment described herein but was difficult to adjust to the correct pressure and should eventually be replaced with a suitable high-pressure valve either purchased or designed a priori. Another commercial valve, or valves designed for this specific purpose, may work equally as well or better and be more suitable. One such valve 250 has been designed based upon the Pneumadyne valve described above. With reference to FIG. 10 in this modification, the high temperature portion 252 of the valve 250 where the needle 254 regulates flow would be filled with epoxy; the needle 254 would be coated lightly with grease to prevent adhesion to the epoxy, and would be inserted into the soft epoxy to form a channel. After the epoxy hardens, the valve 250 would be withdrawn and then scratched one or more times longitudinally with a diamond pencil or other suitable device. If epoxy filled the outlet channel during manufacture it could be drilled out with a very small drill though port 255. These scratches 256 would then form the flow regulating channels when the needle was reinserted into its epoxy seat. Since the epoxy will be somewhat softer than the needle material, exertion of pressure on the needle 254 by firmly threading it into the seat will result (if necessary for further regulation) of an extrusion of the hardened epoxy slightly into the scratched channels, further reducing flow rates to the low values required in this high pressure application. The redesigned flow regulating valves should work effectively, perhaps better than those valves used in working embodiments described herein. It should be understood that the above design is to modify an existing gas valve as a cost savings measure during development. In actual implementation it might be and probably would be more efficacious to design and have machined a similar filled-body, scratched-needle valve from scratch, following the design of FIG. 11. In such a valve header or otherwise move suitable materials (e.g., stainless steel) would be used rather than nickle plated brass.

d. Commercially available PNEUMADYNE valves also have dead volumes. Dead-volumes associated with chromatographic systems generally are undesirable because they reduce resolution by mixing or remixing separated sample components. Although the PNEUMADYNE valve was not designed as a chromatographic valve and does contain significant dead volume, this dead volume is of minimal consequence with respect to the present apparatus, and method for its use, for the following reasons. Pneumatic Focusing is currently achieved in the sample loop and chromatographic column by the helium carrier gas. Pneumatic Focusing in one working embodiment of the apparatus has been achieved at a pressure of from about 300 psi to about 500 psi. Upon flowing past the needle, the carrier gas drops to a pressure near atmospheric (ca. 15 psi). Thus the gas expands by an approximate factor of 20–30, thereby sweeping out the valve dead volume in a minimal amount of time without remixing separated peaks.

The Pneumadyne valve incorporated in working embodiments of PFGC described herein was barely adequate for desired performance. A more suitable valve would allow greater flexibility of adjustment, including computer-controlled adjustments. Shortcomings of the pneumadyne valve included (1) difficulty and irreproducibility of adjustment—the valve had to be adjusted 'off' to obtain low enough flows and (2) temperature stability. Although one valve successfully injected more than 10,000 samples, other valves had a tendency to respond to oven temperature programming by adjusting internal needle position so that flows jumped from set values. Usually this stopped after a break-in period. If not, the valve was removed and reconnected or discarded for another valve. More suitable valves may be commercial available and have likewise been herein designed and described.

It is possible that, in some applications, such as when the column pressure is dropped to lower values and the valve opened after injection of the sample on the column, the dead volume in the current PNEUMADYNE valve may not work as effectively due to lower volume flows. In such cases, more suitable commercial valves could be employed, for instance liquid or SCF chromatograph valves. One such design has been described above, wherein the filled valve interior will significantly reduce dead volume while enabling more precise and reproducible flow regulation. Such a valve could more profitably be designed and built from scratch using more suitable materials without epoxy.

For instance the Pneumadyne valve could be replaced with a low dead volume shut off valve. The valve would be closed during Pneumatic Focusing/injection. Subsequent to focusing/injection the valve would slowly open, as the column head pressure is automatically dropped to 30–60 psi. This would allow bleeding of the high column pressure slowly through the column and into the FID. Subsequent elution would occur under "normal" chromatographic conditions. This application would be suitable for Mass Spectrometric detection.

A pressure gauge (not shown) can be coupled to the valve 30 in FIG. 1. This pressure gauge can be used to adjust the pressure of and/or linear flow rate through the system. The pressure gauge can be placed under computer control to continuously and automatically adjust the pressure and/or linear flow rate through the system. Computer controlled flow regulation is advantageous in pneumatically focused gas chromatography to be able to independently vary flow rate and pressure under computer control. Pressure may be regulated with a computer controlled pressure regulator. In this application, flow would be regulated by computer control of the downstream valve. A Pneumadyne Valve CS70303 was modified as described herein.

This valve also has been modified to include an aperture in the sidewall. With reference to FIG. 11, a valve 220 was tapped for 10–32 threads and fitted to a second hollow 10–32 screw 221 by gluing with high temperature epoxy. See FIG. 11. The outer end 222 of this screw was machined with an internal taper top to accept a graphite ferrule 223. The cap nut was a ¹⁄₁₆" Swagelok cap nut as described previously. This extra port could be connected by a length of shout, open capillary column to a small volume pressure gauge from which the computer could read the pressure. This pressure-to-flow transducer should be calibrated by disconnecting the capillary column from the detector and extending it slightly outside the gas chromatograph and to a flow meter. Flow rate then should be varied with computer control of the modified valve and measured with the flow meter. Concurrently, the computer records the resultant pressure value for each measured flow rate as controlled by the valve setting. This procedure establishes a calibration curve which may be repeated for different oven temperatures and column head pressures. In this fashion, the computer can establish the desired flow rate for any head pressure or column temperature by empirically varying the valve position until the desired pressure reading according to the calibration table is obtained. This valve control may be carried out as desired before or during a chromatogram.

Conventional systems which do not use Pneumatic Focusing commonly use "makeup gas" when operating at more usual pressures of from about 30 psi to about 60 psi. "Make up" gas is used in conventional systems to sweep the column outflow more rapidly into the FID detector. No makeup gas is required with the apparatus and method presently described, a further design simplification.

e. The PNEUMADYNE valve was connected to the FID. In a working embodiment, the PNEUMADYNE valve was connected to the FID by 20 centimeters of capillary tubing. A person of ordinary skill in the art will appreciate that this connection can be made using any suitable method and material. In a working embodiment, a short (ca 20 cm) section of the same column material that was used in the separatory portion was used to connect the PNEUMADYNE valve to the FID. The valve outlet connection was made in the same manner as the valve inlet connection. This column material used to connect the PNEUMADYNE valve to the FID was placed just below the actual flame of the FID. The position of this column material was established empirically to:

i. not burn the column end in the flame;
ii. not extinguish the flame; and
iii. give maximum signal subject to i and ii.

It will be appreciated that other types of tubing could be used to convey the column effluents to the FID or to a manifold, which would direct some fraction of the effluent to any of a number of parallel or serial detectors. Or, the valve could be connected directly to the bottom of the FID housing by suitable connectors thus eliminating the capillary conduit.

Moreover, persons of ordinary skill in the art will appreciate that any of numerous other commercial gas chromatographs [or high pressure or SFC or liquid chromatographs] with a variety of different detectors could be modified as described herein. It also would be possible to construct a more compact, more portable, safer, cheaper, or otherwise more favorably device than the working embodiments of the present apparatus described herein and made by modification of commercial instruments.

11. FIDs Having Fuel and Oxidizer Flow

A FID is operated with fuel flows, such as flows of hydrogen, and an oxidizer, such as air or oxygen. The flow of fuel and oxidizer are empirically optimized to provide maximum response while allowing continuous flame operation. Oxygen is a more expensive oxidizer than compressed air. However, oxygen provides several advantages. For example, oxygen requires lower volume flows and thus less frequent cylinder changes. Oxygen also provides an apparent higher response to the eluting VOC compounds. It has been confirmed that oxygen supplied to the FID in place of the more commonly employed air produces a higher response to at least some hydrocarbons. Substitution of oxygen for air in the FID produces a significantly higher response for some atmospheric VOC hydrocarbons. Since Pneumatic Focusing often will be employed in the measurement of trace gases at very low concentrations, using oxygen would be very advantageous. An additional advantage is that oxygen cylinders will last significantly longer than compressed air cylinders because nitrogen is not required for combustion, but is rather a diluent.

Alternatively, compressed ambient air delivered to the FID may obviate the need to use an air cylinder and regulator. This further simplifies the instrument and may make it less expensive to operate remotely. This compressor could also supply compressed ambient air as the carrier gas. Flows of fuel and oxidizer are passed through the chromatograph's standard inlet valves and conduits. The flow rates of the fuel and oxidizer are regulated by a combination of empirically determined cylinder regulator pressure and chromatographic settings. Currently, suitable operating pressures for fuels and oxidizers are as follows: (a) if hydrogen is used as a fuel, then the operating hydrogen pressure is from about 30 psi to about 60 psi, with about 50 psi being a currently preferred pressure; (b) if air is used as an oxidizer, then the operating air pressure is from about 60 psi to about 100 psi, with about 80 psi currently being preferred; and (c) if oxygen is used as the oxidizer, then the operating oxygen pressure preferably is from about 15 psi to about 30 psi, with about 20 psi being a currently preferred operating pressure for an oxygen oxidizer flow. Such pressures are a function of the original instrument flow control valve settings.

12. Signal Processing, Amplification and A/D Conversion

Working embodiments of the present apparatus used a FID, although other detectors also could be used. For instruments using FIDs, current passing though the FID electrodes is received by a factory-installed coulometer and then passed as a voltage to ports on the side of the instrument. The signal is conducted by coaxial cable into an amplifier, such as a 1000× amplifier. The amplified signal may be filtered, if desired, by an onboard filter.

Figure 12:
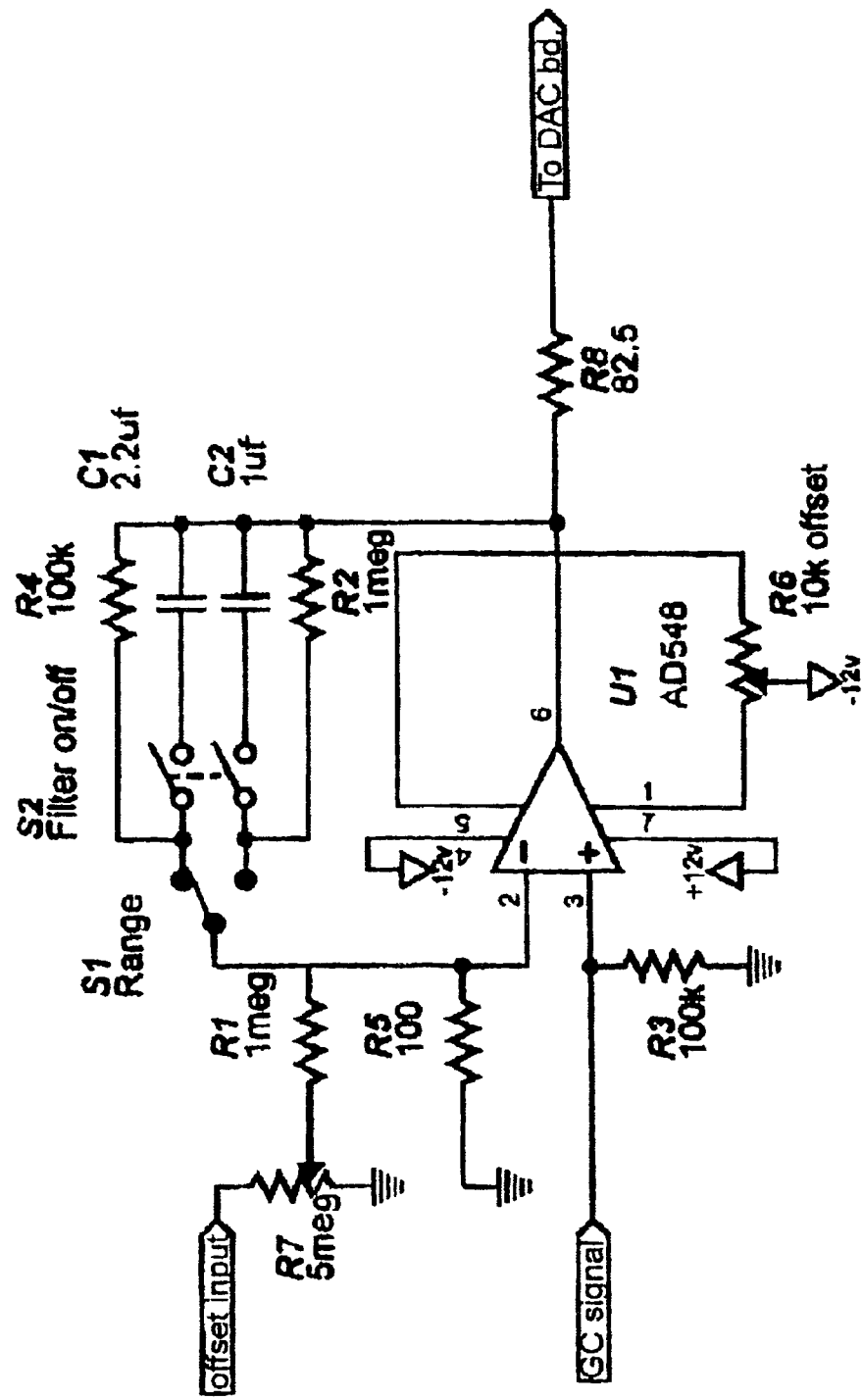
Figure 13:
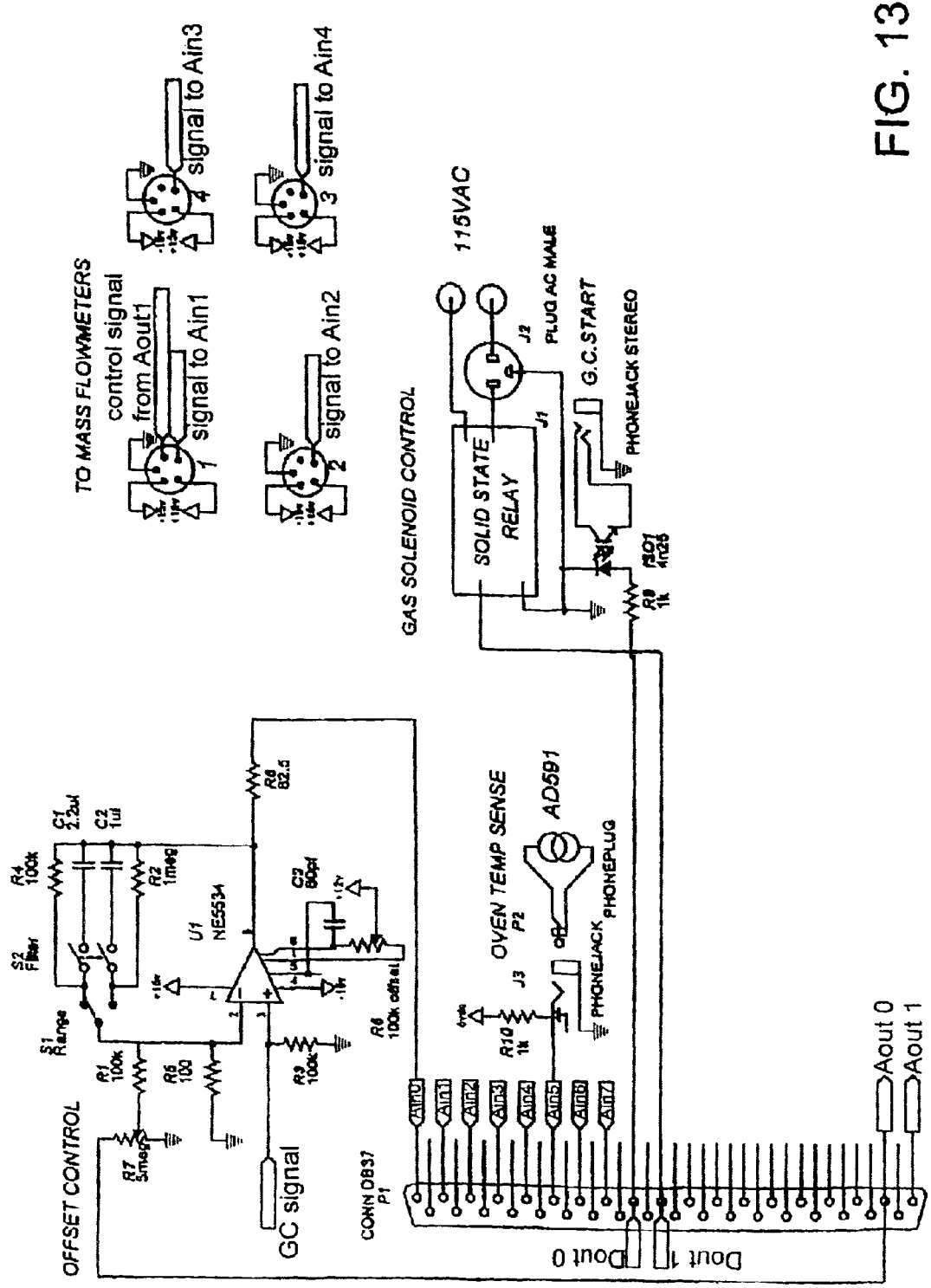

The amplified signal is then passed to an analog-to-digital converter. Any suitable A/D converter can be used. A working embodiment of the present apparatus used a COMPUTER BOARDS analog-to-digital converter, Model No. CIO-DAS08Jr/16-AO. A working embodiment of the current apparatus used a modified 16 bit CIO-DAS08Jr/16-AO A/D converter. The modified 16 bit CIO-DAS08Jr/16-AO A/D converter was modified for an extended range to accommodate either very large peaks or upward drift of the chromatographic baseline associated with temperature programming. This modification consisted of a computer-controlled analog offset to the to the A/D board, which allowed successive voltages greater than the normal range for the A/D board to be accepted. This automatic offset was done by computer control. Using this novel offset procedure, the range of the 16 bit A/D board has been significantly extended beyond the usual 65,000 range, such as to 700,000, i.e., an effective 19 bit board. FIG. 12 is a control circuit for the A/D board, and FIG. 13 is an amplifier circuit to increase voltage of signals for the A/D board.

Another application of this analog offset to a gas chromatograph was carried out by a novel subroutine in the signal acquisition program gc.bas which is described next. This program determines the baseline in a given computer-acquired chromatogram by selecting signal points where no peaks are eluting. A group of these data points are then fitted with a polynomial of desired order, for instance 5th to 15th. This curve fit then becomes the baseline for the next computer acquired chromatogram. Before each point is acquired from the AID board, it is offset by the computer fit baseline value of the previous point. In this way a completely baseline-corrected chromatogram appears on the screen and is stored for later viewing and analysis. The program gc.bas also stores the polynomial coefficients so that the original data may easily be regenerated if desired.

Gradual drift of the baseline is handled in the program by subtracting the polynomial-fitted baseline of the 2nd to last chromatogram from the polynomial-fitted baseline of the last chromatogram so that an absolute reference baseline is maintained.

13. Computer Sampling Control for Baseline Determination and Internal Standard Addition A C Lewis N Carslaw et al. In "A larger pool of ozone-forming carbon compounds in urban atmospheres, Nature 405 (2000) pp. 778–781 have pointed out that the current state of the art in measuring atmospheric VOCs misses a significant fraction of VOCs which are unresolved and form an increased baseline under the resolved peaks. These authors determined the 'missed' unresolved compounds by subjecting an ambient air sample to the powerful new technique of 2-dimensional chromatography. If true, this paper has discovered a significant source of error in VOC measurements and potentially pollution and emission control. This situation has been subsequently discussed by AC Lewis in "New Directions: Novel separation techniques in VOC analysis pose new challenges to atmospheric chemistry" in Atmospheric Environment 34 (2000) pp. 1155–56.

Two types of error should be distinguished.

1. Some compounds because of high molecular weight or high polarity or for other reasons may not elute on a given chromatogram. These compounds remain on the column for extended periods of time, eventually in continuous operation forming a temperature dependent 'baseline' increase (bleed) during temperature programming. These may be termed residual compounds.

2. Other compounds are eluted in the chromatogram in which they were injected, but because of individual low concentration and large numbers are not individually resolved and hence show themselves as an increased baseline (bleed) which is not immediately distinguishable for other causes of baseline shift with temperature programming.

Fully automated Pneumatic Focusing gas chromatography is completely compatible with 2-dimensional analysis of focused ambient air or other gaseous samples. However, another, simpler approach is also possible. In automated Pneumatic Focusing gas chromatography, since the gas chromatograph is under complete computer control it is possible to inject standards or determine the baseline whenever desired. Thus the computer can perform a true baseline measurement by any of several methods. This baseline measurement also serves to detect the presence of any spurious or artifact peaks, such as might be present in the carrier gas. In this approach the 'true' baseline to a chromatogram is determined by injection (under computer control) of a sample which has no significant VOC concentration.

Another application is the injection of calibration standards alternately with actual sample analysis. Such injections can be carried out automatically under computer control, for instance one a day, once a week, or every other sample as the situation warrants. Both baseline determination and standard addition involve similar concepts and procedures. Some of these baseline determinations involve admission of gases from reference cylinders to the Pneumatic Focusing system. This is carried out by the control computer through the parallel port using circuitry shown in FIG. 14.

Figure 14:
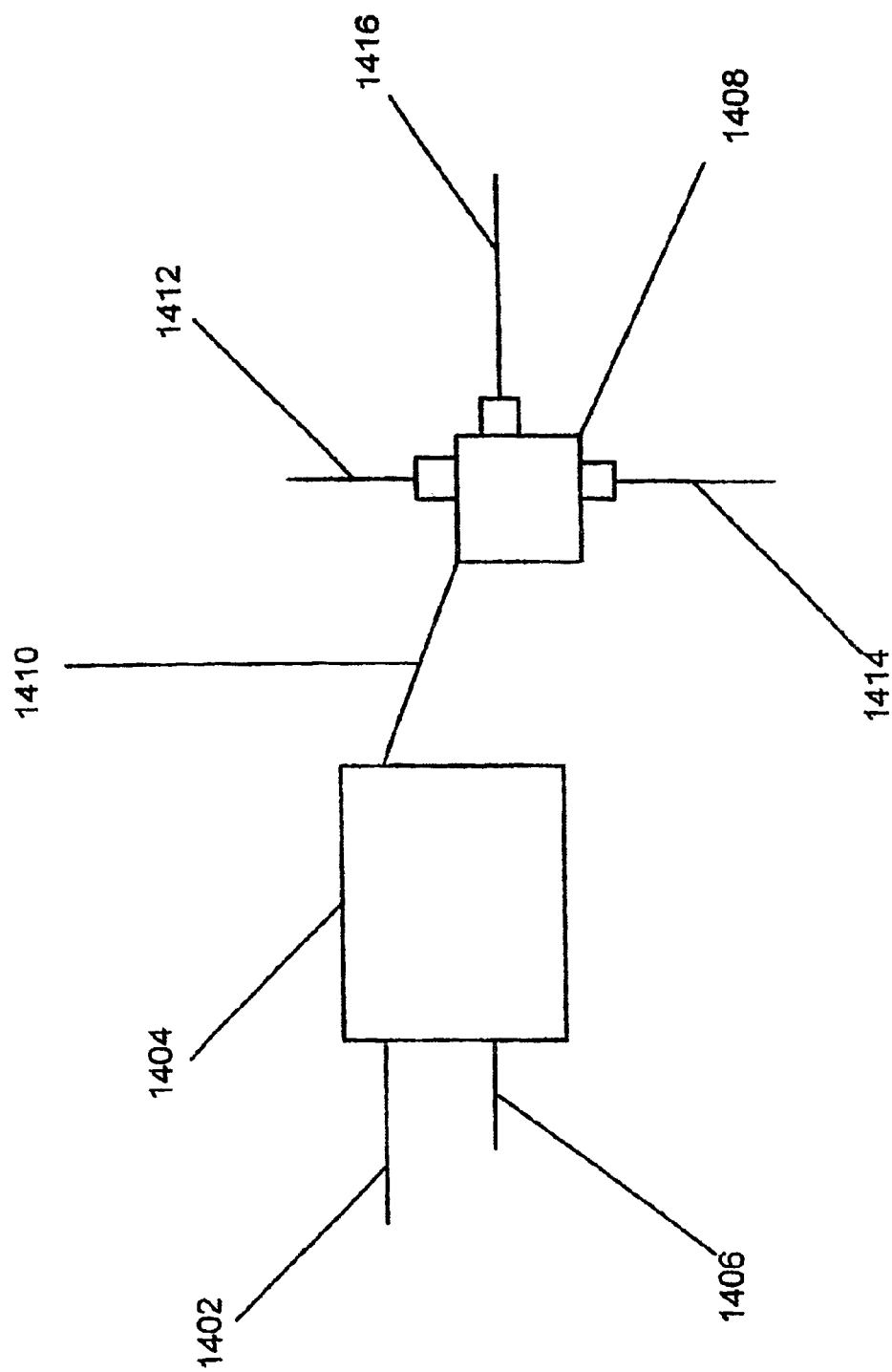

FIG. 14 shows a calibration injection device 1400. Device 1400 includes 25 pin cable 1402, coupled to solenoid control unit 1404, which is powered by a power cable 1406. This device 1404 controls three-way valve 1408 through control cable 1410. Three-way valve 1408 diverts calibration gas inlet 1412 or sample gas inlet 1414 to gas chromatograph 1416.

For either case, any of the following methods may be used.

1. A zero air sample (commercially available) is contained in a pressurized cylinder and periodically injected under computer control instead of a true sample. This sample should show no peaks and represent the true instrumental baseline, incorporating the column baseline bleed as well as baseline 1 above.

2. As in '1' except that any desired standard compounds are added to the zero gas sample. Such compounds are chosen for appropriate retention times and will not interfere with the determination of the 'true' baseline as they will form well behind peaks.

3. The actual sample is passed through a VOC filter containing, for instance, activated carbon such has been described in carrier gas cleanup. This filter may not remove methane quantitatively which presents no problem.

4. As in '3' except any desired standard compounds are added to the purified air sample via permeation tubes or other suitable methods.

5. As in '3' or '4' except that a matched, dual column gas chromatograph is employed with VOCs removed by filtration from one column with an unfiltered air sample going to the other column. These two flows are switched on each injection so that any possible variation between response is seen and so that residual (very slowly eluting compounds) are equally distributed between the two columns.

6. Following analysis of an actual air or other sample the sample valve is NOT returned to the sample mode. Thus pressurized carrier gas (helium) remains in the sample loop and is injected during the next sample processing cycle.

7. As in '6' except that any desired internal standards are added to the helium carrier gas. Such standards need not interfere with the 'true' baseline determination and should be chosen not to elute with target analytes.

8. The sample valve may not be thrown at all, rather the GC goes through a temperature programming cycle with no sample injection at all.

9. As in '8' standards are added to the helium carrier, collect at the column head during cool down of the oven, and form standard peaks upon temperature programming of the oven.

In any of these cases, if the air zero or helium carrier is pure (which is the case with proper filter implementation) then any of these baseline chromatograms can represent the baseline for previous and subsequent chromatograms. Two types of 'unresolved/undetected' compounds are distinguished above. So long as the baseline determination is not performed too frequently, it should distinguish only the second type above, as the high molecular weight compounds from previous injections will still contribute to the baseline during the application of procedures a–h above. Such compounds should be in quasi steady state after several injections, and should not change significantly in their contribution upon the intermittent injection of any of the above 'clean' samples.

If these are significant compounds in case 1 above to be measured, a more appropriate column should be employed so that higher molecular weight, greater polarity, etc. compounds elute during an individual chromatogram.

Figure 15:
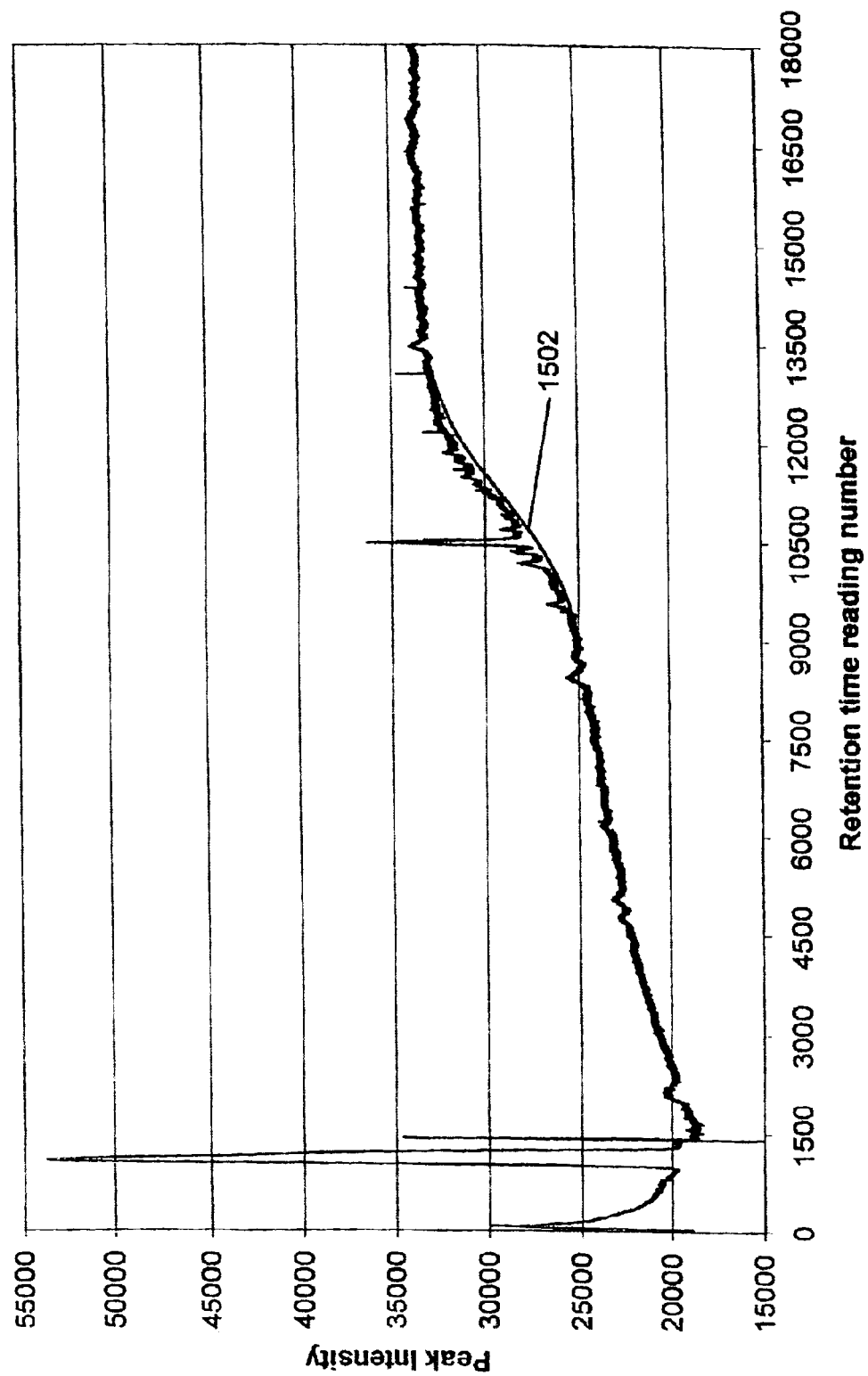

Each of these approaches has its particular advantages and disadvantages. Currently we prefer procedure '6' for its ease of implementation (not requiring an additional gas cylinder) or the setup of FIG. 14 and its positive results. With ambient air sampling '7' is not required as ambient methane forms a satisfactory internal standard. FIG. 15 shows the determination of the baseline 1502 for an ambient air sample 1504. Subtraction of the 'baseline' chromatogram from the sample chromatogram shows (by difference, illustrated graphically in (FIG. 15) that these unresolved compounds make up about 10–30% of the total resolved compounds total concentration. One advantage of procedures '1' or '3' above is that either the ultrapure air sample or the helium carrier gas itself may contain one or more internal standard VOCs which will serve to calibrate the instrument in addition to determining the baseline. For many air pollution applications it is not essential to know the individual identities of the large number of unresolved compounds which 2-dimensional chromatography can resolve. In fact, simply identifying them would be quite an undertaking. Rather, by their approximate retention time these structures and molecular weights can be accurately 'assessed' and their sum total concentration can be determined by the baseline subtraction procedure just described. In either situation, Pneumatic Focusing gas chromatography is the only fully-automated method to obtain information about both resolved and unresolved compounds in a gaseous sample.

14. Continuous Pneumatic Focusing

Most of the working instruments made to date have used what may be termed as 'pulsed' Pneumatic Focusing using pressure from a compressed gas cylinder. Single-stroke piston compression has been described as well. A further type of Pneumatic Focusing, offering advantages in some circumstances, is continuous compression Pneumatic Focusing. A compressor has been used to deliver a continuous pressurized sample to a spectrometric cell. For a given compression/gas delivery capability, the sample pressure may be controlled by an outlet valve on the spectrometric cell. As the valve is closed, pressure rises in the cell. In this application, the focused sample has a residence time in the cell which may be calculated as follows. The STP flow rate of the gas may be expressed as std cc/min as F, the cell volume as V and the compression ratio as R. The residence time tau in the cell (equivalent to the sample averaging time for analysis) is given by Tau=V/(FR). As in any compression, provision for condensed water removal should be made. In this case, since the condensed water may contain analytes whose concentration is to be measured, it may be allowed continuously or periodically (under computer control) to drop through a 2nd valve (FIG. 6) into another spectrometric cell or be delivered to an additional gas or liquid chromatograph, pH or other ionic measurement cell, or any of a multitude of other analytical devices.

In other applications, such as spectroscopy, signal from the detector may be acquired by other types of signal-processing devices. Examples of such additional signal processing devices include, without limitation, coulometers, electrometers, counters, photo-multipliers, etc. Such signals can be subjected to any of several reported digital signal processing procedures, such as described by Lyons in "Understanding Digital Signal Processing," (1997), incorporated by reference herein, to increase sensitivity and reduce noise.

Any of a multitude of other A/D boards of the same or different manufacturer may be employed in signal acquisition. For instance, a COMPUTER BOARDS 12 bit A/D board has been used in working embodiments of the present apparatus. The COMPUTER BOARDS 12 bit A/D board is capable of much more frequent readings, taking and averaging 100 points whereas the 16-bit board only takes and averages 2.

Novel modifications of an analog-to-digital (A/D) board have been made for acquisition and digitization of chromatographic or other analog data, as follows.

Figure 16:
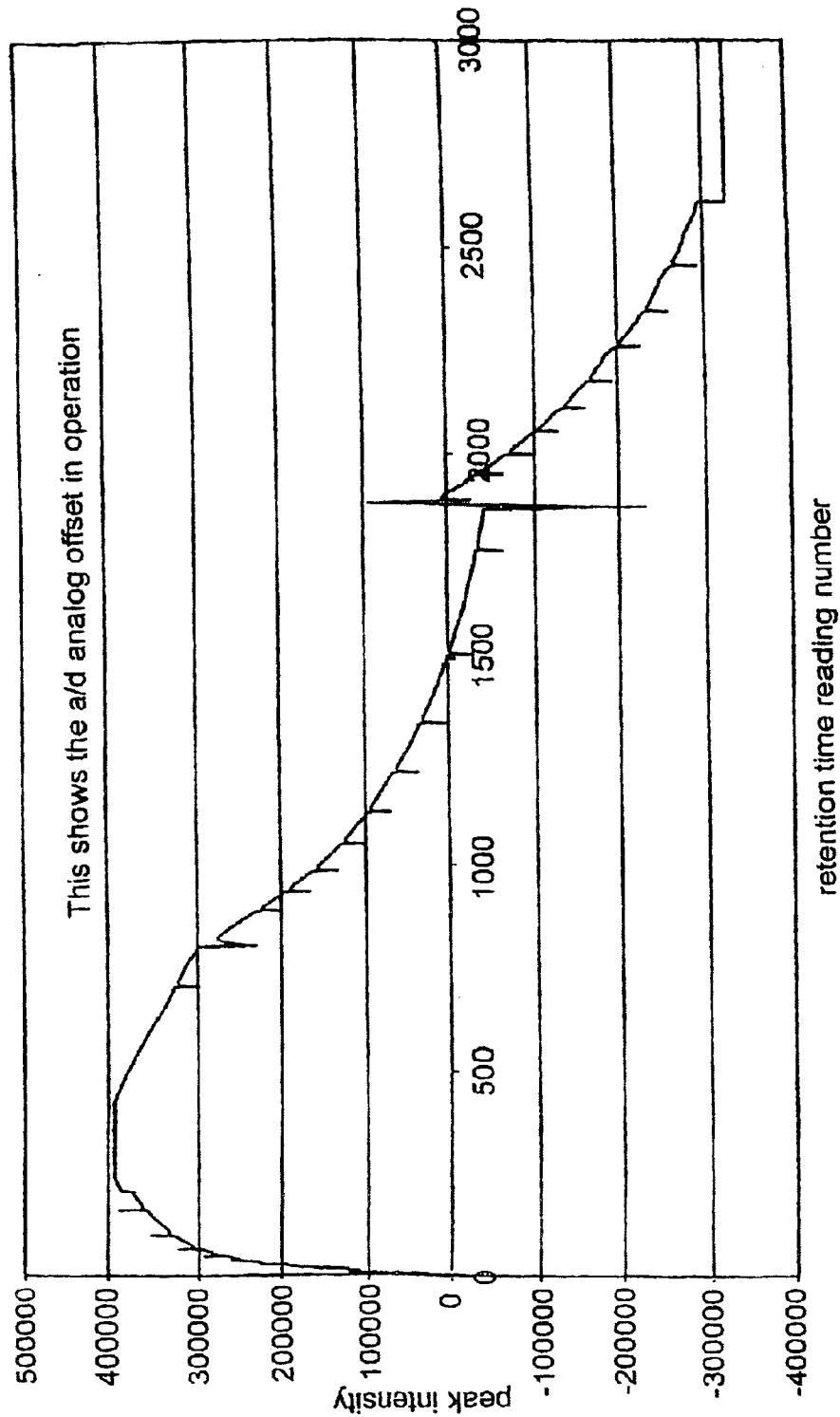

A. In temperature programmed gas chromatography it is common for the detector baseline to increase with temperature due to the increasing elution of compounds strongly adsorbed on the column as the temperature rises. This produces a situation where the baseline itself may approach the maximum signal an A/D board may obtain, typically −5 to 5 volts or 0–10 volts. It is desired to have under computer control an offset voltage to extend the range of the A/D board to accommodate baseline drift. Furthermore, it is common to wish to quantify a wide range of peak intensities. Under situations where large peaks and small peaks are present together, sufficient resolution to adequately capture small peaks may cause large peaks to go off scale on the A/D converter. In this instrument, a circuit (FIG. 12) was designed to offset the range of the −5 to 5 volt A/D board by incremental amounts of 5 volts to produce a total offset range of approximately −50 to 50 volts. Operation of this device is shown in FIG. 16. This illustrates the AID offset applied by the computer program gc.bas whenever it senses that the signal is going off scale of the 16-bit range. The offset was programmed for this figure to show each application as a spike. There is no particular significance to the data itself, other than it shows the high and low ends of the range which saturate the offset. The normal range of a 16 bit A/D board is approximately $2^{16}$ or 65,000. The observed range in this figure is from −32,000 to 40,000 for a total range of 72,000. This is equivalent to approximately 19.5 bits or an extension of a factor of 11 over the normal range.

Figure 17:
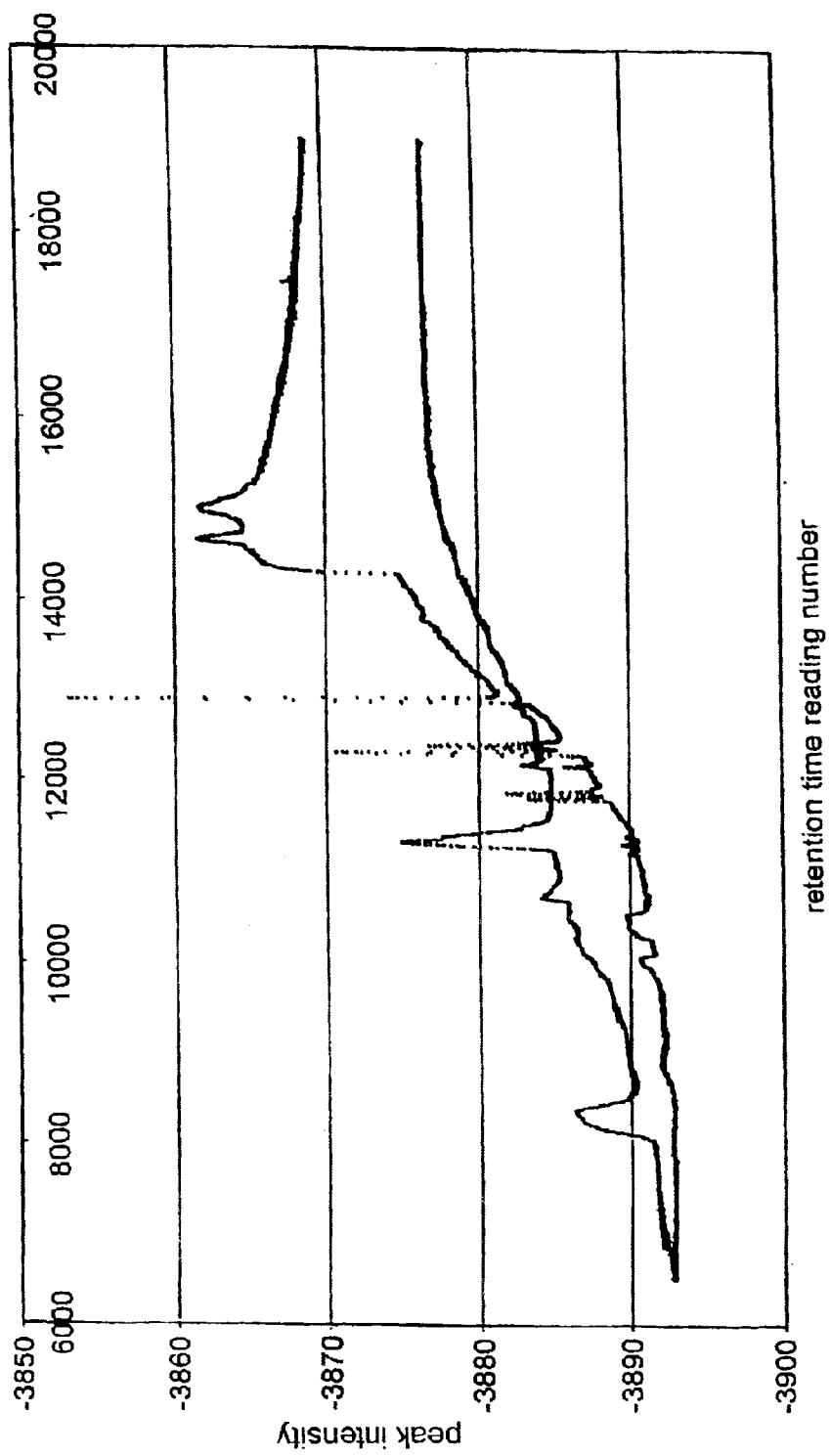
Figure 18:
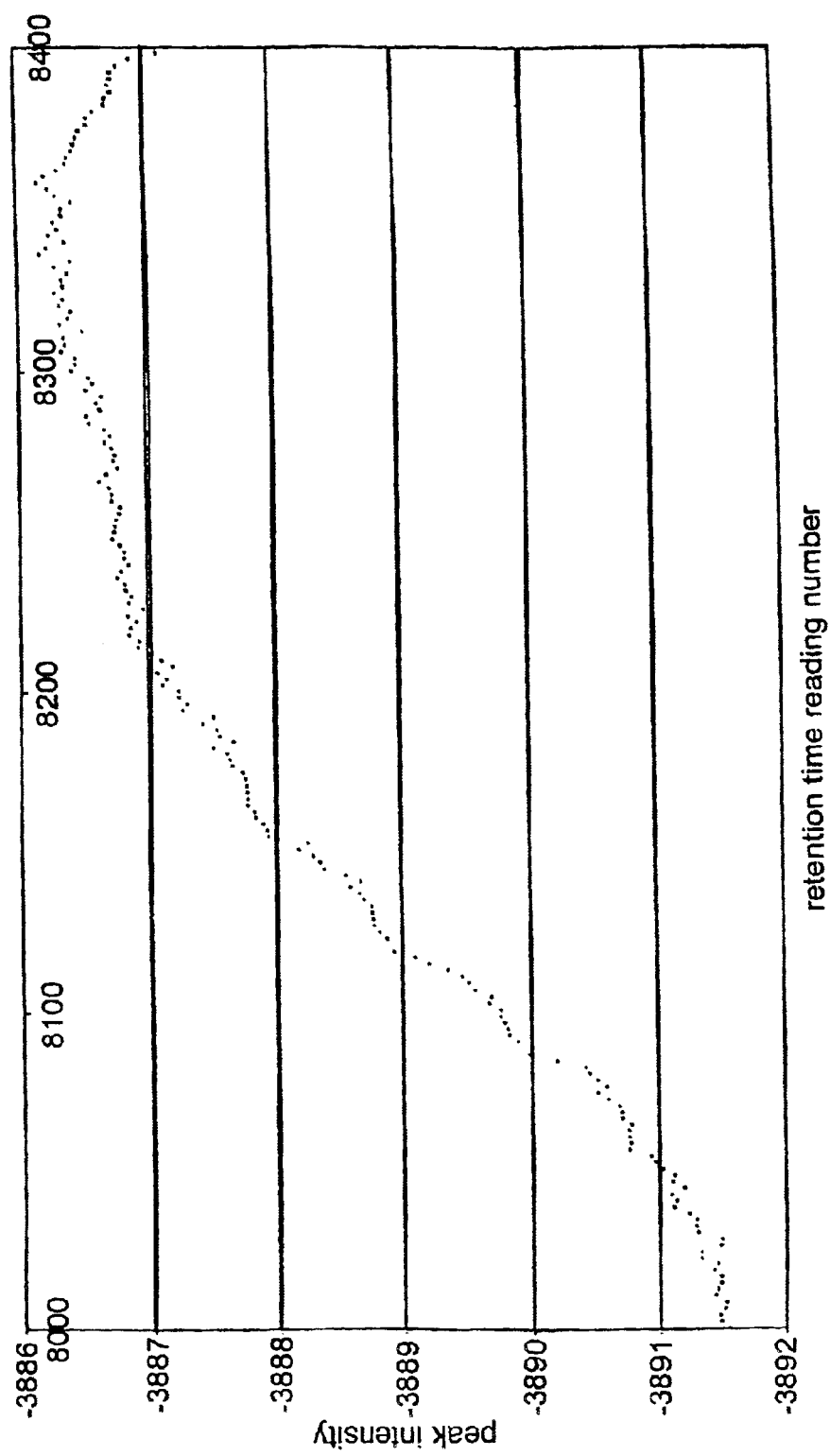

B. It is further desired to provide for interpolation between digital readings on an A/D board of any nominal resolution. For instance a Computer Boards Das08/Jr-AO 12 bit A/D board nominally can record 4095 digital numbers. However, within the program gc.bas, provision is made for taking and averaging 100 readings before recording the numerical value to computer memory and plotting on the computer screen. Although such averaging is not purely linear, its linearity is sufficient for the present instrument. With this averaging procedure it has been possible to record an entire gas chromatogram using only the 35 digital numbers between −3895 and −3860 (out of 4095 available on the A/D board) since averaged values are usable to interpolate between the nominal integer values returned by digital reading (see FIG. 17). To clarify, for a 10 v full scale 12 bit A/D board such as the Das08/Jr-AO, the minimum sensitivity is $10/4095$ or 2.4 mv. However, using the averaging procedure within gc.bas and choosing an average of 100, it was possible to increase the minimum sensitivity to between $1/10$ and $1/20$ of the nominal 2.4 mv, that is to 0.24 mv or even 0.12 mv, depending upon the rate of change of the voltage being read. This is accomplished in the program gc.bas (enclosed) within the subroutine 'das8' that acquires data from the A/D board. In operation with the slower 16-bit A/D board only an average of 2 readings was taken (line 1105). However, with the 12 bit board discussed here, it was possible to take 100 readings per save (ii=100 in line 1105) and still faithfully record the chromatogram. Typical peak data taken with this averaging procedure is shown in FIG. 17 and an enlargement thereof in FIG. 18. In FIG. 17 are displayed two chromatograms taken with an average of 100 readings per saved data point. The fastest rising peaks (e.g. at 13,000) have sufficient data for accurate representation of their areas. These peaks would have benefited from a reduction in the averaging times perhaps. However, for the slowly rising peak around 8,000, which is expanded in FIG. 18, between 10 and 20 readings are taken per nominal integer A/D reading. There is an inherent and fairly reproducible nonlinearly in these data which could easily be linearized in software within the program or in postprocessing, giving better linearity.

15. Chromatographic System Control

The entire chromatographic system in a working embodiment was controlled by two computer programs. Most chromatographic functions of the Varian 3400 are entered through a keypad on the front of the gas chromatograph (GC). Other commercially available GCs employ other types of control, including dials on the instrument front. Virtually all of these instruments can be adapted to provide the present apparatus, and can be used to practice the present method. Or, such a chromatograph could be designed and constructed from scratch.

Other functions of Pneumatic Focusing, including timing of valve operation, are controlled by a personal computer. A working system used a 486 personal computer running WINDOWS 98. The computer program also acquired data from the A/D board.

A working embodiment of the present apparatus used a computer program, gc.bas, to further control apparatus functions. GC.bas was programmed in the basic language TekBasic, running in a DOS window. However, suitable operating programs may be written in other languages, such as True Basic, Visual Basic, GWbasic, other basics, Fortran, C, C+, C++, etc. GC.bas first sends a start signal to the chromatograph and then moves the valve from a "sample air" mode to an "inject sample" mode.

The following keypad program was run on the Varian 3400 GC used to make a working embodiment of the present apparatus. Such programs can be altered, if desired, for optimization for use with particular applications. A program used with a working embodiment is described. Through the keypad, the following functions were entered to perform a continuous sampling of the atmosphere using a working embodiment of the present apparatus.

1. initial range setting—10–10 amperes (low amplification for methane measurement);
2. initial GC oven start temperature—35° C.;
3. auto zero output signal;
4. initial oven temperature hold time—3 minutes;
5. amplifier range—change to 10–12 amperes;
6. auto zero output signal;
7. initial temperature ramp speed—20°/minute;
8. intermediate column temperature—100° C.;
9. intermediate column temperature hold time—zero minutes;
10. secondary temperature ramp speed—5° C./minute;
11. final column temperature—200° C. (maximum recommended by manufacturer);
12. final hold time—20 minutes;
13. reset oven to initial conditions, wait for start signal from PC;

Additional chromatographic functions were performed by the personal computer, e.g., a 486 computer, running the laboratory-written Tekbasic program gc.bas (see the appendix) through the das16 a/d board. Certain of these functions are as follows:

1. A file is created on the computer's hard drive and named with the month, day, hour and minute a particular sample is injected. ASCII files are automatically created and named to hold the individual sample data (i.e., the chromatogram), along with the date and time a sample is injected. For example, a sample injected on December 25 at 5:30 am would have a file named as 12250530.asc. Such files may be 'zipped' or otherwise compressed to require less storage space.
2. A sample inject signal is sent to the sampling valve.
3. A GC start signal is sent to the GC.
4. A signal is acquired from A/D board, with a pause command of 30 ms. The pause allows a stable A/D board reading to be obtained. Plural readings may be taken and averaged for storing in the computer memory. In a working embodiment, two readings were taken, averaged and saved. The average value is converted to an integer to save storage space. 9.09 values are stored per second, each an average of 2 readings. "Readings per second" are controlled by software and may by reprogrammed to suit the application.
5. A sample signal is sent to the sample valve. This returns sample flow through the sample loop and carrier flow directly through the sample valve to the chromatographic column. The time this signal is sent to the sample valve can be an important consideration. For example, upon "inject signal" to the VALCO sampling valve from the computer, the following functions occur:
    a. Carrier gas is diverted from a direct path through the sample valve to the column and required to pass through the sample loop before entering the column. The air sample is diverted in the valve so it no longer passes through the sample loop, but rather directly through the valve to the sample pump.
    b. Carrier gas, such as helium carrier gas, enters the sample loop, which contains a sample, such as ambient air at ambient pressure for analysis. The carrier gas drives the sample before it to the end of the sample loop, through the sample valve and onto the head of the separatory column.
    c. The sample is compressed, and upon compression, the sample both heats and loses ambient water vapor through condensation. The extent to which the sample is heated is controlled by the compression rate, thermal conductivity of the apparatus and the temperature at which the apparatus is maintained. Ambient water vapor condensation can occur either to a fog, to the sides of the conduit, or a combination of both. If desired, the end of sample loop could be packed with material, such as glass beads, to collect condensed water vapor.

U.S. Pat. No. 5,498,279 states that:

"High speed gas chromatography system for analysis of polar organic compounds" describes Gas chromatography systems which provide for high speed separation of polar compounds of interest from samples which also include non-polar compounds. Efficient separation is achieved through the use of a tandem series connected combination of analytical columns, one of which having a polar stationary phase material and another having a non-polar stationary phase material. In two systems the order of the analytical columns is reversed. Fluid flow conduits, valves and vents are provided in a manner which eliminates mechanical valves in a sample stream."

Such patented process would work more effectively if coupled to analyze either the total condensed moist air sample or the water fraction thereof.

a. The timing of the valve return to the sampling position is determined experimentally. For ambient air samples, the valve return timing generally is set to a point at which the (probably unretained) methane has all entered the column. This is determined by experiments in which the valve timing is changed, chromatograms are obtained and the end of the methane peak on such chromatograms is examined to see whether the methane peak has been truncated. The sampling valve is returned to the sample position at the earliest possible time. In a working embodiment, the sample valve was returned to the sample position after the 799th readings of the FID, about 80 seconds. Returning the sampling valve to the sample position at the earliest possible time helps prevent condensed water from entering the chromatographic column, and instead conducts it to the waste stream entering the sampling pump. Returning the sampling valve to the sample position at the earliest possible time helps (1) eliminate much of the water in the initial sample from the column; (2) deliver a constant amount of water to the column, independent of the ambient humidity; and (3) quantiation depends simply upon the quantity of sample in the sample loop volume, which thereby allows for consistent chromatographic separations from injection-to-injection, day-to-day, etc.
b. A preset number of readings is acquired. While acquiring the preset number of readings, some, or all, readings are sequentially displayed in real time on the computer screen. Each reading is saved in computer memory. After the readings are recorded, the program waits a sufficient period to allow the GC oven to cool to a predetermined temperature. In a working embodiment, a 7-minute waiting period was initiated by the computer to allow the Varian 3400 GC oven to cool to a temperature of about 35° C. The sampling cycle is then repeated. In a working embodiment of the present apparatus, 38,000 FID readings are taken over a sampling period of approximately 37 minutes, and the average of each pair stored in computer memory for 19,000 stored readings. A person of ordinary skill in the art will realize that the software can be changed to vary the number and timing of readings, averaging of readings before storage, and length of chromatogram.
c. The stored chromatograph can, such as through remote computer access, be downloaded, such as through a network, to another computer and processed as desired. Continuous computer data may be acquired from the automated instrument operating anywhere accessible by phone line, cellular phone, or satellite-linked communication system. Continuously operating instruments may be placed anywhere in the world with data acquisition occurring at a central facility. The only normal human intervention required to operate the system is to change the cylinder gases, if so equipped, at regular intervals, such monthly. The computer can be configured for automatic restart upon power interruption. This processing includes a novel data analysis procedure, which is described below.
d. Another application of this analog offset to a gas chromatograph could be carried out by a novel subroutine (Sub basetrack) in the signal acquisition program gc.bas which is described below. This program determines the baseline in a given computer-acquired chromatogram by selecting signal points where no peaks are eluting. A group of these data points are then fitted with a polynomial of desired order, for instance 5th to 15th. This curve fit then becomes the baseline for the next computer acquired chromatogram. Before each point is acquired from the A/D board, it is offset by the computer fit baseline value of the previous point. In this way a completely baseline corrected chromatogram appears on the screen and is stored for later viewing and analysis. The program gc.bas also stores the polynomial coefficients so that the original data may easily be regenerated if desired.

e. The ambient air sample is drawn through a modified aquarium pump FIGS. 3 and 4 to the Valco sampling valve and then to outdoor air through ¼" TEFLON tubing. This pump pulls about 0.2–1.0 liters/minute of outside air continuously through the sample loop, except during the short time during each measurement cycle when the sampled air in the sample loop is pressurized and injected into the chromatographic column. In this embodiment, any type of pump may be employed, since the sample does not pass through the pump before entering the sample loop/chromatographic column. In another application a pump was modified (FIGS. 3 and 4) for suction rather than pressurization by interchanging the internal check valves. FIG. 4 illustrates a cross section of the pump 100. Housing holds diaphragm 114, which is maintained in position by retainer 116. Retainer 116 is coupled in position by pin 118.

With reference to FIG. 3, a pump 100 is illustrated for drawing air through the system. Pump 100 includes a housing 102 having an inlet 104. A tubing 106 houses spring 108, adjacent to which is positioned bb110. In other applications, the sample pump is replaced by any of several types of compressors or pistons that serve to pneumatically focus the sample without the requisite of consumable high-pressure carrier gases. The sample loop in two embodiments consisted of 50' of ¼" of ⅛" copper tubing connected to the Valco valve. As stated above, the sample loop may be made of other metals, TEFLON or other plastics. The chosen sample loop must withstand the Pneumatic Focusing pressures to be employed. Especially, the sample loop may be made of nickel tubing or nickel-plated copper tubing, since nickel has low adsorption efficiency for many VOCs or other gaseous sample analytes, or of copper to remove ozone. The sample loop can be maintained at any desired constant temperature by a thermostated heater thereby delivering a know volume and mass of gas sample as governed by the ideal gas law PV=NRT or it's nonideal equivalents.

In one application the sample tube could consist of an optical or infrared waveguide connected to a light absorption spectrometer so that the wavelength-dependent absorption of the Pneumatically Focused sample could be determined after pressurization and before injection into the chromatograph. Such a cell also could be applied downstream of the column to measure absorbance of the separated analyte components as they elute from the column still at high pressure.

16. Piston Compression of Sample Gas for Pneumatic Focusing

In most embodiments to date compressed gases (often helium carrier gas in chromatography) have been used for Pneumatic Focusing. In this situation care must be taken not to mix the focusing gas-with the sample as described elsewhere. An alternate approach, which avoids the need for consumable gas cylinders, is the employment of a compression piston/cylinder situation. One such prototype arrangement was constructed using a cylinder and a 12V electronic trailer jack (Atwood company, purchased from a trailer supply distributor) to provide the compression force. In one embodiment the jack was attached to an available cast iron table leg with stainless steel hose clamps. The cylinder, which contained an o-ring-sealed piston, was similarly attached. Application of 12V to the jack compressed the prototype piston, which would drive the contained air sample into either a spectrometric sample cell or onto the head of a GC column.

The previous piston arrangement (available as surplus) is satisfactory for injections of small volumes into a chromatograph. However, in the case of spectrometric Pneumatic Focusing it may be desirable to use cells of fairly large volumes (to minimize wall effects) and to use high focusing pressures. In this case larger piston/cylinder arrangements are preferred. The ability to compress at varying speed will be useful in controlling compression heating of the gas as well as aerosol formation/growth via water condensation, which follows compression.

17. Computer Programs used for Data Interpretation

In addition to the program gc.bas, described above, which runs the measurement cycle, acquires and stores the data, several other basic language programs have been written for data interpretation. For example, the program, gc_mplot.bas plots a set number of chromatograms on the computer screen, and sends a graphic file to a printer to provide a hard copy of the set number of chromatograms. In a working embodiment, gc_mplot.bas plotted 20 chromatograms on the computer screen before sending a graphic file to a printer. The program gc_avg.bas first writes a text file containing the names of all files acquired on a given day. The gc_avg.bas program then sequentially averages each chromatogram to get a composite average for VOC data collected over a desired time period, such as daily or weekly. Chromatogram averaging reduces noise and smoothes the chromatographic baseline. This averaging procedure is a novel way of increasing the sensitivity for multiple averaged samples, e.g., for daily, weekly, etc., chromatogram averaging. The gc_avg.bas program then sequentially plots each individual chromatogram on the computer screen in comparison to the daily average concurrently plotted. The gc_avg.bas program then saves the daily average with a file name, such as 1225.avg. This average chromatogram, due to averaging, will be relatively noise free and show the extant analyte peaks unambiguously relative to the baseline. As such it may be subjected to any of a number of chromatographic peak integration programs, including our own and commercial ones, for accurate determination of peak beginnings and ends. These beginnings and ends may be then returned to the program integpro.bas (see FIG. 49) as starting points in its own peak search and integrate routine.

Certain programs have been written to prepare, for example, statistical information concerning acquired data. For example, the program baseline.bas conducts a polynomial fit to the baseline of an individual chromatogram or average chromatogram, subtracts the baseline, and then plots and saves the baseline-subtracted chromatogram as a file name, such as 1225.bsl. Most chromatograms provided by the drawings were baseline corrected.

Finally, commercially available programs may be used to plot the chromatograms. A working embodiment of the present apparatus used the EXCEL Microsoft program to plot the individual, averaged, or baseline-subtracted chromatograms. Individual chromatograms can be integrated by commercial programs or programs written for a particular application. For example, the commercially available program CHROMPERFECT can be used to integrate chromatograms.

18. Quantification of Analyte Concentrations from Chromatograms

Fully automated Pneumatic Focusing gas chromatography as described here generates huge amounts of raw data. For instance, one automated instrument has run for over 1 year measuring Portland's air pollution and generating 40 or so chromatograms per day. This represents approximately 14,000 chromatograms per year per column. Another instrument utilizes two columns. Several computer programs are commercially available for integration of GC peak areas for quantification of analytes, and the following have been used:

1. Chrom Perfect
2. Peak Simple
3. Peak Fit

Figure 19:
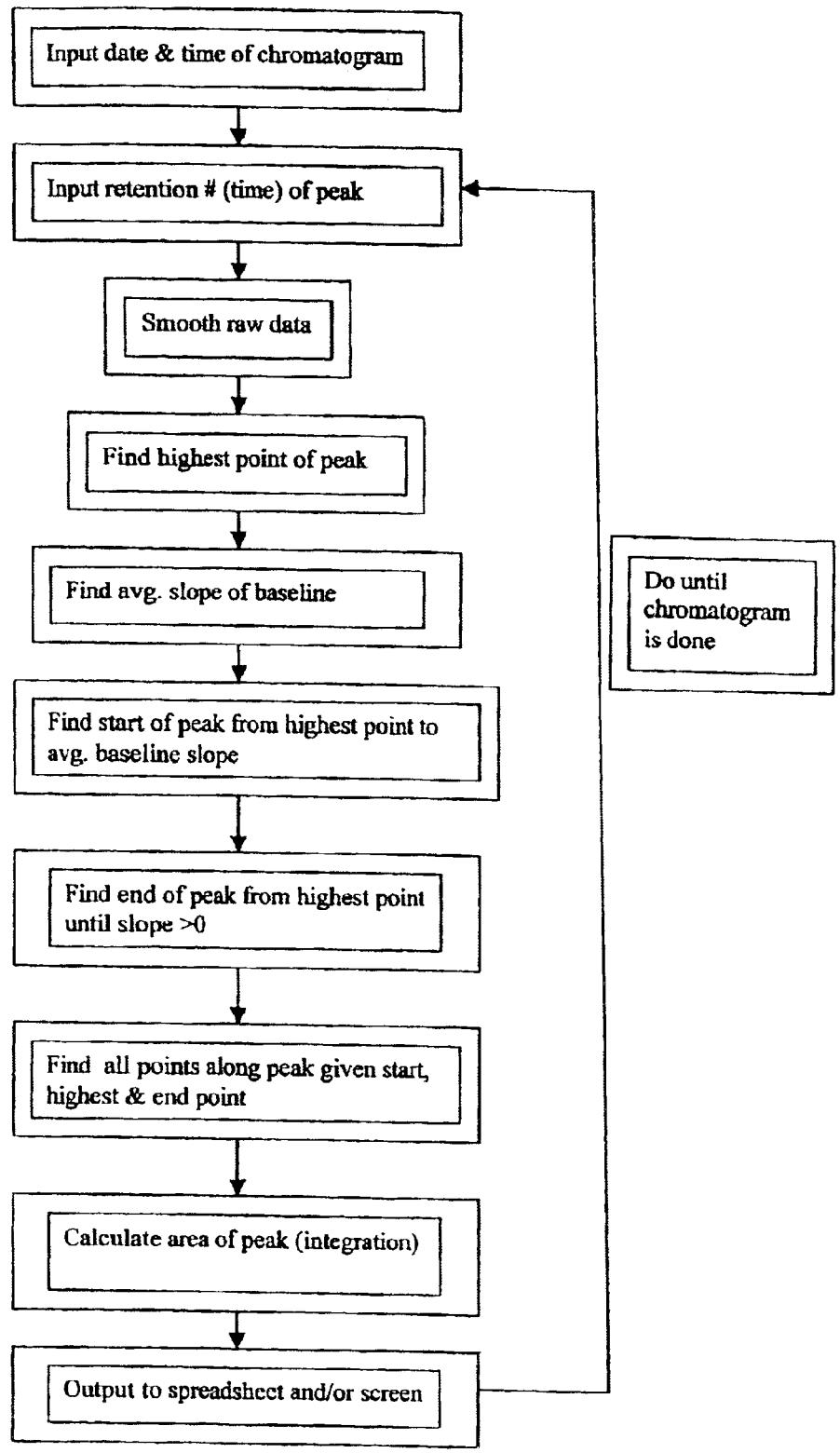
Figure 20:
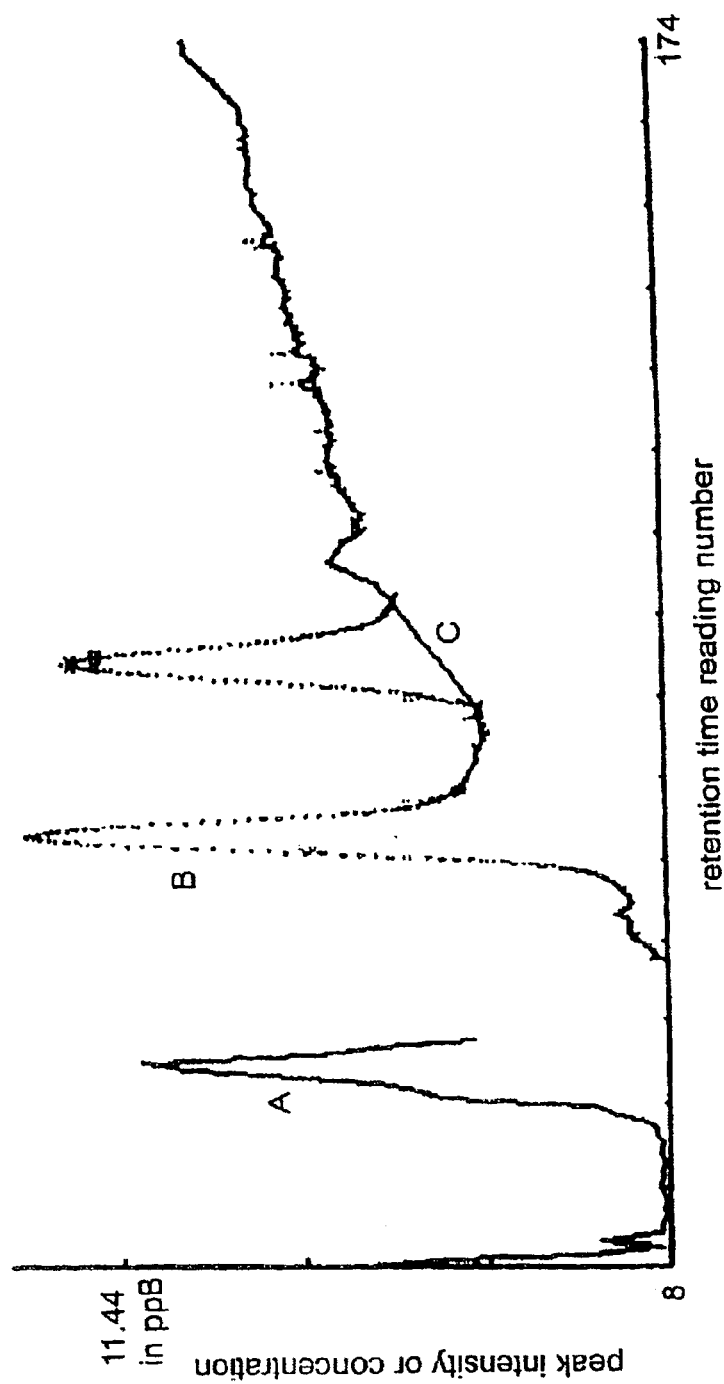

While these programs are well written and quite useful, none are adequate to process the huge volume of data produced by automated Pneumatic Focusing gas chromatography. The reason for this is that each of these programs is geared to significant user intervention in the determination of the beginning and end of peaks, split peaks, etc. as a necessary prerequisite for area integration. All these programs necessarily allow for user override of computer selected peak beginnings and ends. However, none allow the easy application of user selections to subsequent chromatograms, which are frequently quite similar. Consequently we have written a prototype integration program Integpro.bas (FIG. 19) in the basic language. This program initially approaches a set of chromatograms differently from commercial programs which attempt to quantify all peaks in a given chromatogram. Integpro.bas rather focuses on a single peak which will then appear in a potentially very large number of similar chromatograms. Thus, once recognition and integration of a given analyte peak is optimized, the program can process without significant human intervention a large number of chromatograms. An example of the output of a single program recognition and integration is shown in FIG. 20. Integpro.bas displays and integrates subsequent chromatograms in rapid order. An operator may observe this display (if necessary or desired) and adjust 'standard' parameters as desired to optimize correct integration. Once a given analyte's peak is successfully integrated the program then moves to another peak. This program, once optimized for a large number of peaks, can successfully recognize and integrate all peaks in a given chromatogram for realtime determination of all analyte peaks in a given chromatogram. Output from Integrpo.bas is shown in FIG. 20. The horizontal axis represents reading number in a single chromatogram. Sample number 28 is being processed. Curve B is being processed, a short portion of chromatogram 28. Peak C is being integrated note the baseline drawn by the program. Concurrently the program plots a continuing concentration graph of the concentration corresponding to peak "C" as measured in all previous chromatogram.

19. Identifying Chromatogram Peaks

Once a chromatogram is obtained, peaks are identified that correspond to analytes of interest. Individual peaks in the chromatograms are identified in several ways including, without limitation:

1. Using sample VOC chromatograms, available commercially, which give analyte elution order;
2. Spiking samples with reference VOC compounds. For example, air samples have been selectively spiked with reference VOC compounds of known identity. Examples of reference VOC compounds include, but are not limited to, individual alkanes, alkenes, etc. See Tables 1 and 2 above.
3. The pneumatically focused chromatograph may be connected to other instruments used for chemical identification, such as mass spectrometers. By connecting the chromatograph to a mass spectrometer, the molecular weight, fragmentation pattern and presumably the identity of compounds corresponding to each peak, may be identified as it elutes from the column using standard gc/ms procedures. For GC/MS applications, the sample exiting from the valve is split to the MS and other detectors, or the excess discarded, or the STP gas flow rate is dropped to 1–2 cc/minute by computer controlled decrease in carrier pressure and opening of the flow control valve as described above. A person of ordinary skill in the art is familiar with GC/MS identification of unknown VOCs and other compounds.

It is not necessary to use Pneumatic Focusing itself to determine peak identities in a PFGC. Thus if the quantity of an unknown analyte delivered to a mass spectrometer is below such instrument's detection limit, unknown compounds discovered in PFGC may still be identified. To this end a PFGC may also incorporate into the sample loop or separately a standard 'freeze-out loop'. Such loop would be used in standard cryogenic focusing to capture and deliver to the GC/MS instrument a larger quantity of target analytes in case such concentrations delivered by the Pneumatic Focusing technique remains below the detection limit of the mass spectrometer. Identification of these analytes then may be carried out (assuming the same or a similar column is used) in a standard fashion. Once unknown compounds with known retention times are identified using standard procedures, these retention times will be transferred to all PFGCs using the same column and temperature/pressure programs.

20. Quantifying Amounts of Individual Compounds on Chromatograms

Individual peaks (i.e., compounds) are quantified in one or more of the following ways:

1. Internal reference standards, such as those listed in Tables 1 and 2, may be added at known concentrations to a sample, such as a sample air volume. This method is known to those skilled in the art as "known addition," and is exact for each compound. In the rest of the methods, previously measured or known per-carbon responses of individual VOC compounds are applied to each individual peak compared to one of the internal standards.

Figure 21:
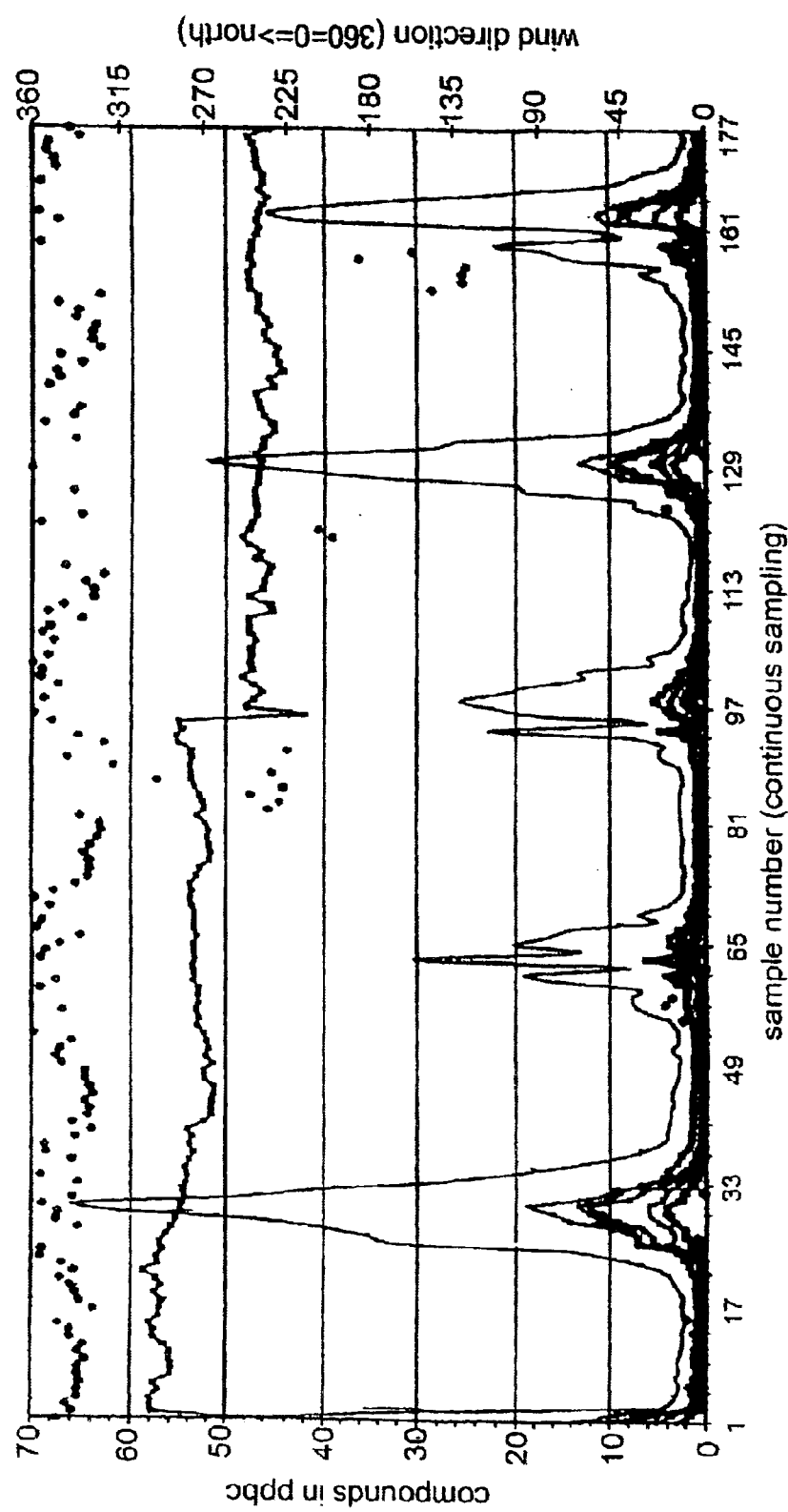

2. For air analysis, the methane peak can be used as an internal standard for quantifying the amount of other compounds on a chromatogram. This is because the concentration of methane is relatively constant at about 1.8 ppm for all but the most polluted air samples. Thus, areas of individual peaks can be compared to the area of the methane peak area for that same chromatogram to determine the amount of a compound corresponding to a particular peak. Methane forms an excellent internal standard for many atmospheric sampling situations in which air is not too highly polluted. Such is the case in FIG. 21 which shows the methane concentration measured over a several day period as part of atmospheric sampling. Note that the methane peak area varies only slightly except when the oxygen cylinder for the flame was changed, (about sample 96) in spite of considerable variations in atmospheric pollutant concentrations. Thus normalizing each pollutant peak area to the methane peak area, which represents 1.8 ppm will make correction for FID response. A sample calculation may be shown. Say, for instance the area under a methane peak was 1,100 units and the area under a target analyte peak was 11 units. Typically methane is attenuated 10× relative to other analyte peaks due to its high concentration. Then the target analyte concentration would be given by:

11/1100*1.8 ppmC/10=0.0018 ppmC=1.8 ppbC. If the target analyte were propane $C_3H_8$ then its concentration would be equivalent to 1.8 pppC/3=0.9 ppb=900 ppt.

3. (Methane is slowly varying seasonally and yearly on the order of 1% or so. If necessary this variation may taken into account in a calibration procedure). Methane is an abundant pollutant from auto exhaust so that in areas with very high automobile traffic (such as Los Angeles) the variability of methane may be significant but its use as an internal standard can still prevent gross errors in instrument calibration. Methane would not be a suitable internal standard for breath analysis, since humans produce varying amounts of methane metabolically. In this case an internal standard may be employed as described previously and next.

4. An internal standard may be added to the carrier gas, such as any VOC compound not normally present in the sample and chosen to elute in a region of the chromatogram where no other analytes are presented. This internal standard is prevented from stratifying in the carrier gas cylinder by, for example, placing a small heater at the cylinder bottom, which causes continuous convective air movement within the cylinder. This internal standard will, of course, always be entering the chromatograph, but can be focused thermally at the column head so that it elutes to form a quantitative peak upon column temperature programming. The quantity of internal standard collected at the column head, and hence the precision and reproducibility of the calibration, is dependent upon exactly reproduced column hold and programming times. In laboratory operation such internal standards at not practical. In fully automated Pneumatic Focusing gas chromatography they may be routinely employed.

5. An additional standard can be added to the carrier gas separately by a gaseous permeation device of standard design.

6. Gas from a reference compressed gas cylinder containing various internal standards may be periodically injected onto the GC column under computer control instead of an ambient air sample.

21. Injection Details

In order to maximize resolution and shorten analysis time, the sample should be injected onto a chromatographic column in a minimum of time. Pneumatic Focusing allows the injection of a large quantity of sample in a minimum time. It is further advantageous that the sample should be injected as a 'plug' with a minimum of 'broadening' at the edges. Such broadening is produced by turbulent or molecular diffusion into the sample plug by the focusing or carrier gas in the case of pneumatic injection from a sample loop. For instance with the setup described in FIG. 1, when the multiport valve is switched, several processes occur.

1. The carrier gas currently passing through the column backflows into the 'downstream' end of the sample loop. This results in column depressurization and dilution of the sample near the downstream end of the loop and produces a broadened chromatographic detector output.

2. At the upstream end of the loop, the focusing gas mixes turbulently with the sample gas as well, also producing a sample gas plug broadened at the edge. Such mixing is worsened in wider bore sample loops.

Such Broadening can be Minimized by at Least Two Approaches

Figure 22:
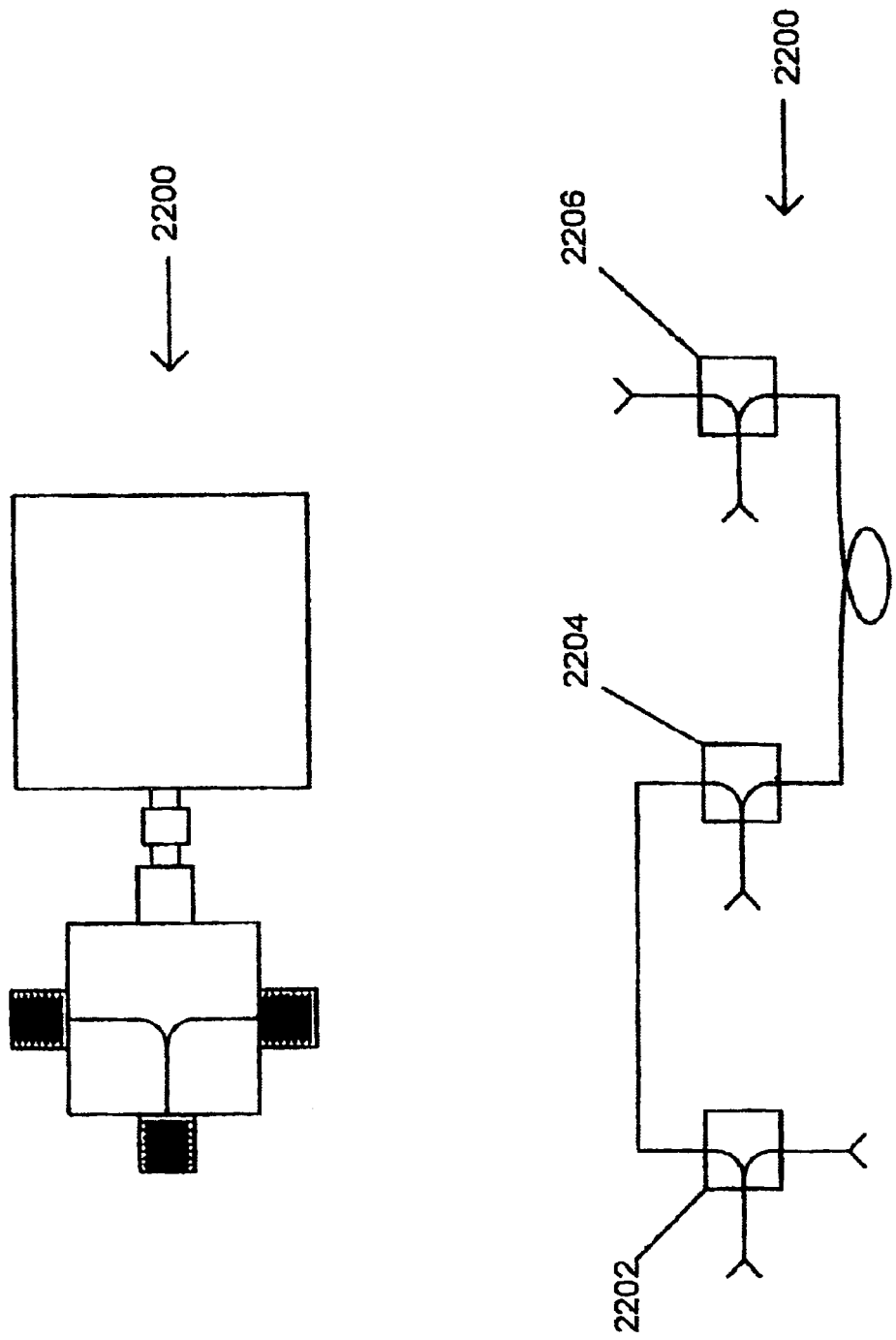

1. Rather than using a single multiport valve, which switches all ports simultaneously, use several individual '3-way' valves, which switch under computer control at slightly different times. For instance using controller 2202 in FIG. 22, valve 1 (2202) switches to isolate the sample pump, valve 2 (2204) switches to focus the sample up to valve 3 (2206), meanwhile maintaining column pressure. Finally, after an appropriate time (e.g. several seconds) v3 injects the sample onto the column. This approach minimizes backflow from the column into the sample loop, but turbulent mixing may still occur at the upstream end of the sample loop. This mixing can be combated either by the use of a pneumatic piston (described elsewhere) or by curtailing the injection before the tail end (turbulently mixed region) of the sample is injected. This can be done under computer control.

Figure 5:
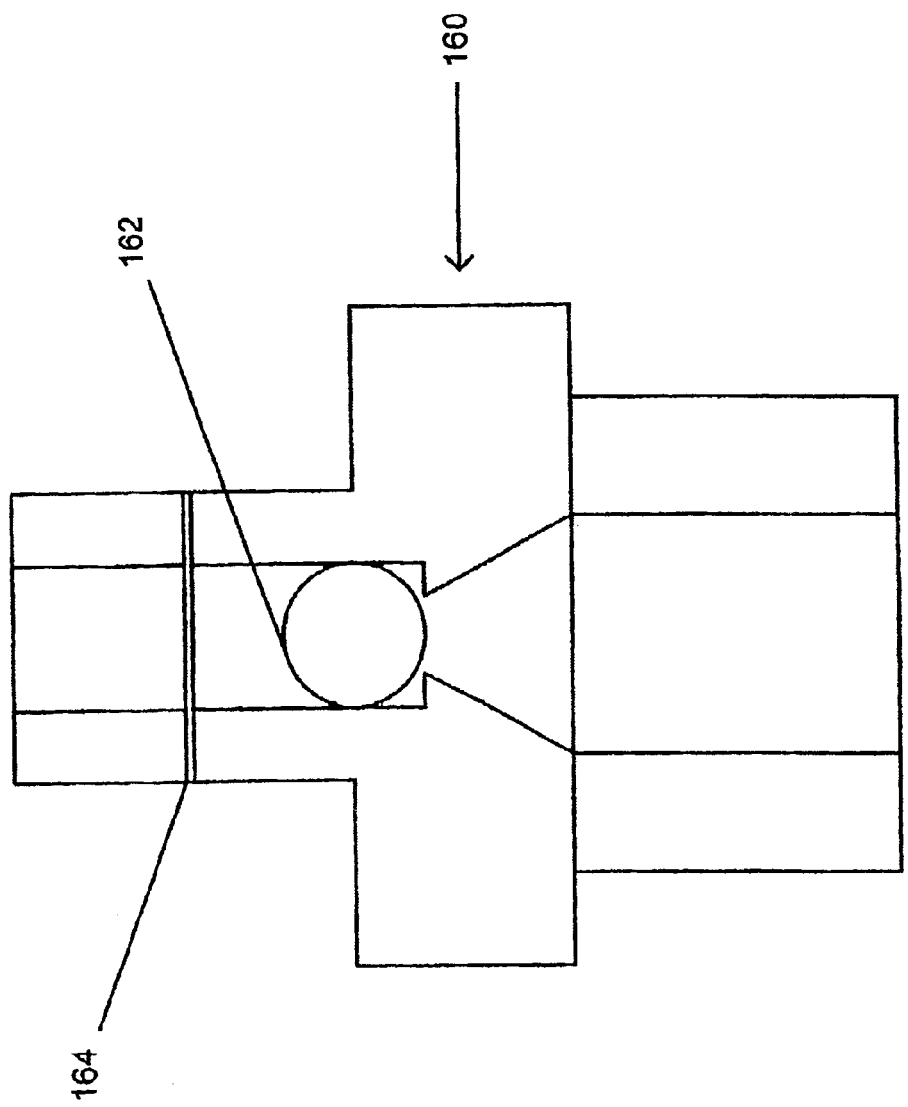

2. A multiport valve may still be used with minimal turbulent mixing using appropriate check valves, which have been designed for this purpose. These check valves consist (as is customary) of a spherical object (beebee) of appropriate composition (e.g. metal or plastic) which when forced in one direction forms a seal, but in the opposite direction allows gas passage. We have designed inexpensive but highly efficient check valves using simple materials. In one manifestation a small spring is held in a piece of tubing by swaging a ferrule around it or other means. This spring allows passage of gas past the beebee and through the spring. In the other direction another swaged ferrule stops beebee passage, effectively stopping flow. This check valve can prevent backflow of the Pneumatic Focusing gas (e.g. helium) into the sample line from a chromatographic column. In another application we have modified a standard 'Swagelok' fitting to perform a check function while maintaining its fluid connectivity between two pieces of tubing by drilling axially into the fitting to enlarge a region to accept the beebee and then transversely through the fitting (FIG. 5) for insertion of a small wire. A beebee is placed into the drilled out region of the fitting, and a small wire is inserted through the drilled hole and soldered or epoxied place in a leak-free fashion. The wire stops the beebee and allows flow in one direction, while in the opposite direction the beebee stops flow when it encounters the internal surface of the modified Swagelok fitting. This check valve can prevent backflow of the column carrier gas (helium) into the sample loop. Such valves function more simply and more appropriately than any commercial valves we have encountered.

Figure 23:
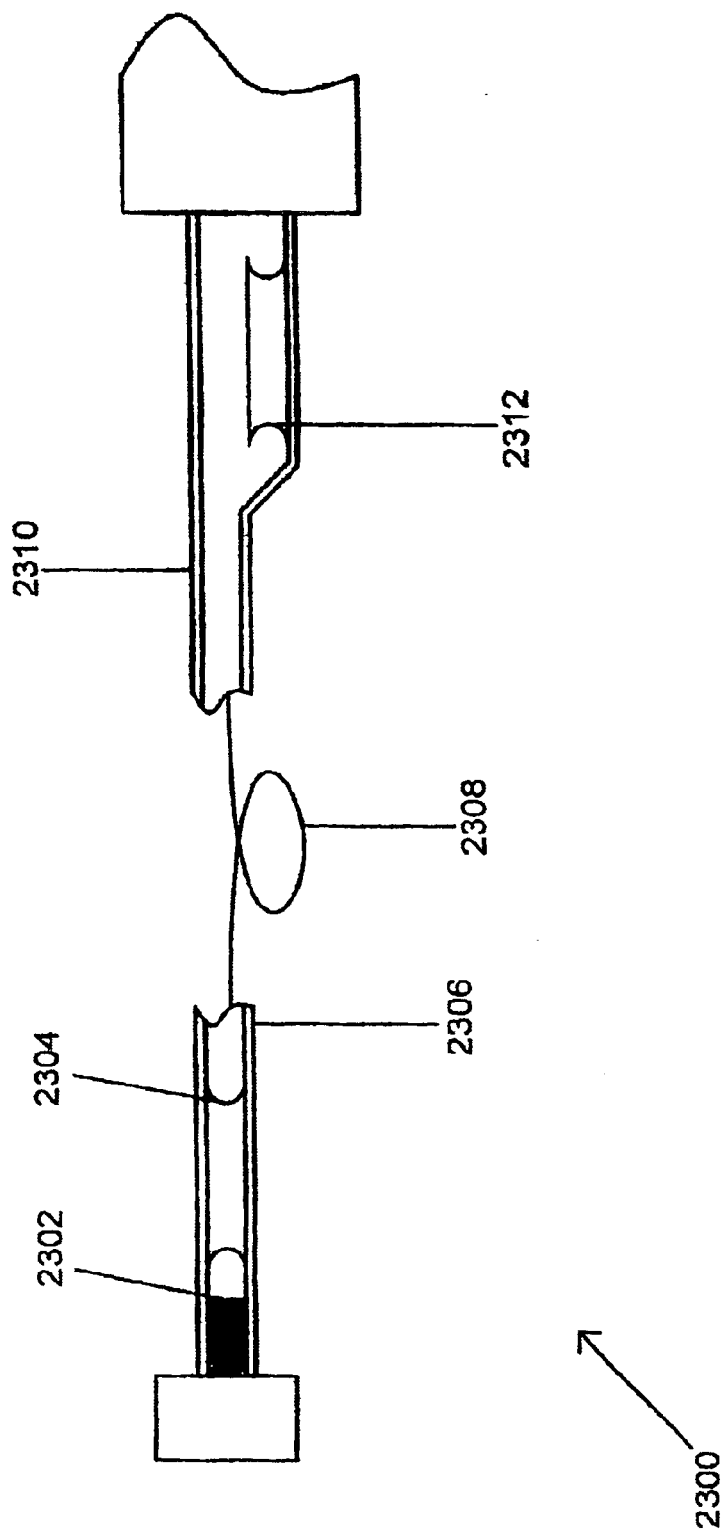

Mixing of the Pneumatic Focusing gas with the sample may be eliminated with a device referred to as a 'pneumatic piston'. This device (illustrated in FIG. 23) is expanded and driven by the compression gas and in so doing expands and compresses the sample gas into the GC column, spectrometric cell, etc. Such a pneumatic piston may be formed from any suitable material. For instance Rulon J (sold by Small Parts, Inc. Miami Lakes Fla.). Rulon J is a plastic which according to the Small Parts 2000 catalogue p. 144 was expressly developed to run against soft materials such as brass, type 318 stainless steel, aluminum, zinc, plastics and other materials which are worn rapidly by existing filled PTFE (Teflon) compounds. In the case of chromatography, once pressurization of the gas sample contained in the sample loop has reached the column pressure, the compression gas via the pneumatic piston will continue to force sample into the column at the overall flow rate as determined by the downstream flow restriction valve. Since this flow is know by experience, computer control of the valve switching can thereby determine the sample size injected to the column. For instance, in air monitoring, if the air is relatively clean a relatively large sample should be injected. If the air is polluted, a smaller sample may be injected to improve resolution and minimize detector saturation. Thus sample size may be completely controlled by the computer which measures concentrations in the previous sample and adjusts the next sample size accordingly. Actual sample size can be approximately determined by computer timing and more accurately determined (if desired) by an internal standard already present in or added to the sample stream, for instance by the methane peak area for atmospheric pollution analysis.

V. Pneumatic Focusing Thermodynamic Details

Fundamental thermodynamics of phase transitions, specific heat and heat transfer govern the details of Pneumatic Focusing. When a gas is compressed it heats as pressure-volume work is done on the gas. As the gas heats, it transfers heat to the surrounding containment vessel. The time/temperature profile of the gas depends upon the relative rates of compression and heat transfer. Concurrently, compression may cause condensable vapors (especially water vapor) to exceed its saturation vapor pressure at the pneumatic focused temperature. This supersaturation will cause water to seek the condensed phase. Details of this process will depend upon preexisting condensation nuclei in the sample (which may be removed by filtration if desired), the size of the compression chamber, turbulence induced by compression, and the rate of compression. This process, especially as it may involve turbulence, is quite complex and difficult of quantitative numerical modeling. Maintaining the compressing gas at a temperature, which will be above the condensation point for the ultimate pressure ratio achieved, may control condensation. Alternately, if it is desired to remove water from the sample for subsequent analysis, such water may be removed either by allowing aerosol formation/growth and subsequent filtration, or by inducing condensation on surfaces (cooled surfaces, for instance) from which water can be later treated as desired. Once water is collected by either method it may be either reevaporated by the carrier gas in a chromatographic application and transferred to the same or a different column from the noncondensables, or it may be allowed to run/drip into another chamber for subsequent spectrometric analysis or injection into another chromatographic column or chromatograph (e.g. a pH meter, then a liquid chromatograph, etc.). In the case of water condensation, polar compounds may themselves be included in the condensed water, even if they do not themselves exceed their 100% saturation pressure, due to vapor pressure lowering as in Henry's Law. These polar compounds would then be analyzed with the 'water fraction'. Examples of compounds to be found in the water fraction in atmospheric sampling might be methanol, ethanol, acetone, etc. Depending upon their Henry's Law coefficients at the applicable temperature these polar compounds may partition between the condensed and gas phases and be quantified in both. Details of such partitioning are familiar to persons experienced in thermodynamics and are described in detail elsewhere herein.

VI. Water in Chromatographed Systems

Some columns in chromatography (gas or liquid) are either harmed by the presence of significant water or have their performance impeded, such as through the variation of retention times. As an example, the RT-alumina columns used in disclosed embodiments for VOC analysis are very sensitive to water vapor in the sample. This water vapor control is ideal for analysis of nonpolar VOCs. However, if polar compounds (e.g. alcohols, aldehydes, ketones, etc.) are to be analyzed then they must obviously be injected onto the column with the rest of the sample. This may involve injection of significant quantities of water vapor. On some columns this presents no problem. On an alumina VOC column, however, retention time variation may occur if the correct approach is not employed. An abrupt rise in the baseline towards the end of the chromatogram is due to water 'breakthrough' into the FID. If significant polar VOC compounds are present in the sample they often are 'pushed through' by the water producing a large conglomerate peak. After water passes into the detector, subsequent retention times on that sample may be variable. However, they can be prevented from varying on subsequent samples if the column is maintained a sufficiently long time at its highest temperature before cooling for the next sample injection. This may require operating the column for a significant length of time (e.g. 5–10 min) at this temperature even though no analyte components are eluting. If water is too much of a problem (e.g. as with alumina columns) an alternate column (e.g. the J&W 'Gas Pro' column may be used. This column has greatly reduced water sensitivity with somewhat less desirable separatory properties).

V. Using Pneumatic Focusing to Chromatographically Analyze Gas Samples

The apparatus described above can be used in a number ways to focus and analyze gas samples. One embodiment of the present system used a sample collection system. A sample pump is used to draw about 0.1–5.0 liters per minute into a sample line. A TEFLON sample line was used in a working embodiment. This sample line was then connected to a collection coil, such as the ⅛ inch collection coil described above. Flow of the collected sample is directed by the Valco multiport valve discussed above. While the system is in sampling mode, the pump draws air samples from ambient air through the valve and into the collection coil. Meanwhile, the carrier gas, such as a helium carrier gas, goes directly through the valve and onto the column. Periodically, such as about every 40 minutes and upon completion of the elution/analysis of the previous sample, the control computer switches the valve, and the helium carrier gas is diverted to pass through the collection coil. The valve remains in this position so that the carrier gas is compressing (pneumatically focusing) the gas sample and carrying it onto the column. The length of time that the carrier gas is diverted through the collection coil is an important consideration. Empirically, it has been determined that for nonpolar, water-insoluble analytes analyzed on a water-sensitive alumina column, this time should be just sufficient to allow methane in the sample to enter the column. As soon as the methane peak is on the column, then the valve is switched back to sampling mode. In this manifestation the sample volume and hence the resultant analyte signal response is determined by the volume of the sample loop-in this case 40 cc. By this timing sequence, condensed water vapor from the compressed sample can be almost entirely prevented from entering the column. Alternately, with water-soluble, polar analytes, the water may be prevented from condensing by elevated temperatures or be reevaporated into the carrier gas so that it all enters the separatory column, as described elsewhere.

Sometimes when the concentration of a particular analyte is low, baseline noise is sufficient to mask the presence of analyte peaks. This can be mitigated by averaging individual detector readings or by concurrent or post-processing digital signal processing of the data for a single chromatogram. As part of this new technology chromatograms have been averaged over some pre-selected period of time, such as daily. By averaging the data, a stable baseline can be generated with greater peak measurement precision. Furthermore, the analyte retention times so determined may be fed back into the program Integpro.bas which then uses them to measure the areas under individual peaks which are not so clearly defined due to poorer signal-to-noise ratios on an individual chromatogram relative to the averaged chromatogram.

VI. EXAMPLES

The following examples are provided to exemplify certain features of various methods and apparatuses. A person of skill in the art will recognize that the invention is not limited to those particular features exemplified.

Example 1

This example concerns a method for continuously monitoring air quality using a pneumatically focused gas chromatography (PFGC) apparatus and method. An apparatus as described above, capable of pneumatically focusing to pressures of about 100 to about 500 psi was provided. The chromatograph was placed in automatic mode so that it was continuously sampling ambient air. Ambient air samples were collected and analyzed approximately every 40 minutes using the sampling system described above. For this particular example, the TEFLON collection tube was passed through the roof so that ambient air could be drawn into the tube using the sampling pump. The TEFLON tube was connected to an ⅛" coiled copper tubing, approximately 50 feet in length through an 8-port Valco rotary valve. With the system in sampling mode, the copper tubing continuously receives gaseous sample that is drawn into the copper tubing via the TEFLON tube as a result of the sampling pump's action. The copper tube served to destroy ozone in the air sample and prevent its reaction with alkene VOCs during Pneumatic Focusing. Collected samples periodically were injected via Pneumatic Focusing onto a column. In this embodiment the chromatogram took approximately 33 minutes with a 7 minute over cool down period for a total sampling period of 40 minutes.

Figure 24:
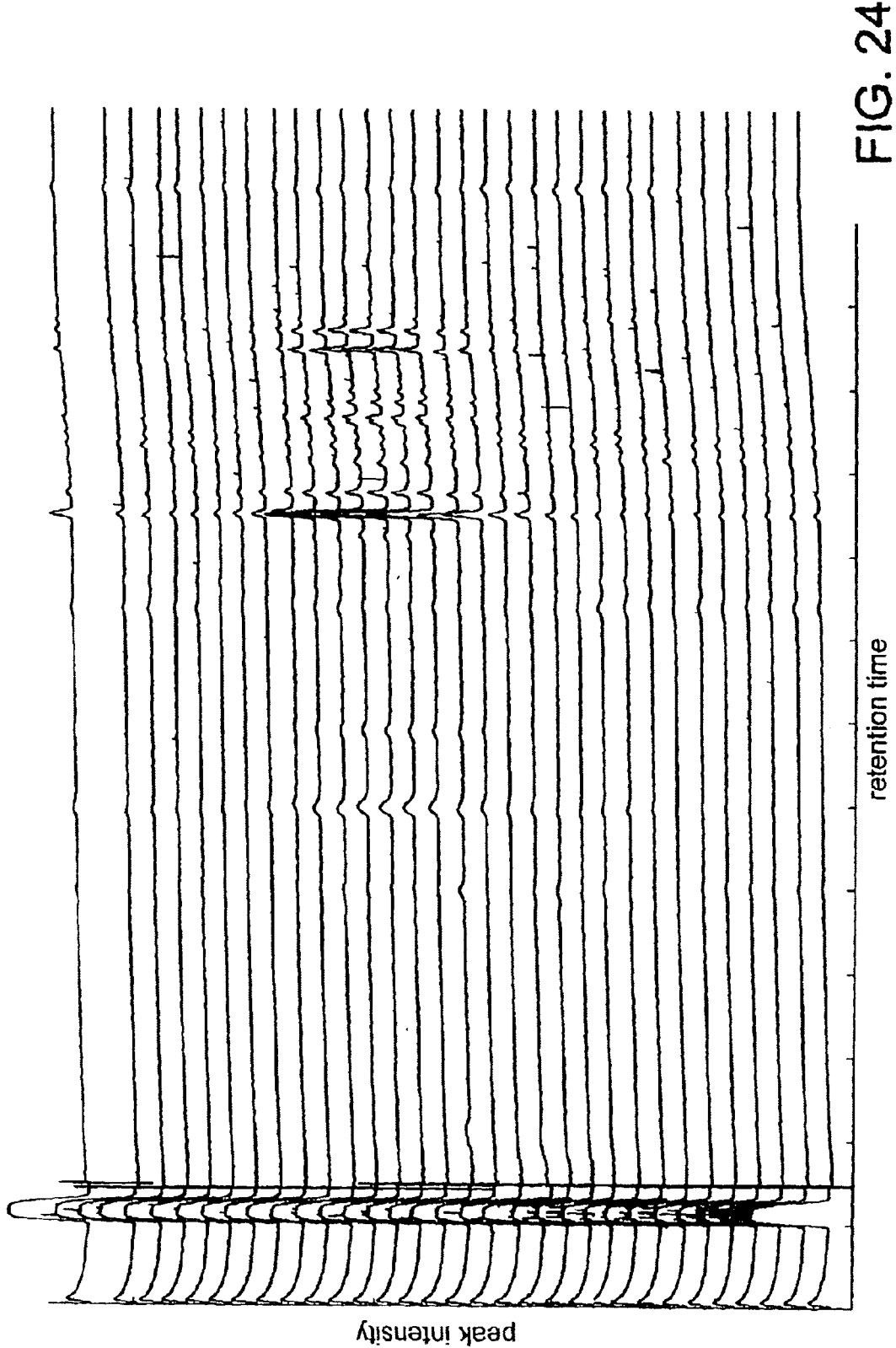
Figure 25:
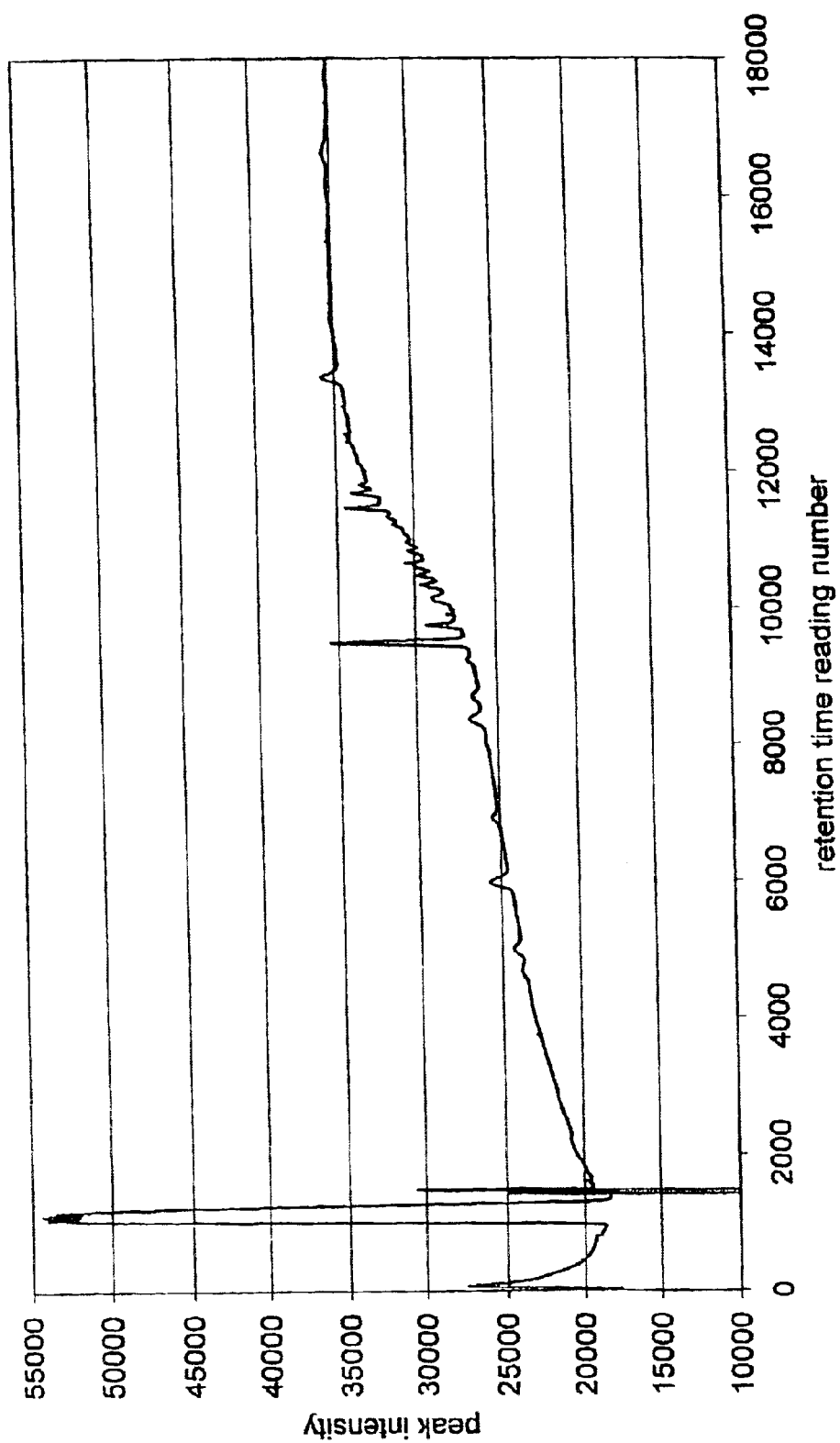
Figure 26:
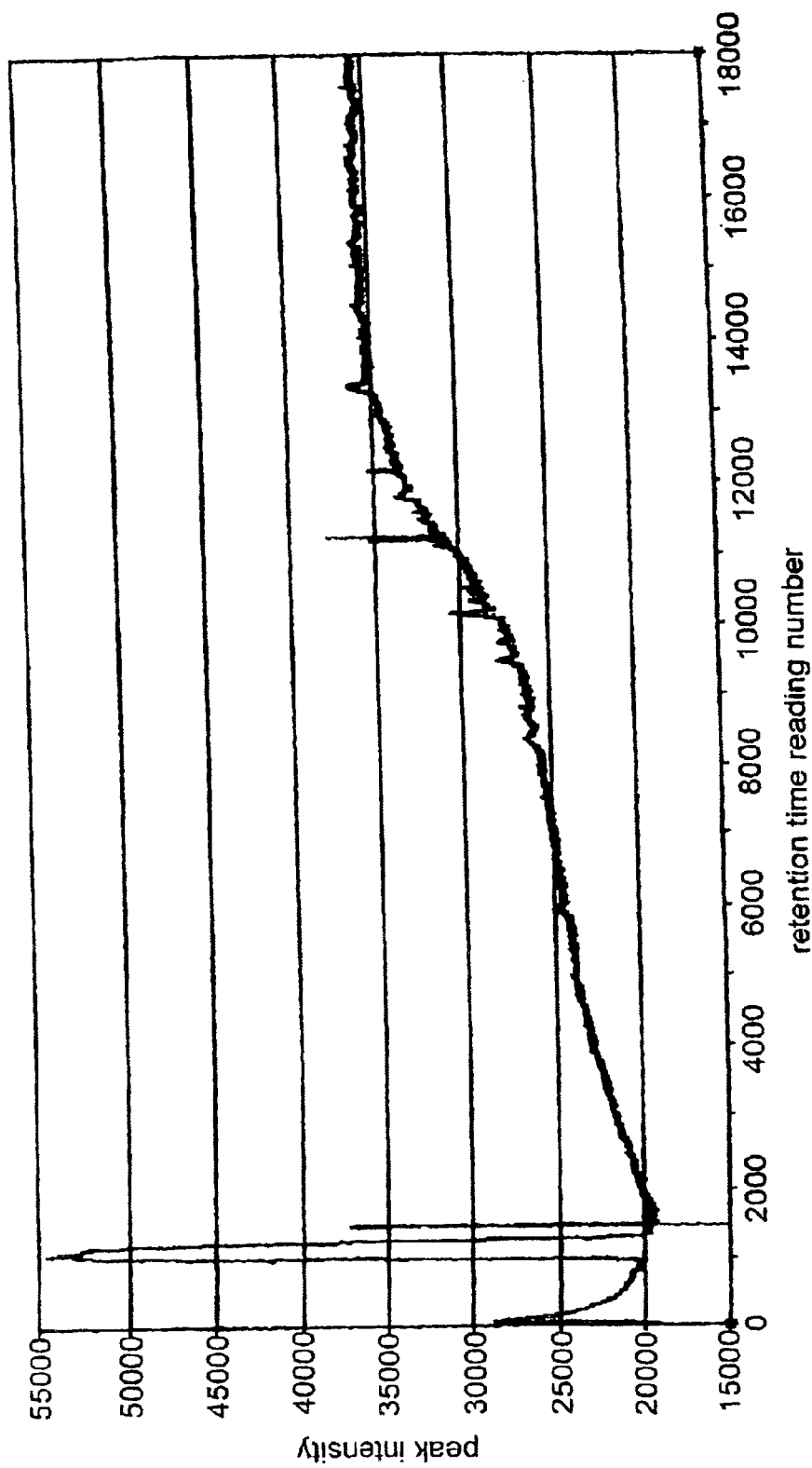

A system as described in this Example 1 has been continuously operating for >12 months collecting ambient air samples and providing chromatograms of each analyzed sample. FIG. 24 provides a series of such chromatograms that have been prepared in the manner described in this example. FIG. 26 is one chromatogram of the plural chromatograms provided by FIG. 24 and FIG. 25 is an averaged chromatogram as prepared for the 20 plural chromatograms of FIG. 24. FIGS. 24, 25 and 26 show that a continuous method for collecting and sampling ambient air can be practiced using Pneumatic Focusing and the apparatus described above, without having to cryofocus or absorbent-focus the ambient air sample prior to injection on the GC column. In this embodiment, sample analytes do not leave the gas phase until they begin the adsorption/desorption cycle within the chromatographic column, which individually resolves them from one another and then quantifies each in the FID. These individual chromatograms were then subsequently integrated with the program Integpro.bas described elsewhere herein. They are discussed further in a later example.

Example 2

Figure 27:
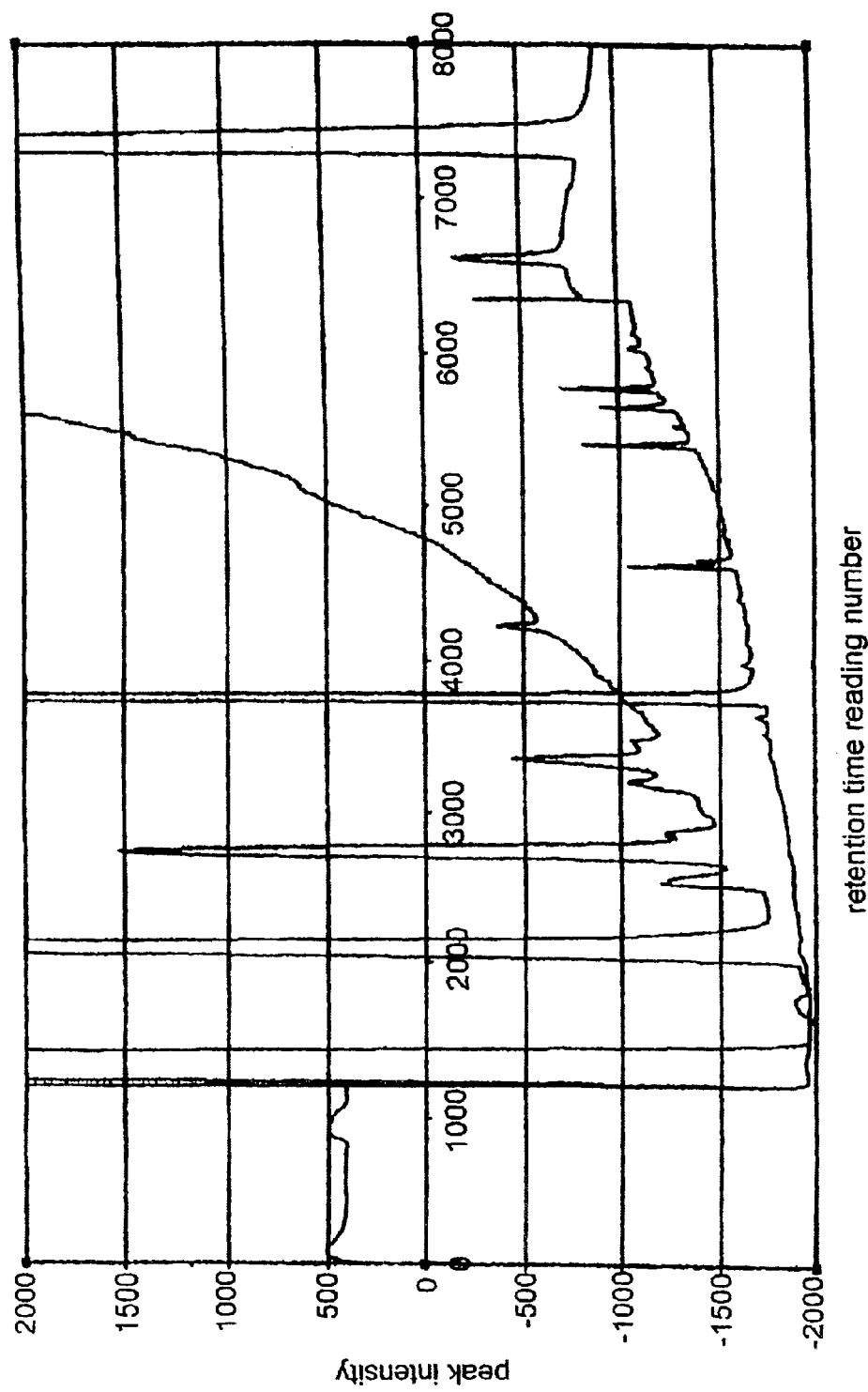
Figure 28:
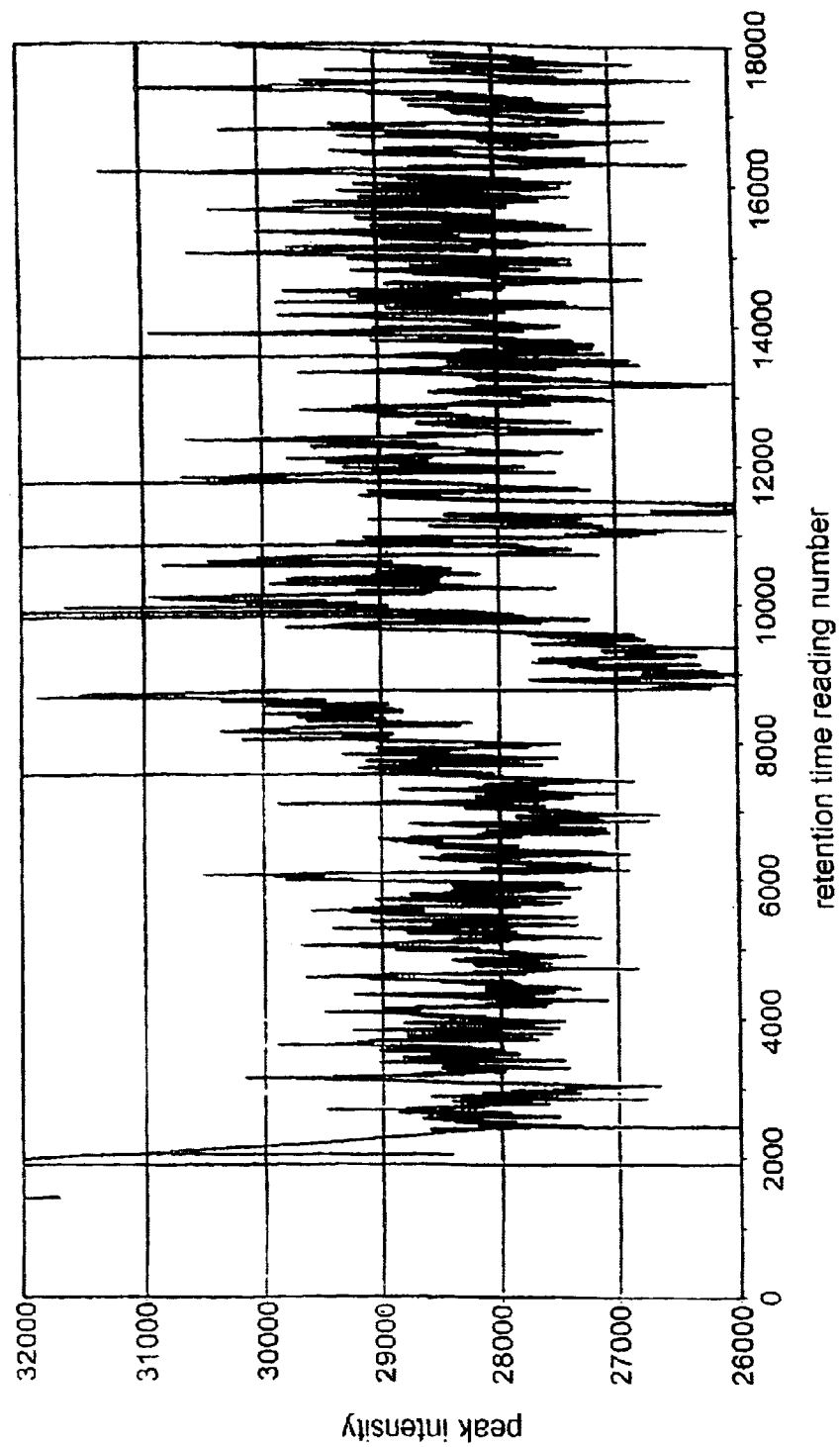
Figure 29:
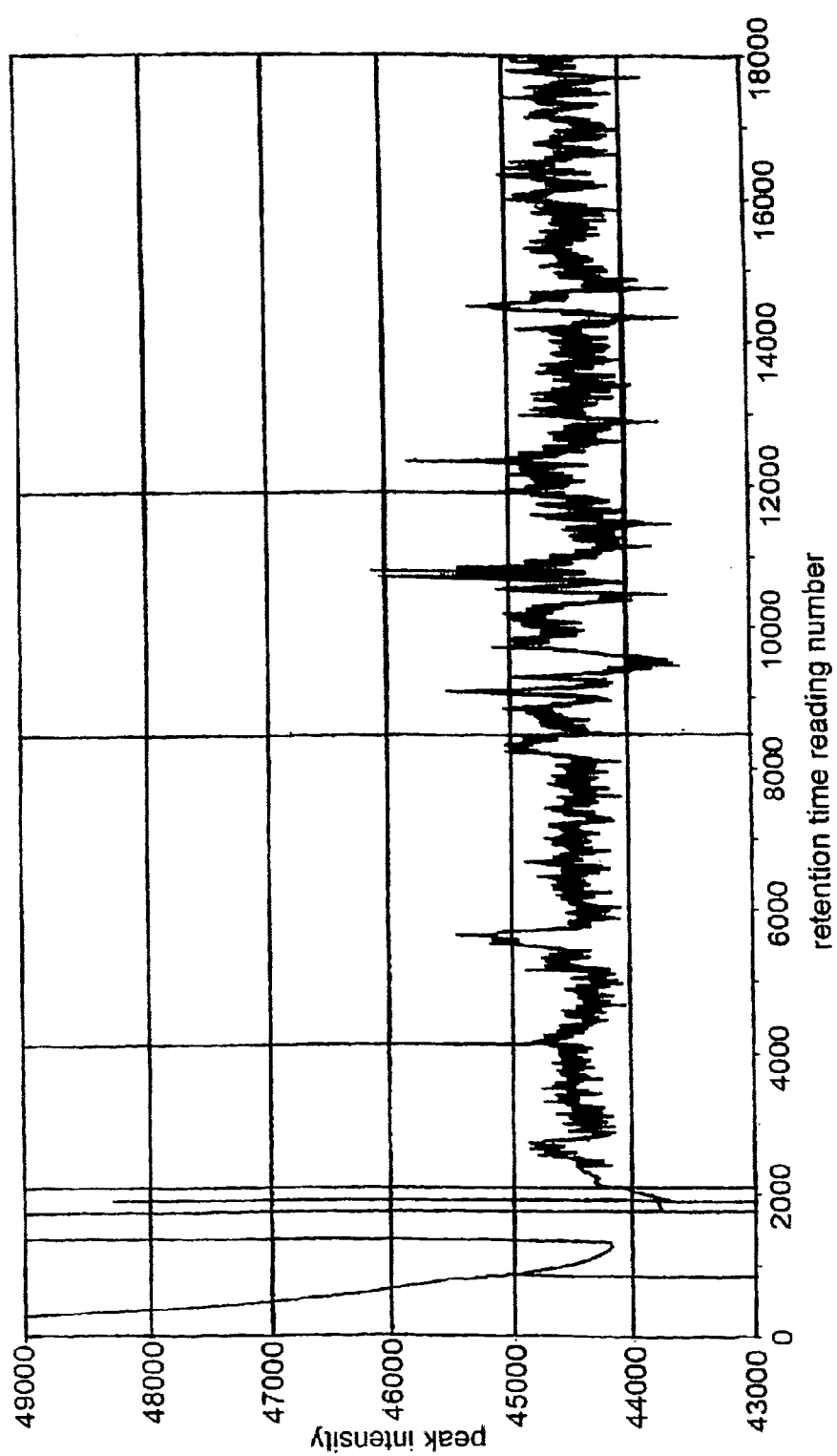
Figure 30:
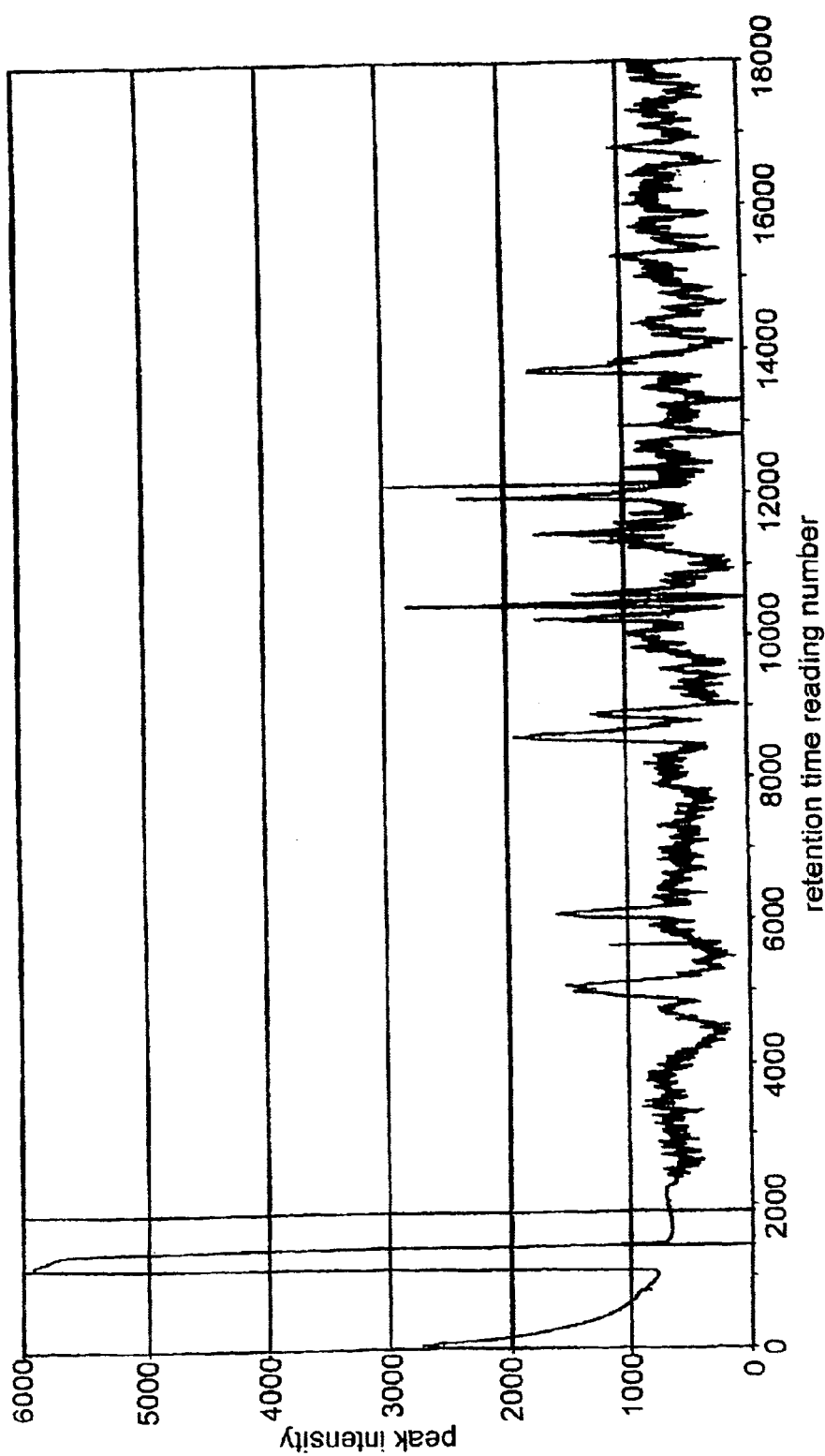
Figure 31:
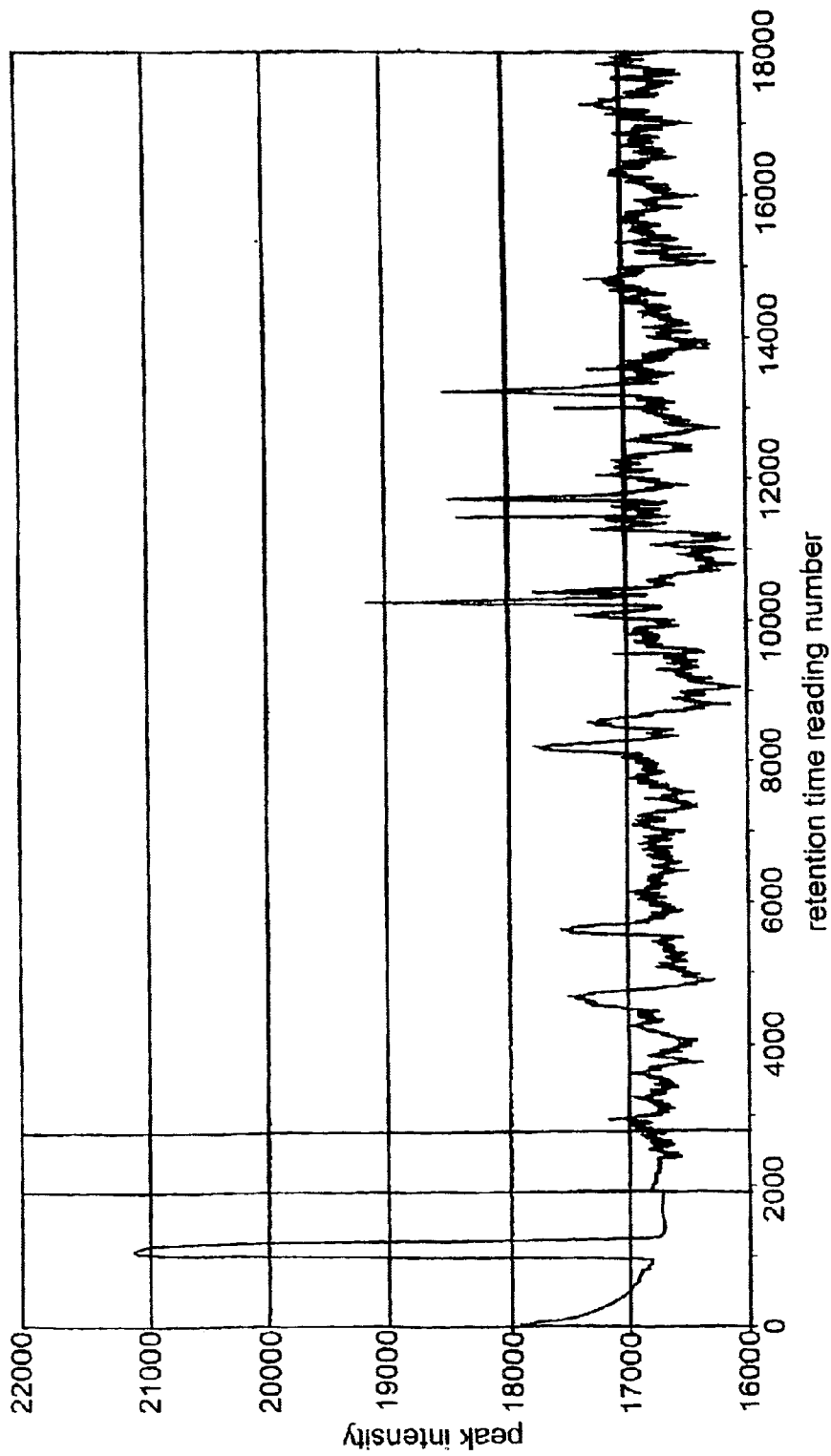

A second embodiment of an apparatus has been used for continuously sampling ambient air. This second embodiment works in substantially the same manner as that described in the preceding paragraphs except that the second embodiment included 2 separatory columns and two sample collection loops. One such separatory column is suitable for non-polar VOC compounds (Restek RT Alumina 60 m×0.32 mm id Serial number 183143) while the other is suitable for polar OVOC compounds (Supelcowax-10 fused silica capillary column serial #15702-10 60 m×0.32 mm id×1.0 um film thickness). Typical chromatographic results are shown in FIG. 27. In both these manifestations the volume of air drawn into the copper tubing is the sample volume for Pneumatic Focusing, and subsequent GC analysis. Thus, the sample size is determined by the interior volume of the sample coil.

Example 3

This example illustrates injection of a varying size ambient air sample from a sample loop which consisted of 50' or ¼" id copper tubing. The sample loop of example 1 was replaced with a the larger diameter column just described. This allows for the injection of up to 10× larger samples. The interior volume of the ⅛" sample loops is approximately 40 cc while the larger sample loop is approximately 500 cc in volume. When operated in the same mode as in example 1, the entire sample loop volume was injected. Under these conditions, water removal was not as successful as in Example 1 with the ⅛" sample loop and retention times show some variability after water eluted from the chromatographic column. In variable volume injection the program GC.bas was modified slightly to switch the sample valve back into air-sample mode at earlier and earlier times thereby terminating sample transfer to the chromatographic column with a resultant smaller sample volume injected. This experiment showed that injection of 10× larger sample volume results as expected in 10× larger peaks and 10× greater sensitivity. However, also as expected, resolution of the earlier eluting compounds is degraded since Pneumatic Focusing pressure was not increased in inverse proportion to the sample size. This degradation in resolution could be remedied by using higher Pneumatic Focusing pressures, not performed in these experiments.

Example 4

This example illustrates the degree of Pneumatic Focusing that occurs with increasing pressure. A dilute gasoline vapor sample was prepared by evaporating about 0.000001 liter liquid gasoline into 847 liters of air. This sample was then analyzed chromatographically while varying the degree of Pneumatic Focusing. The pressures used to generate the data for this example were 200 psi, 250 psi, 350 psi and 400 psi. For this example, the flow/pressure control valve was not adjusted. As a result, the resolved peaks move forward on the chromatograms with increasing pressure due to faster column flow rate at higher Pneumatic Focusing pressures.

FIGS. 28–32 are chromatograms of data collected at each pressure indicated above. The chromatograms are shown to the same vertical and horizontal scale. VOC components decreased significantly in concentration during this 5-hour experiment due to continuing dilution of the air sample.

By comparing FIGS. 28–32, the effects of increasing Pneumatic Focusing on the sensitivity and noise level are clear. Larger peaks just barely discernible in the chromatograms with the lowest pressures become much more discernible as the pressure increases. Noise levels are high in FIG. 28, which is at 200 psi. This may be due to flow instabilities through the pressure-regulating valve. Noise levels are much less in the rest of the chromatograms of FIGS. 29–32. Resolution of peaks occurs for certain compounds as the pressure increases. For example, a trio of peaks appears at approximately 10,900 reading numbers in FIG. 29. This same trio of peaks (which appear at about 10,500 reading numbers) is much better resolved in FIG. 31, collected at 400 psi. Thus, the data of FIGS. 28–31 shows that Pneumatic Focusing provides significant benefits for resolving and quantifying analytes in gaseous samples. These samples could have been pneumatically focused to even higher pressures with continuing improvement in sensitivity but such high pressures were not employed in this particular prototype instrument. Such limitation is not generally a limitation in Pneumatic Focusing with suitably designed apparatus.

Example 5

This example concerns gasoline vapor chromatograms made at pressures of 500 psi and 900 psi using a sample comprising 0.000001 liter liquid gasoline evaporated into 847 liters of air. Specifically, these chromatograms were taken at:

a. 500 psi, 30 standard cubic centimeters/minute;
b. 900 psi, 30 standard cubic centimeters/minute;
c. 900 psi, ~40 standard cubic centimeters/minute; and
d. 900 psi, ~standard cubic centimeters/minute.

Figure 32:
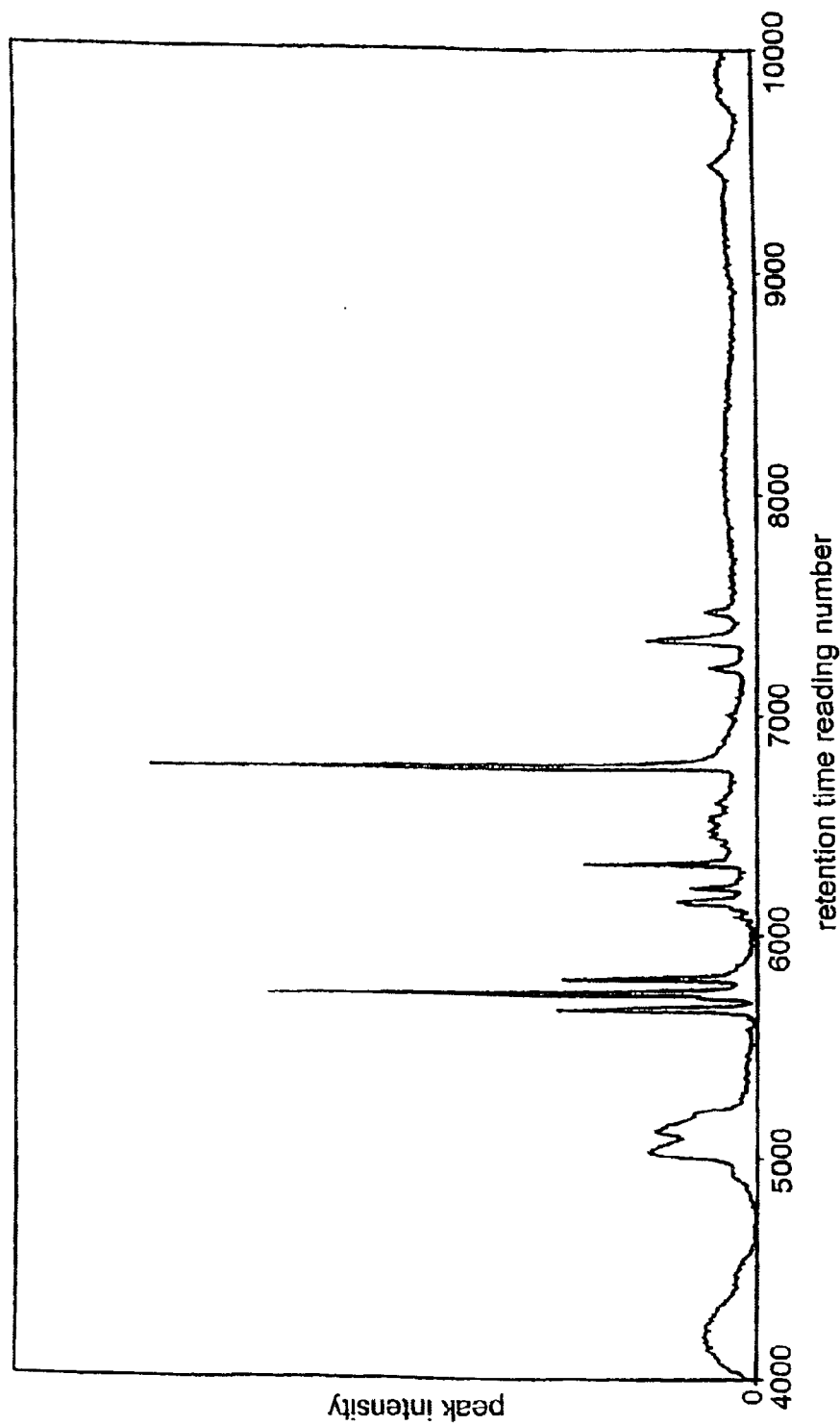
Figure 33:
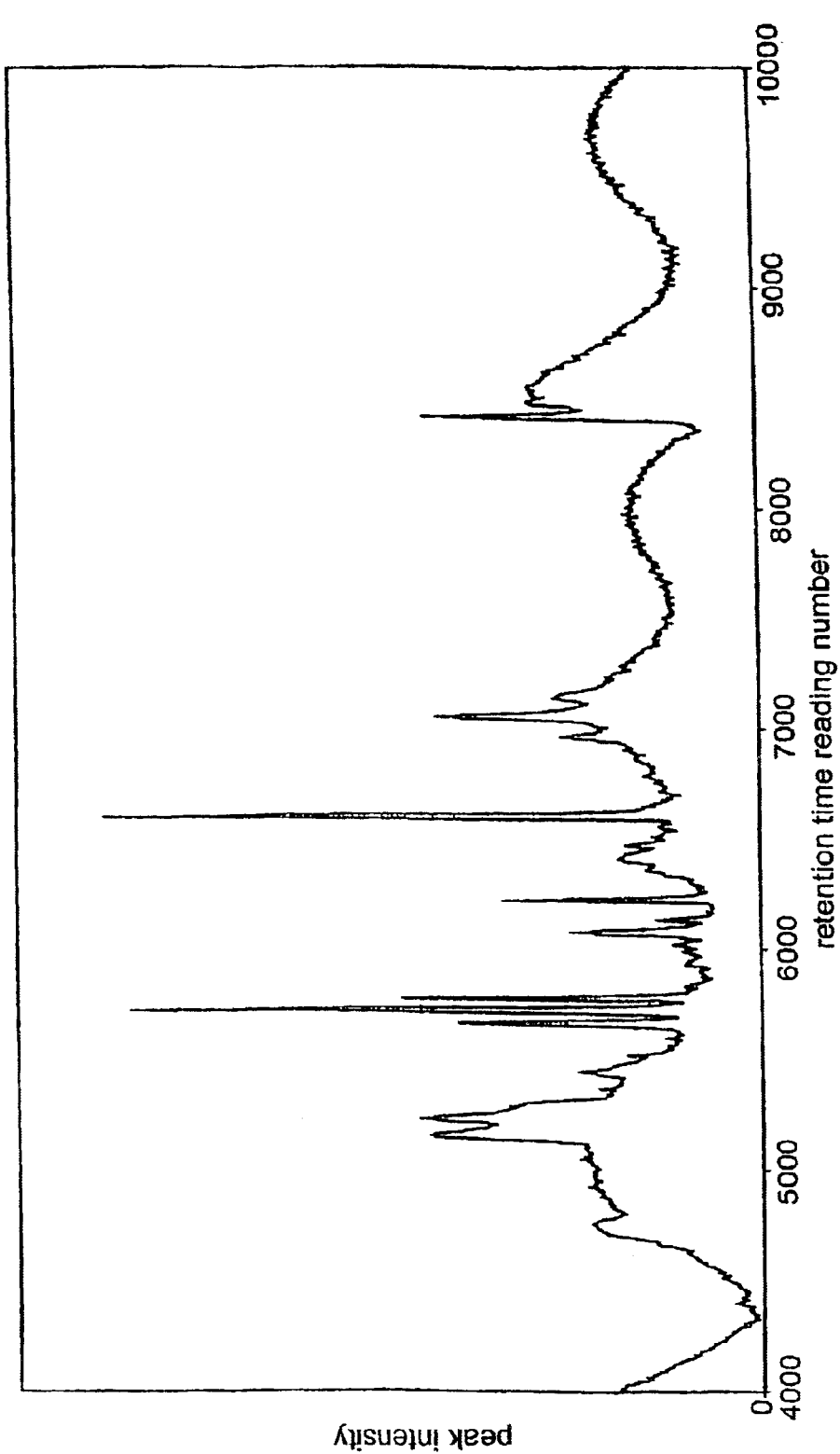

Linear flow was adjusted with the downstream valve to be about 30 standard cubic centimeters/minute in cases (a) and (b) to compare the effects of varying pressure and maintaining flow rate. These two chromatograms are shown in FIGS. 32 and 33. By comparing FIGS. 32 and 33 it can be seen that superior resolution is achieved for the peaks eluting between reading numbers 4,600 to 5,200 at 900 psi versus 500 psi. This is because of greater Pneumatic Focusing and narrower bandwidth occurs upon injection onto the separatory column at the increased pressure.

Figure 34:
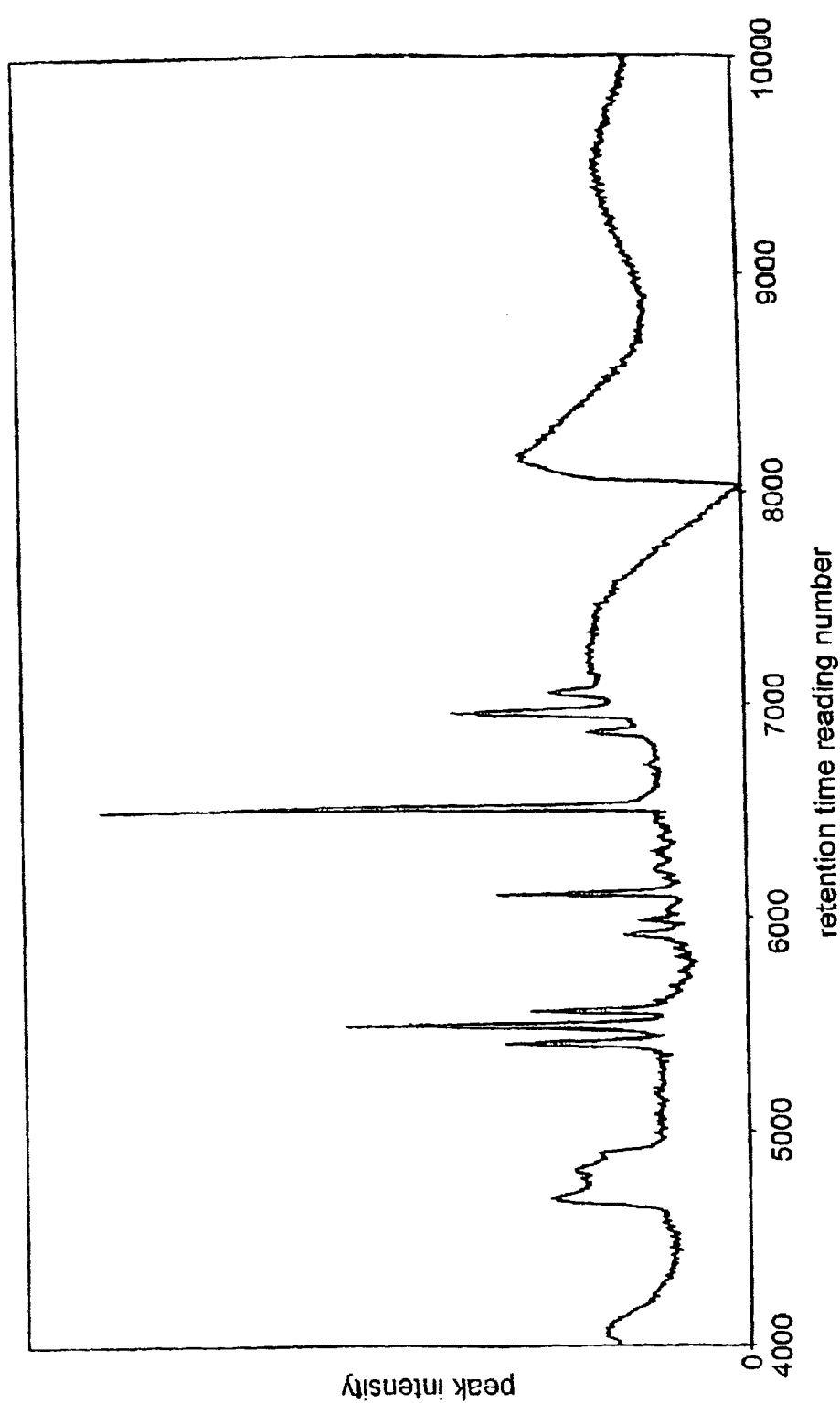

Pressures were maintained constant and linear flow rates were changed to investigate the effects of linear flow rate at a constant pressure on resolution. For example, by comparing FIG. 34 with FIG. 35 one can determine that the resolution is degraded even at the same column pressure. This likely is because a faster linear velocity prevents equilibration of the analytes with the column walls.

Figure 35:
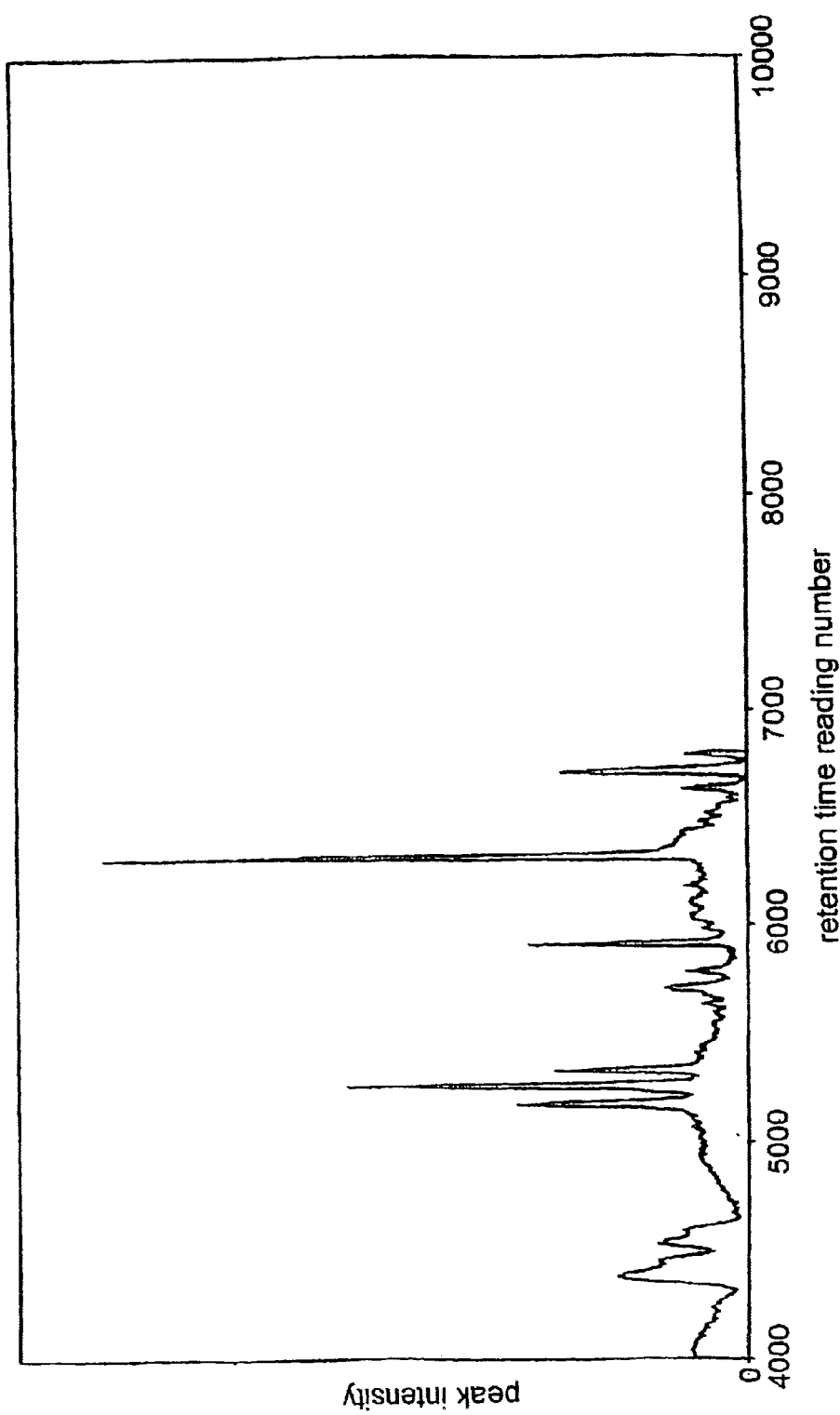

The elution time of FIG. 35 is much shorter than the elution time of FIG. 32 because of the higher flow rate at the same valve setting. The peak between reading numbers 4,000 and 5,000 is moved earlier in time and is better resolved than in FIG. 32, but not as well as in FIG. 34. FIG. 35 terminates early because the high flow rate carrier gas extinguished the flame at reading ~6800 reading number.

In all chromatograms of FIGS. 32–35 the tallest peak eluting between 6,000 and 7,000 has identical shapes (full width at half height). This indicates that this analyte is focused by concentration at the column head, independent of the carrier focusing pressure.

Persons familiar with chromatography will realize that resolution and analysis time are determined by balancing column pressure, linear flow rate, temperature, column length and diameter to name a few chromatographic parameters. FIGS. 32–25 indicate that in pneumatically focused chromatography, computer-controlled variations in column pressure, flow rate, and temperature can be optimized to suit the needs of a particular separation and quantification, just as in other types of chromatography.

The data discussed in this example was collected over a period of about 5 hours, drawing sample from a test vessel. Sample withdrawal over time decreased the concentration of the gasoline components, and their signal in the chromatographic system decreased as well. All chromatograms of FIGS. 32–35 have been normalized to constant peak height. This explains the variation in the relative noise in the baseline.

Example 6

Figure 36:
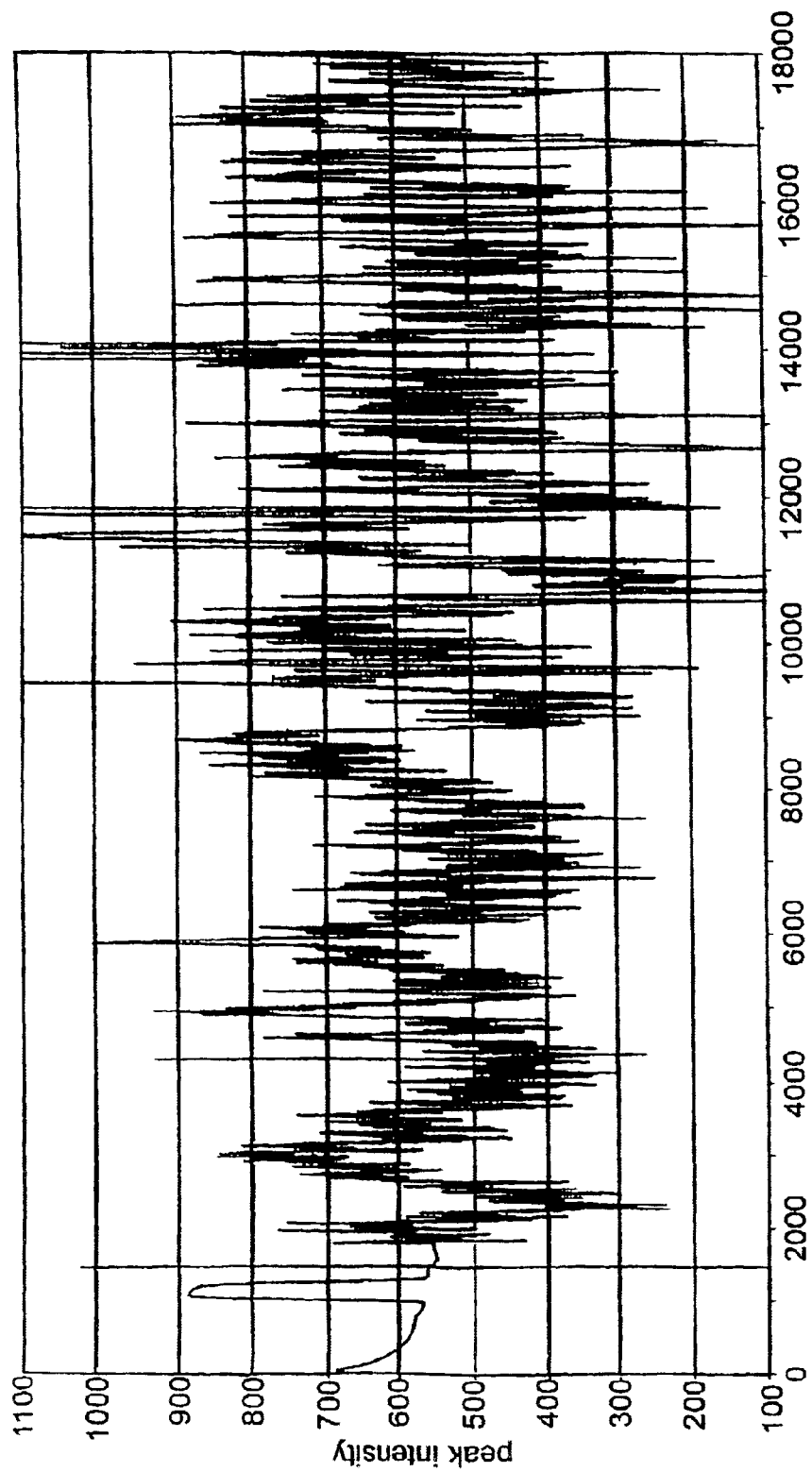
Figure 37:
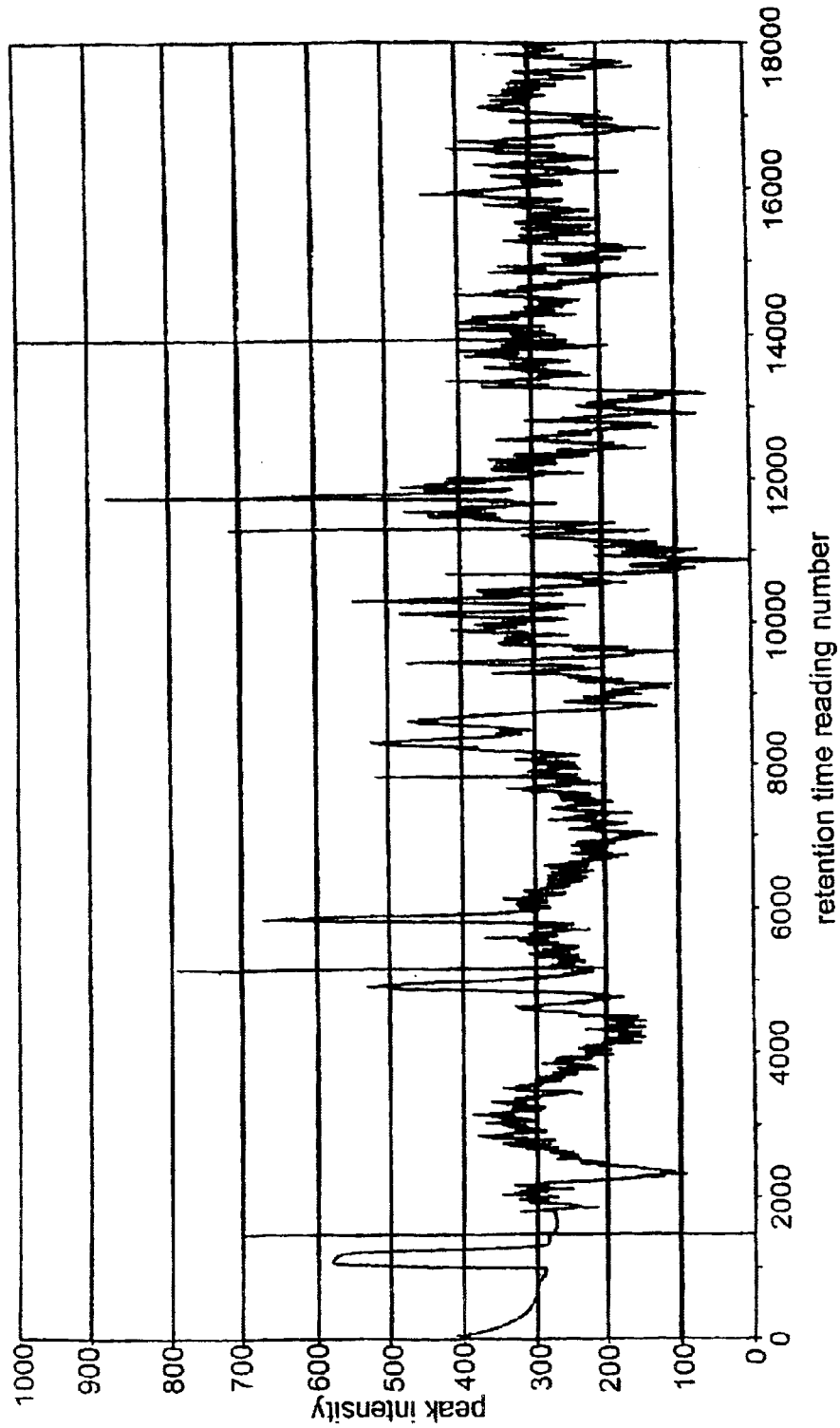
Figure 38:
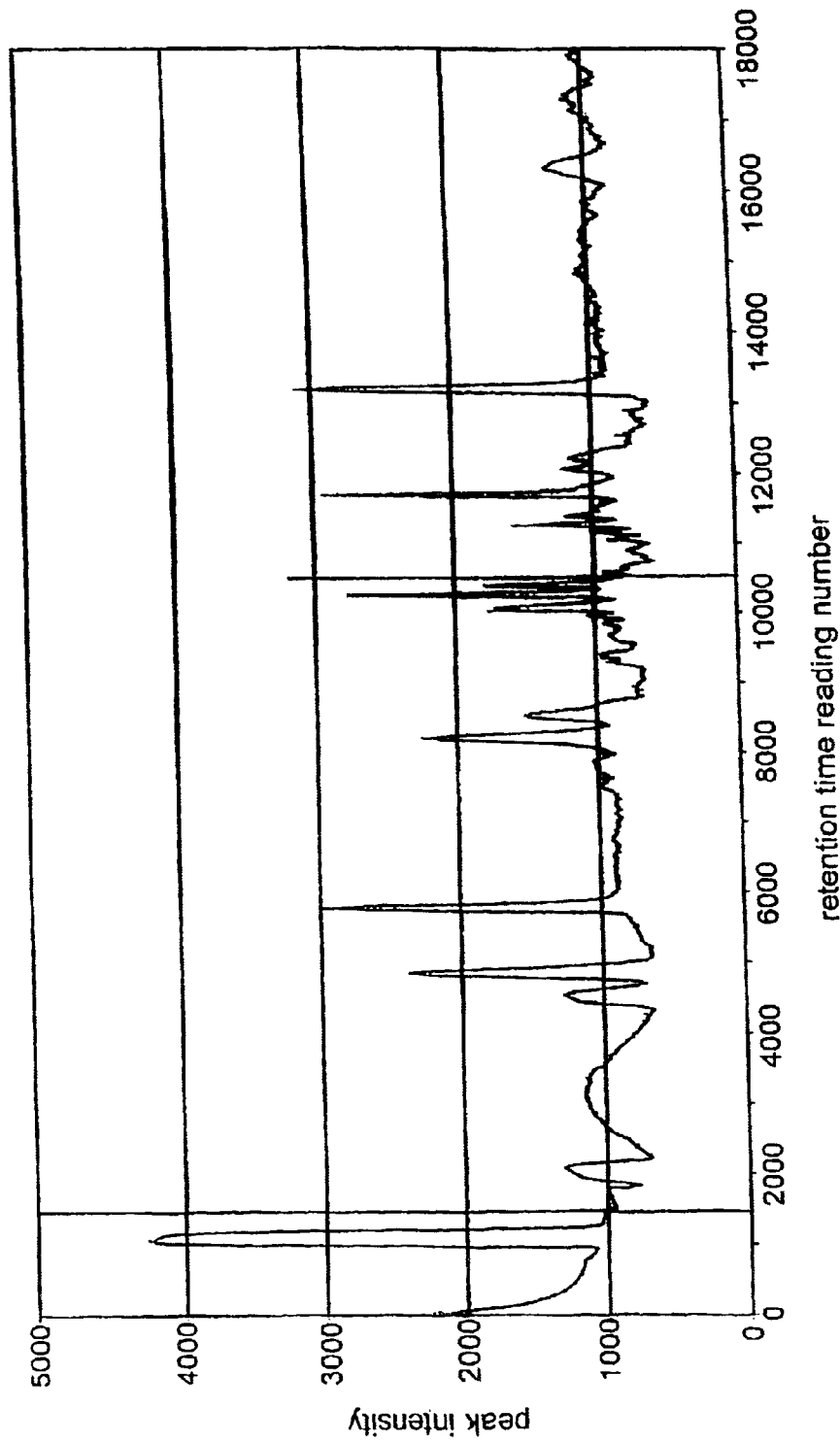

This example describes and illustrates the effect of chromatogram averaging. Air samples were continuously taken in Portland, Oreg., during a stormy period where wind speeds varied from about 30 miles per hour to about 80 miles per hour. The air sampled represents background Pacific Ocean air rapidly transported from the Oregon Coast to the Portland area, a distance of 100–200 miles. This air is quite clean, as evidenced by the virtual absence of a toluene peak in FIGS. 36–37. Toluene, often the most prevalent VOC in automobile fuel, normally is one of the most abundant VOCs in Portland Air. See FIG. 38.

a. FIG. 36 is a chromatogram taken in the middle of the windstorm.
b. FIG. 37 is an average of 10 chromatograms taken before and after the chromatogram shown in FIG. 36.
c. FIG. 38 is an average of 37 typical chromatograms of Portland, Oreg.'s polluted air for reference to FIGS. 36 and 37. By comparing FIG. 36 with FIGS. 37 and 38, it can be seen that chromatogram averaging improves the signal-to-noise ratio. Chromatogram averaging also increases the detection limit for individual VOCs by about a factor of 3, which is consistent with the appropriate square root of sample number statistical theory.

The methane peak has been attenuated by 1000× relative to the rest of the chromatogram in FIG. 36 and 37, but only by 100× in FIG. 38. In all but the most polluted atmospheres, methane ($CH_4$) is present at about 1.8 ppm. Thus, in FIGS. 36 and 37, equal areas on the rest of the chromatogram represent about 1.8 ppb carbon atoms (e.g., for hexane $C_6H_{14}$, an equal area would be 1.8 ppb C/6 or 300 ppt compound. The detection limit on the averaged chromatograms of FIGS. 37 and 38 is about 10–20 ppt for hexane without any further digital signal processing.

Example 7

This example describes using Pneumatic Focusing to concentrate and analyze analytes in gas exhalations of human subjects or patients. Although it is possible for a patient to breath directly into a sample loop, the ⅛ inch sample loops present significant flow resistance. We have designed a breath sampling device to overcome this difficulty. The sampling device, shown in FIG. 39, consists of a commercially available 100 cc ground glass plunger equipped syringe. A 4-way valve has two positions:

1. Sampling mode. In this position the sample pump purges room air through the sample loop (to remove adsorbents from previous samples) and the sampling syringe is connected to the breath sample line. In this mode the subject is given an individual breathing tube (sterile) which is then connected to the sample line. The patient breaths through this tubing, thereby inflating the syringe with 100 cc breath air. Greatest sensitivity and reproducibility is obtained in this breath sample if the subject exhales the last 100 cc of breath air that she can conveniently provide. This air has been in most intimate contact with blood vessels through the alveoli and contains the greatest (equilibrated) concentrations of metabolites, in contrast with the tidal lung air, which has made little blood contact. In this example the 100 cc sample volume is suitable to fill the two 40 cc sample loops.

2. Injection mode. When the syringe reaches its uppermost, 'full' position, the 4-way valve is switched to the inject mode. In this mode the syringe containing the breath sample is fluidly connected to the sample loops and the breath sample is pulled by the sample pump through the sample loop. Just as the syringe reaches the lowest 'empty' position, the computer is triggered to pneumatically focus the breath samples in the two sample loops into the chromatograph. In this example manual valve switching is employed. The breath sample is obtained in about 10–20 seconds and the sample pump requires 20–30 seconds to pull the sample into the sample loop. Pneumatic Focusing and injection into the chromatograph takes approximately an additional minute. The first VOC to elute from the column end then emerges about 2 additional minutes later. Remaining VOC and OVOC compounds emerge from their respective columns and are quantified by the respective FIDs as is normal in chromatography. This breath sampling device has the advantage that the syringe walls are only exposed to the breath sample for a brief period. This minimizes loss of condensable components in the current breath sample or addition of undesired components remaining from a previous subject. Additionally, the sample loops are purged with room air (or any other desired) gas during sample analysis, also minimizing carryover of adsorbed breath components from previous subjects.

Figure 39:
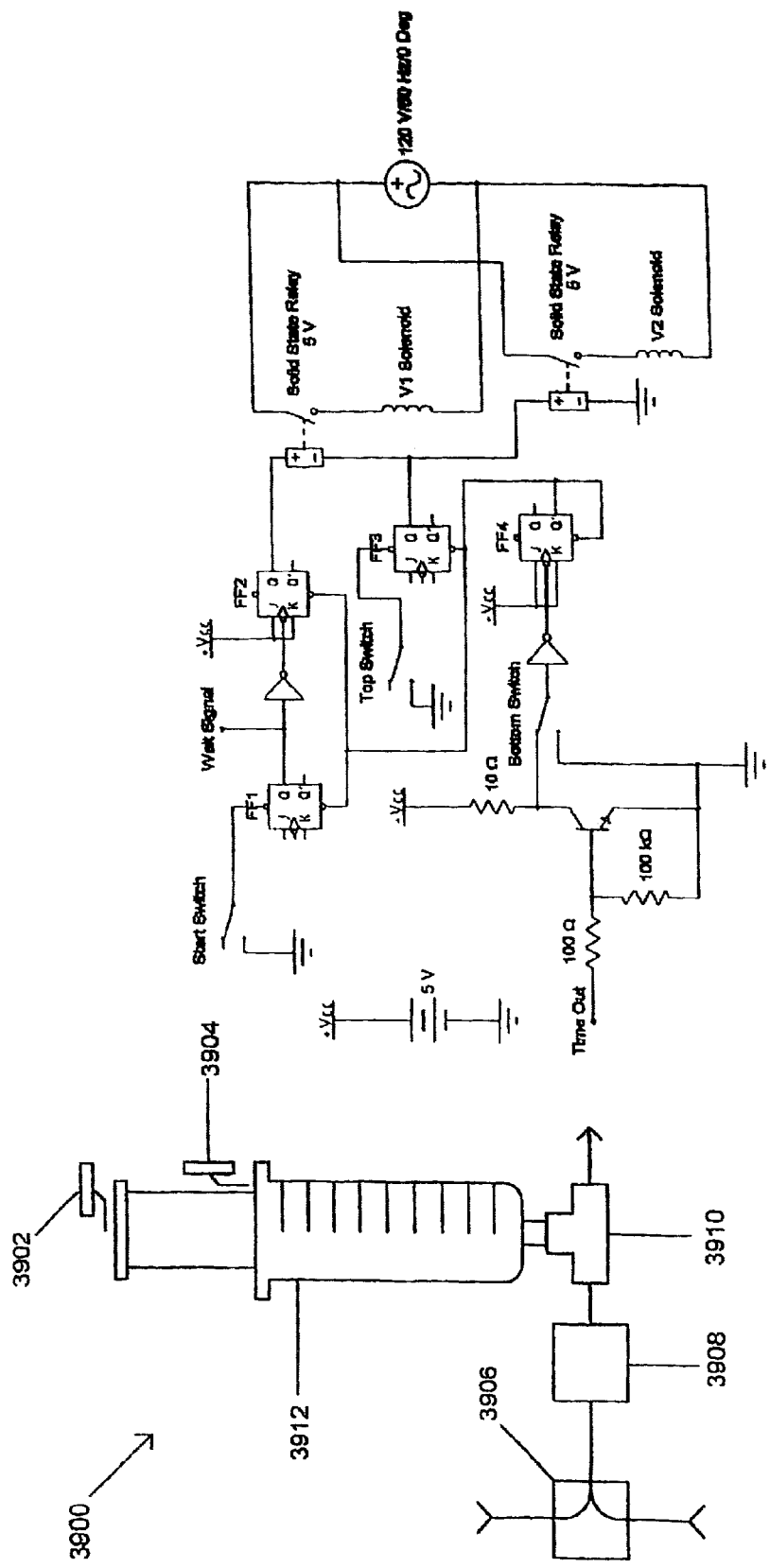

3. The valve switching was automated so that it is completely run by the computer. The only user intervention is to push a single button on the chromatogram to inform the machine that a breath sample is to be taken (FIG. 39).

Breath Analysis System

This system allows the GC to automatically process a breath sample by pressing a button and exhaling into the breath intake tube when prompted. Feedback allows the computer to acknowledge that a breath sample is being induced so that it may adjust sensitivity settings and appropriately annotate the file where it writes the data. If the system expects a breath sample, but does not receive one in a proper time period, then it will reset itself and continue with normal automatic operation sample b cal air.

Structure

The syringe is suspended within a chassis comprised of three equally spaced columns between a top and bottom plate. Peg holes in the column allow for the height of the syringe and top plate to be adjusted as necessary. The syringe and piston act as an expanding chamber to collect the breath sample. Switches at the top and bottom of the piston's range of motion allow the system to recognize the completion of the various steps in the breath analysis intake cycle. As the steps are completed, the system opens and shuts two electric solenoid valves to properly direct the breath sample as it's collected and processed.

Operation

Normal analysis of atmospheric impurities in local ov air is unchanged by this system.

Breath analysis begins when the user presses the "Breath Analysis Start Button." This causes a logic zero to be applied to the set input of Flip-Flop 1, causing its Q output to go high. This output is sensed by the computer as the "Wait Signal." When the computer detects the Wait Signal it enters a sub program that adjusts the data files and sensitivity ranges to those appropriate for breath analysis. Also, the computer begins counting until the Wait Signal disappears after the completion to the breath analysis intake cycle. If the computer finishes its count before the Wait Signal disappears then the computer will issue a brief 5Vdc "Time Out" signal to the system. This Time Out signal causes the saturation of a high gain transistor that places a logic zero on the clock input of Flip-Flop Four. When the computer removes the Time Out signal, Flip-Flop Four will toggle due to the collector voltage on the transistor returning to 5Vdc. When Flip-Flop Four toggles, it places a logic zero on the clear inputs of all the flip-flops. This causes the system to reset and the Wait Signal disappears. If the Wait Signal does not go away, then the system can tell that it is in the process of a breath sample since the piston is depressing the bottom switch.

When the wait signal appears, after pressing the start button, the change in voltage is sensed by Flip-Flop Two's clock and causes it to toggle. This makes the second flip-flop produce 5Vdc on its Q output. This 5Vdc is applied directly to the input of a 5Vdc to 120Vac solid state relay, forcing it to conduct since its negative input is tied to Flip-Flop Three's Q output at logic zero. When the solid state relay conducts, 120 Vac is applied to Valve One. Valve One is normally orientated to pass only outside air, but when energized it opens a path between the Breath Intake tube and the syringe. Breathing into the tube causes the piston to rise until it closes the top switch.

When the top switch closes, a logic zero is applied to the set input of Flip-Flop Three. This causes Flip-Flop Three's Q output to go high and stop the conduction through the relay powering valve one and cause the solid state relay for valve two to conduct. When valve two is energized, the syringe is sealed from further gas intake and a pump draws the breath sample into the system's sample loops. As the sample is drawn from the syringe, the piston lowers until it clears the bottom switch. When the bottom switch opens the clock input on Flip-Flop Four goes from logic zero to logic one, toggling the flip-flop, and resetting the system. When the system is reset, the Wait Signal drops to zero. The computer then initiates the sample injection sequence and continues according to its internal program.

Figure 40:
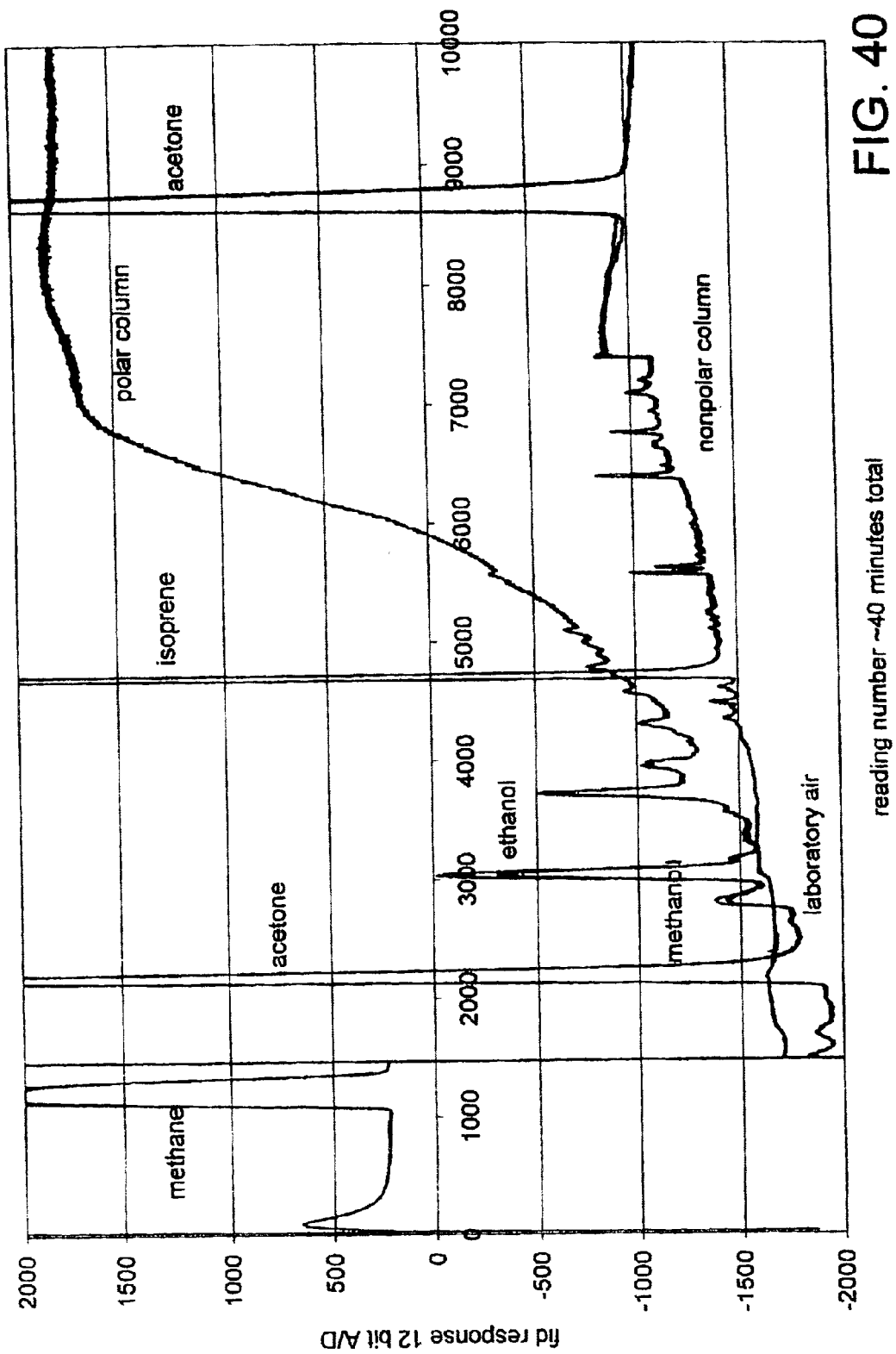
Figure 41:
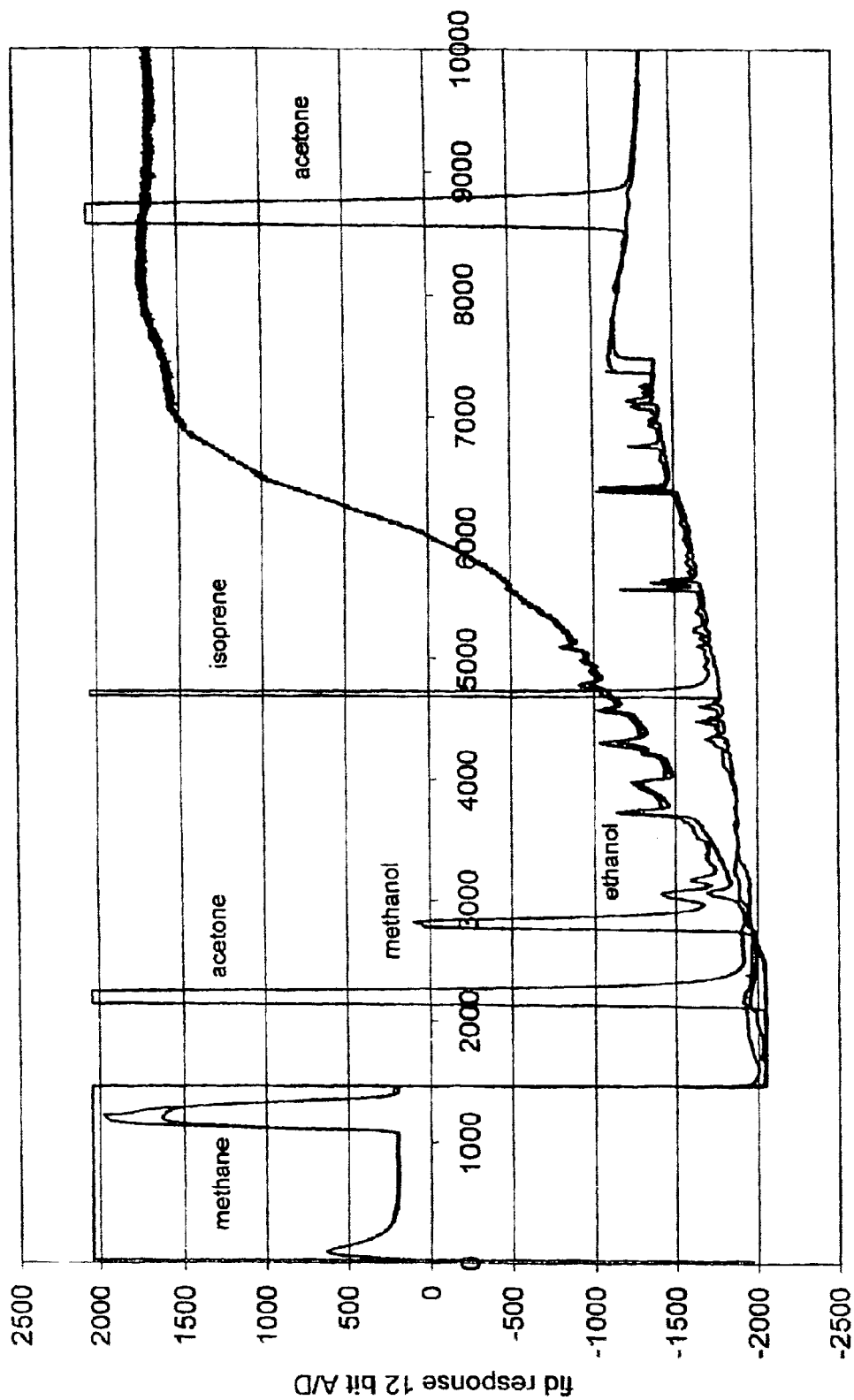
Figure 42:
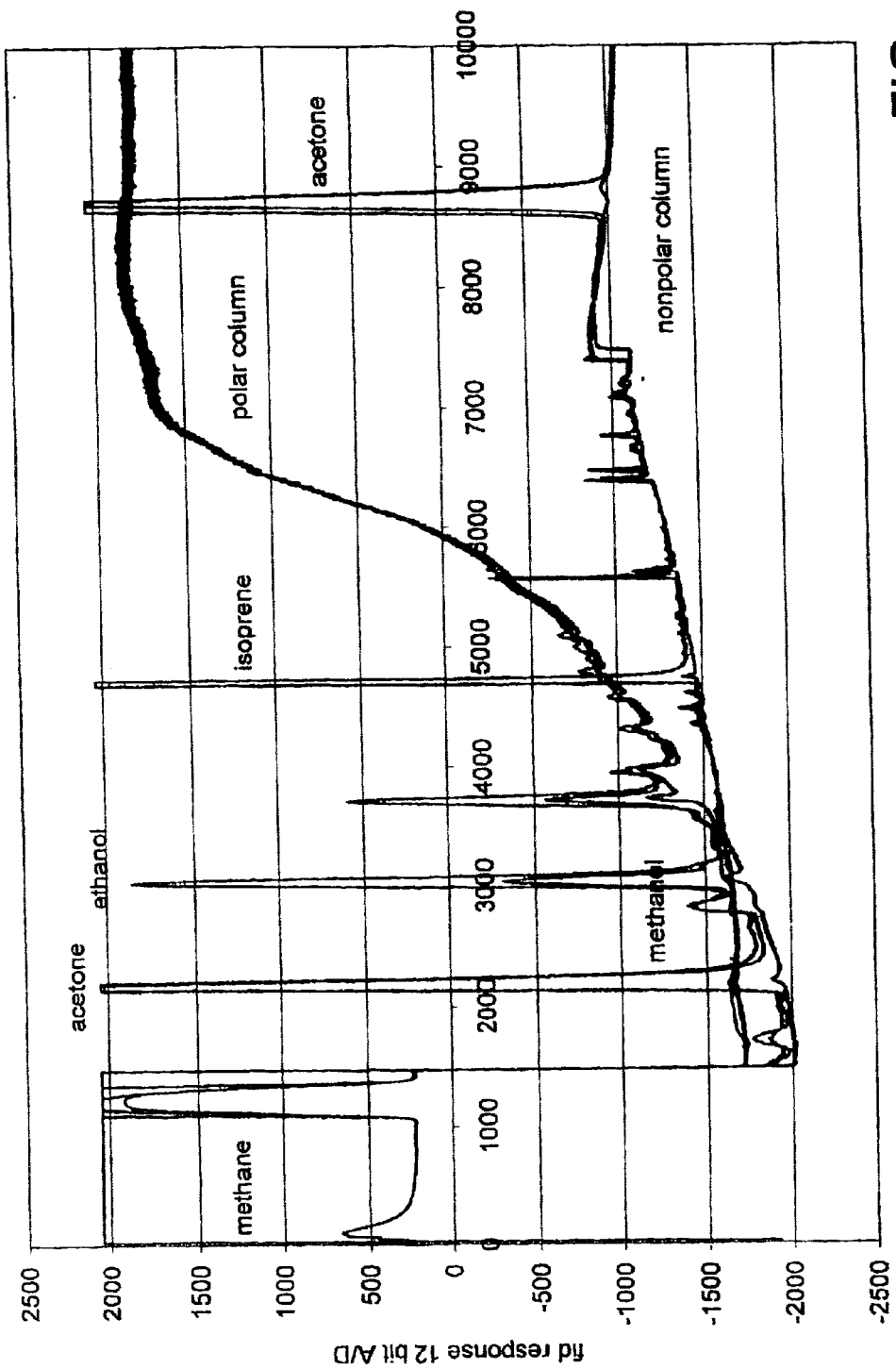
FIG. 42 is a chromatogram of breath exhalation from a person indicating metabolic effects.
Figure 43:
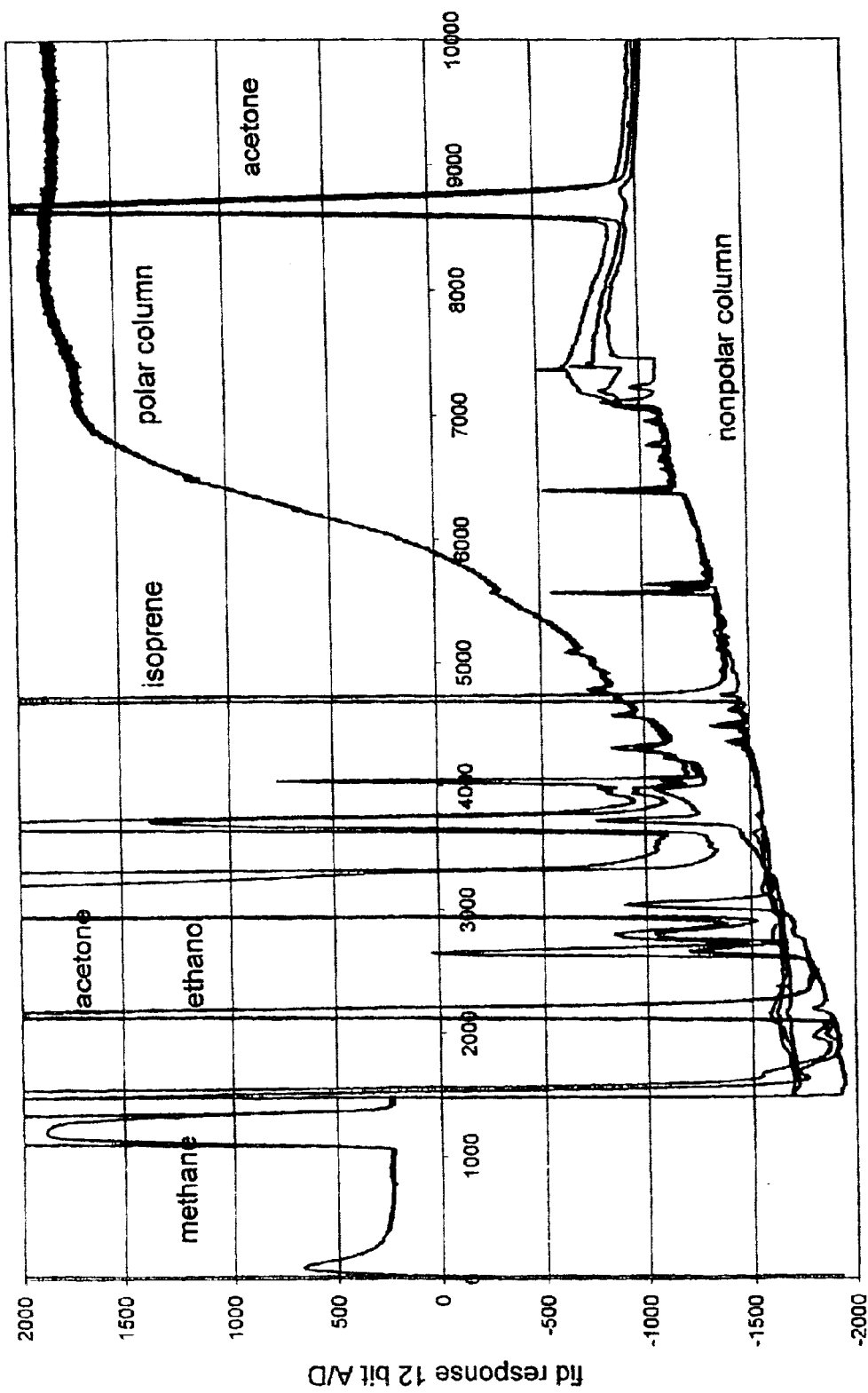
FIG. 43 is a chromatogram of breath exhalations illustrating the detection of alcohol following consumption.
Figure 44:
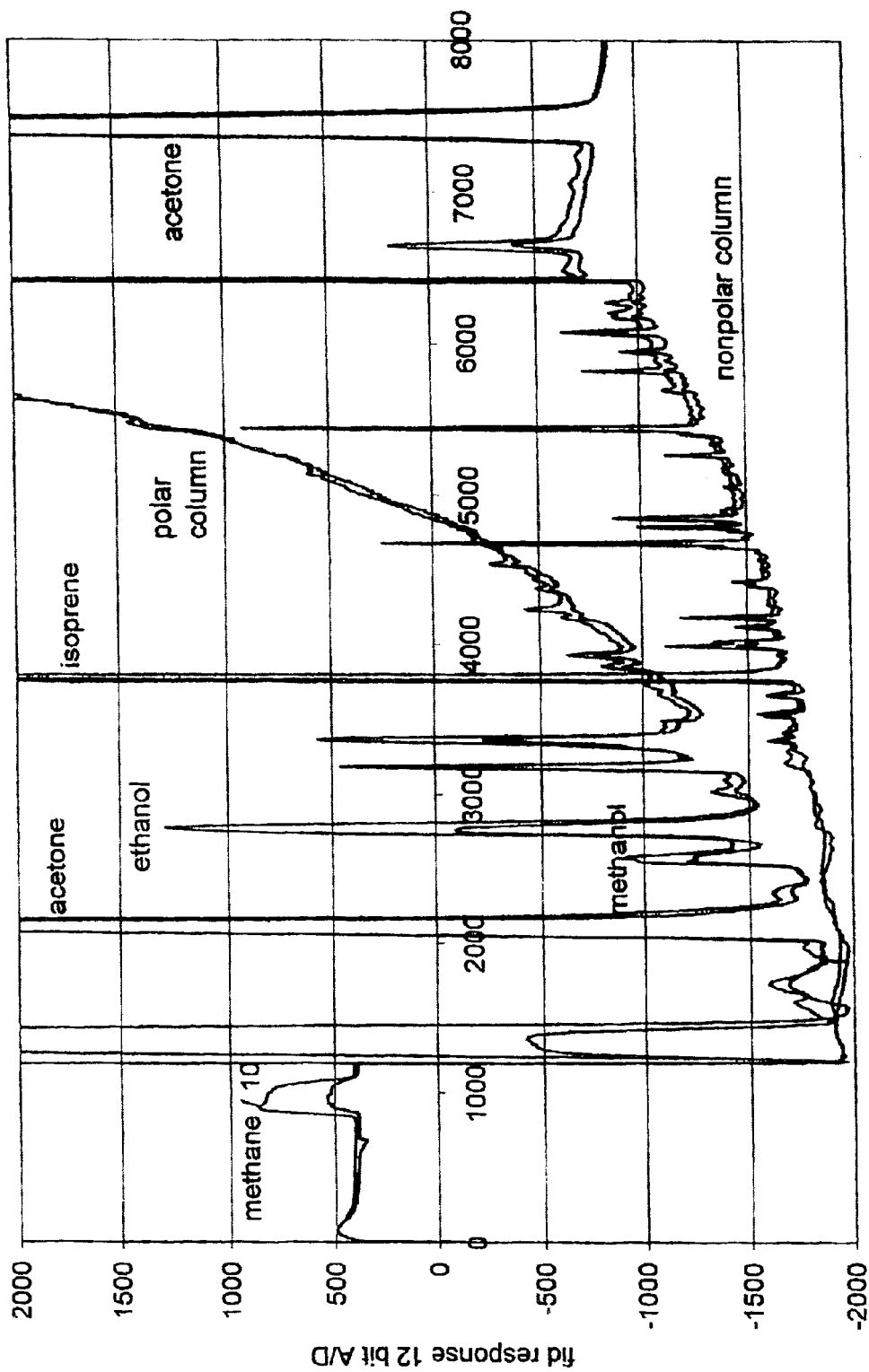
FIG. 44 is a chromatogram of breath exhalations from two heavy smokers.

1. One working embodiment of the breath analysis system just described was utilized to analyze human subjects' breath. FIG. 40 presents two chromatograms of a subject's breath taken 50 minutes apart and a third chromatogram of laboratory air inhaled by the subject. Each breath sample was analyzed on two columns, one for nonpolar (VOC) compounds and the other for polar (OVOC) compounds. Thus there are 6 total chromatograms. Major components are acetone (which appears on both columns), isoprene and methanol, all concentrations virtually identical in the subject's two breath samples; and ethanol, which differs by about 10% between the two samples. All of these compounds had very small concentrations in laboratory air. Among the minor compounds, many but not all were present in laboratory air and were therefore simply inhaled by the patient. Detailed analysis will be required of those minor compounds not inhaled which could be quite important in, for instance, disease diagnosis. The methane peak is reduced 10× in all these chromatograms and in laboratory air serves as an internal standard at 1.8 ppm. Methane in this subject's breath is about twice the ambient concentration. A breath sample from another subject is compared with laboratory air in FIG. 41. Major components are the same as FIG. 40, except for methanol which far exceeds the ethanol concentration. This subject suffers from Addison's disease. No other subjects analyzed so far have shown this methanol/ ethanol concentration inversion, but further analysis is required before any conclusions can be reached about potential disease diagnosis. FIG. 42 compares breath samples from the same subject as FIG. 40, in this case samples taken resting and after vigorous exercise. Laboratory air inhaled by subject is shown as well. There are a total of 6 chromatograms, 3 each on two columns as in B1. Methanol, acetone and isoprene concentrations were unaffected by vigorous exercise. Methane and ethanol were reduced by ~⅔ following vigorous exercise. Minor components require further detailed analysis. FIG. 43 shows ethanol metabolism in a beer-drinking subject. These chromatograms were taken after drinking 3 cans of beer over 120 minutes. Laboratory air is shown as well. Samples taken 50 minutes and 1 beer apart. The nonpolar column shows only very small changes in breath compounds. The polar column shows significant changes. Methanol, isoprene and acetone concentrations were unchanged by beer consumption. Ethanol shows large further increase after consuming 3rd beer. Notice the appearance of several apparent metabolites, which appear before methanol and after ethanol and whose concentration increases with time. Finally, FIG. 44 compares breath samples from a husband and wife, heavy smokers, about 30–60 minutes after smoking. In this case the nonpolar (VOC) column shows a large number of compounds while the polar column also shows several compounds not present in the breath of nonsmokers.

It is clear from these examples that the most efficacious analysis of patients' or subjects' breath for native compounds would be to expose the patient to air zero for a sufficient length of time that the body is purged of extraneous compounds. Such experiments are known in the art. What is not realized is that a more efficient approach would be to carry out these breath characterization experiments in regions which naturally have ultra clean air so that minimal non-native VOCs, OVOCs, etc. would be present. Some suitable locations would be the west coast of the Pacific NW, Hawaii, etc. Such areas are exposed under correct wind conditions to air which has remained over the Pacific Ocean for a long period and has been purged of many background compounds in natural processes.

Example 8

This example concerns the absorption spectroscopy of several gases subjected to Pneumatic Focusing in a UV/VIS absorption cell.

Figure 49:
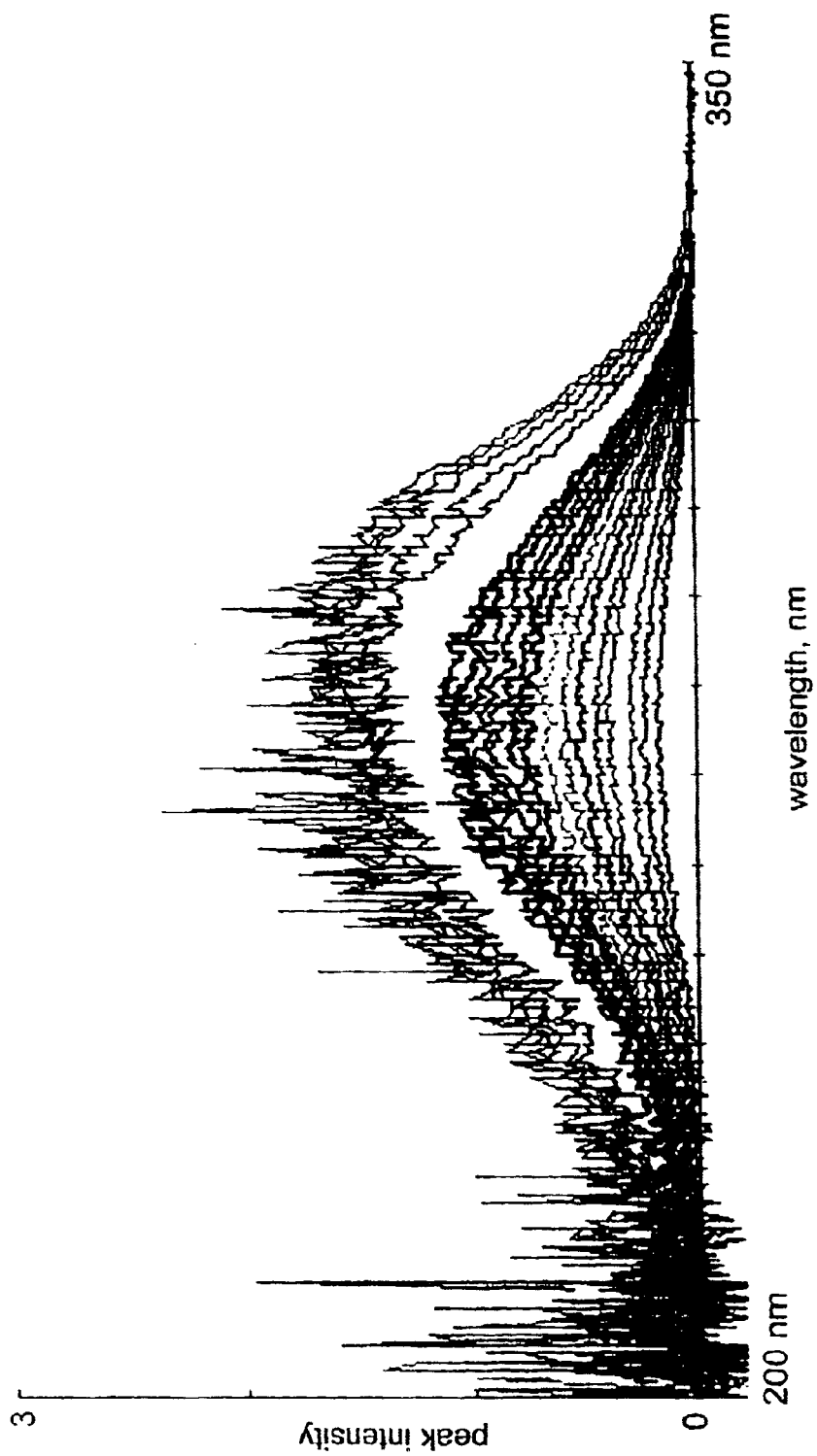
FIG. 49 illustrates pneumatic focusing of acetone at pressures of 15 to 600 psi.

FIG. 49 illustrates Pneumatic Focusing of acetone in room air at focusing pressures ranging from 15 to 600 psi.

Figure 45:
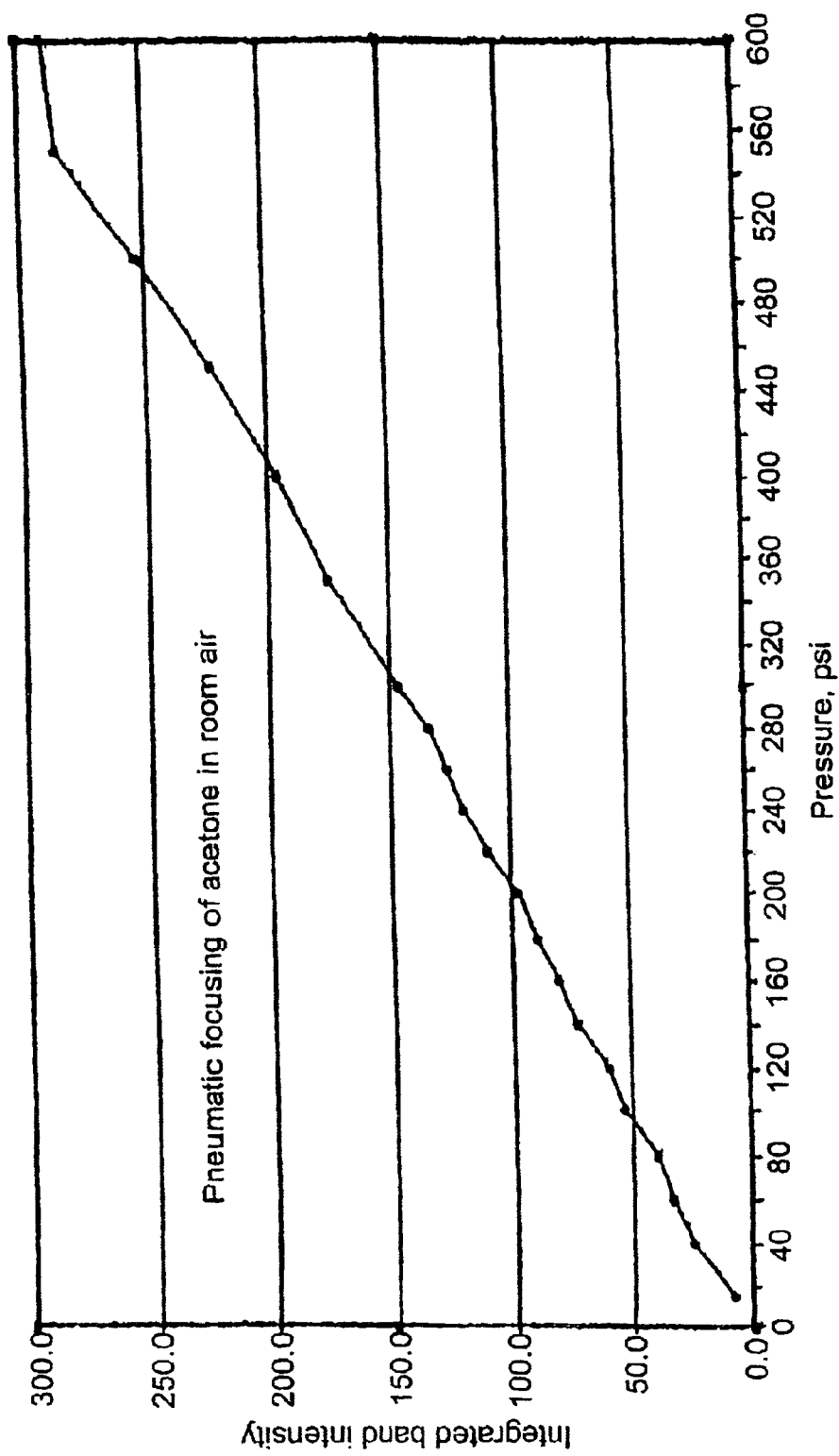
FIG. 45 is a calibration curve.

FIG. 45 is a calibration curve based Pneumatic Focusing of acetone in FIG. 49.

Figure 46:
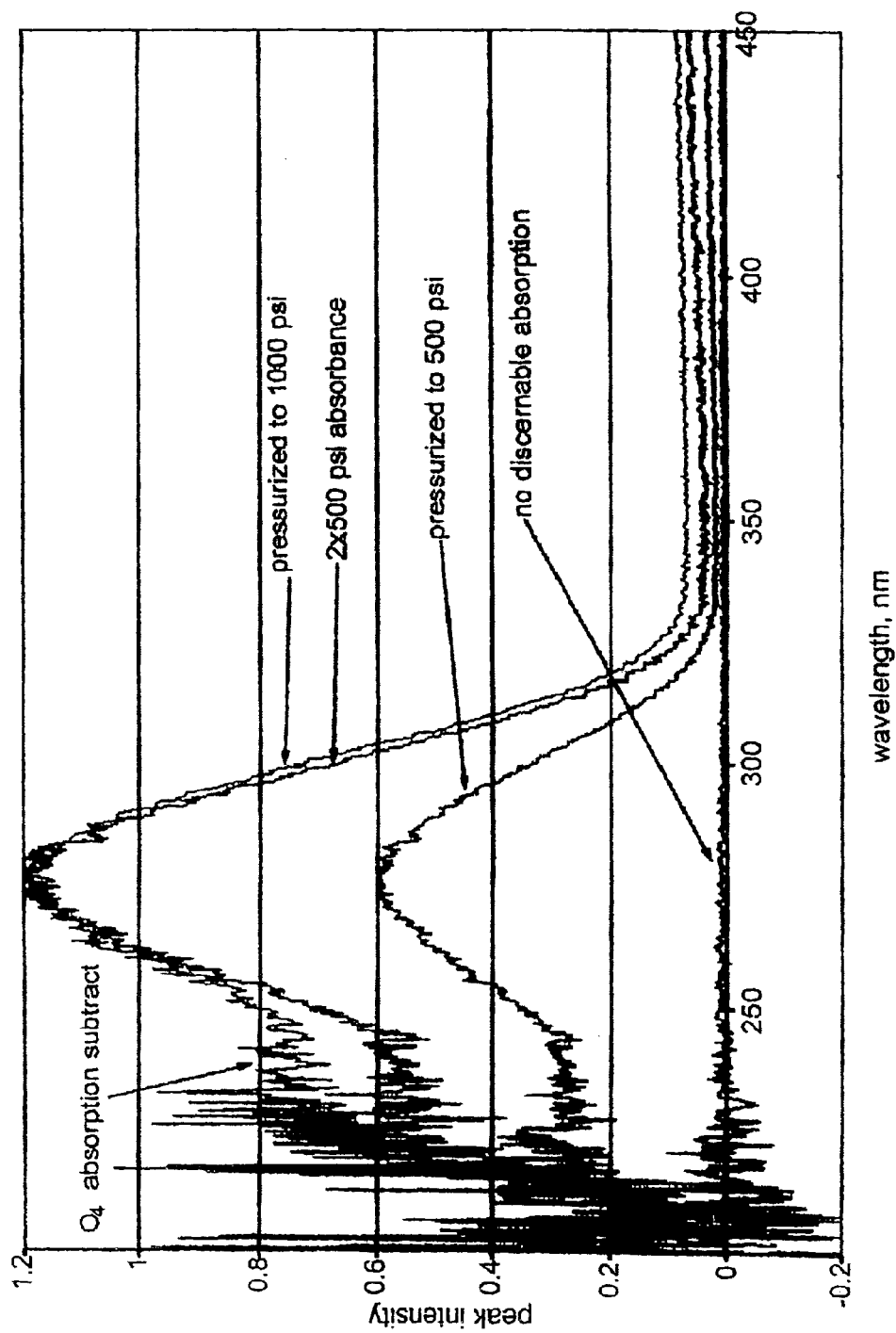
FIG. 46 is a chromatogram of acetone focused to 1,000 psi.
Figure 47:
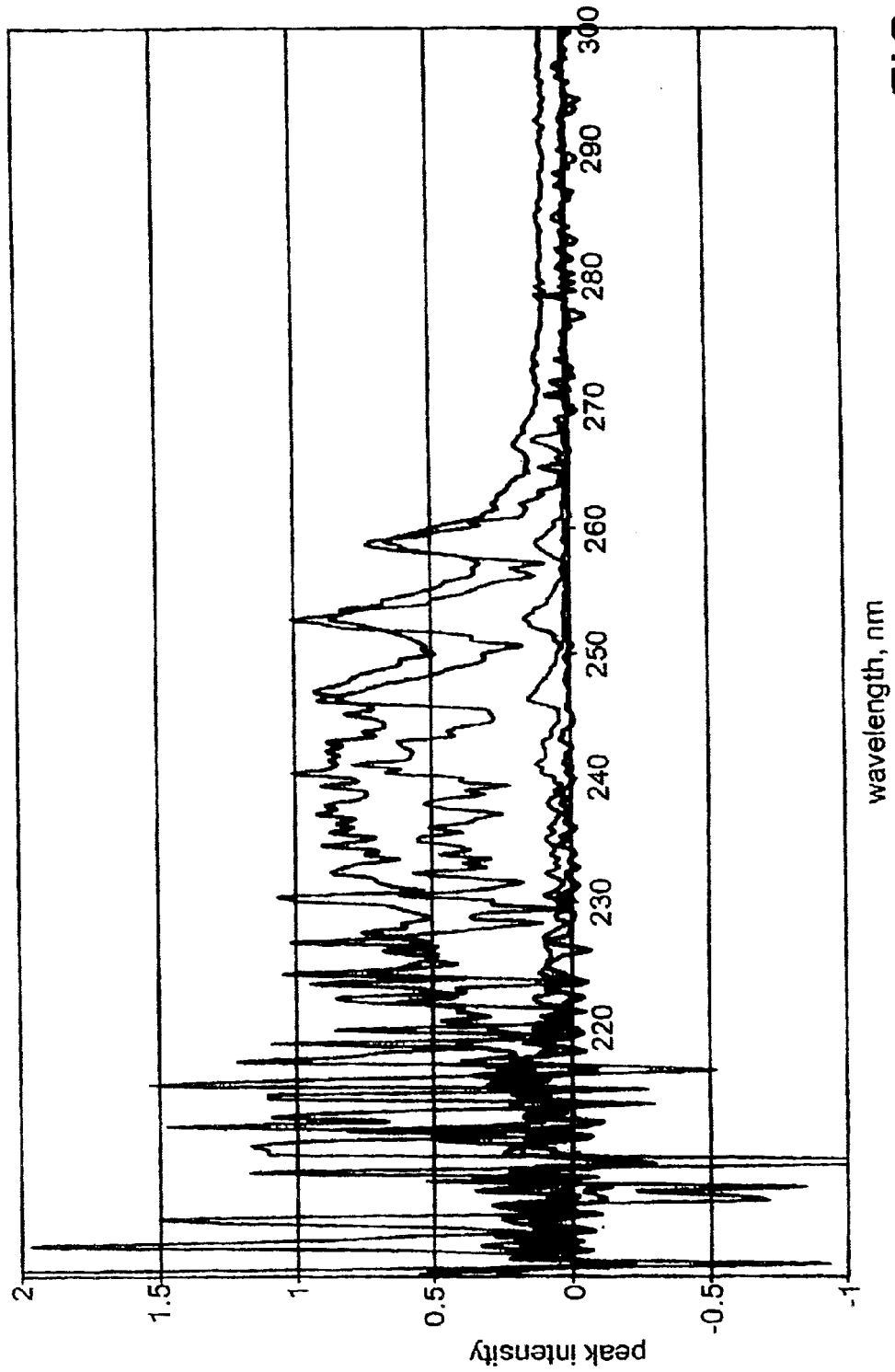
FIG. 47 is chromatogram of benzene focused to 1,500 psi.

FIG. 46 shows Pneumatic Focusing of acetone in room air: the lower curve at atmospheric pressure shows no discernable acetone absorption due to low concentration. Significant absorption occurs in the middle curve focused to 500 psi. The upper 1000 psi focusing curve is in excellent agreement with twice the 500 psi curve, indicating good linearity. The acetone absorption band is contaminated by O4 UV absorption at the short wavelength end. Although not required for quantification (which can occur at longer wavelengths), this O4 absorption could be subtracted as is familiar to those experienced in spectroscopy.

Figure 48:
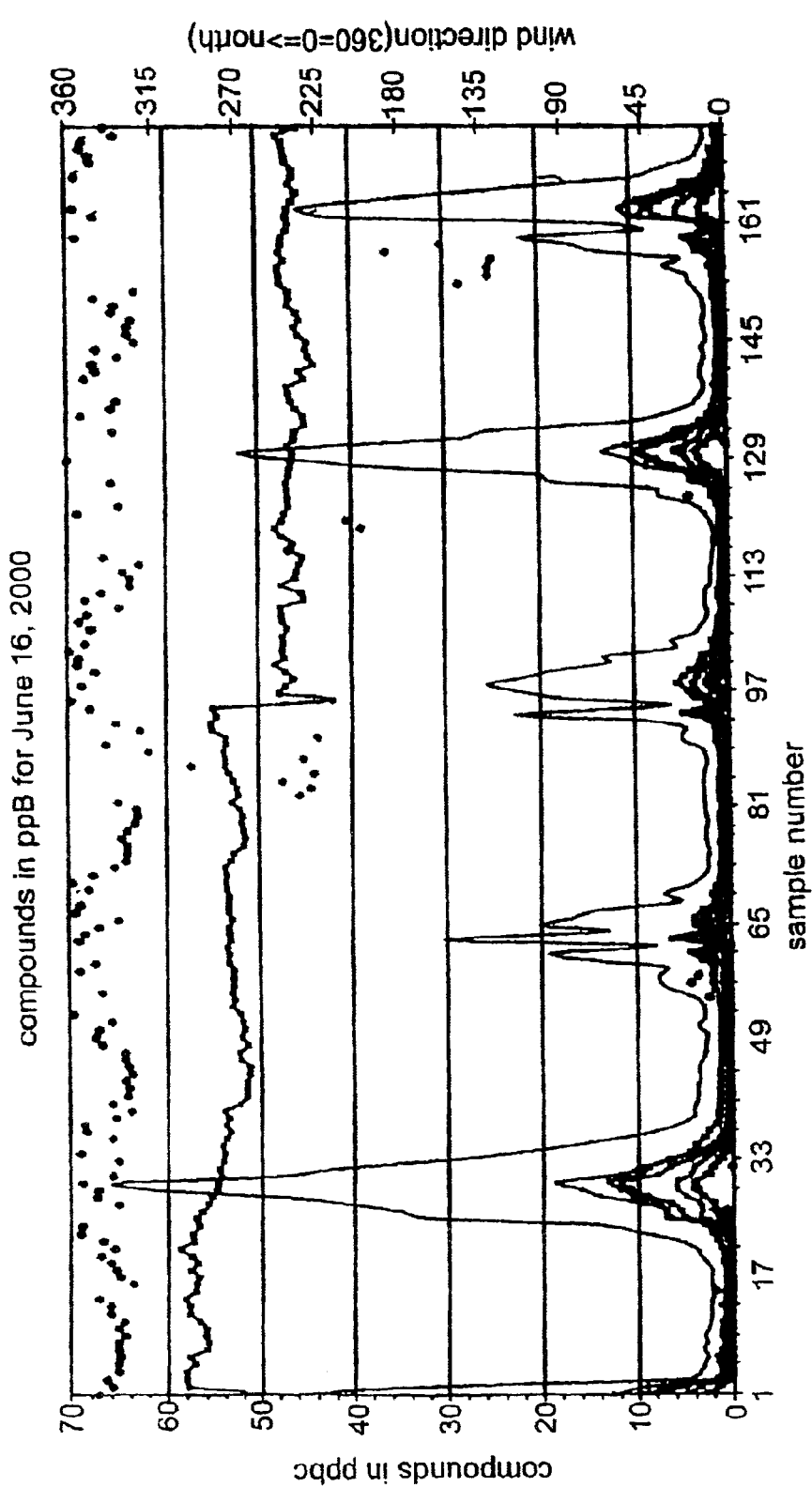
FIG. 48 is a chromatogram illustrating determination of a sample and accounting for wind direction.

FIG. 48 illustrates benzene pneumatically focused in room air with spectral interference at short wavelengths by O4 absorption. The lower curve is at atmospheric pressure. The next curve illustrates 250 psi and the upper curves 1,500 psi compared with 6 times the 250 psi curve. Good linearity in band structure at the long wavelength end although the 1500 psi curve shows considerable broadening (shallower valleys) compared to 6*250 psi spectrum. At 1,500 psi the short wavelength spectrum shows interaction bands with oxygen which result in enhanced absorption and different band structure.

Example 9

Figure 6:
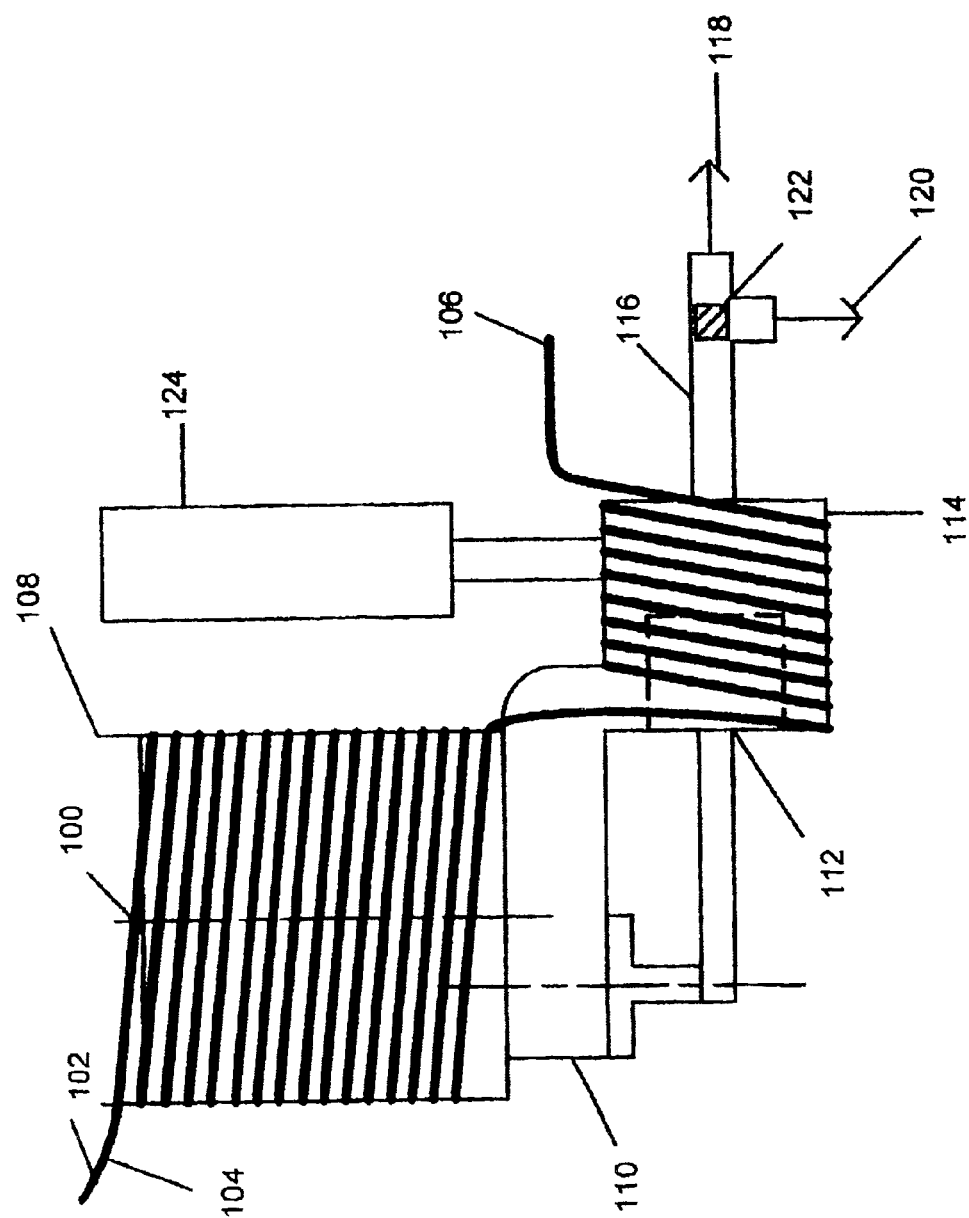

This example describes using Pneumatic Focusing to continuously condense water vapor, with continuous separation of the condensed water from the pneumatically focused gas sample for separate analysis. A gaseous sample containing water vapor is obtained. The gaseous sample is then pneumatically focused as described above. Condensed water is continuously separated from the pneumatically focused sample as illustrated in FIG. 6. Each part of the sample could be analyzed separately. For instance (without limitation) the focused gas sample could be directed to a gas chromatograph as described above. The condensed water would then be directed to another analytical device. An illustrative delivery calculation is given here. Consider a miniature compressor pneumatically focusing 1 liter of ambient air per minute. Assume this sample has 1% water vapor by volume. (Saturation at STP is about 3% so this would be about 33% RH). Compression to 45 psi would just start water to condense. Pressurization to 500 psi would condense virtually all the water vapor. Using PV=nRT, this would produce $$n=0.01 \text{ atm}*1 \text{ L}/(0.082 \text{ L-atm/K-mole}*298K)=4.1 \text{ e}-4 \text{ mole H2O}$$

$$4.1 \text{ e}-4 \text{ mole}*18 \text{ g/mole}=7.4 \text{ e}-3 \text{ g H2O}=7.4 \text{ e}-3 \text{ ml}=7.4 \text{ uL}=7.4 \text{ e3 nL H2O}$$

This is sufficient for pH and other ionic measurements by microelectrodes. Assume, for instance, that gaseous nitric acid was present at a concentration of 1 ppbV in the same liter of air. This is a very modest concentration. 1 ppb=1 e−9 atm of nitric acid $$n=1 \text{ e}-9 \text{ atm}*1 \text{ L}/(0.082 \text{ L-atm/K-mole}*298K)=4.1 \text{ e}-11 \text{ mole}=0.041 \text{ nmole nitric acid}$$

Nitric acid is extremely water soluble and all would dissolve (see above) to produce a concentration of 0.041 nmole/7.4 e3 nL H2O. This is a molarity of 5.4 e−6 with a pH of 5.3-acid condensate whose pH would be easily measured by a microelectrode described below.

This analysis could be made as the condensed water flowed continuously past the microelectrode which would not alter the solution. Since pH measurement can be made on 10 uL by commonly available microelectrodes, the averaging time of the pH measurement in Pneumatic Focusing system would be 1 minute. One example of a microelectrode source is Lazar Products (http://www.lazarlab.com/). Their literature states that pH may be determined using their Micro combination pH (BNC Conn) PHR-146B electrode. They offer numerous other electrodes for specific ions of atmospheric interest. These electrodes can make measurements in as little as ¹⁄₁₀ of a drop (5 uL) at a depth of 0.1 mm. In addition to pH, a variety of other specific ions could be determined in a nondestructive fashion as the water sample passed to another analytical device such as a spectrometer cell which also performs a nondestructive analysis. Finally, the water sample could pass to a the sample inlet of a destructive device such as a Pneumatic Focusing or other gas or liquid chromatograph.

The previous considerations would apply equally if some additional acidic material were present in the air sample in either the gas or the particulate phase, as Pneumatic Focusing would capture all water soluble materials.

Example 10

This example demonstrates and illustrates a method for determining the directional distribution and emission strength of emission sources around a single PFGC monitoring station. As such the method can be useful for locating and quantifying pollution sources without reference to emission inventories, stack monitoring, or any direct or in situ analysis. It is thus useful for confirming or denying the validity of emission inventories which are notoriously unreliable. (Employment of two of more PFGCs provides a much more powerful system and is discussed in the next example).

In a proof of principle demonstration we have used PFGC to locate and quantify an intermittently operating source upwind from our PFGC. An automatically operating, continuous, Pneumatic Focusing analysis system was set up to analyze samples taken from the roof of our building. Wind speed and direction were also measured and recorded every 10 minutes using commonly available instrumentation. Samples were continuously obtained about every 40 minutes, pneumatically focused and analyzed as described above.

The distribution of such pollutants downwind from a source is commonly described by a Gaussian Plume Model in which the pollutants diffuse vertically and horizontally as they are carried downwind toward a receptor site. (See, for instance, J H Seinfeld and S N Pandis, Atmospheric Chemistry and Physics, John Wiley & Sons, 1998 pp. 880–957, especially pp. 945–47 which treats multiple source plume models). Essentially, the pollutant distribution follows a gaussian distribution both horizontally or vertically and this gaussian half-width, standard deviation, or other measure of dispersion increases with downwind flow. Spreading is caused by turbulent diffusion and appropriate diffusion coefficients are available which are a function of surface structure (roughness) and wind speed. Such models are commonly employed in the field of air pollution science and engineering and are familiar to those experienced in this field. This gaussian behavior may be exploited to characterize pollutant emission sources as measured downwind by a single PFGC.

FIG. 24 presents an exemplary subset of chromatograms obtained in the ambient atmosphere during a period of about 10 days. As described above, FIG. 20 shows the integration of a single GC peak by Integpro.bas. FIG. 48 presents concentrations of pollutants as determined with reference to the methane concentration by the program Integpro.bas described above. Several variables are shown on this graph. The points represent wind direction as determined about every 10 minutes. The right hand axis indicates that wind was substantially from the north (360 degrees, occasionally wrapping around to zero degrees) during this period. Methane is taken constant at 1.8 ppm and drift in its concentration (shown as the continuous line in the center of the figure) is taken as due to instrumental drift. The abrupt drop in methane response at about sample 97 is due to a change of cylinder gas to the FID. Pollutant concentrations are normalized to this changing response. The remainder of the curves are a subset of individual pollutants as determined in this study. Note that some pollutant species are identified as to chemical identity while others are currently unidentified and expressed in terms of their retention time on the GC analysis. Reference to a map of the subject area indicated that the major pollution sources probably originated in an industrial area approximately 5 miles upwind. With a single site and no significant shift in wind direction it is not possible to determine exactly the location of the source or the source strength, since it is unknown how far the source is from the vectored wind direction. However, it is possible to determine a lower limit to the emission source strength by assuming it is centered directly upwind and that emissions originated in the industrial area. If the source is not directly up wind, the maximum would not be received at the PFGC monitoring site and the actual source rate would be larger. This emission source strength could be determined for each of the individual pollutants measured by PFGC assuming they all could be assigned to the same source. In this particular situation, the emission site would have to be located by ground truthing. Once this were done, the Gaussian Plume Model could be used to quantify emission sources for each individual compound, assuming they originated from the same single source. The next example carries the analysis a step further.

Example 11

The previous description deals only with the actual pollutant concentrations measured by PFGC. A more informative and more thorough approach may build upon those results. To carry out this more complete analysis the output concentrations from the integration of each sample by Integpro.bas is fed a Microsoft Excel spreadsheet file. These data are then output as a text file and fed to the program UNMIX described previously. Table III gives the source distributions as determined by the program UNMIX operating on the data of Example 8.

TABLE III

| Compounds | Source 1 | Source 2 | Source 3 |
| --- | --- | --- | --- |
| Acetylene | 0.13728 | 2.29486 | 0.80171 |
| Benzene | 0.08900 | 0.00005 | 0.54703 |
| rtx#11660 | 0.01430 | 1.49792 | −0.00520 |
| rtx#11456 | 0.00007 | 2.16476 | 0.06542 |
| rtx#10970 | 0.00620 | 0.35692 | 0.00352 |
| T-2Hexene | 0.01759 | 0.53155 | 0.03835 |
| rtx#10345 | 0.16815 | −0.05546 | 1.27916 |
| rtx#9750 | 0.06894 | 1.68992 | 0.51805 |
| rtx#9486 | 0.23377 | 8.80221 | 1.12259 |
| rtx#8360 | 0.28109 | −0.19686 | 2.58218 |
| Pentane | 0.15852 | 0.00144 | 1.45255 |
| rtx#9229 | 0.00306 | 0.50905 | 0.03779 |
| Butane | 0.18095 | −0.15603 | 1.93525 |
| Isobutane/Propene | 0.11334 | −0.01207 | 0.74688 |
| MysteryBump6862 | 0.04162 | 0.85410 | 0.17550 |
| Toluene | 0.30667 | 0.04077 | 1.82316 |
| Hexane | 0.07787 | −0.00298 | 0.52961 |
| Octane | −0.00465 | 0.47018 | 0.09961 |
| rtx#11100 | 0.01564 | 0.00597 | 0.10944 |
| rtx#11358 | 0.44013 | −0.00115 | 0.04843 |
| rtx#11225 | 0.01291 | 0.04984 | 0.14702 |
| TOTAL | 2.36244 | 18.84499 | 14.05805 |

The computer program UNMIX was then used to analyze the data and determine the distribution of emission sources upwind from the PFGC monitoring station during this period. The program UNMIX is publicly available from, for example, Ronald C. Henry, Civil Engineering Department of the University of Southern California. Its use has been described in: (1) R. Henry et al. "Vehicle-Related Hydrocarbon Source Compositions from Ambient Data: The GRACE/SAFER Method", Environmental Science and Technology, 28:823–832 (1994); and (2) Henry et al. "Reported Emissions of Organic Gases are not Consistent with Observations," Proc. Natl. Acad. Sci., 94:6596–6599 (1997); both of which are incorporated herein by reference. Dr. Henry provides a operation manual with the program.

Next, each individual sample is analyzed by least squares to determine the contribution of each of the three sources found by UNMIX to describe the PFGC data of example 8. This analysis is not provided by UNMIX but is a form of Source Reconciliation or Chemical Mass Balance as discussed by for instance, J H Seinfeld and S N Pandis, Atmospheric Chemistry and Physics, John Wiley & Sons, 1998 pp. 1248–58). This process, more properly called multiple linear regression analysis is familiar to those knowledgeable in statistics and is illustrated here only by example. Four sets of variables are defined. Some of these variables are unitless (e.g. % or fractions) while others are expressed in parts per billion as carbon atoms ppbC or ppbC/min. These units are familiar to those experienced in air pollution and are roughly proportional to FID response as determined by the PFGC FID analysis of example 8. Thus ethane C2H6 produces approximately twice the FID response of methane CH4, hexane C6H14 produces approximately 6 times the response as methane, etc. The four variables are

- $E_i$ emission sources: E1, E2, E3, relative units, these are found by UNMIX
- $P_i$ individual pollutants: P1, P2, P3, P10 units are ppbC measured by PFGC
- $S_i$ individual samples analyzed: S1, S2, S3, S174 no units, just an identifier
- $X_i$ source contributions to each sample $S_i$: X1, X2, X3 ppbC/min UNMIX identifies three sources: which contribute to the samples $S_i$.

For purposes of example assume the following array of emissions were found by UNMIX

|    | P1  | P2  | P3  |                          |
|----|-----|-----|-----|--------------------------|
| E1 | 0.2 | 0.4 | 0.4 | note that the Ei sum to unity |
| E2 | 0.3 | 0.1 | 0.6 |                          |
| E3 | 0.2 | 0.3 | 0.5 |                          |

Now the contribution of each emission source $E_i$ to each sample $S_i$ is found by least squares minimization. For illustrative purposes this will be done in reverse. Assume that in S1, E1 contributed 2.0, E2 contributed 7.0, and E3 contributed 5.0 ppbC total pollutants P1+P2+P3 that is, X1=2, x2=7 and x3=5 ppbC

Thus S1 contains $$P1 = x1*0.2 + x2*0.4 + x3*0.4 = 5.2$$

$$P2 = x1*0.3 + x2*0.1 + x3*0.6 = 1.6$$

$$P3 = 1*0.2 + x2*0.3 + x3*0.5 = 5.0$$

These three quantities (ppbC) would be the areas under the under the peaks P1, P2, and P3 in PFGC-analyzed sample S1 as ratioed to the internal standard methane concentration of 1.8 ppbC.

In the general case the goal is to find $X_i$ (which would of course be unknown) from the measured values $P_i$. To do this the following is to be minimized:

$$[(P1-(x1*0.2+x2*0.4+x3*0.4))^2+((P2-(x1*0.3+x2*0.1+x3*0.6))^2+((P3-(x1*0.2+x2*0.3+x3*0.5))^2]$$

This is a familiar problem which has a well know solution yielding the values of X1, X2, and X3.

Using the created emission sources here it is of course equal to zero:

$$[(P1-(2*0.2+7*0.4+5*0.4))^2+((P2-(2*0.3+7*0.1+5*0.6))^2+((P3-(2*0.2+7*0.3+5*0.5))^2]=0 \text{ (as defined for this illustrative example)}$$

Each term in the previous equation is identified with the residuals for P1, P2, and P3.

Thus in finding X1, X2, and X3 the residuals are minimized. However, in a real world case they will not equal zero because of measurement error, variation in emission rates and composition, the presence of more than the 3 sources found by UNMIX, errors in UNMIX, variation in wind direction, and numerous other effects. These residuals then allow a goodness of fit calculation to be made. From them may be calculated the standard deviation, standard error of the mean, uncertainties in the coefficients $X_i$, etc, as is described in any statistics book.

Once the above analysis has been performed for all samples $S_i$, the next step in source location is to plot all the $X_i$ values for each emission source for all the samples vs. wind direction. If the wind is variable in direction and a given source is upwind at least some of the time, this curve will produce a true maximum at the compass direction between the receptor site where the PFGC is located and the individual emission source $E_i$. If the maximum is found at the extreme angle of wind direction which occurred (not a true maximum) then the source was not directly upwind. In this case the actual maximum may be found by extrapolation of the Gaussian Plume Model. In the event that no variation in emission source strength is seen with wind direction, then an area source (such as traffic or vegetation) has been located.

If there is no variation in wind direction during the sampling period then the exact location of an individual emission source cannot be exactly located without ground truthing since the source could be off the wind compass direction and the center of the plume is not being encountered. In this case a lower limit emission rate could be calculated on the assumption that the source was located directly upwind in the constant wind field at a distance from ground truthing. In this situation a map could be referred to and potential emission sources looked for. If a possible source is located, then application of the Gaussian Plume Model will allow that source to be quantified from the collected sample data $S_i$.

Example 12

This example describes the location of an emission source by the process of triangulation which is allowed by employment of two or more PFGCs. In this manner, analyses are conducted at plural monitoring stations, for instance in a linear, crosswind orientation downwind from an industrial area, city, or other multiple pollutant source area. Such data could then be used, along with triangulation, to determine the source location and strength of a particular measured analyte or analytes. We have not yet employed two PFGCs in the method described next, but the approach is described.

Triangulation of emission sources may be accomplished (without limitation) as follows.

1. Establish two or more automatic pneumatically focused gas chromatographs at several locations. These instruments could be placed, for instance, downwind from a source area, such as an industrial area, transversely oriented with the normal wind direction for the given season. It is by no means necessary that there be a constant wind direction. In fact, if wind direction is variable more spatial information may be obtained simply by segregating data into various wind direction coordinates as described in previous examples.

Spacing between instruments could be decided by application of the Gaussian Plume model to determine diffusional spreading vs. downwind direction based upon distance from suspected emission sources. With variable winds in a city, for instance, placement might be chosen at random. Take samples under varying wind, atmospheric temperature-inversion, and emission conditions for periods ranging from days to weeks to months.

2. Apply the program UNMIX to determine the range of emission sources contributing to the observed pollutant concentrations at each site by analyzing all the data samples over selected time periods of days to weeks. This analysis should be employed to the entire data set, regardless of wind direction, and to specific subsets based upon wind direction, weekdays vs. weekends, etc. Such approaches are familiar to those involved in study and regulations of air polution.

3. For each individual sample, determine the emission sources contributing to the observed total pollutant concentration at each precise time at each site as described in the previous example. Plot individual absolute source contribution to each analyzed sample as wind direction as described above. With variation in wind direction, this curve should produce a maximum in source contribution when the specific source is directly upwind.

4. Use the wind direction which produces a maximum absolute source contribution to draw the two upwind vectors leading from all pairs (trios may be employed as well) of adjacent monitoring instruments. As in any triangulation, these two vectors will cross at the point of emission impacting each pair of adjacent measurement stations for the particular wind direction and pollutant concentrations of that pair of measurements.

5. Once the source location has been, determined, source strength may be determined from an application of the Gaussian Plume model using dispersion parameters appropriate for the local topography and measured wind speeds. With these given constraints, pollutant concentrations at a receptor site are simply a function of the downwind distance (known from triangulation) and the emission source strength, which of course may be time varying.

6. It is expected that some sources will not produce maxima in the source contribution with wind direction, or that such maxima will be quite broad. In this case such sources represent area sources, such as traffic or vegetative emissions. These sources should have compositions which are currently associated with such emissions as recognized to those familiar with air pollution.

7. It is further expected that some source vs. wind direction graphs will produce maxima at the extrema of wind direction encountered. Such sources were never directly up wind. Their actual location may be determined two ways.

a. By extrapolating a Gaussian curve through the observed points to find the maximum, or b. by moving an appropriate pair of PFGC instruments in the direction of the actual maximum.

1. There will be some uncertainty in an individual triangulation due to shifts in wind direction, variation in emission strengths or composition. This is to be expected. However, by averaging over all sources, all compounds, all wind directions, considerably confidence can be built up in the sum total results of a large number of triangulations.

2. Finally, use a standard Gaussian plume model fixed on the estimated emission site to model the predicted pollutant concentrations at adjacent sites. Compare predicted pollutant concentrations with observed. Perform appropriate statistical calculations.

3. Finally, if necessary or desired, move at least pairs of instruments in directions (closer if necessary) to suspected emissions sites for improvement in precision and accuracy.

4. Lastly, (or even firstly) ground truth the calculations qualitatively by visiting the suspected emission sites and by consulting emission inventories maintained by local air pollution control districts.

Example 13

This example concerns the identification of intermittent sources which due to their sporadic rate of emission are not detected by the statistical program UNMIX. Such sources might include, for instance, illegal drug synthesis labs which intermittently boil off solvents or pour them on the ground from which they evaporate. Detection of these emissions proceeds substantially as example 8, except that such sources will not be identified by the program UNMIX. Rather they may be detected by examination of the residuals determined from source distribution analysis using the output of UNMIX. This is done by examining the best-fit residuals calculated in the fitting procedure of item 3, example 8. These extrema in the residuals will represent occasional or intermittent sources of an individual pollutant P. These intermittent sources may then be spatially located as described in Example 8. Lastly, the exact nature of the sporadic emissions could be discussed with local pollution and law enforcement agencies.

Example 14

This example concerns the use of PFGC to locate harmful outgassing substances in an indoor environment. Such environments might include without limitation residential buildings, office buildings, factories, etc. Such outgassing substances can contribute to what is termed Sick Building Syndrome and might include active substances such as molds and fungi and passive substances such as paint, particle board, carpets, drapes, household products, pesticides, etc. In some cases the outgassed chemical compounds may themselves be irritating and/or harmful. In other cases the detected pollutants (e.g. heptanol from bacteria) may not themselves be harmful but may serve as indicators or surrogates for the presence of harmful organisms which produce spores or other materials which are indeed harmful but which are harder to detect.

Provide a PFGC, most suitably including two columns and two detectors, one each to sample incoming and outgoing building air. Choose a pair of separatory columns most suitable for the range of pollutants to be encountered. Numerous manufacturers of these columns can provide detailed advice and sample chromatograms. In some cases two separate columns might be required to completely cover the range of target analytes as in the breath analysis of a previous example. In such case the PFGC might contain 4 columns and 4 detectors. All four detectors could be accommodated by a single A/D board. Analysis would most beneficially be done by attachment to the building ventilation system. One sample line draws a continuous air sample from the incoming building air and the other from the outgoing (exhaust) air. Carry out continuous sampling and analysis of this air for a period of days to weeks. Data taken in the outgoing (exhaust) air stream will allow human exposure to measured pollutants to be calculated. Comparison of these two sets of continuous samples will allow the origin of all building air components to be assigned either to outgassing within the building or transfer from outdoors through the ventilation system determine sources using UNMIX. These data will allow risk assessment, liability or other litigious issues to be settled. The data will also suggest the most effective remediation measures to be taken. If the pollution source is indoors and cannot be deduced from initial measurements. Then the PFGC could be dedicated to monitoring individual rooms or areas of the building. In this case individual sample lines could be directed to separate areas to speed the detection process.

Example 15

This example concerns the identification and quantification of common outgassing substances from respiratory organisms such as various bacteria, molds, fungi, etc. such as might be present in damp buildings prone to exhibit sick building syndrome. Obtain a culture of a suitable living organism from a commercial source or by scraping from a building which exhibits sick building syndrome. Establish a culture medium with suitable humidity and nutrients in an enclosed situation such as a beaker, fish tank, etc. Suspend the culture within the culture vessel on a suitable light-weight substrate that may be periodically weighed to determine colony growth rate. Slowly pass purified, pre-humidified air through said culture vessel at a low volume flow rate. This rate may be chosen to establish reasonable, measurable levels of gaseous metabolic products. Such flow rate may be chosen from the following theoretical calculation familiar to those involved in the art. Consider a culture vessel volume V(L), a purge flow rate F(L/min), and an offgassing rate for a target compound G(ng/min). These will establish a steady-state concentration P(ng/L)=G/F of the pollutant with the sampling time (tau) to reach (1/2.7) of equilibrium given by the residence time V/F (min). Of course offgassing rates may vary significantly with time as the culture grows. The flow response time tau represents an averaging time for the determination of these changing offgassing rates. This above growth chamber is essentially a metabolic chamber which could be applied without limitation to a variety of higher organisms (including humans) whose gaseous metabolic by-products in breath and otherwise were quantitatively and continuously determined by PFGC.

Example 16

This example concerns the application of PFGC to continuous automated analysis of water samples. As an example, consider a river subjected to natural and anthropogenic pollution sources. Such a moving body of water will continuously transport varying quantities of natural or anthropogenic pollutants past any fixed point. Concentration of such pollutants may vary with depth in the river, river flow, season, etc. Such variations may be determined as in Example 1 by modifications of the PFGC described for gaseous analysis as shown in FIG. 8. To do these modifications one should:

1. Choose a chromatographic column which is impervious to the action of high-temperature, high-pressure water vapor and which will preferably have a polarity such that the vaporized water sample passes through ahead of the desired analytes. Alternately, the column could pass the water vapor subsequent to the analytes. Finally superheated water could form the mobile phase. Water is not commonly injected onto chromatographic columns. Rather such water samples are 'stripped' of their organic components by either 'trap and purge' or by extraction to a hydrophobic phase. Such methods are slow, complex, expensive, and prone to artifacts and error. Appropriate columns for water injection are not currently in widespread use. Nonetheless, such separations are possible. See the paper "Supercritical fluids in separation science—the dreams, the reality and the future" Journal of Chromatography A 856 (1999) pp. 83–115 and references contained therein. To quote from this authoritative source, Superheated water can also be used as a mobile phase for reversed-phase liquid chromatography (references) with both UV and fluorescence spectroscopic detection and universal FID (references). The eluent can also be buffered (ref) and the separation applied to a range of analytes including pharmaceuticals (ref). Thus water with the appropriate stationary phase can be used as an eluent. For Pneumatic Focusing two situations can be envisioned:

a. A liquid water sample is automatically injected into a PFGC. In this case water is simply the 'native' vehicle to transfer the analytes (water pollutants) to the Pneumatically Focused separatory column. Thus in this application it is only necessary that the water not destroy the column when passing through prior to the analytes to be separated chromatographically using any of a variety of sub or supercritical mobile phases.

b. A liquid water sample is transferred directly to a liquid chromatograph which may employ superheated water as the eluent. This situation would duplicate the non-automated analysis referenced in the just described J. Chromatography article.

2. Substitution of a sample loop of approximately 1 cc volume. The most appropriate volume will be determined by experimentation. This sample loop will perform direct river water injection into the PFGC.

3. Adjusting the sample injection block temperature to a temperature which will 'flash' evaporate the water at high pressure upon transit through the sample block. Such temperature may be determined either theoretically (consult stream tables) and/or by experimentation with temperature and flow rate through such sample block. Flow rate and heat transfer may be varied by the diameter of the sample inlet tube from the sample loop to the chromatographic column.

4. Said sample loop will inject the river water sample through a heated injection sample block (modification described above) such as is common for syringe injection. When the water sample passes through this heated sample block it will be vaporized as is common in liquid injection. However, the high pressure within the PFGC will reduce the gaseous water expansion factor (relative to injection into a 'normal' gas chromatograph by a factor proportionate to the internal GC pressures. For instance, if a 'standard' GC uses a head pressure of 30 psi and a PFGC uses a head pressure of 300 psi this compression ratio will be a factor of 10. Essentially (and to a first order approximation) the PFGC allows a sensitivity increase (relative to a standard GC) of 10×. Correspondingly, a PF pressure of 3000 psi will allow a sensitivity increase of 100×.

Example 17

This example, being substantially similar to Example 10, is only briefly described. In this method continuous monitoring of river pollutant concentrations is used to determine sources. Two methods (without limitation) are described.

1. In this case, rather than plural PFGC instruments located at different locations, on or more such instruments, containing (if desired) plural columns are located at a single site with sample lines running to different positions in the river. Typically these sample lines would have to be at a depth such as would not interfere with boat traffic.

2. Instruments are located at different downstream locations, sampling one or more transverse or depth locations within the flowing stream.

As in Example 10, choose an appropriate liquid phase transport model to analyze such data. In particular, a series of instruments located along the river's course, could pick up pollution sources with much simpler analysis than in the case of air monitoring.

Sample lines should admit no light to prevent algal growth and sample flow should be appropriately filtered to prevent clogging. Sample flow through the sample loop may be continuous as in gas phase analysis or intermittent following each previous sample analysis.

Example 18

Figure 50:
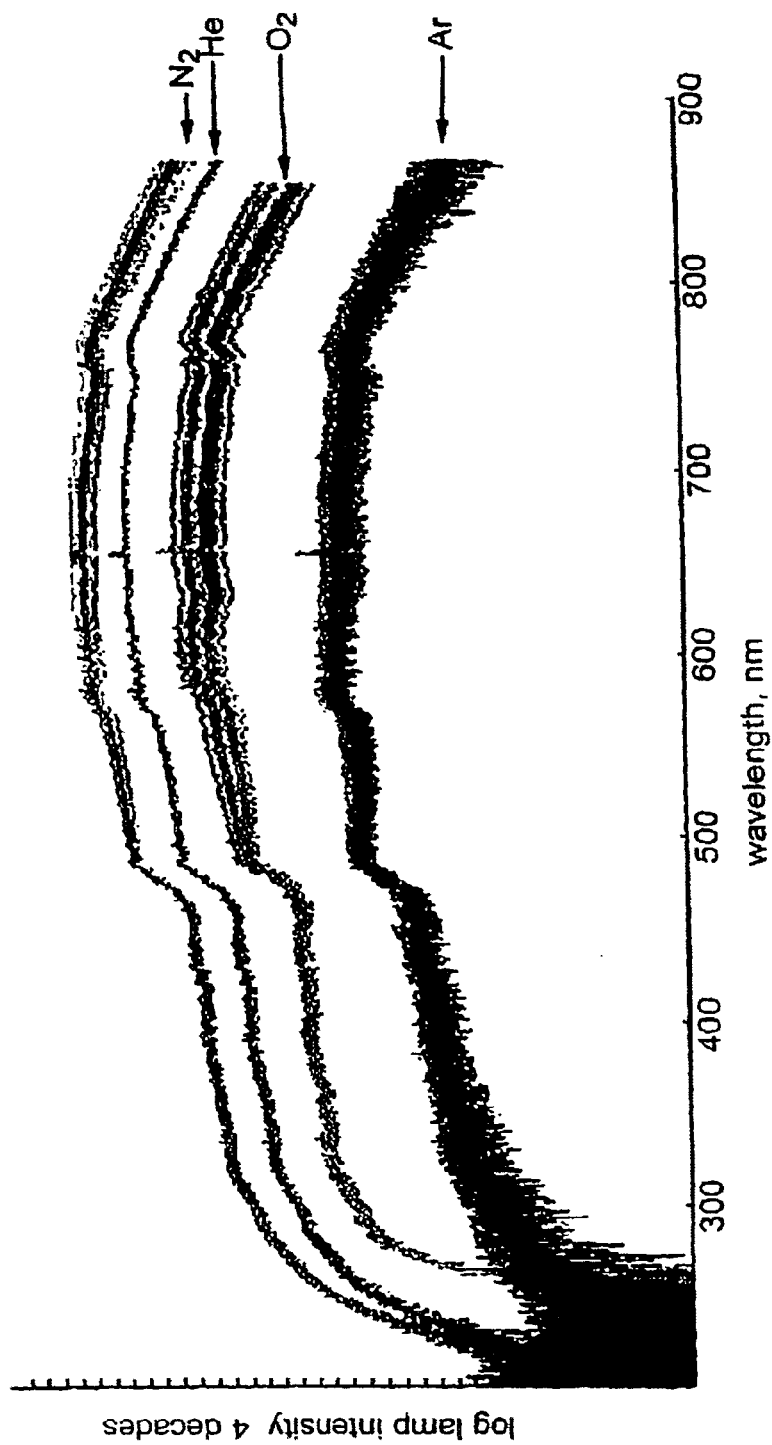
FIG. 50 shows variations in light transmission with wavelength.

This example illustrates fluctuation in transmission of lamp intensity as determined using the apparatus of FIG. 2. No unusual fluctuations were observed with helium. Other gases (as shown in FIG. 50) exhibited quasi random or chaotic variation in transmission (or absorbance) which varied in magnitude with wavelength. When UV/VIS emitting lamp 84 in FIG. 2 was replaced with a source of visible radiation only, these fluctuations did not occur.

Example 19

This example describes particular embodiments of pneumatic focusing systems contained substantially within commercially available personal computer cases. Constructing pneumatic focusing instruments within commercially available computer cases is an example of a more general approach to providing instrumentation that is both portable and less expensive. Modification and use of a personal computer case to house the components of an analytical instrument is not solely suitable for pneumatic focusing gas chromatography.

Instruments that may be constructed within personal computer cases include gas chromatographs in general, pneumatic focusing spectrophotometers, gas chromatography/mass spectrometry instrumentation, mass spectrometers, particulate detection systems, fluorescence spectrophotometers and infrared spectrophotometers. Another example is an atomic absorption/atomic emission/ atomic fluorescence (AA/AE/AF) spectrometer. Such an instrument may include, for example, a multiple lamp turret, a graphite furnace, and spray/flame device that is very similar to a Flame Ionization Detector (FID) mounted within a personal computer case. These components can easily be contained in a standard tower ATX case, server case, etc, and as the components are further shrunk, such as in "lab on a chip" technologies, the more the 'in a pc' becomes a viable alternative. A suite of spectrometers including infrared (IR), near-infrared (NIR), x-ray, and ultraviolet-visible (UV-Vis) spectrometers, as well as a fluorescence spectrometers using broadband source excitation and emission monochromators may be contained within a personal computer case. Various laser spectroscopic instruments, for example, intracavity absorption; Raman; resonance ionization, fluorescence and chemiluminescence spectrometer also may be constructed in a personal computer case. Further, various mass spectrometers, using mass detection techniques such as quadrupole, ion-trap (inverted quadrupole), and time-of-flight may be housed in a personal computer case. A high pressure liquid chromatographic (HPLC) system and its associated solvent sources, pumping system, and HPLC column, would easily fit within personal computer cases. Similarly, an ion chromatograph (IC) would be an excellent companion to an HPLC in a pc, and would only need a different detector and column. For example, a dual HPLC-IC could be constructed in a personal computer case. Other embodiments of an "instrument in a PC" include a microscope (wherein, for example, the personal computer case is modified to include a large port for access to a sample stage; internal optics and camera chip, and a display screen, with focus, translation, and magnification controlled from a keyboard or mouse). An ion selective electrode (ISE) may be constructed in a personal computer case, and used, for example, continuously sample various ions that are tracked by regulatory agencies such as the EPA. Such an ISE/PC combination would permit for continuous data logging and display for process effluents or downstream tracking of pollutants.

A case for a pneumatic focusing gas system is desired for a number or reasons, including protection of system components. Typically, such systems are run by external personal computers, such as laptop personal computers, or the systems are in large containers that contain computer processors. However, as demonstrated herein, all the components for a pneumatic focusing gas chromatograph may be contained within a commercial personal computer case along with the components that are normally present in a personal computer. Commercially available computer cases often include a power supply, and the power supply may be used not only to power the computer, but components of the pneumatic focusing system. In one embodiment, modifications to a computer case to permit introduction of samples and to provide gases (such as FID gases, sample, and pneumatic focusing gases) were made, and the resultant instrument incorporated all the normal functions of a personal computer as well as all the functions of a pneumatic focusing gas chromatograph, a highly desirable combination.

A personal computer (PC) is generally contained within a personal computer case and contains some or all of the following computer components, which constitute in whole or in part what is termed a "computer." The computer case refers to an enclosure, such as a metal or plastic enclosure, that provides or is designed to accommodate at least some of the following components:

1. Power Supply: A unit which plugs into wall line voltage (e.g. 110 V, 60 Hz) and provides a variety of types of electric power to the computer and its components such as 6V and 12V DC. The power supply is typically sold as an integral part of a computer case.
2. Fan: a small device for circulating air inside the computer case for the purpose of removing excess heat and cooling the computer; several such fans may be employed; an alternative is a water cooling system.
3. Operating System or OS: a computer program that controls the processor. An example would be Microsoft Windows 98, 2000, etc.
4. Hard Drive: a magnetic storage device for permanently storing (1) computer operating systems, (2) programs or software, (3) data.
5. Mother Board: a circuit board, commonly mounted within a computer case to which various other components are themselves mounted.
6. Memory: a magnetic storage device for storing programs, software and data while the computer is operating; also called RAM, or random access memory. This memory refreshes or resets itself when the computer is turned off. It is commonly mounted on the motherboard.
7. Processor: the actual electronic device that operates the computer, runs programs, and causes the various computer components to communicate with one other. This is mounted on the Mother Board. Example would be any of the processors manufactured by Intel (Santa Clara, Calif.) or AMD (Sunnyvale, Calif.).

8. Graphics display card, sound card, network card, etc. Control cards for display, sound, communication with other computers, etc. These may be separate circuit boards or 'cards' mounted within the case, or their functionality may be incorporated onto the mother board directly without requiring additional cards.

9. AID & D/A conversion or cards: these additional circuit boards may be mounted within the case and allow the computer to acquire analog or digital data from instrumentation (such as from a GC) and to communicate with or operate instruments, such as a GC.

As is commonly the commercial situation, computers may be purchased directly from a distributor fully constituted so that they contain some, all, or more than the above components, and such a device is commonly called a "computer." Alternatively, any or all of the above components may be purchased separately from a distributor and the computer assembled from its component parts. This may be done by a reseller or by the end user.

In all cases of the existing art, the computer used to run a GC is attached as a peripheral to or is contained within a case designed for the GC. In contrast, the disclosed instrument consists of constructing a GC within a case designed to house a commercial personal computer (PC); that is, constructed within a personal computer case by modifying the computer case to provide, for example, inlets and outlets as necessary to supply gases, samples etc. and to exhaust waste gases.

A wide variety of computer cases (enclosures) are available that, although not designed for the purpose, nevertheless may be used to house a wide range of analytical instrumentation in place of the specialized cases currently employed. For example, such cases may be obtained from Colorcase (Rowland Heights, Calif.) and CaseDepot (Santa Fe Springs, Calif.). Computer cases suitable for enclosing scientific instruments such as pneumatic focusing gas chromatographic, include AT, BATX, ATX, MATX, LPX and microATX compatible cases (referring to their compatibility with particular types of motherboards), and (full) tower, mid-tower, microtower, desktop, rackmount and server chassis cases (referring to their size and configurations). Particularly suitable computer cases are portable cases having a built-in screen, keyboard and carrying handle. Such computer cases are available from CaseDepot (Santa Fe Springs, Calif.). Additional manufacturers/suppliers of suitable computer cases include Antec (Fremont, Calif.), Avus (City of Industry, Calif.), Cables Unlimited (Bohemia, N.Y.), Chieftec (Fletcher, Ohio), CrazyPC (Walled Lake, Mich.), FuturePower (Glendale Heights, Ill.), Kingwin (Walnut, Calif.), Koolance (Federal Way, Wash.), pcToys (Woodinville, Wash.), Soyo Tek (Fremont, Calif.) and Zerus Hardware (Springfield, Mo.). Any of these cases may be modified to house scientific instruments. In a particular embodiment, the computer case may also be modified to include an integral video screen, such as a 5-inch video screen, available, for example, from Parts Express (Springboro, Ohio). If a small monitor is present on the computer case, an external monitor is not necessary (although one may still be employed in parallel with the incorporated 5 inch monitor), providing greater portability for the instrument. In other particular embodiments, appropriate computer cases have a volume (based on external dimensions) of not more than 4500 in$^3$, such as not more than 3500 in$^3$, for example, not more than 2500 in$^3$.

In a working embodiment, a pneumatic focusing gas chromatographic system as previously shown in FIG. 1 was constructed within an ATX compatible, tower computer case having the outer dimensions of 20 inches by 19 inches by 8 inches (volume=3040 in$^3$). A handle was affixed to the top of the case.

Figure 51:
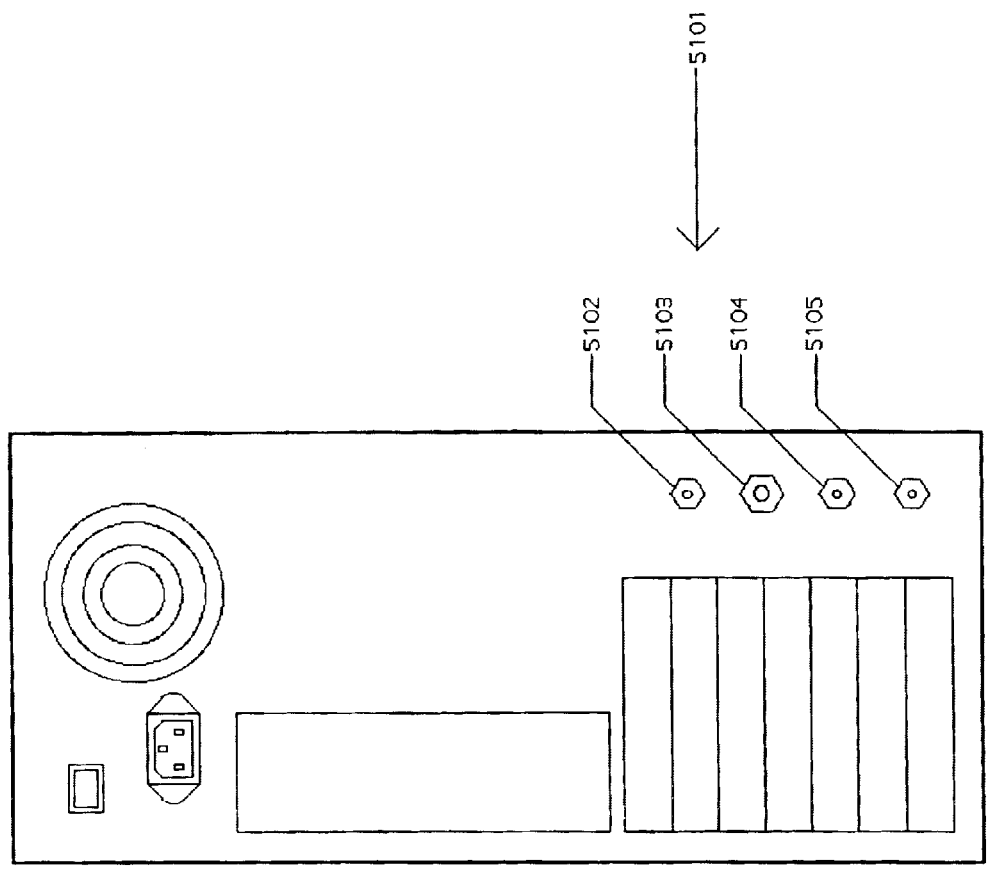
FIG. 51 is a diagram showing a rear view of a personal computer case modified with a particular layout of inlet ports for sampling and gas lines

Referring now to FIG. 51, a rear view of a computer case 5101 is shown with a particular layout of inlet and outlet ports for sampling and gas lines that were provided by modifying the computer case. The modified computer case includes helium inlet 5102. Helium inlet 5102 was added to the case by drilling a hole to accept a Swagelok Bulkhead Union SS-200-61. Sample inlet 5103 was added to the PC case by drilling a hole to accept a Swagelok Bulkhead Union B-400-61. Hydrogen inlet 5104, like helium carrier gas inlet 5102 was added by drilling a hole to accept a Swagelok Bulkhead Union B-200-61, as was oxygen inlet 5105.

Figure 52:
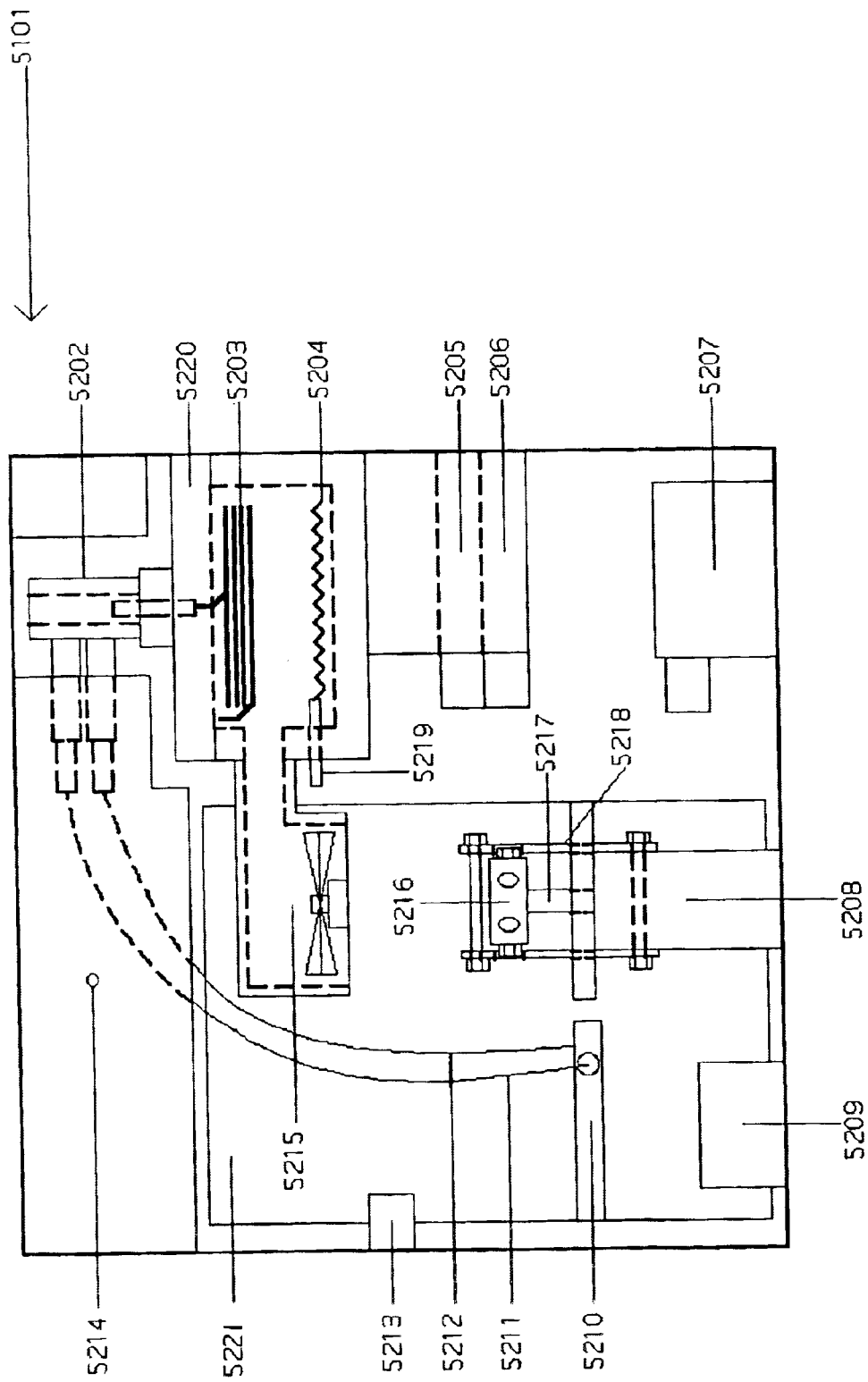
FIG. 52 is a diagram showing a side cutaway view of a modified personal computer case housing components of both a personal computer and a pneumatic focusing gas chromatograph.

FIG. 52 shows a side cut-away view of computer case 5101 modified to enclose the major components of a pneumatic focusing gas chromatograph as illustrated previously in FIG. 1. FID assembly 5202 was added to the PC case by drilling vent holes through the top panel and cutting away the bulkhead side wall of the PC case to allow the FID assembly to easily slide into place when mounted atop oven unit 5220. Within the oven unit 5220 is column assembly 5203, and resistive heating element 5204. Resistive heating element is electrically connected to circuit assembly 5209 through resistive heating element power supply terminals 5219 (electrical connections not shown).

Column assembly 5203 is fluidly connected between 6-port gas valve 5216 (Swagelok Ball Valve SS-4346FS2) (connection not shown) and FID assembly 5202. 6-port gas valve 5216 also is fluidly connected to sample inlet 5103 of FIG. 51 through a sample loop that is located in the sample loop assembly 5214 (loop not explicitly shown) Helium carrier gas inlet 5102 of FIG. 51 is also fluidly connected to 6-port gas valve 5216 (not shown). FIG. 1 illustrates the connections to 6-port gas valve 5216 that are not explicitly shown in FIG. 52. Although not shown in FIG. 52, a flow restrictor valve is present in the conduit that extends between column assembly 5203 and FID assembly 5202, as was shown in FIG. 1.

Below oven unit 5220 are mounted removable media (e.g. CD-ROM or floppy disk drive) data storage device 5205 and non-removable media (i.e. hard-drive) data storage device 5206. Below the data storage devices 5205 and 5206 is a circuit assembly 5207 for automation of 6-port gas valve 5216, which was added to the PC case by drilling mounting holes for a circuit enclosure box.

Actuation motor 5208 for controlling 6-port gas valve 5216 was added to the PC case by drilling mounting holes to attach it to the PC case. Motor/valve shaft coupler 5217, a custom fabricated part used to connect the motor and valve shafts. Motor/Valve Bracket Assembly 5218 is a custom fabricated part used to rigidly connect motor 5208 and 6-port gas valve 5216.

An electrometer 5210 is shown mounted in a PCI slot mounted to the computer motherboard 5221. FID/Electrometer signal cable 5211 and FID/Electrometer reference voltage cable 5212 electrically connect electrometer 5210 to FID assembly 5202. A 120V AC power inlet 5213 for actuator motor 5208 was added to the PC case by cutting away the mounting hole for the bulkhead plug assembly. FID Heater Block Temperature Control Unit 5213 was added to the PC case by drilling mounting holes for attaching the control unit and allowing the control knob of the control unit to extend through PC bulkhead wall. Oven Cooling Fan/Duct Unit 5215 was added to the PC case to prevent heat from the oven and the FID from building up inside the case.

Figure 53:
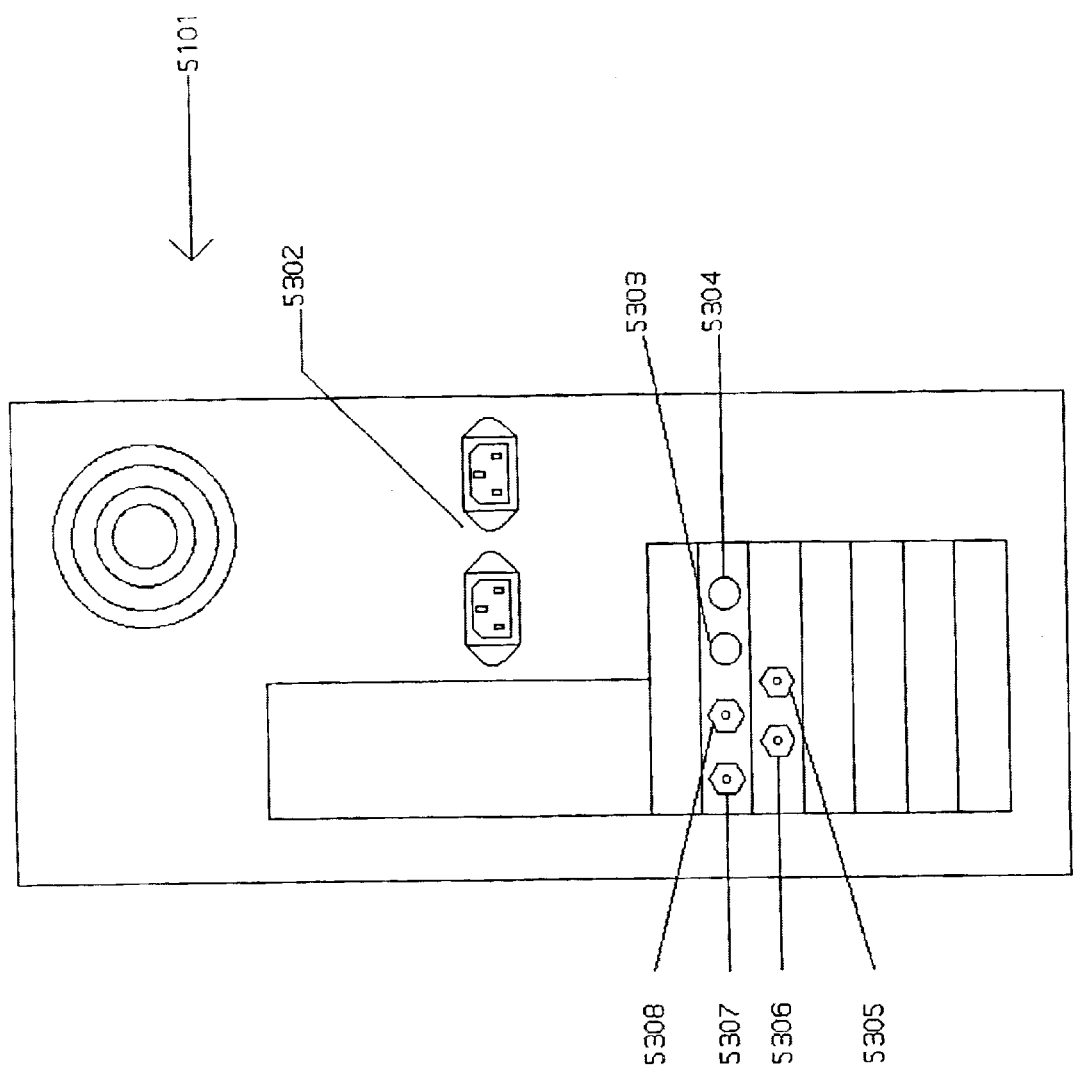
FIG. 53 is diagram showing a rear view of a personal computer case modified with another particular layout of inlet ports for sampling and gas lines, and flow control valves, for including a pneumatic focusing gas chromatograph in the case.

FIG. 53 is another rear view of a computer case 5101 showing an alternative set of modifications made to add gas inlets and gas flow control units to the computer case for the pneumatic focusing gas chromatograph of FIG. 52. Bulkhead AC plug assemblies 5302 were added to the computer case by cutting away mounting holes in the rear exterior panel. In this embodiment, oxygen flow control valve 5303 is fluidly connected to and between oxygen inlet 5308 and FID assembly 5202 of FIG. 52, and is used to control oxygen flow to the FID during operation of the FID. Similarly, hydrogen flow control valve 5304 is fluidly connected to and between hydrogen inlet 5307 and FID assembly 5202 of FIG. 52, and is used to control hydrogen flow during operation of the FID. Sample inlet 5305 is fluidly connected to 6-port gas valve 5216 of FIG. 52.

Figure 54:
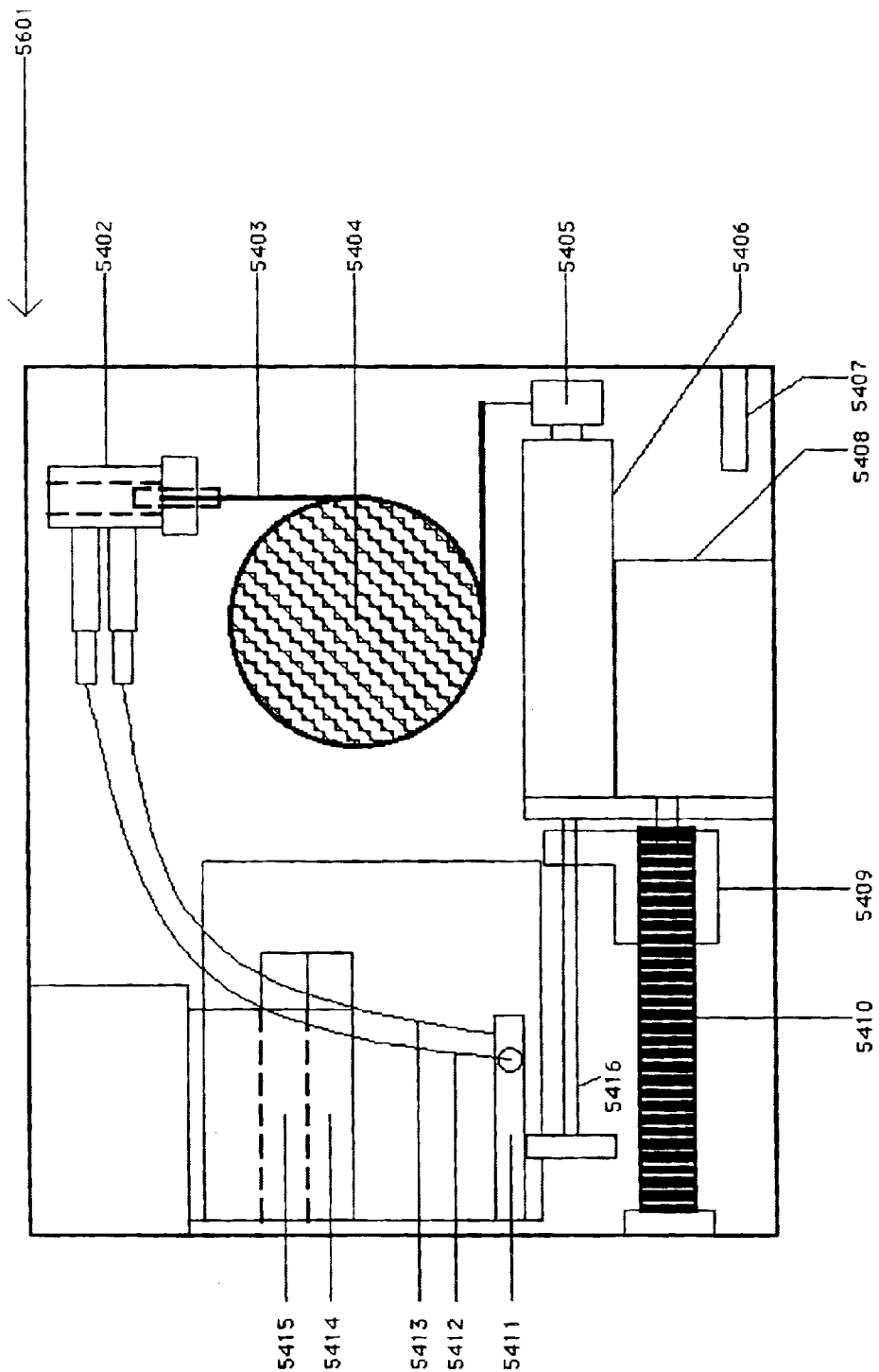
FIG. 54 is a diagram showing a side view of a pneumatic focusing gas chromatograph including a piston inlet that is constructed within a modified personal computer case.

FIG. 54 shows a side cut-away view of an alternative embodiment of a pneumatic focusing gas chromatograph within a modified computer case 5601. In this embodiment a piston apparatus is used to pneumatically focus samples instead of a sample loop and a pneumatic focusing gas as in FIG. 52. FID assembly 5402 is added to the computer case by drilling vent holes through the top panel and cutting away bulkhead side wall of computer case 5601 to allow FID assembly 5402 to easily slide into place when mounted atop circular oven unit 5404. Column 5403 is fluidly connected to and between FID assembly 5402 and piston valve inlet assembly 5405. Piston housing 5406 is fluidly connected to piston valve inlet assembly 5405. During operation, piston plunger 5416 is moved by motor 5408, which is connected to jack screw 5410 through thrust collar 5409. Also shown in FIG. 54 are removable media data storage device 5407, electrometer 5411, FID/Electrometer signal cable 5412, FID/Electrometer reference voltage cable 5413, non-removable data storage device 5414, and A/D conversion unit 5415.

Figure 55:
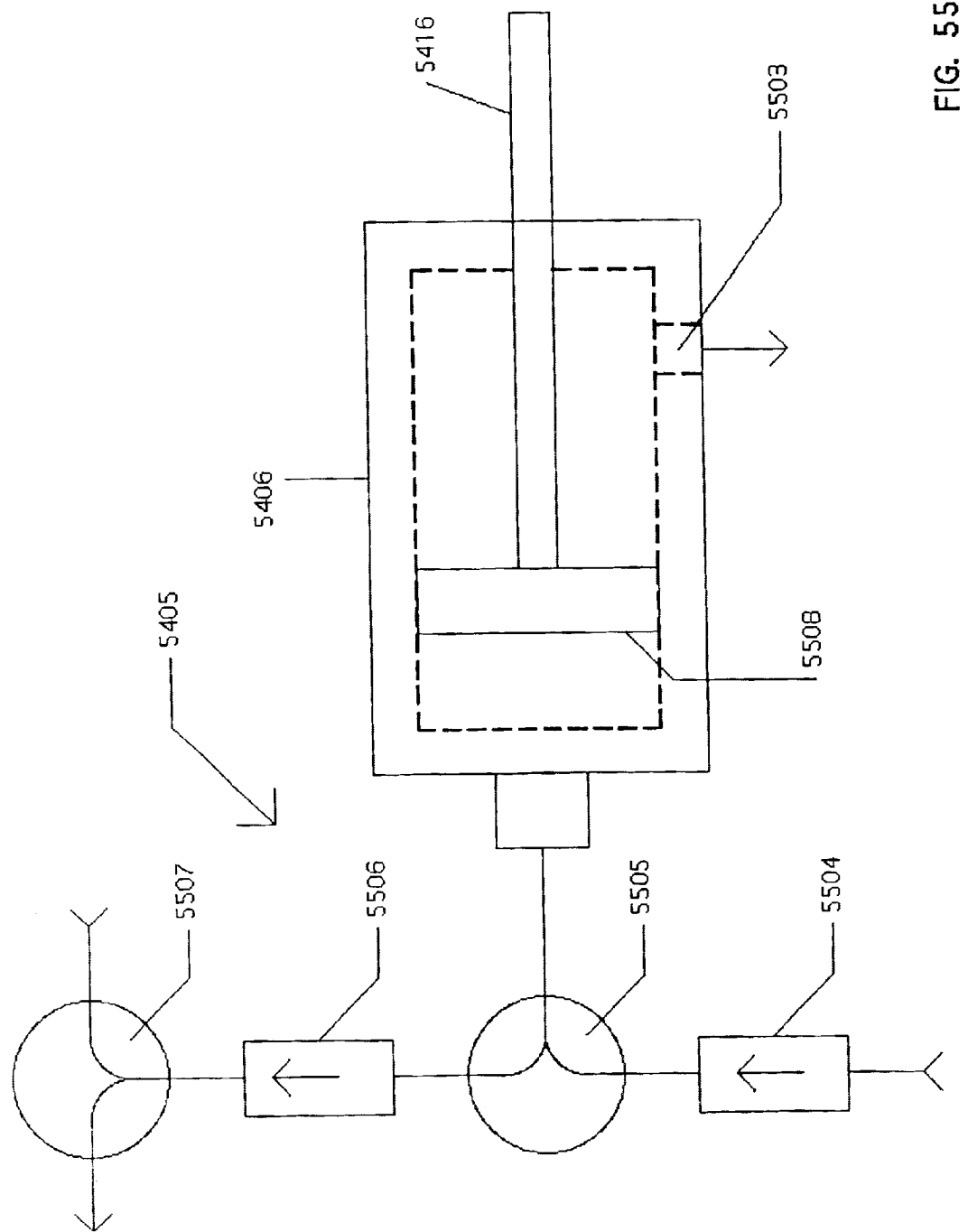
FIG. 55 is diagram showing a side view of an embodiment of a piston inlet assembly.

FIG. 55 shows a particular embodiment of piston valve inlet assembly 5405 of FIG. 54, fluidly connected to piston housing 5416 of FIG. 54. Piston housing 5406 encloses piston 5508, which can move within the piston housing. Piston 5508 is connected to piston plunger 5416 which may be used to move the piston within the housing. Piston housing 5406 also includes sample line 5503, which during operation is fluidly connected to a pump (not shown) that generates a suction in the sample line, thereby drawing sample into the piston housing through the piston valve inlet assembly 5405. Piston valve inlet assembly 5405 includes check valve 5504, which allows gas sample flow only in the direction shown by the arrow. Check valve 5504 is fluidly connected to a sample inlet (not shown). 3-port Tee 5505, is fluidly connected to check valve 5504, piston housing 5406, and check valve 5506, which allows gas flow only in the direction shown by the arrow. 3-port Tee 5507 is fluidly connected to check valve 5506. Tee 5507 is also fluidly connected to a pneumatic focusing/carrier gas supply. During operation, piston plunger 5416 is used to withdraw piston 5508 until the space between the piston and the piston valve inlet assembly 5405 is fluidly connected to sample line 5503. The vacuum pump connected to sample line 5503 draws a gas sample through check valve 5504 and 3-port Tee 5505, into piston housing 5406. At the same time, the pressure of the pneumatic focusing/carrier gas flowing through 3port Tee 5507 in the direction shown is greater than the pressure in 3-port Tee 5505, causing check valve 5506 to close, thereby preventing flow of the pneumatic focusing/carrier gas into piston housing 5406. Once the gas sample fills piston housing 5406, piston plunger 5416 is used to drive piston 5508 further into the housing and past sample line 5503. Once piston 5508 is past sample line 5503, the gas sample is no longer entering piston housing 5406. As piston 5508 is driven further into housing 5406, the pressure in the housing increases and closes check valve 5504 which prevents loss of sample. Piston 5508 is further driven into housing 5406 until the pressure within the housing increases and reaches the pressure in 3-port Tee 5507, at which point, check valve 5506 opens and sample enters 3-port Tee 5507. Once sample enters 3-port Tee 5507 it is swept into the chromatographic column for analysis. This embodiment may be constructed from pre-existing components. For example, any commercially available check valve or solenoid controlled valve that may be opened or closed under computer control to provide the correct timing may be employed as check valves 5504 and 5506. In one embodiment, the check valves are Alltech soft seat check-valves (part # 02-0129, Alltech, Deerfield, Ill.). The check valves (e.g. solenoid controlled valves) can be mounted in orientations other than vertical if the check valves retain their functionality.

Figure 56:
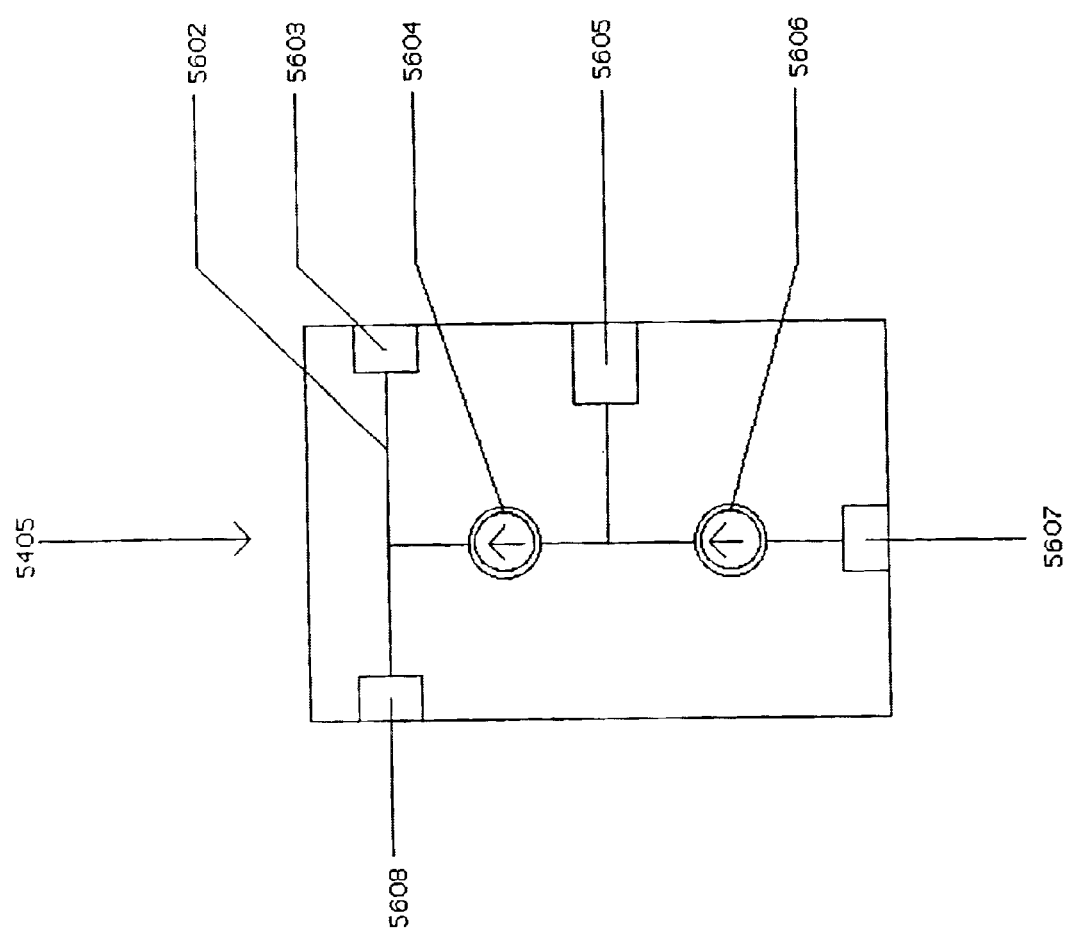

FIG. 56 shows an alternative embodiment of piston valve inlet assembly 5405 of FIG. 54, which may be constructed within a stainless steel block or similar machinable stock. This embodiment includes machined path for gas flow 5602 fluidly connected to inlet port 5603, which receives pressurized carrier gas. Machined path 5602 is also fluidly connected to outlet port 5608, which is fluidly connected to a chromatographic column. Included within the machinable stock are additional machined paths 5609, 5610, 5611 and 5612 which fluidly connect the remaining components of the piston inlet valve assembly 5405. Machined path 5609 fluidly connects machined path 5602 to check valve 5604, which may be a ball bearing-like sphere in a machined seat that permits gas flow only in the direction shown by the arrow. This sphere may be made from any suitable material, for example, rubber, Teflon, viton, sapphire, delrin, etc. that can withstand the pressures and temperatures to which it is exposed. Machined path 5611 is fluidly connected to machined path 5610, which is fluidly connected to port 5605, which is fluidly connected to piston housing 5406 (not shown). Machined path 5611 is also fluidly connected to check valve 5606, which also may be a ball bearing in a machined seat that permits gas flow only in the direction shown by the arrow. If necessary, an o-ring or grommet could be added to the seat to provide a better seal with the ball bearing. For example, the o-ring may be fabricated to fit into the interior of the hole and could include a lip to prevent it from fully entering the machined path. Sealing would occur with pressure from the ball bearing pressing down on the lip of the O-ring/grommet. Such o-rings may be obtained, for example, from O-rings West (Seattle Wash.). Machined path 5612 fluidly connects check valve 5606 to gas sample inlet port 5607. Dead volumes in the assembly 5405 may be minimized by the use of appropriate filler poured into the cavities and removed as necessary.

During operation, the piston valve inlet assembly of FIG. 56 functions in a manner similar to the embodiment shown in FIG. 55. Application of a pneumatic focused sample closes check valve 5606 and opens check valve 5604, allowing the sample to enter chromatographic column 5603. In some embodiments, dead-volume at 5603 is sufficiently small that backflow will be negligible. If the dead-volume is too large, a check valve, such as illustrated at 5604 and 5606, may be installed at the head of column 5603 to enable forward carrier gas flow but to block reverse sample flow into the carrier gas feed line. Any of several commercial check valves (e.g., Alltech soft seat checkvalve, part # 02-0129, Alltech, Deerfield, Ill.) may be used as check valves 5604 and 5606, or such check valves may be fabricated. For example, the check valve illustrated in FIG. 58 may be used.

Example 20

This example describes an apparatus including a check valve and one or more crimped flow regulators that may be used for pneumatic focusing of a sample followed by analysis of the pneumatically focused sample at a lower pressure. This method may also be employed with the check valves to pneumatically focus a sample into a gas chromatograph operating at typical gas chromatographic pressures, for example, at column head pressures of between 10 and 60 psi. In this approach, the high focusing pressure will close suitable check valves, diverting the column flow into a flow restrictor which will allow on-column focusing of analytes, particularly higher molecular weight analytes (e.g., greater than 16 amu), as discussed below. Then, when the high pressure sample has bled through the flow restrictor, sample pressure will drop, the check valves will open (or be opened under computer control), and typical column pressures will be attained, allowing separation of analytes previously adsorbed at the column head.

Figure 57:
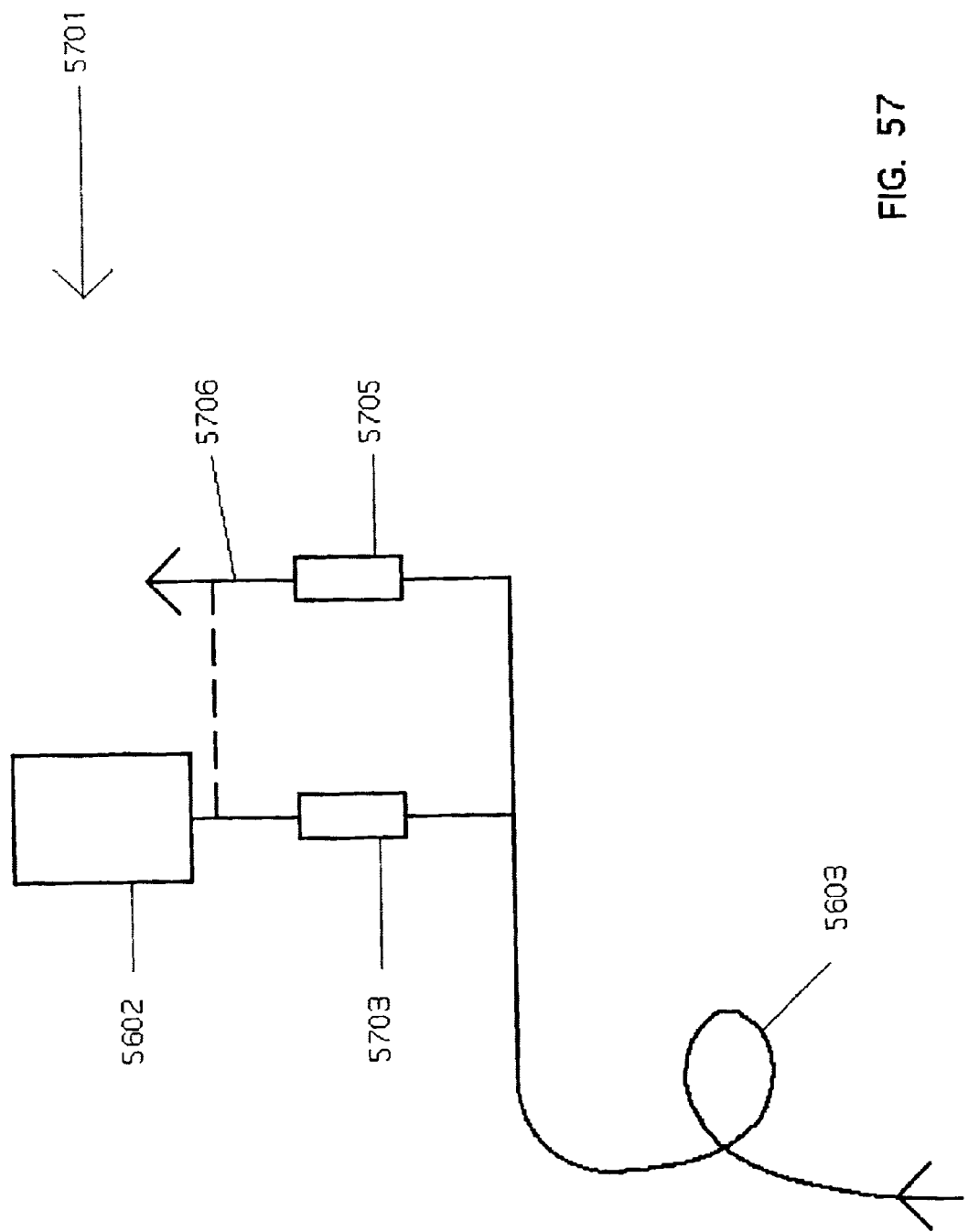
FIG. 57 is a diagram showing an a check valve and crimp flow regulator.

FIG. 57 shows a schematic diagram of one embodiment of such an apparatus. In FIG. 57, flow control assembly 5701 is fluidly connected downstream of column 5603 of FIG. 56, and upstream of FID assembly 5602 of FIG. 56. Flow control assembly 5701 includes check valve 5703 and flow regulating device 5705. In this embodiment, check valve 5703 is configured to prevent flow at high pressures (e.g. 150 psi and above) from column 5603 to FID assembly 5602, but allow flow at low pressures (for example, below 150 psi, such as below 100 psi, 80 psi, 60 psi ,40 psi, or 20psi) from the column to the FID assembly. Flow regulating device 5705 can be a solenoid driven needle valve, a calibrated leak, a frit restrictor, a tapered capillary restrictor, a feedback regulator, a manually operated needle valve, or a crimped capillary flow regulator. Flow regulating device serves to increase the pressure inside the column and reduce the high flow rate in the direction of the arrow through the column which would otherwise occur upon application of a pneumatically focused sample. As shown in FIG. 57, gas flow through flow regulating device 5705 may be diverted to FID assembly 5602 (dashed line) or may be directed, for example, to an atmospheric vent or to another detector, for example, a mass spectrometer.

In an alternative embodiment, two flow regulating devices 5705 may be connected in parallel to the gas line coming from column 5603. In this embodiment, under high pressure operation, the flow from one of the flow regulating devices is directed to FID assembly 5602 (for example, as shown by the dashed line in FIG. 57), and the flow from the other flow regulating device is directed to a second detector, for example, a mass spectrometer. By adjusting the relative flow rate of the two flow regulating devices, sample emerging from the chromatographic column may be apportioned to the two detectors as appropriate. For example, if the second detector is a mass spectrometer, the flow directed to the mass spectrometer will be adjusted to a lower level than the flow directed to FID assembly 5602 to maintain the low pressure needed for operation of a mass spectrometer.

In yet another embodiment, one (or more) additional measurement device may be connected through suitable flow regulating devices to the sample line between 5703 and 5602. This additional device (for instance a mass spectrometer, could sample a suitable proportion of the flow leaving the chromatographic column under the low pressure conditions which apply after the pneumatically focused sample pressure drop has occurred and flow through flow restrictor 5705 has been transferred to check valve 5703. In this embodiment, the main flow passes through valve 5703 to FID 5602 while a suitably regulated flow is directed through the flow regulating device (not shown) to a second detector, for example, a mass spectrometer. By adjusting the relative flow rate of this flow regulating device, sample emerging from the chromatographic column operating under low pressure conditions may be apportioned to the two detectors as appropriate. For example, if the second detector is a mass spectrometer, the flow directed to the mass spectrometer will be adjusted to a lower level than the flow directed to FID assembly 5602 to maintain the low pressure needed for operation of a mass spectrometer.

During operation of flow control assembly 5701, a pneumatically focused sample is introduced to column 5603. Pneumatic focusing of the sample involves increasing the pressure applied to the sample as it is introduced to the column. At the time the pneumatically focused sample is introduced, operational column pressure may be any pressure, for example, a low pressure (e.g., 10–60 psi), an intermediate pressure (e.g., 60–120 psi), a high pressure (e.g. 120–1200 psi) or an extremely high pressure (e.g. greater than 1200 psi). Regardless, application of increased column pressure of the pneumatically focused sample will close check valve 5703 when the sample pressure rises above the column pressure. This will divert flow of the pneumatically focused sample through flow restrictor 5705. This flow is desirably at a rate sufficiently low to concentrate analytes, particularly higher-weight analytes (e.g., greater than 16 amu), at the head of the column. When the pneumatically focused sample is exhausted, that is, most of the sample volume has passed through flow restrictor 5705, column pressure will drop, check valve 5703 will open, and carrier gas flow through the system will resume. Then, for example, when the column temperature is increased, such as by temperature programing, separation of the analytes adsorbed at the head of the column will occur.

At the pressures used for pneumatic focusing, check valve 5703 will be closed, preventing direct flow to FID assembly 5602. Instead, flow is directed to flow regulating device 5705, which is functioning as an inline pressure increasing/ flow decreasing valve. For example, flow regulating device 5705, by restricting flow, maintains the pneumatic focusing pressure that is applied to the sample by either a pneumatic focusing gas or a piston device. Once the sample is introduced to column 5603 it may be desirable to lower the pressure to aid in chromatographic separation of sample components, to reduce consumption of the carrier gas associated with high pressure flow, or to reach a flow more suitable for a mass spectrometer. Once the pressure is lowered, check valve 5703 will open, permitting direct flow of sample components from the column into FID assembly 5602 or other associated detectors such as described in the previous paragraph.

When a sample contained in a sample loop is pneumatically focused by a high pressure gas, and then introduced into a chromatographic column, high pressure gas remains in the sample loop. The high pressure gas must then be vented to allow additional sample to enter the sample loop. Venting may be accomplished by allowing gas to escape from one end of the sample loop. However, in some applications it may be undesirable to let the high pressure gas enter the sample pump or the sample line. Gas flow into the sample pump or sample line may be prevented by a check valve. A second check valve that permits venting to atmosphere also may be employed.

Figure 58:
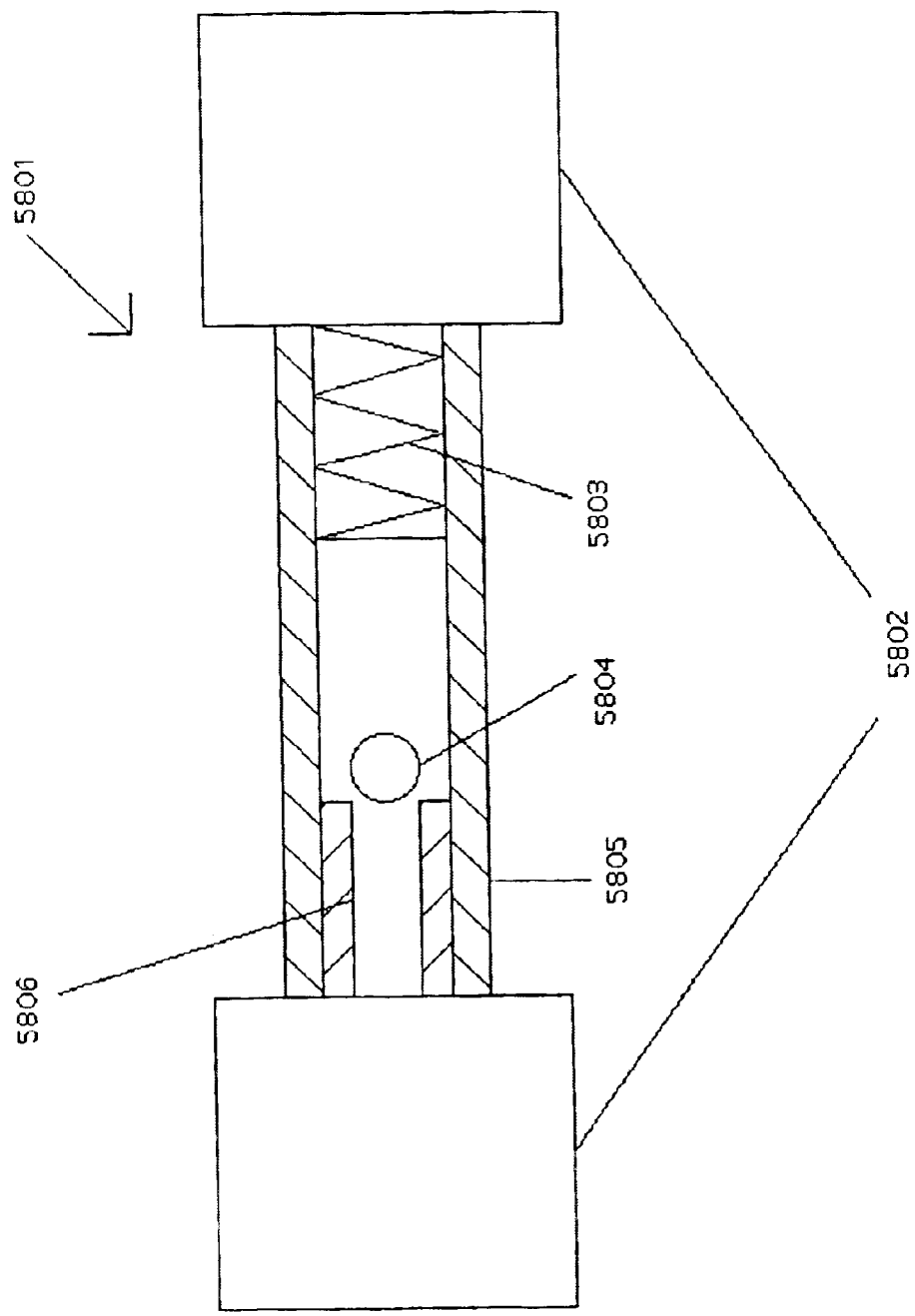
FIG. 58 is diagram showing a side view of an embodiment of a check valve.

FIG. 58 is a diagram showing a particular embodiment of a check valve that can be used, for example, in pneumatic focusing gas analysis systems such as the apparatus of FIG. 57, or the apparatus of FIG. 55. For example, the check valve may be used to prevent backflow of high pressure gas into a sample line or sample pump. Check valve 5801 includes Swagelock tube fittings 5802, spring 5803, ball bearing 5804, outer Teflon tubing 5805 and inner Teflon tubing 5806. Outer Teflon tubing 5805 is connected to the two Swagelock tube fittings 5802 at both ends. Inside of outer Teflon tubing 5805 is fitted inner Teflon tubing 5806. The outer diameter of inner Teflon tubing 5805 is such that it fits tightly within the outer Teflon tubing 5805 and prevents gas flow between the outer surface of the inner tubing and the inner surface of the outer tubing. Ball bearing 5804 is of a diameter that is larger than the inner diameter of inner Teflon tubing 5805. Spring 5803 prevents ball bearing 5804 from forming a seal against the Swagelock tube fitting 5802 shown at right in FIG. 58, but ball bearing 5804 may form a seal when it is pressed against the end of inner Teflon tubing 5805 at left. Thus, in operation, gas flow is permitted from left to right in FIG. 58.

It should be recognized that particular check valves are not needed to establish the functionality of the apparatus shown in FIG. 57. Rather, any gas valve (commercial or fabricated) can function to regulate flow during pneumatic focusing of analytes at the column head. As will be appreciated by one of ordinary skill in the art, the molecular weights of compounds that are concentrated at the head of the column during pneumatic focusing will depend, for example, on the column type, the stationary phase and the temperature.

Figure 59:
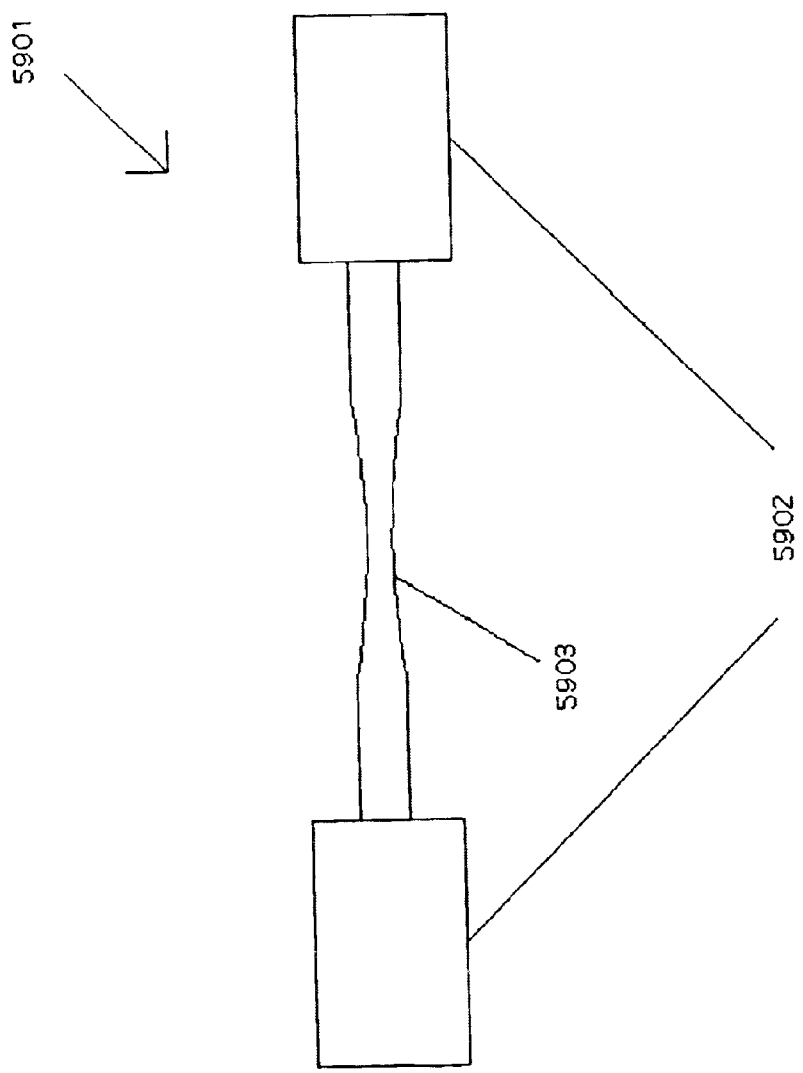
FIG. 59 is a diagram showing an embodiment of a crimped flow control fitting.

FIG. 59 shows a particular flow regulating device that may be used in pneumatic focusing apparatuses such as those shown in the systems of FIG. 1 and FIG. 57. Crimped flow regulating device 5901 includes two Swagelok tube fittings 5902, which are disposed at either end of metal tubing 5903, which may, for example, be copper tubing or steel tubing. In operation, the flow rate through crimped flow regulating device 5901 is adjusted by the following method.

1. Metal tubing 5903 is crushed in a first direction, such as in a vice or a press, so that no flow is observed (or possible) through crimped flow regulating device 5901 at the desired pressure (e.g. the pneumatic focusing pressure desired). Flow through crimped flow regulating device 5901 may be monitored by connecting one end of the device to a supply of gas at the desired pressure, and connecting the other end to a flow meter, such as a soap bubble flow meter known in the art.

2. While observing the flow meter, tubing 5903 is crushed in a second direction, such as a direction substantially perpendicular to the first direction, until flow through device 5901 is observed. Crushing in the second direction is conveniently done using a pair of pliers. As the tubing is crushed in the second direction, the flow will increase, and crushing is ceased once the desired flow rate at the desired pressure is observed. In practice, there is some elasticity of the tubing, and the flow rate should be monitored for a period after crushing in the second direction that is sufficient for the flow rate to stabilize. If the desired flow rate is exceeded, the process may be repeated.

An advantage of a crimped flow regulating device is its relative temperature insensitivity. Thus, the flow regulating device may be placed inside of a pneumatic focusing instrument, such as between a heated column oven and a heated FID. In contrast, commercially available needle type valves used for flow regulation, such as the PNEUMA-DYNE valve described above, are temperature sensitive in that they show unacceptable variation in flow rate with temperature and typically include components that are not resistant to temperatures as high as may be desired for a column oven or an FID.

With reference to FIG. 52, when a separated sample is transported directly from a metal chromatographic column such as 5203 to a detector such as FID 5202, the crimping procedure may be applied directly to the end portion of the column itself. Crimping the column itself eliminates the need for flow regulating device 5901 by accomplishing its function directly. If so crimped, the column should not contain packing material in the portion to be crimped. That is, a substantial end portion of column should remain unpacked. Thus it would be possible to cut and remove an unusable end portion of the column and still have additional unpacked column for remaking the crimp. In addition to simplifying the overall design, direct column crimping provides for a more leak-free system, as potential leaks at the high pressure, upstream end of flow regulating device are circumvented.

Example 21

This example describes additional embodiments of analytical instrumentation contained within a personal computer case. In particular, this example concerns the construction of a mass spectrometer based upon a commercial residual gas analyzer (RGA) within a commercial personal computer case. The computer would also contain typical computer components such as a processor, RAM, hard drive, etc., which would be used to control and pass data to and from the incorporated RGA. This example is based upon the commercial RGA offered for sale by Extorr (New Kensington, Pa.) having the dimensions 3.3"×4.8"×7.5". This small quadrupole mass spectrometer is provided with a negative pressure (relative to atmospheric pressure) to allow its operation. In this example, the negative pressure is provided in a chamber, the chamber also provided within a commercial personal computer case. Furthermore, a source of sample, such as a gas chromatograph, for example, a pneumatic focusing gas chromatograph is also provided within the personal computer case.

A suitable negative pressure is provided using any standard set of components as would be familiar to someone skilled in the art. Such components include, but are not limited to, a hermetically sealed metal container coupled to the vacuum connection of the commercial RGA. Provision for vacuum pumping of the vacuum chamber by, for instance, a turbomolecular pump, is supplied by suitable and standard vacuum fittings welded or otherwise affixed to the metal vacuum chamber. Provision for sample introduction from either an external sample source, or from the effluent of a chromatographic column, such as a gas chromatographic column is provided as well.

Pumping for the RGA and associated vacuum housing is provided, for example, by a vacuum pump such as a turbomolecular pump. Any such pump may be employed, with small pumps which would easily fit within the commercial computer case being advantageous, leaving more room for other system components. A particularly suitable pump has been described by NASA. This particular pump has approximately cubic dimensions of 2.25 inches. Such a device easily fits inside the commercial computer case and be coupled to the Extorr RGA, also within the case. As described in the NASA brief, this miniature turbomolecular pump could be combined with a miniature diaphragm fore pump which would also fit within the personal computer case.

The NASA-described turbomolecular pump is proposed rather than extant, but shows the miniaturization possible within the current mass spectrometric/pumping art. Slightly larger turbomolecular pumps are now available. For example, the turbomolecular pump may be an ATH 31 pump by Alcatel (Hingham, Mass.) which fits within a 4" cubed space.

Example 22

This example describes a system and method for detecting particulate matter in a gas sample. More particularly, this example describes a method for visualizing and counting the number of spores, such as mold and bacterial spores, in an air sample.

Aerosols may be defined as solid or liquid particles suspended in air. As such they can encompass such terms as aerosol particles, particles, particulate matter, dust, haze, smoke, etc. Particles are naturally present in outdoor air and are also introduced into outdoor or indoor air by human activities. Inhalation of certain types and sizes of particles can be hazardous to health. Atmospheric particles range in size from millimeter to nanometer sizes. Larger particles soon fall to earth unless maintained airborne by high wind turbulence. Smaller particles may remain airborne indefinitely. Details of atmospheric particle sizes, formation and loss, and human health implications are described in such texts as *Smoke, Dust and Haze* by Sheldon Friedlander.

In typical 'integrating' particle detectors such as nephelometers and condensation nuclei counters, a number of particles collectively absorb or scatter measurable amounts of light. Such instruments are neither sensitive to individual aerosol particles nor to low numbers of aerosol particles. Although optical particle counters can detect and 'size' individual aerosol particles, such instruments are expensive and complex. In contrast, the disclosed methods and systems are simple and inexpensive, capable of detecting very low numbers of particles (such as 1 particle per cubic centimeter) and capable of operating for very long periods completely unattended.

When air is compressed rapidly, adiabatic heating occurs. Such heating more than compensates for the increase in water vapor concentration associated with the volume reduction. Adiabatic heating prevents water condensation. However, subsequent to the compression step, heat will be lost to the surroundings, cooling will occur, and water may condense in the system. This effect has been used herein to selectively condense such water on certain types of aerosol particles.

When water vapor saturations greater than 100% occur, water vapor is inclined to condense to the liquid phase. Due to the Kelvin Effect (see *Smoke, Dust & Haze,* Sheldon Friedlander), such water will tend to condense on preexisting surfaces rather than homogeneously form new water vapor droplets. This is the phenomenon involved in so-called "cloud-seeding." According to the Kelvin Effect, larger aerosols will be more favored thermodynamically to condense water vapor and at lower supersaturation. This effect is described by a simple mathematical equation, the Kelvin Equation. However, one term in this equation, the surface tension of the resultant liquid droplet, is difficult or impossible to predict for the wide range of aerosol particles present in the atmosphere. Expressed another way, the physical nature of the aerosol that can potentially serve as a condensation nucleus is an important parameter in determining whether that aerosol particle will condense water vapor at any given supersaturation. In general, such effects must be determined experimentally rather than theoretically.

A system for the controlled pressurization or depressurization of an air sample at a controlled rate is provided. In the case of pressurization, the rate of pressurization will determine the development of controlled supersaturation with the ability to condense water vapor selectively on particles. This controlled pressurization may be obtained either by compressing at a slow rate, or by compressing at a faster rate, and then stopping the pressurization step and waiting for cooling and condensation. In the case of depressurization, since adiabatic cooling enhances water condensation, the method consists of slowly expanding the volume containing the air sample. In either situation the air sample may be contained in a small piston-containing chamber to which it is introduced before the measurement begins.

Particles are drawn with the associated air sample into a cell constructed for that purpose. Details of the cell are given in the examples below. The cell is connected to a piston device for drawing the air sample into the cell by piston expansion. Following influx of the air sample, a valve is closed and the piston is compressed to the desired pressure to initiate hydration of the particles. No special coating on the inside of the cell and piston has been found necessary, but may be used in some embodiments. If desired, the inside of the apparatus may be coated with Teflon or some other hydrophobic coating which prevents water condensation of the surface of the piston and cell itself. Particles may visualized by the light beam from an inexpensive laser pointer which enters and exits the cell through windows placed opposite each other for that purpose. Particles may be detected by a webcam whose viewing axis is 90 degrees from the light beam propagation line, also through a window provided for that purpose. Concurrently, additional light sensors could be present in the cell. Such sensors could be constructed, for instance, from the receiving end of an optical fiber connected to a computer spectrometer. Alternately, they could be any of a number of light sensing diodes or other devices. These additional light sensors could provide measurements of light scattering or attenuation as in a condensation nuclei counter or an integrating nephelometer. In this case they could be provided either along the line of propagation of the light source or at angles, such as right angles, to measure, respectively, transmission and/or scattering of the propagated light beam.

The examples described below involve controlled pressurization of air samples containing 'normal' room air, or room air to which spores have been intentionally added. Additionally, such air samples could be subjected to depressurization or expansion by withdrawing the piston. Under these controlled conditions, selective hydration of certain types of aerosols such as spores may be accomplished.

In some embodiments, the methods include recording of individual particles grown up by water condensation to a size viewable by a webcam. A computer continuously records a bitmap (or other format) image from the camera and software parses the individual bits of the image for the presence of a strong light signal. Typical webcams record images at 30 Hz, or 30 frames per second. Such rates are suitable for this method. For this method to work, it is not necessary to magnify an individual particle to a size where it would occupy more than 1 bit in the image. Rather, a single bit records the presence of a light scattering aerosol particle actually much smaller than the area visualized by the bit itself. However, spores and other aerosol particles upon which condensation has not occurred are too small to produce significant scattering to be recorded with the web cam. Thus, in the absence of the water condensation step, spores or similar particles produce no signal, i.e. the bitmap is 'empty' or all black. The number of particles in the field of view of the camera/beam system is easily determined from geometrical and optical considerations. Viewed volumes on the order of a cubic centimeter have been typically viewed in prototype instruments and one or more particles are routinely visualized after water condensation. Thus, the prototype instruments have a 'nominal' detection limit of ~1 spore per cubic centimeter, although much higher numbers of spores per cubic centimeter may be detected. An upper limit may occur when individual spores overlap in the bitmap image. Under many circumstances, however, if the spore count were this high, there would be no need to measure it accurately. However, if there was need to measure spore concentration accurately, the air sample could be diluted, for example, quantitatively, with filtered air before it enters the visualization cell.

The disclosed methods and systems are described further in the following examples. These examples are provided for illustrative purposes and are not meant to limit the invention in any way.

1. Particulate Detection System

FIG. 60 is a schematic of a working embodiment of a system useful for measuring the number and size of particulates, including spores, for any given gas sample, including air. The following components, as well as their connections, will be discussed with reference to FIG. 60. A more detailed explanation of certain components is also included.

FIG. 60 illustrates the aerosol detection system 6013. A working embodiment of system 6013 has been used to nucleate spores of mold grown in a 1-pint jar on a carbohydrate medium in room air. The system 6013 pressurizes air in the cylinder 6003, after which the pressurized air cools with heat lost to the surroundings. Upon compression, room air undergoes adiabatic heating. The air inside cylinder 6003 then goes through a period of controlled cooling and heterogeneous nucleation, wherein water vapor condenses on aerosol particles in the air. Laser pointer 6005 is used to illuminate the particles once they have nucleated, and web cam 6007 is used to record a bitmap (or equivalent) image the nucleated particles as they are illuminated. The web cam is interfaced with desktop computer 6002, and the movies can be viewed from monitor 1, using, for example, the INTEL Auto Snapshot program. Valve 6008 is used to release the pressurized air, and draw in new samples.

Cylinder 6003 is pressurized by means of trailer jack 6004; cylinder 6003 is fastened to trailer jack 6004 by u-clamp 6006.

Relay box 6012 is interfaced with trailer jack 6004 to allow remote control of trailer jack 6004, by means of the relay box 6012. Relay box 6012 is also interfaced with the computer 6002, by means of parallel port cable 6014. The interface allows trailer jack 6004 to be controlled remotely by computer 6002, for example, with the use of the TEK-BASIC programming language. Relay box 6012 is connected to trailer jack 6004 by means of power cable 6017. Relay box 6012 is also connected to Variac 6015, by means of power cord 6016. Variac 6015 is then plugged into the wall outlet 6018. The Variac 6015 regulates the voltage down to 12V. Relay box 6012 is then powered at 12V from the Variac 6015.

The system also includes components that may be used to cool the compression cylinder 6003. Water at a temperature lower than the cylinder may be flowed through tubing 6010, from water source 6011. Water travels through tubing 6010 into copper coil 6009 which surrounds cylinder 6003. Water then continues through tubing 6010, and is disposed for example in a drain or sink.

In an alternative embodiment, the system components described above are all contained within the case of computer 6002.

Expanded views of different portions of FIG. 60 are shown in FIGS. 61 and 62. These FIGS. refer to the description just given and are described further below.

FIG. 61 is an illustration of the end of cylinder 6003 in FIG. 1 and components attached thereto. All the following components, as well as their connections, will be discussed with reference to FIG. 61.

When air is compressed in cylinder 6103, and particle nucleation has begun to occur, the particles are illuminated by means of the laser pointer 6105, which is attached to cylinder 6103 by interface 6106. The illuminated particles are then filmed and documented by the web cam 6101, which is attached to cylinder 6103 through interface 6102 and is in electrical connection with the desktop computer 6108. The nucleation of particles inside cylinder 6103 can then be viewed on desktop computer 6108 by using the INTEL Auto Snapshot program. Air samples in the cylinder are exchanged by the use of the screw valve 6103. An optional filter 6104 can be attached to screw valve 6103 in order to filter out any larger aerosol particles. In a working embodiment, all of the aforementioned components that are connected to the cylinder 6103 were attached by drilling into the side of the cylinder 6103, then tapping the holes for ¼ inch pipe fittings.

FIG. 62 is an illustration of interface 6102 in FIG. 61, which is used to fasten the web cam 6101 to cylinder 6103. All of the following components, as well as their connections will be discussed with reference to FIG. 62. In FIG. 62, webcam 6201 is attached with fitting 6202 to housing 6205 held together by bolts 6203 and connecting plates 6204.

2. Operation of the System

Experimental images and graphs obtained using the system described in FIGS. 60–62 are shown FIG. 63. FIG. 63 depicts three different experiments. Each experiment is depicted by a chart (charts 1–3) as well as two sets of web cam images for each experiment. Each set of three images stacked vertically refers to each of 3 exemplary experiments. The bottom set of 3 web cam images are shown as recorded by the webcam. These images have a black background with blotchy areas where the laser beam reflects off the cell walls. These reflections have nothing to do with aerosol particles and can be eliminated through further cell design. In addition, each webcam image shows a number of individual particles. Image 1 shows a single particle indicated by an arrow. Images 2 and 3 show a plurality of particles, only a few of which are indicated by arrows. The middle set of photos are color reversals of the bottom set. These are included only for clarity in that the lower, black set may not reproduce well. These middle images present the same information as the lower set.

Chart 1, Chart 2, and Chart 3 illustrated in FIG. 63 are graphical and bitmap representations of data collected using the system 13.

Referring back to FIG. 60, when the trailer jack 6004 compresses the cylinder 6003 in the system 6013, and a subsequent waiting period for cooling is employed, the gas inside the cylinder goes through a period of heterogeneous nucleation. The waiting period typically comprises anywhere from 10 seconds to several minutes.

An exemplary procedure follows:

1) Cylinder 6003 is compressed to a certain compression ratio during which time the gas heats substantially adiabatically. This compression pressure is indicated in the charts in units of 10 psi above atmospheric pressure which is approximately 15 psi.
2) The relative humidity inside said cylinder 6003 initially decreases due to this heating process. This heating has a stronger effect than the volume compression on the relative humidity.
3) Heat is lost to the cooler surroundings, which causes the compressed gas to cool. When, due to this cooling, the sample relative humidity increases to a particular value that is higher than one hundred percent, the moisture in the gas begins to condense on selected aerosol particles that may be in the sample. Depending upon the size and character and type of aerosol particles, water will condense on those particles at a characteristic pressure, time, temperature or relative humidity following compression.

While cylinder 6003 is in the process of being compressed adiabatically, the moisture will not condense on the particles due to the fact that the heat created by the increasing pressure will cause the vapor pressure of the water to rise fast enough so that no water is allowed to condense on the particles in the sample. When the sample inside cylinder 3 is compressed and then allowed to cool for a short period of time, heat is lost from the sample to the walls of cylinder 6003. When enough heat is lost from the gas, the vapor pressure of the water lowers to a point where it will begin to condense on some of the aerosol particles in the gas. The condensation that occurs in the sample tends to happen to the largest and/or most hygroscopic particles first. As sample temperature drops, and in turn the relative humidity increases, the more hydrophilic and/or larger particles nucleate and are visualized first. So by compressing the cylinder 6003 to varying pressures it is possible to cause the water in the air sample to condense on different types of particles in the sample.

The disclosed embodiment of the spore detector included a trailer jack that had only a single compression speed. Hence, the procedure of compression, followed by waiting for cooling and condensation, was employed. A more general approach is to use a variable speed motor to enable compression at any desired rate. At sufficiently low compression rates, heat loss to the surroundings will occur substantially as compression heating occurs. In this mode, no waiting period for cooling and condensation is needed; rather, condensation on particles occurs at a particular pressure or compression ration without any waiting period. Such a compression mode is isothermal in nature rather than adiabatic in nature. In the "isothermal" mode, the presence of spores would be detected by their hydration at a lower compression ratio relative to other, non-spore aerosol particles in a gas sample, such as an air sample.

Figure 60:
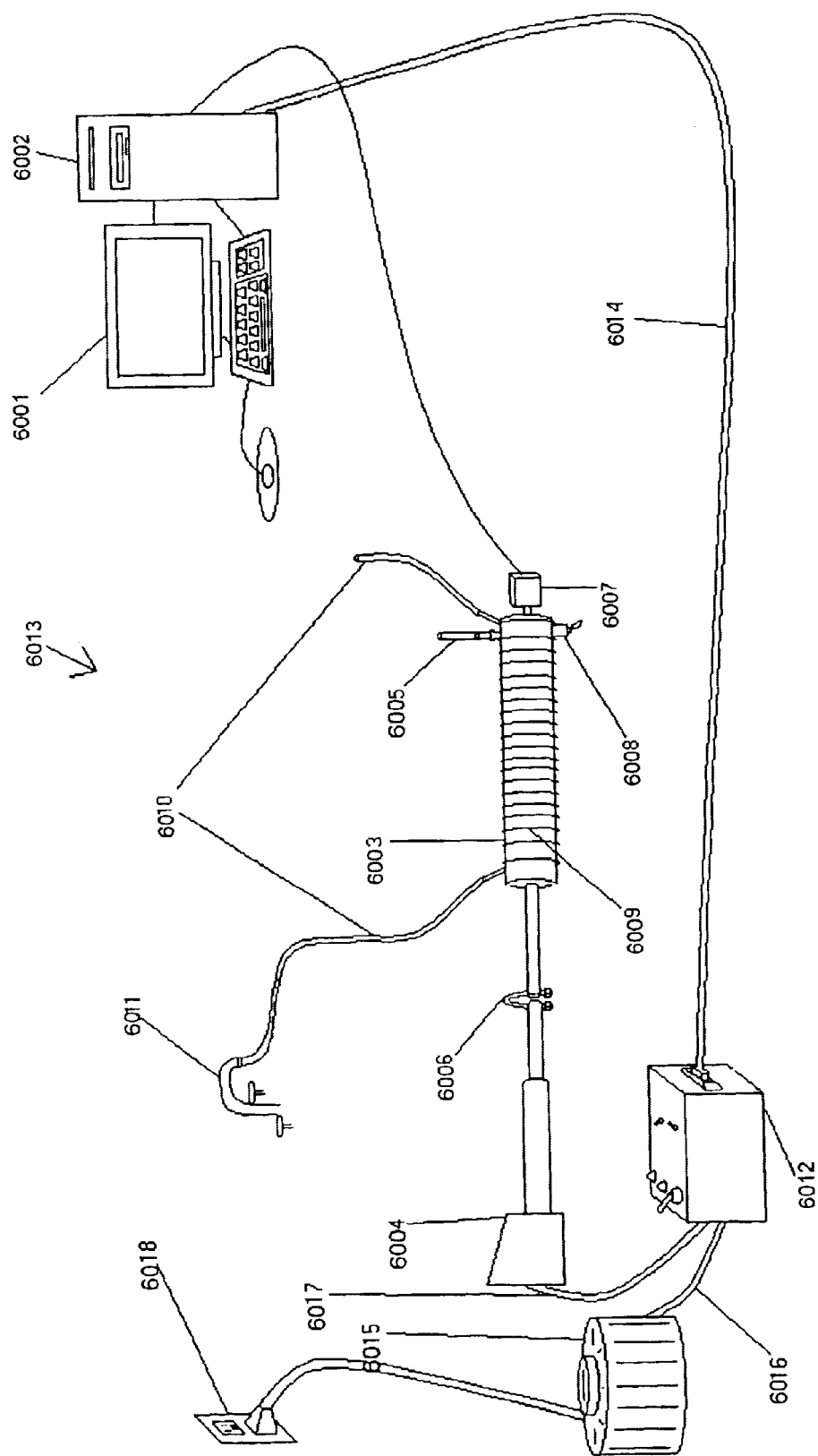
FIG. 60 is a diagram showing connections and circuitry of a system for visualizing, identifying and counting spores in a gas sample.
Figure 61:
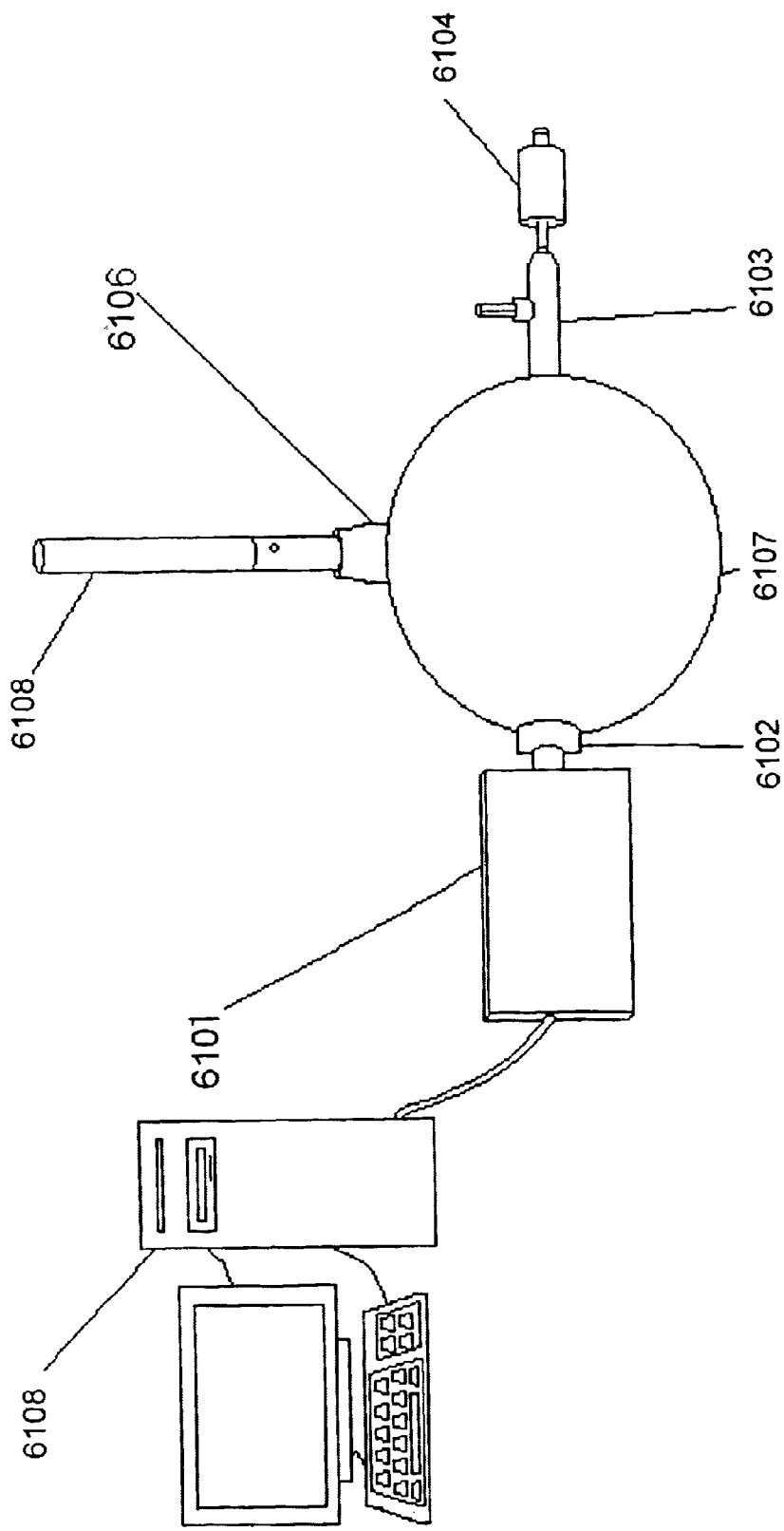
FIG. 61 is a cross-section of the end of a compression cylinder.
Figure 62:
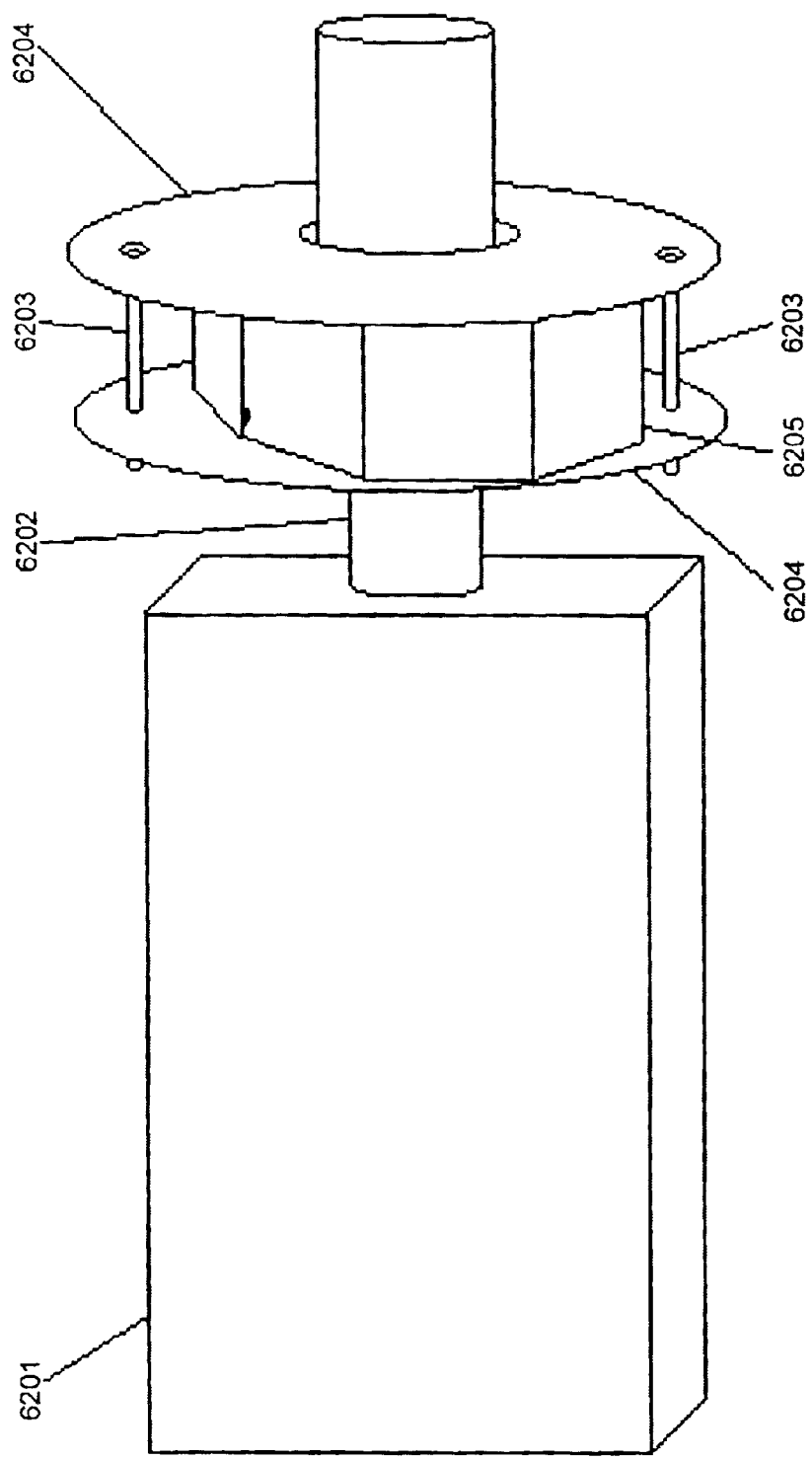
FIG. 62 is a detailed magnification of a fitting used to secure a web camera to the compression cylinder of FIG. 62.

Referring still to FIG. 60, it is possible to inject a sample of normal room air that has been contaminated with spores into cylinder 6003 using the valve 6008, and compress the sample to a point where the spores will begin to nucleate. The pressure required to nucleate and visualize these particles in the laser beam has been shown to be significantly lower than the pressure that is required to allow the ambient particles in a normal sample of room air to nucleate. This means that it is possible to identify the presence of spores in a sample of room air.

Figure 63:
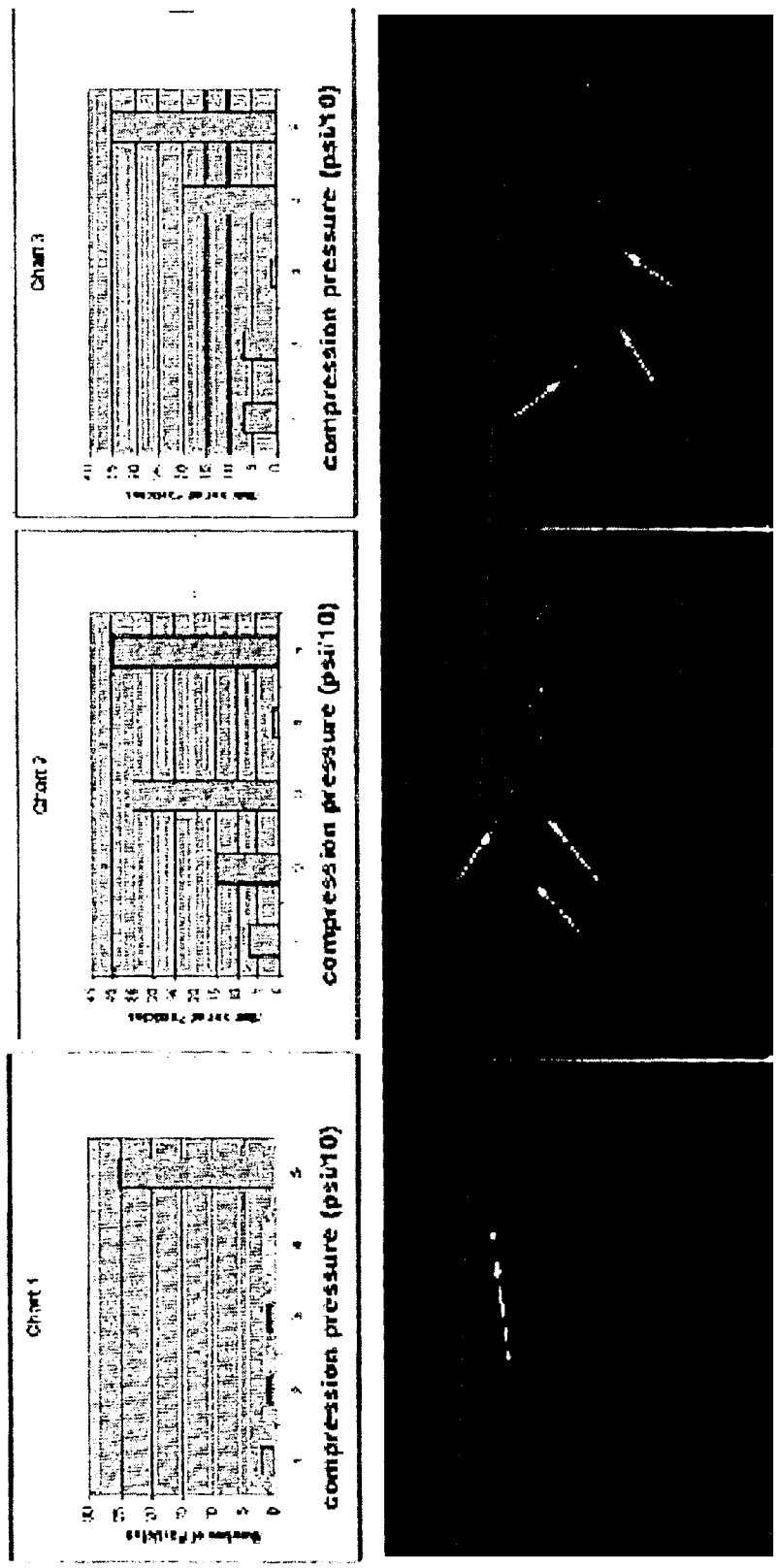
FIG. 63 is a graph showing particle counts obtained in three separate experiments using ordinary room air as a sample, and two samples where room air was passed through a small jar containing spores formed by mold growing on a carbohydrate medium. Also shown are the web camera images of the aerosol particles produced by compression/condensation of the air samples in the apparatus ill

Chart 1 of FIG. 63 is a representation of an experiment in which ordinary room air was injected into cylinder 6003 using valve 6008 of FIG. 60. The sample was then compressed in cylinder 6003 using trailer jack 6004, in increments of 10 PSI. Chart 1 shows that there are literally no spores seen nucleating at any of the lower pressure intervals. Then, at roughly 50 PSI above normal atmospheric pressure, the production of nucleated aerosol particles jumps up rapidly. This is because in this sample of normal room air no ambient particles exist that are large enough, or hygroscopic enough, to nucleate at pressures lower than 50 PSI above atmospheric pressure. After the sample reaches pressures higher than 50 PSI above atmospheric pressure, and the cell is allowed to cool, the relative humidity rises to a point high enough that water will begin to condense on the ambient particles in the air.

Chart 2 of FIG. 63 is a representation of another experiment in which spores were hydrated and visualized at pressures lower than those required to hydrate aerosols present in the same room air.

Spores were prepared for this experiment by storing a piece of bread, about 2 cm×2 cm, in a glass container for a period of several weeks. During this time, mold grew on the bread and eventually formed spores. These spores were suspended by shaking the jar. Air from the jar was drawn into the visualization chamber by the piston through a tube provided for that purpose. This tube connected the spore jar fluidly with the compression chamber. Air withdrawn from the mold chamber was replaced through another inlet to the mold chamber. This replacement air originated from the room. Air originating from the room could either be taken directly, in which case it contained ambient aerosols; or it could be filtered before entering the mold growth chamber, thereby removing the larger room aerosol particles. In this spore experiment, it was not determined whether the spores existed individually as supendedaerosols, or whether they were present as agglomerates of multiple spores. In normal spore release by, for example, molds, individual spores are released. However, in terrorist application of virulent spores, it is often difficult to disperse individual spores, and less effective agglomerates of spores are released. It may be possible to differentiate single spores and agglomerated spores on the basis of their relative hydration pressures.

In this experiment room air that had been contaminated with spores was injected into cylinder 6003 using valve 6008 of FIG. 60. The sample was then compressed in cylinder 6003 using trailer jack 6004, in increments of 10 PSI. Chart 2 indicates that numerous particles are nucleating at pressures as low as 20 PSI above atmospheric pressure. At 20 PSI above atmospheric pressure, Chart 1 shows that no particles were seen nucleating when room air with no added spores constituted the sample. The experiment that produced Chart 1 was identical to the experiment that produced Chart 2, except that there were no spores added to the air sample used in the experiment for Chart 1. So, the only particles that could have been nucleating at pressures as low as 20 PSI above atmospheric pressure were the foreign spores that were contaminating the air sample that was used in the experiment for Chart 2. This demonstrates that it is possible to identify spores in a gas sample through the use of the system 6013 of FIG. 60.

Chart 3 of FIG. 63 is a representation of a third experiment. This experiment was run in a manner identical to the experiment that produced Chart 2. The data in Chart 3 shows results that are consistent with those found in Chart 2, and shows that the data in Chart 2 is reproducible. This means that the conclusions drawn from Chart 2 can be drawn from another, identical experiment that was performed at a different time than the experiment that produced Chart 2.

In addition to simply identifying the presence of foreign particles in a sample of gas, it is possible to count the particles in the photo and use an equation to give an estimate of particles per cubic cm in the original air sample. The equation describes the volume of compressed air in which the spores are counted. The compressed air sample illuminated by the laser pointer has a volume of $pi*r^2*1$. Here, r is the laser beam radius, 1 is the length of the laser beam that falls within the field of view of the web camera. The values of r and 1 may be measured with a millimeter scale by directing the laser pointer beam onto the scale, and by viewing the scale at the appropriate distance with the web cam. This calculation provides the volume in which the spores were detected. Since the air during detection has been compressed, correction for this compression step will give the original number of spore particles per unit volume. This calculation, for example, would then be $N=pi*r^2*1*P/atm$ psi. The quantities r and 1 are defined previously. P is the pressure to which the cell was pressurized and atm is atmospheric pressure in the same units. Alternatively, P/atm is the isothermal compression ratio utilized for a particular hydration event.

In addition to counting the number of aerosol particles per unit volume it is possible to estimate their size with use of the equation, $D=2((0.0525343*P)/(N*T))$. In the equation, D represents the diameter of the individual particles being nucleated. N represents number of particles being seen hydrated at any point in time. P represents the pressure of the gas at the time when you are trying to determine the size of the particles. T represents the absolute temperature of the gas. By taking a picture of the nucleating particles as captured by the web cam 21 it was possible to determine the approximate size of the particles being seen in the picture.

A program for counting the number of particles in a picture has been developed using the MATLAB programming language which offers image processing software. With this program, it is possible to find the number of particles that are hydrating in the cylinder 6003 of FIG. 60 at any point in time. This is done by parsing the individual bits of the webcam bitmap image and looking for high light intensities. Then, given the pressure and temperature in said cylinder 6003, it is possible to determine the average size for the particles hydrating.

The aforementioned experiments describe pressurization of a room air sample to varying pressures above atmospheric pressure followed by a delay waiting time for cooling and condensation to occur. This waiting time typically represents a few seconds to a few minutes.

Alternatively, the methods may be practiced by slow expansion of the piston in a chamber into which room air has been introduced. In this case, condensation may occur without a waiting period, since adiabatic cooling should immediately produce an increase in relative humidity by decreasing the water vapor pressure. The principal variable in this system will simply be the rate of piston expansion. Thus, a piston chamber in which the piston movement rate can be controlled is required, for example by use of a variable voltage dc motor. These experiments may, for example, be conducted as follows:

1) The piston is compressed to its minimum distance to expel most of the air from the previous sample.
2) The piston is drawn back a predetermined distance, such as ½ way between its fully compressed and fully expanded positions. During this expansion air from the sample enters the chamber.
3) The valve connecting the piston to the atmospheric or other sample is then closed and the air sample is allowed to reach room temperature.
4) The web camera is initiated, obtaining images of the cell contents every 1/30 second.
5) The piston is then slowly further withdrawn towards full expansion.

Adiabatic cooling produces condensation upon selected preexisting particles. The camera then records the condensation of water vapor onto preexisting aerosol particles or spores. With a record of piston position and/or cell pressure and/or temperature, the point at which various types of aerosol particles or spores hydrate may be determined, and used to determine whether spores can be distinguished from 'normal' room aerosols. Furthermore, different types of spores/particles may be distinguished by the recorded piston position, cell pressure and/or temperature at which they hydrate.

6) In an alternative approach, following step 4), the piston is slowly compressed rather than withdrawn. If such compression is done slowly, the compression may proceed substantially isothermally, rather than (semi) adiabatically, and hydration of spores will occur at a characteristic isothermal compression ratio.

Either 5) or 6) may be employed successively in a particular spore detection experiment. That is, one air sample may be subjected to steps 1–5, and the next subjected to steps 1–4, then 6.

3. Webcam Detection of the Hydration Process

Figure 64:
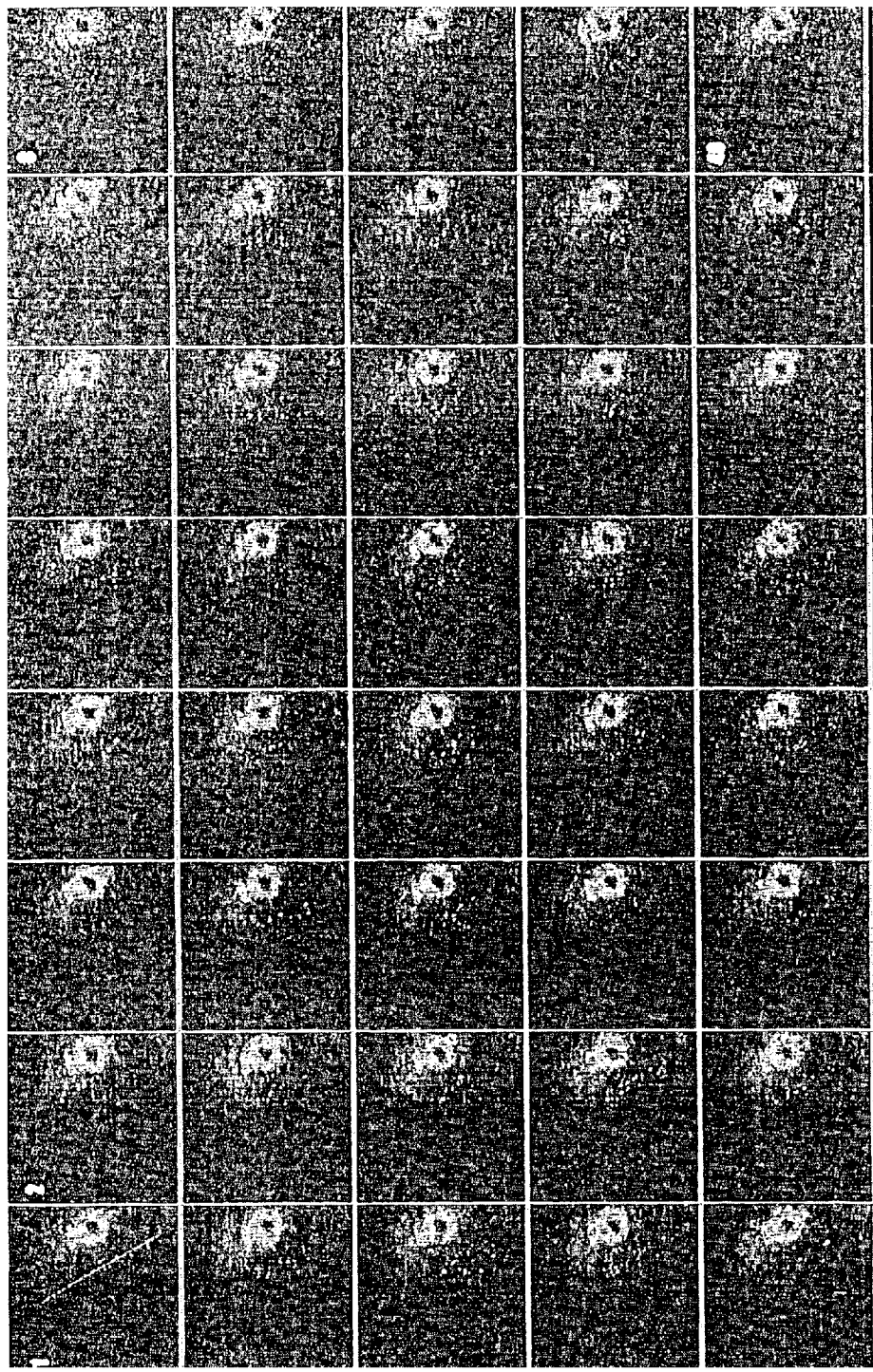
Figure 65:
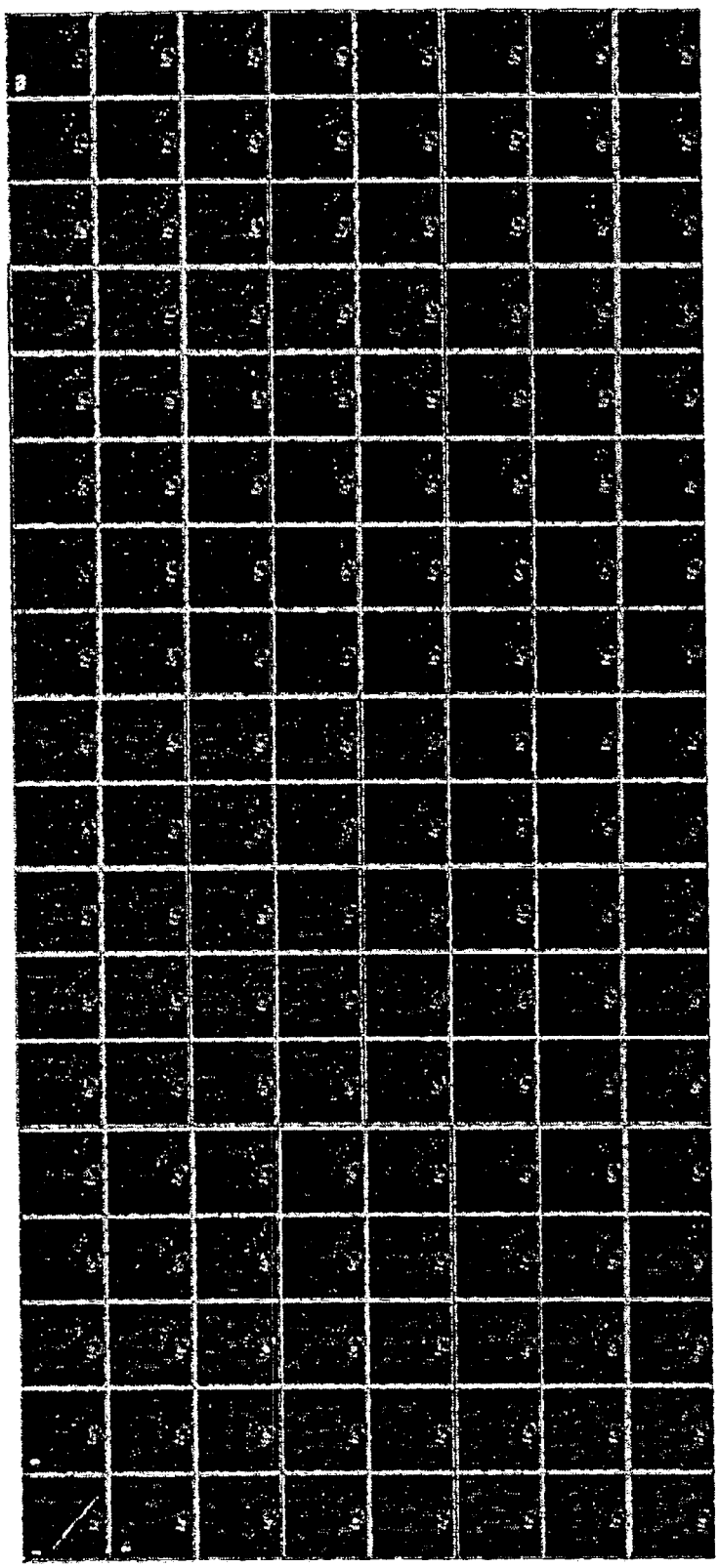

FIGS. 64 and 65 depict a series of webcam photos taken during the hydration of spores from moldy bread at 40 psi. This is a different experiment from the experiments shown in FIG. 63. FIG. 64 shows a sequence of frames taken at 30 Hz, the base frequency of the webcam. Each frame is taken 1/30 of a second after the previous frame and after the onset of hydration after the cell was pressurized to 40 psi. FIG. 65 shows a longer sequence of the same experiment, this time showing only every $10^{th}$ frame so that ⅓ second elapses between frames. The direction of laser beam propagation is illustrated in the first frame of each sequence. A few frames are individually numbered to illustrate the sequence.

4. Continuous Monitoring to Detect Sudden or Occasional Exposure to Extraneous Spore Aerosol Particles This example describes a method of continuous monitoring for the presence of extraneous spores which could potentially be harmful to health. The apparatus described in this section is operated continuously by a personal computer using the methods described above. A human individual may be automatically notified by said computer if an unusual particle situation occurs.

Compression of an air sample produces adiabatic heating that raises the vapor pressure of water vapor present in the air sample. In spite of the volume decrease associated with compression, water will not condense under adiabatic conditions. However, if the sample is allowed to cool at a controlled rate during the compression step it is possible to regulate the sample relative humidity so that a well-controlled time/temperature/relative humidity profile occurs. Thus, particles in the air sample will be exposed to gradually increasing relative humidity. In principle, for particles of a homogenous chemical composition, the largest particles should hydrate first, followed successively by increasingly smaller particles. This phenomenon can be followed by the laser illumination, webcam recording described above. Alternatively, this phenomenon can be followed by monitoring the light scattering particles with a standard, low-tech photometer as used in a condensation nuclei counter. An inexpensive laser-pointer type light source may be employed in either case. Thus a particular intensity/time curve would represent a particular size distribution for a size-polydisperse, chemically-homogeneous aerosol. The details of this curve would depend upon the hygroscopic properties of the original "seed" aerosol. This combination of size distribution and hydroscopicity for a size-polydisperse aerosol could easily be measured for a given chemically-homogeneous aerosol. If components of the original aerosol particle are water soluble they would dissolve during this hydration/growth period. If the aerosol particle is not soluble per se, as is the case with a bacterial spore, then the particle size and surface free energy of the particle would determine its particular temporal light scattering curve.

Another approach is to use slow, gradual expansion of the original air sample within the piston chamber with concurrent measurement of either particle number via web cam and/or total light scattering via a photometer. This expansion would be carried out either by drawing a fresh air sample through the chamber with an auxiliary pump, followed by gradual expansion, or by drawing a new air sample into the chamber by partial expansion of the piston, following by closure of the valve to prevent more incoming air, followed by subsequent expansion of the piston. This expansion would be neither adiabatic or isothermal, but in-between these limiting cases, with the extent of cooling dependent upon the expansion rate and the rate of heat transfer to the surroundings.

In the open atmosphere there will be a mix of particle sizes and particle chemical composition that would produce a varying time/hydration/light scattering curve. Gradual compression or expansion of an air sample would record a light intensity hydration curve which could be stored and then compared by pattern- or source-recognition software to previous history to look for something quantitatively out of the ordinary. The system could be extensively tested on both ambient aerosols and upon selected nonvirulent spores which will serve as anthrax or other virulent spore surrogates.

Once an automated compression/light scattering system as described above was operational, it would continuously and repeatedly record connected data records of light scattering and/or number of condensation nuclei. This data would form a continuous record which could then be compared in real time with each new data file using pattern or source recognition software. In this way any unusual circumstance would be immediately recognized.

Certain preferred embodiments are described herein. Persons of ordinary skill in the art will realize that the scope of the present invention can vary from the particular embodiments described herein. The true scope of the present invention should be determined by reference to the attached claims.

We claim:

1. A gas chromatograph and gaseous sample analysis system, comprising:
   a sample loop for receiving a gaseous sample;
   a separatory column fluidly connected to and downstream of the sample loop;
   an inline pressure-increasing device which is located downstream of the separatory column and which is configured to increase system pressure to at least 150 psi to pneumatically focus the gaseous sample; and
   a detector downstream or upstream of the pressure increasing device for detecting analytes.

2. The system of claim 1 where the inline pressure-increasing device is further configured to reduce linear flow rate to lower than linear flow rate through the system prior to increasing the pressure with the inline device.

3. The system of claim 1 where the inline pressure-increasing device is further configured to increase linear flow rate to higher than linear flow rate through the system prior to increasing the pressure with the inline device.

4. The system of claim 1 where the inline pressure-increasing device is further configured to maintain linear flow rate substantially the same as linear flow rate through the system prior to increasing the pressure with the inline device.

5. The system of claim 1 where the sample loop is of sufficient capacity to provide adequate analyte sensitivity once the sample is pneumatically focused, and wherein the system is further configured to inject all of or a portion of the pneumatically focused sample into the separatory column.

6. The system of claim 1 including plural separatory columns.

7. The system of claim 1 including plural detectors.

8. The system of claim 1 and including a vacuum pump to draw a gas sample through the column.

9. The system of claim 1 and further comprising plural separatory columns.

10. The system of claim 1 and further comprising plural sample collection coils and plural separatory columns.

11. The system of claim 1 and further including a sample collection pump for drawing the gaseous sample into the gas sample loop.

12. The system of claim 1 and further including a computer for controlling the system.

13. The system of claim 12 where the computer is operated by a neural network and expert systems.

14. The system of claim 1 where the gas chromatograph is located on a microchip.

15. The system of claim 12, wherein the system is contained within a computer case.

16. The system of claim 1, wherein the inline pressure increasing device is selected from the group consisting of a calibrated leak, a frit restrictor, a tapered capillary restrictor, a feedback regulator, a needle valve, and a crimped capillary flow regulator.

17. The system of claim 15, wherein the computer case is selected from the group consisting of AT, BATX, ATX, MATX, LPX and microATX compatible cases.

18. The system of claim 15, wherein the computer case is selected from the group consisting of full tower, tower, mid-tower, microtower, desktop, rackmount and server chassis cases.

19. The system of claim 1 where the sample loop is configured to withstand system pressure used to pneumatically focus the sample.

20. The system of claim 19 where the sample loop is configured to withstand pressures from 200 psi to 2,000 psi.

21. The system of claim 1 where the inline pressure-increasing device is configured to increase system pressure to a pressure of 150 psi to 15,000 psi.

22. The system of claim 1 where the inline-pressure-increasing device is configured to increase system pressure to a pressure of 200 psi to 2,000 psi.

23. The system of claim 1 further including a valve configured to direct a carrier gas through the sample loop containing the first volume of the gaseous sample as the inline pressure-increasing device increases system pressure.

24. The system of claim 1 where the inline-pressure increasing device is further configured to decrease system pressure after the gaseous sample is pneumatically focused and injected into the separatory column.

25. The system of claim 23 where system pressure is increased and decreased under computer control.

26. The system of claim 1 where the inline-pressure increasing device comprises a needle valve under computer control.

* * * * *